(12) United States Patent
Singh et al.

(10) Patent No.: US 11,884,744 B2
(45) Date of Patent: Jan. 30, 2024

(54) COMPOUND TARGETING IL-23A AND B-CELL ACTIVATING FACTOR (BAFF) AND USES THEREOF

(71) Applicants: Boehringer Ingelheim International GmbH, Ingelheim Am Rhein (DK); MacroGenics, Inc., Rockville, MD (US)

(72) Inventors: Sanjaya Singh, Sandy Hook, CT (US); Qi Pan, Chappaqua, NY (US); Rachel Rebecca Barrett, Bethel, CT (US); Leslie S. Johnson, Damestoen, MD (US); Pankaj Gupta, Scarsdale, NY (US); Sarah Low, Carmel, NY (US); Haixia Wu, Danbury, CT (US)

(73) Assignees: Boehringer Ingelheim International GmbH, Ingelheim Am Rhein (DK); MacroGenics, Inc., Rockville, MD (US)

( * ) Notice: Subject to any disclaimer, the term of this patent is extended or adjusted under 35 U.S.C. 154(b) by 550 days.

(21) Appl. No.: 17/076,894

(22) Filed: Oct. 22, 2020

(65) Prior Publication Data
US 2021/0107998 A1   Apr. 15, 2021

Related U.S. Application Data

(62) Division of application No. 16/278,216, filed on Feb. 18, 2019, now Pat. No. 10,844,138, which is a division of application No. 15/215,690, filed on Jul. 21, 2016, now Pat. No. 10,280,231.

(60) Provisional application No. 62/355,302, filed on Jun. 27, 2016, provisional application No. 62/201,067, filed on Aug. 4, 2015, provisional application No. 62/196,170, filed on Jul. 23, 2015.

(51) Int. Cl.
| | |
|---|---|
| *A61K 39/395* | (2006.01) |
| *C07K 16/46* | (2006.01) |
| *C07K 16/28* | (2006.01) |
| *C12N 15/63* | (2006.01) |
| *C12N 5/10* | (2006.01) |
| *C07K 16/24* | (2006.01) |
| *C12P 21/00* | (2006.01) |
| *C12N 15/00* | (2006.01) |
| *A61K 39/00* | (2006.01) |

(52) U.S. Cl.
CPC .......... *C07K 16/468* (2013.01); *C07K 16/241* (2013.01); *C07K 16/244* (2013.01); *C07K 16/2875* (2013.01); *C12N 5/10* (2013.01); *C12N 15/63* (2013.01); *A61K 2039/505* (2013.01); *C07K 2317/31* (2013.01); *C07K 2317/524* (2013.01); *C07K 2317/53* (2013.01); *C07K 2317/56* (2013.01); *C07K 2317/60* (2013.01); *C07K 2317/62* (2013.01); *C07K 2317/76* (2013.01); *C07K 2317/92* (2013.01); *C12N 15/00* (2013.01); *C12P 21/00* (2013.01)

(58) Field of Classification Search
CPC .................................................... A61K 39/395
See application file for complete search history.

(56) References Cited

U.S. PATENT DOCUMENTS

| | | |
|---|---|---|
| 2003/0059937 A1 | 3/2003 | Ruben et al. |
| 2010/0028359 A1 | 2/2010 | Gu et al. |
| 2010/0174053 A1 | 7/2010 | Johnson et al. |
| 2010/0303777 A1 | 12/2010 | De Creus et al. |
| 2011/0236388 A1 | 9/2011 | Baehner et al. |
| 2013/0129723 A1 | 5/2013 | Blankenship et al. |
| 2013/0280256 A1 | 10/2013 | Barrett et al. |
| 2013/0330335 A1 | 12/2013 | Bremel et al. |
| 2014/0363444 A1 | 12/2014 | Barrett et al. |
| 2014/0377269 A1 | 12/2014 | Mabry et al. |
| 2015/0017169 A1 | 1/2015 | Humphreys et al. |

FOREIGN PATENT DOCUMENTS

| | | |
|---|---|---|
| WO | 2009081201 | 7/2009 |
| WO | 2010/080538 | 7/2010 |
| WO | 2011098762 | 8/2011 |
| WO | 2012/018687 A1 | 2/2012 |
| WO | 2012076883 | 6/2012 |
| WO | 2012083370 | 6/2012 |
| WO | 2012135345 | 10/2012 |
| WO | 2013120929 | 8/2013 |
| WO | 2013/158577 A1 | 10/2013 |
| WO | 2013/177101 A1 | 11/2013 |

OTHER PUBLICATIONS

Lubberts, Erik. "The IL-23-IL-17 axis in inflammatory arthritis." Nature reviews. Rheumatology vol. 11,7 (2015): 415-29. doi:10.1038/nrrheum.2015.53.

Du et al. "Molecular basis of recognition of human osteopontin by 23C3, a potential therapeutic antibody for treatment of rheumatoid arthritis." Journal of molecular biology. Oct. 17, 2008;382(4):835-42.

Caldas et al. "Humanization of the anti-CD18 antibody 6.7: an unexpected effect of a framework residue in binding to antigen." Molecular Immunology. May 1, 2003;39(15):941-52.

(Continued)

*Primary Examiner* — Prema M Mertz
(74) *Attorney, Agent, or Firm* — Robin L. Teskin; Baker, Donelson, Bearman, Caldwell & Berkowitz PC

(57) ABSTRACT

The disclosure relates to compounds specific for IL23A and BAFF, compositions comprising the compounds, and methods of use thereof. Nucleic acids, cells, and methods of production related to the compounds and compositions are also disclosed.

20 Claims, 5 Drawing Sheets
Specification includes a Sequence Listing.

(56) References Cited

OTHER PUBLICATIONS

Kunik et al. "Structural consensus among antibodies defines the antigen binding site." PLoS computational biology. Feb. 23, 2012;8(2):e1002388.
Casadevall et al. "Immunoglobulin isotype influences affinity and specificity." Proceedings of the national academy of sciences. Jul. 31, 2012;109(31):12272-3.
Dall'Acqua, WF, et al. "Properties of human IgG1s engineered for enhanced binding to the neonatal Fc receptor (FcRn)," J Biol Chem Aug. 18, 2006;281(33):23514-24.
Lai Kwan Lam Q, et al. "Local BAFF gene silencing suppresses Th17-cell generation and ameliorates autoimmune arthritis," Proc Natl Acad Sci U S A. Sep. 30, 2008;105(39):14993-8.
Oganesyan V, et al. "Structural characterization of a human Fc fragment engineered for extended serum half-life," Mol Immunol. May 2009;46(8-9):1750-5.
Su DL, et al. "Roles of pro- and anti-inflammatory cytokines in the pathogenesis of SLE," J Biomed Biotechnol. vol. 2012; Article ID 347141, 15 pages.
Brummell DA, et al. "Probing the combining site of an anti-carbohydrate antibody by saturation-mutagenesis: role of the heavy-chain CDR3 residues," Biochemistry. Feb. 2, 1993;32(4):1180-7.
Kobayashi H, et al. "Tryptophan H33 plays an important role in pyrimidine (6-4) pyrimidone photoproduct binding by a high-affinity antibody," Protein Eng. Oct. 1999; 12(10):879-84.
Brorson K, et al. "Mutational analysis of avidity and fine specificity of anti-levan antibodies," J Immunol. Dec. 15, 1999;163(12):6694-701.
Colman PM. "Effects of amino acid sequence changes on antibody-antigen interactions," Res Immunol. Jan. 1994;145(1):33-6.

* = p< 0.05 One-way ANOVA followed by Dunnett's multiple comparisons test vs. huBAFFmc control { # COMPOUND TARGETING IL-23A AND B-CELL ACTIVATING FACTOR (BAFF) AND USES THEREOF

CROSS REFERENCE TO RELATED APPLICATIONS

This application is a divisional of U.S. patent application Ser. No. 16/278,216, filed Feb. 18, 2019, which is a divisional of U.S. patent application Ser. No. 15/215,690, filed Jul. 21, 2016, now U.S. Pat. No. 10,280,231, which is a which claims priority to U.S. Provisional Appl. Nos. 62/355,302, filed Jun. 27, 2016; 62/201,067, filed Aug. 4, 2015; and U.S. Provisional Appl. No. 62/196,170, filed Jul. 23, 2015, the disclosures of each of which are hereby incorporated by reference in their entireties.

This application includes as part of its disclosure a biological sequence listing which is being concurrently submitted through EFS-Web. Said biological sequence listing is contained in a file named "11574430001205.txt" which was created Oct. 21, 2020, and has a size of 296,867 bytes, and is hereby incorporated by reference in its entirety.

BACKGROUND

Inflammation involves an innate and adaptive immune response that is required for fighting infection. However, when the inflammation becomes unchecked autoimmune or autoinflammatory diseases, neurodegenerative disease, and even cancer can develop. It is known that proinflammatory cytokines such as ILL BAFF, TNF-alpha, IL6, IL12, IL17, IL18, and IL23 are involved in inflammation and specific pathways that activate immune cells. However, it is unclear whether or how the inhibition of one or more of these cytokines could result in treatment of autoimmune or auto-inflammatory diseases.

Interleukin 23 (IL23) is a heterodimeric cytokine consisting of two subunits, p40 and p19. The p19 subunit is also referred to as IL-23A. While the p19 subunit is unique to IL23, the p40 subunit is shared with the cytokine IL12. IL23 is emerging as a key regulator of pathogenic Th17, γδ T and innate lymphoid cells (ILCs) driving the production of IL17, IL22 and other cytokines that lead to local tissue inflammation and damage. IL23 promotes upregulation of the matrix metalloprotease MMP9, increases angiogenesis, reduces CD8+ T cell infiltration, and has been implicated in the development of cancerous tumors. In addition, in conjunction with IL6 and TGFβ1, IL23 stimulates naive CD4+ T cells to differentiate into Th17 cells. In turn, the Th17 cells produce IL17, a proinflammatory cytokine that enhances T cell priming and stimulates the production of proinflammatory cytokines such as IL1, IL6, TNF-alpha, NOS-2, and also induces expression of chemokines resulting in inflammation and disease pathogenesis. IL23 exerts its effects via a cell surface receptor composed of the IL12β1 subunit of IL12 receptor partnered with a unique IL23R subunit. Expression of the IL23R is restricted to specific populations of immune cells and is found primarily on subsets of T cells (αβ and γδ TCR+) and NK cells.

In mice, genetic ablation of the IL23p19 gene results in selective loss of IL23 function accompanied by severely compromised T-dependent immune responses, including reduced production of antigen-specific immunoglobulins and impaired delayed type hypersensitivity responses (Ghilardi N, et al. (2004) J. Immunol. 172(5): 2827-33). Knockout mice deficient in either IL23p40 or IL23p19, or in either subunit of the IL23 receptor (IL23R and IL12β1), develop less severe symptoms in animal models of multiple sclerosis, arthritis and inflammatory bowel disease. Similar results have been obtained using an antibody specific for IL23p19 in EAE and a T cell mediated colitis model further substantiates the role of IL23 in these disease settings (Chen Y. et al. (2006) J. Clin. Invet. 116(5):1317-26; Elson C O. Et al. (2007) Gastroenterology 132(7): 2359-70). This highlights the importance of IL23 in chronic inflammation (Langowski et al. (2006) Nature 442 (7101): 461-5; Kikly K, et al. (2006) Curr. Opin. Immunol. 18 (6): 670-5). In addition, elevated IL23 production has been implicated as being a major factor in inflammatory arthritis and in inflammatory autoimmune diseases (Adamopoulos et al. (2011) J. Immunol. 187: 593-594; and Langris et al. (2005) J. Exp. Med. 201:233-240). A connection between IL23, its downstream cytokine IL22, and bone formation has been published in a mouse model system in which IL23 is overexpressed (Sherlock et al. (2012) Nat. Med. 18: 1069-76).

B-cell activating factor (BAFF) is a cytokine that belongs to the tumor necrosis factor (TNF) ligand superfamily and acts as a ligand for receptors BAFF-R (BR3), TACI (transmembrane activator and calcium modulator and cyclophilin ligand interactor) and BCMA (B-cell maturation antigen). The interaction between BAFF and its receptors triggers signals essential for the formation and maintenance of B cells, which in turn synthesizes immunoglobulins in response to invasion by a foreign substance. Appropriate levels of BAFF in a patient help maintain normal levels of immunity whereas inadequate levels can lead to immunodeficiency and excessive levels can result in abnormally high antibody production. When a patient exhibits autoimmunity, it produces antibodies against the tissues or organs of its own body. Autoimmune diseases, including lupus erythematosus and rheumatoid arthritis, result from excessive levels of BAFF in the body. Thus it is important to modulate the production of BAFF in order to treat the patients having these diseases.

BAFF can exist in three forms: membrane bound (mb-BAFF), soluble trimeric BAFF (sBAFF) and a multimeric form consisting of 60 BAFF monomers (BAFF 60 mer). The relative importance of the various forms of BAFF in normal and disease physiology is not well understood. As noted, BAFF binds to three receptors, BAFFR (BR3), TACI and BCMA. A proliferation-inducing ligand (APRIL), a related member of the TNF receptor ligand family, has been shown to bind with high affinity to TACI and BCMA. In contrast to the high affinity APRIL:BCMA interaction, the BAFF:BCMA interaction is of low affinity (1-2 μM) and is not believed to be play an important role in vivo (Bossen and Schneider, 2006).

Soluble BAFF is expressed at high levels in individuals with systemic lupus erythematosus (SLE) and in inflamed target organs such as the kidney. Soluble BAFF serves as a critical factor for B cell homeostasis and survival (Kalled et al., 2005; Mackay et al., 2003; Smith and Cancro, 2003; Patke et al., 2004). Autoantibody formation by BAFF-dependent B cells results in glomerular IC deposits, initially at the glomerular basement membrane (GBM), mesangium and interstitial tissue within the proximal tubular epithelial cells (PTEC). These IC deposits lead to complement fixation and neutrophil activation resulting in local kidney damage. Inflammatory mediators (e.g. IL6, IL8, MCP-1) produced by the damaged kidney cells (MC, PTEC, renal fibroblasts, endothelial cells) fuel an inflammatory cycle by increasing immune cell infiltration (e.g. B cells, T cells, dendritic cells, neutrophils and macrophages).

Anti-BAFF monoclonal antibody belimumab (Benlysta®) has the demonstrated ability to decrease autoantibody formation and has provided significant benefit to patients with systemic lupus erythematosus (SLE). However, efficacy of belimumab in SLE patients is moderate at best, and there is substantial room for improvement (Furie et al., 2011). Therefore, there remains a need for new compositions with increased efficacy for treating and preventing autoimmune or inflammatory diseases. Furthermore, identification of more efficacious treatments should allow for administration of reduced dosages, as well as lower costs associated with the treatment.

SUMMARY

Provided herein are compounds specific for BAFF and IL23A, compositions comprising such compounds, as well as methods of use and production thereof.

Aspects of the disclosure relate to a compound comprising a first polypeptide and a second polypeptide, wherein:
(A) said first polypeptide comprises:
  (i) a light chain variable domain of a first immunoglobulin (VL1) specific for a first target protein;
  (ii) a heavy chain variable domain of a second immunoglobulin (VH2) specific for a second target protein; and
  (iii) a hinge region, a heavy chain constant region 2 (CH2) and a heavy chain constant region 3 (CH3); and
(B) said second polypeptide comprises:
  (i) a light chain variable domain of the second immunoglobulin (VL2) specific for said second target protein;
  (ii) a heavy chain variable domain of the first immunoglobulin (VH1) specific for said first target protein;
wherein:
  a) said VL1 and VH1 associate to form a binding site that binds said first target protein;
  b) said VL2 and VH2 associate to form a binding site that binds said second target protein;
  c) said heavy chain constant region 2 (CH2) comprises a tyrosine at position 252, a threonine at position 254 and a glutamic acid a position 256, numbered according to the EU index as in Kabat; and
  d) said first target protein is BAFF and said second target protein is IL-23A or said first target protein is IL-23A and said second target protein is BAFF,
and wherein:
  (i) said VL1 comprises SEQ ID NO:2, said VH1 comprises SEQ ID NO:1, said VL2 comprises SEQ ID NO:4 and said VH2 comprises SEQ ID NO:3; or
  (ii) said VL1 comprises SEQ ID NO:4, said VH1 comprises SEQ ID NO:3, said VL2 comprises SEQ ID NO:2 and said VH2 comprises SEQ ID NO:1; or
  (iii) said VL1 comprises SEQ ID NO:85, said VH1 comprises SEQ ID NO:84, said VL2 comprises SEQ ID NO:4 and said VH2 comprises SEQ ID NO:4; or
  (iv) said VL1 comprises SEQ ID NO:4, said VH1 comprises SEQ ID NO:3, said VL2 comprises SEQ ID NO:85 and said VH2 comprises SEQ ID NO:84; or
  (v) said VL1 comprises SEQ ID NO:87, said VH1 comprises SEQ ID NO:86, said VL2 comprises SEQ ID NO:4 and said VH2 comprises SEQ ID NO:3; or
  (vi) said VL1 comprises SEQ ID NO:4, said VH1 comprises SEQ ID NO:3, said VL2 comprises SEQ ID NO:87 and said VH2 comprises SEQ ID NO:86; or
  (vii) said VL1 comprises SEQ ID NO:89, said VH1 comprises SEQ ID NO:88, said VL2 comprises SEQ ID NO:4 and said VH2 comprises SEQ ID NO:3; or
  (viii) said VL1 comprises SEQ ID NO:4, said VH1 comprises SEQ ID NO:3, said VL2 comprises SEQ ID NO:89 and said VH2 comprises SEQ ID NO:88; or
  (ix) said VL1 comprises SEQ ID NO:91, said VH1 comprises SEQ ID NO:90, said VL2 comprises SEQ ID NO:4 and said VH2 comprises SEQ ID NO:3; or
  (x) said VL1 comprises SEQ ID NO:4, said VH1 comprises SEQ ID NO:3, said VL2 comprises SEQ ID NO:91 and said VH2 comprises SEQ ID NO:90.

In some embodiments, said first polypeptide further comprises a first linker between said VL1 and said VH2 and said second polypeptide further comprises a second linker between said VL2 and said VH1. In some embodiments, said first linker or said second linker comprises the amino acid sequence GGGSGGGG (SEQ ID NO:69). In some embodiments, said first linker and said second linker comprise the amino acid sequence GGGSGGGG (SEQ ID NO:69). In some embodiments, said first polypeptide further comprises a third linker between said VH2 or said VL1 and said hinge region, and said second polypeptide further comprises a fourth linker after said VH1 (at its C-terminal end) or said VL2 (at its C-terminal end). In some embodiments, said third linker of said first polypeptide comprises the amino acid sequence GGCGGGEVAACEKEVAALEKEV-AALEKEVAALEK (SEQ ID NO:82), and said fourth linker of said second polypeptide comprises the amino acid sequence GGCGGGKVAACKEKVAALKEKVAALKEK-VAALKE (SEQ ID NO:83). In other embodiments, said third linker of said first polypeptide comprises the amino acid sequence GGCGGGKVAACKEKVAALKEK-VAALKEKVAALKE (SEQ ID NO:83), and said fourth linker of said second polypeptide comprises the amino acid sequence GGCGGGEVAACEKEVAALEKEVAALEKEV-AALEK (SEQ ID NO:82). In some embodiments, said third linker of said first polypeptide comprises the amino acid sequence GGCGGGEVAACEKEVAALEKEVAALEKEV-AALEK (SEQ ID NO:82) or the amino acid sequence GGCGGGKVAACKEKVAALKEKVAALKEKVAALKE (SEQ ID NO:83). In other embodiments, said forth linker of said second polypeptide comprises the amino acid sequence GGCGGGEVAACEKEVAALEKEVAALEKEVAALEK (SEQ ID NO:82) or the amino acid sequence GGCGGGK-VAACKEKVAALKEKVAALKEKVAALKE (SEQ ID NO:83). In some embodiments, said third linker comprises the amino acid sequence VEPKSC (SEQ ID NO:72) or the amino acid sequence FNRGEC (SEQ ID NO:71). In some embodiments, said fourth linker comprises the amino acid sequence FNRGEC (SEQ ID NO:71) or the amino acid sequence VEPKSC (SEQ ID NO:72). In some embodiments, said third linker comprises the amino acid sequence VEPKSC (SEQ ID NO:72) and said fourth linker comprises the amino acid sequence FNRGEC (SEQ ID NO:71).

In some embodiments, said first polypeptide further comprises a heavy chain constant region 1 domain (CH1) between said VH2 or said VL1 (depending on the configuration) and the hinge region and said second polypeptide further comprises a light chain constant region domain (CL) at the C-terminal end of said VH1 or VL2 (depending on the configuration), wherein said CL and said CH1 are associated together via a disulfide bond to form a C1 domain. In some embodiments, said first linker (between said VL1 and said VH2) or said second linker (between said VL2 and said VH1) comprises the amino acid sequence GGGSGGGG (SEQ ID NO:69). In some embodiments, said first linker and said second linker comprise the amino acid sequence GGGSGGGG (SEQ ID NO:69). In some embodiments, said first polypeptide further comprises a third linker between said VH2 or said VL1 (depending on the configuration) and said CH1, and said second polypeptide further comprises a fourth linker between said VH1 or said VL2 (depending on the configuration) and said CL. In some embodiments, said third linker or said fourth linker comprises the amino acid sequence LGGGSG (SEQ ID NO:70). In some embodiments, said third linker and said fourth linker comprise the amino acid sequence LGGGSG (SEQ ID NO:70). In some embodiments, said third linker and/or said fourth linker comprise an optional cysteine residue. In some embodiments, said third linker and/or said fourth linker comprise the amino acid sequence GGCGGG (SEQ ID NO:135) or LGGCGGGS (SEQ ID NO:136).

In some embodiments, said heavy chain constant region 2 (CH2) comprises an alanine at positions 234 and an alanine at position 235, numbered according to the EU index as in Kabat for a conventional antibody.

In some embodiments, the amino acid sequence of said hinge region, said heavy chain constant region 2 (CH2) or said heavy chain constant region 3 (CH3) is derived from a IgG1 or from a IgG4. In some embodiments, said hinge region comprises the amino acid sequence EPKSCDKTHTCPPCP (SEQ ID NO:76). The hinge region of SEQ ID NO:76 is present in, for example, SEQ ID NO:5 polypeptide. In other embodiments, the hinge region comprises the amino acid sequence LEPKSSDKTHTCPPCP (SEQ ID NO:130). The hinge region of SEQ ID NO:130 is present in, for example, SEQ ID NO:9 polypeptide. In still other embodiments, the hinge region comprises the amino acid sequence ESKYGPPCPPCP (SEQ ID NO:134). The hinge region of SEQ ID NO:134 is present in, for example, SEQ ID NO:13 polypeptide.

In some embodiments, said compound comprises two said first polypeptides and two said second polypeptides, wherein said two first polypeptides are associated together via at least one disulfide bond. In some embodiments, said compound comprises two said first polypeptides and two said second polypeptides, wherein said two first polypeptides are associated together via at least one disulfide bond and wherein each of said first polypeptide is associated to one said second polypeptide via at least one disulfide bond.

In some embodiments,
(i) said first polypeptide comprises the amino acid sequence of SEQ ID NO:5 and said second polypeptide comprises the amino acid sequence of SEQ ID NO:6; or
(ii) said first polypeptide comprises the amino acid sequence of SEQ ID NO:7 and said second polypeptide comprises the amino acid sequence of SEQ ID NO:8; or
(iii) said first polypeptide comprises the amino acid sequence of SEQ ID NO:9 and said second polypeptide comprises the amino acid sequence of SEQ ID NO:10; or
(iv) said first polypeptide comprises the amino acid sequence of SEQ ID NO:11 and said second polypeptide comprises the amino acid sequence of SEQ ID NO:12; or
(v) said first polypeptide comprises the amino acid sequence of SEQ ID NO:13 and said second polypeptide comprises the amino acid sequence of SEQ ID NO:14; or
(vi) said first polypeptide comprises the amino acid sequence of SEQ ID NO:15 and said second polypeptide comprises the amino acid sequence of SEQ ID NO:16; or
(vii) said first polypeptide comprises the amino acid sequence of SEQ ID NO:17 and said second polypeptide comprises the amino acid sequence of SEQ ID NO:18; or
(viii) said first polypeptide comprises the amino acid sequence of SEQ ID NO:19 and said second polypeptide comprises the amino acid sequence of SEQ ID NO:20; or
(ix) said first polypeptide comprises the amino acid sequence of SEQ ID NO:21 and said second polypeptide comprises the amino acid sequence of SEQ ID NO:22; or
(x) said first polypeptide comprises the amino acid sequence of SEQ ID NO:23 and said second polypeptide comprises the amino acid sequence of SEQ ID NO:24; or
(xi) said first polypeptide comprises the amino acid sequence of SEQ ID NO:25 and said second polypeptide comprises the amino acid sequence of SEQ ID NO:26; or
(xii) said first polypeptide comprises the amino acid sequence of SEQ ID NO:27 and said second polypeptide comprises the amino acid sequence of SEQ ID NO:28; or
(xiii) said first polypeptide comprises the amino acid sequence of SEQ ID NO:29 and said second polypeptide comprises the amino acid sequence of SEQ ID NO:30; or
(xiv) said first polypeptide comprises the amino acid sequence of SEQ ID NO:31 and said second polypeptide comprises the amino acid sequence of SEQ ID NO:32; or
(xv) said first polypeptide comprises the amino acid sequence of SEQ ID NO:33 and said second polypeptide comprises the amino acid sequence of SEQ ID NO:34; or
(xvi) said first polypeptide comprises the amino acid sequence of SEQ ID NO:35 and said second polypeptide comprises the amino acid sequence of SEQ ID NO:36; or
(xvii) said first polypeptide comprises the amino acid sequence of SEQ ID NO:37 and said second polypeptide comprises the amino acid sequence of SEQ ID NO:38; or
(xviii) said first polypeptide comprises the amino acid sequence of SEQ ID NO:39 and said second polypeptide comprises the amino acid sequence of SEQ ID NO:40; or
(xix) said first polypeptide comprises the amino acid sequence of SEQ ID NO:41 and said second polypeptide comprises the amino acid sequence of SEQ ID NO:42; or
(xx) said first polypeptide comprises the amino acid sequence of SEQ ID NO:43 and said second polypeptide comprises the amino acid sequence of SEQ ID NO:44; or (xxi) said first polypeptide comprises the amino acid sequence of SEQ ID NO:45 and said second polypeptide comprises the amino acid sequence of SEQ ID NO:46; or
(xxii) said first polypeptide comprises the amino acid sequence of SEQ ID NO:47 and said second polypeptide comprises the amino acid sequence of SEQ ID NO:48; or
(xxiii) said first polypeptide comprises the amino acid sequence of SEQ ID NO:49 and said second polypeptide comprises the amino acid sequence of SEQ ID NO:50; or
(xxiv) said first polypeptide comprises the amino acid sequence of SEQ ID NO:51 and said second polypeptide comprises the amino acid sequence of SEQ ID NO:52; or
(xxv) said first polypeptide comprises the amino acid sequence of SEQ ID NO:53 and said second polypeptide comprises the amino acid sequence of SEQ ID NO:54; or
(xxvi) said first polypeptide comprises the amino acid sequence of SEQ ID NO:55 and said second polypeptide comprises the amino acid sequence of SEQ ID NO:56; or
(xxvii) said first polypeptide comprises the amino acid sequence of SEQ ID NO:57 and said second polypeptide comprises the amino acid sequence of SEQ ID NO:58; or
(xxviii) said first polypeptide comprises the amino acid sequence of SEQ ID NO:59 and said second polypeptide comprises the amino acid sequence of SEQ ID NO:60; or
(xxix) said first polypeptide comprises the amino acid sequence of SEQ ID NO:61 and said second polypeptide comprises the amino acid sequence of SEQ ID NO:62; or
(xxx) said first polypeptide comprises the amino acid sequence of SEQ ID NO:63 and said second polypeptide comprises the amino acid sequence of SEQ ID NO:64; or
(xxxi) said first polypeptide comprises the amino acid sequence of SEQ ID NO:65 and said second polypeptide comprises the amino acid sequence of SEQ ID NO:66; or
(xxxii) said first polypeptide comprises the amino acid sequence of SEQ ID NO:67 and said second polypeptide comprises the amino acid sequence of SEQ ID NO:68.

In some embodiments, wherein said compound comprises two said first polypeptides and two said second polypeptides, wherein said two first polypeptides are associated together via at least one disulfide bond.

In some embodiments, said compound comprises two said first polypeptides and two said second polypeptides, and wherein the hinge, CH2 and CH3, of one of the first polypeptides associates with the hinge, CH2 and CH3, of the other of the first polypeptides to form a tetravalent molecule. In some embodiments, said compound comprises two said first polypeptides and two said second polypeptides, wherein each of said first polypeptides comprises a CH1, a hinge, a CH2 and a CH3 and each of said second polypeptides comprises a CL and wherein the hinge, CH2 and CH3 of one of the first polypeptides associates with the hinge, CH2 and CH3 of the other of the first polypeptides and the CH1 of each said first polypeptides associates with the CL of one said second polypeptides to form a tetravalent molecule (e.g., a monomer, a monomeric antibody as described in the Examples section) (e.g., compounds E and V). In some embodiments, said compound comprises two said first polypeptides and two said second polypeptides, wherein each of said first polypeptides comprises a third linker, a hinge, a CH2 and a CH3, and each of said second polypeptides comprises a fourth linker and wherein the hinge, CH2 and CH3 of one of the first polypeptides associates with the hinge, CH2 and CH3 of the other of the first polypeptides and the third linker of each said first polypeptides associates with the fourth linker of one said second polypeptides to form a tetravalent molecule (e.g., a monomer, a monomeric antibody as described in the Examples section) (e.g., compounds U and T).

Other aspects of the disclosure relate to a first compound that competes with a second compound for binding to IL-23A and to BAFF, wherein said first compound comprises a third polypeptide and fourth polypeptide, wherein:
(A) said third polypeptide comprises:
 (i) a light chain variable domain of a first immunoglobulin (VL1) specific for a first target protein;
 (ii) a heavy chain variable domain of a second immunoglobulin (VH2) specific for a second target protein; and
 (iii) a hinge region, a heavy chain constant region 2 (CH2) and a heavy chain constant region 3 (CH3); and
(B) said fourth polypeptide comprises:
 (i) a light chain variable domain of the second immunoglobulin (VL2) specific for said second target protein;
 (ii) a heavy chain variable domain of the first immunoglobulin (VH1) specific for said first target protein;
and wherein
 (i) said VL1 and VH1 associate to form a binding site that binds said first target protein;
 (ii) said VL2 and VH2 associate to form a binding site that binds said second target protein; and
 (iii) said first target protein is BAFF and said second target protein is IL-23A or said first target protein is IL-23A and said second target protein is BAFF,
and wherein said second compound comprises a first polypeptide and a second polypeptide, wherein:
 (i) said first polypeptide comprises the amino acid sequence of SEQ ID NO:5 and said second polypeptide comprises the amino acid sequence of SEQ ID NO:6; or
 (ii) said first polypeptide comprises the amino acid sequence of SEQ ID NO:7 and said second polypeptide comprises the amino acid sequence of SEQ ID NO:8; or
 (iii) said first polypeptide comprises the amino acid sequence of SEQ ID NO:9 and said second polypeptide comprises the amino acid sequence of SEQ ID NO:10; or
 (iv) said first polypeptide comprises the amino acid sequence of SEQ ID NO:11 and said second polypeptide comprises the amino acid sequence of SEQ ID NO:12; or
 (v) said first polypeptide comprises the amino acid sequence of SEQ ID NO:13 and said second polypeptide comprises the amino acid sequence of SEQ ID NO:14; or
 (vi) said first polypeptide comprises the amino acid sequence of SEQ ID NO:15 and said second polypeptide comprises the amino acid sequence of SEQ ID NO:16; or (vii) said first polypeptide comprises the amino acid sequence of SEQ ID NO:17 and said second polypeptide comprises the amino acid sequence of SEQ ID NO:18; or
(viii) said first polypeptide comprises the amino acid sequence of SEQ ID NO:19 and said second polypeptide comprises the amino acid sequence of SEQ ID NO:20; or
(ix) said first polypeptide comprises the amino acid sequence of SEQ ID NO:21 and said second polypeptide comprises the amino acid sequence of SEQ ID NO:22; or
(x) said first polypeptide comprises the amino acid sequence of SEQ ID NO:23 and said second polypeptide comprises the amino acid sequence of SEQ ID NO:24; or
(xi) said first polypeptide comprises the amino acid sequence of SEQ ID NO:25 and said second polypeptide comprises the amino acid sequence of SEQ ID NO:26; or
(xii) said first polypeptide comprises the amino acid sequence of SEQ ID NO:27 and said second polypeptide comprises the amino acid sequence of SEQ ID NO:28; or
(xiii) said first polypeptide comprises the amino acid sequence of SEQ ID NO:29 and said second polypeptide comprises the amino acid sequence of SEQ ID NO:30; or
(xiv) said first polypeptide comprises the amino acid sequence of SEQ ID NO:31 and said second polypeptide comprises the amino acid sequence of SEQ ID NO:32; or
(xv) said first polypeptide comprises the amino acid sequence of SEQ ID NO:33 and said second polypeptide comprises the amino acid sequence of SEQ ID NO:34; or
(xvi) said first polypeptide comprises the amino acid sequence of SEQ ID NO:35 and said second polypeptide comprises the amino acid sequence of SEQ ID NO:36; or
(xvii) said first polypeptide comprises the amino acid sequence of SEQ ID NO:37 and said second polypeptide comprises the amino acid sequence of SEQ ID NO:38; or
(xviii) said first polypeptide comprises the amino acid sequence of SEQ ID NO:39 and said second polypeptide comprises the amino acid sequence of SEQ ID NO:40; or
(xix) said first polypeptide comprises the amino acid sequence of SEQ ID NO:41 and said second polypeptide comprises the amino acid sequence of SEQ ID NO:42; or
(xx) said first polypeptide comprises the amino acid sequence of SEQ ID NO:43 and said second polypeptide comprises the amino acid sequence of SEQ ID NO:44; or
(xxi) said first polypeptide comprises the amino acid sequence of SEQ ID NO:45 and said second polypeptide comprises the amino acid sequence of SEQ ID NO:46; or
(xxii) said first polypeptide comprises the amino acid sequence of SEQ ID NO:47 and said second polypeptide comprises the amino acid sequence of SEQ ID NO:48; or
(xxiii) said first polypeptide comprises the amino acid sequence of SEQ ID NO:49 and said second polypeptide comprises the amino acid sequence of SEQ ID NO:50; or
(xxiv) said first polypeptide comprises the amino acid sequence of SEQ ID NO:51 and said second polypeptide comprises the amino acid sequence of SEQ ID NO:52; or
(xxv) said first polypeptide comprises the amino acid sequence of SEQ ID NO:53 and said second polypeptide comprises the amino acid sequence of SEQ ID NO:54; or
(xxvi) said first polypeptide comprises the amino acid sequence of SEQ ID NO:55 and said second polypeptide comprises the amino acid sequence of SEQ ID NO:56; or
(xxvii) said first polypeptide comprises the amino acid sequence of SEQ ID NO:57 and said second polypeptide comprises the amino acid sequence of SEQ ID NO:58; or
(xxviii) said first polypeptide comprises the amino acid sequence of SEQ ID NO:59 and said second polypeptide comprises the amino acid sequence of SEQ ID NO:60; or
(xxix) said first polypeptide comprises the amino acid sequence of SEQ ID NO:61 and said second polypeptide comprises the amino acid sequence of SEQ ID NO:62; or
(xxx) said first polypeptide comprises the amino acid sequence of SEQ ID NO:63 and said second polypeptide comprises the amino acid sequence of SEQ ID NO:64; or
(xxxi) said first polypeptide comprises the amino acid sequence of SEQ ID NO:65 and said second polypeptide comprises the amino acid sequence of SEQ ID NO:66; or
(xxxii) said first polypeptide comprises the amino acid sequence of SEQ ID NO:67 and said second polypeptide comprises the amino acid sequence of SEQ ID NO:68.

Other aspects of the disclosure relate to a compound comprising two first polypeptides and two second polypeptides;
wherein said two first polypeptides are associated together via at least one disulfide bond and wherein each of said first polypeptide is associated to one said second polypeptide via at least one disulfide bond;
wherein each of said first polypeptides comprises:
(i) a light chain variable domain of a first immunoglobulin (VL1) specific for a first target protein;
(ii) a heavy chain variable domain of a second immunoglobulin (VH2) specific for a second target protein;
(iii) a heavy chain constant region 1 (CH1), a hinge region, a heavy chain constant region 2 (CH2) and a heavy chain constant region 3 (CH3); and
wherein each of said second polypeptides comprises:
(i) a light chain variable domain of the second immunoglobulin (VL2) specific for said second target protein;
(ii) a heavy chain variable domain of the first immunoglobulin (VH1) specific for said first target protein;
(iii) a light chain constant region domain (CL);
wherein the hinge, CH2 and CH3 of one of the first polypeptides associates with the hinge, CH2 and CH3 of the other of the first polypeptides and the CH1 of each said first polypeptides associates with the CL of said each second polypeptides to form a tetravalent molecule;
wherein
  a) said VL1 and VH1 associate to form a binding site that binds said first target protein;
  b) said VL2 and VH2 associate to form a binding site that binds said second target protein;
  c) said heavy chain constant region 2 (CH2) comprises a tyrosine at position 252, a threonine at position 254 and a glutamic acid a position 256, numbered according to the EU index as in Kabat; and
  d) said first target protein is BAFF and said second target protein is IL-23A or said first target protein is IL-23A and said second target protein is BAFF,
and wherein:
  (i) said VL1 comprises SEQ ID NO:2, said VH1 comprises SEQ ID NO:1, said VL2 comprises SEQ ID NO:4 and said VH2 comprises SEQ ID NO:3; or
  (ii) said VL1 comprises SEQ ID NO:4, said VH1 comprises SEQ ID NO:3, said VL2 comprises SEQ ID NO:2 and said VH2 comprises SEQ ID NO:1; or
  (iii) said VL1 comprises SEQ ID NO:85, said VH1 comprises SEQ ID NO:84, said VL2 comprises SEQ ID NO:4 and said VH2 comprises SEQ ID NO:4; or
  (iv) said VL1 comprises SEQ ID NO:4, said VH1 comprises SEQ ID NO:3, said VL2 comprises SEQ ID NO:85 and said VH2 comprises SEQ ID NO:84; or
  (v) said VL1 comprises SEQ ID NO:87, said VH1 comprises SEQ ID NO:86, said VL2 comprises SEQ ID NO:4 and said VH2 comprises SEQ ID NO:3; or
  (vi) said VL1 comprises SEQ ID NO:4, said VH1 comprises SEQ ID NO:3, said VL2 comprises SEQ ID NO:87 and said VH2 comprises SEQ ID NO:86; or
  (vii) said VL1 comprises SEQ ID NO:89, said VH1 comprises SEQ ID NO:88, said VL2 comprises SEQ ID NO:4 and said VH2 comprises SEQ ID NO:3; or
  (viii) said VL1 comprises SEQ ID NO:4, said VH1 comprises SEQ ID NO:3, said VL2 comprises SEQ ID NO:89 and said VH2 comprises SEQ ID NO:88; or
  (ix) said VL1 comprises SEQ ID NO:91, said VH1 comprises SEQ ID NO:90, said VL2 comprises SEQ ID NO:4 and said VH2 comprises SEQ ID NO:3; or
  (x) said VL1 comprises SEQ ID NO:4, said VH1 comprises SEQ ID NO:3, said VL2 comprises SEQ ID NO:91 and said VH2 comprises SEQ ID NO:90.

In some embodiments relating to the above aspect, each of said first polypeptides further comprises a first linker between said VL1 and said VH2, and each of said second polypeptides further comprises a second linker between said VL2 and said VH1. In some embodiments, said first linker or said second linker comprises the amino acid sequence GGGSGGGG (SEQ ID NO:69). In some embodiments, said first linker and said second linker comprise the amino acid sequence GGGSGGGG (SEQ ID NO:69). In some embodiments, each of said first polypeptides further comprises a third linker between said VH2 (or said VL1) and said CH1, and each of said second polypeptides further comprises a fourth linker between said VH1 (or said VL2) and said CL. In some embodiments, said third linker or said fourth linker comprises the amino acid sequence LGGGSG (SEQ ID NO:70). In some embodiments, said third linker and said fourth linker comprise the amino acid sequence LGGGSG (SEQ ID NO:70). In some embodiments, said third linker and/or said fourth linker comprise an optional cysteine residue. In some embodiments, said third linker and/or said fourth linker comprise the amino acid sequence GGCGGG (SEQ ID NO:135) or LGGCGGGS (SEQ ID NO:136). In some embodiments, said heavy chain constant region 2 (CH2) comprises an alanine at positions 234 and an alanine at position 235, numbered according to the EU index as in Kabat. In some embodiments, the amino acid sequence of said hinge region, said heavy chain constant region 2 (CH2) or said heavy chain constant region 3 (CH3) is derived from a IgG1 or from a IgG4. In some embodiments, said hinge region comprises the amino acid sequence EPKSCDKTHTCPPCP (SEQ ID NO:76), the amino acid sequence LEPKSSDKTHTCPPCP (SEQ ID NO:130) or the amino acid sequence ESKYGPPCPPCP (SEQ ID NO:134).

In some embodiments,
  (i) each of said first polypeptides comprises the amino acid sequence of SEQ ID NO:5 and each of said second polypeptides comprises the amino acid sequence of SEQ ID NO:6; or
  (ii) each of said first polypeptides comprises the amino acid sequence of SEQ ID NO:7 and each of said second polypeptides comprises the amino acid sequence of SEQ ID NO:8; or
  (iii) each of said first polypeptides comprises the amino acid sequence of SEQ ID NO:13 and each of said second polypeptides comprises the amino acid sequence of SEQ ID NO:14; or
  (iv) each of said first polypeptides comprises the amino acid sequence of SEQ ID NO:15 and each of said second polypeptides comprises the amino acid sequence of SEQ ID NO:16; or
  (v) each of said first polypeptides comprises the amino acid sequence of SEQ ID NO:21 and each of said second polypeptides comprises the amino acid sequence of SEQ ID NO:22; or
  (vi) each of said first polypeptides comprises the amino acid sequence of SEQ ID NO:25 and each of said second polypeptides comprises the amino acid sequence of SEQ ID NO:26; or
  (vii) each of said first polypeptides comprises the amino acid sequence of SEQ ID NO:29 and each of said second polypeptides comprises the amino acid sequence of SEQ ID NO:30; or
  (viii) each of said first polypeptides comprises the amino acid sequence of SEQ ID NO:33 and each of said second polypeptides comprises the amino acid sequence of SEQ ID NO:34;
  or
  (ix) each of said first polypeptides comprises the amino acid sequence of SEQ ID NO:37 and each of said second polypeptides comprises the amino acid sequence of SEQ ID NO:38; or
  (x) each of said first polypeptides comprises the amino acid sequence of SEQ ID NO:41 and each of said second polypeptides comprises the amino acid sequence of SEQ ID NO:42; or
  (xi) each of said first polypeptides comprises the amino acid sequence of SEQ ID NO:45 and each of said second polypeptides comprises the amino acid sequence of SEQ ID NO:46; or
  (xii) each of said first polypeptides comprises the amino acid sequence of SEQ ID NO:49 and each of said second polypeptides comprises the amino acid sequence of SEQ ID NO:50; or
  (xiii) each of said first polypeptides comprises the amino acid sequence of SEQ ID NO:53 and each of said second polypeptides comprises the amino acid sequence of SEQ ID NO:54; or
(xiv) each of said first polypeptides comprises the amino acid sequence of SEQ ID NO:55 and each of said second polypeptides comprises the amino acid sequence of SEQ ID NO:56; or
(xv) each of said first polypeptides comprises the amino acid sequence of SEQ ID NO:57 and each of said second polypeptides comprises the amino acid sequence of SEQ ID NO:58; or
(xvi) each of said first polypeptides comprises the amino acid sequence of SEQ ID NO:59 and each of said second polypeptides comprises the amino acid sequence of SEQ ID NO:60; or
(xvii) each of said first polypeptides comprises the amino acid sequence of SEQ ID NO:61 and each of said second polypeptides comprises the amino acid sequence of SEQ ID NO:62; or
(xviii) each of said first polypeptides comprises the amino acid sequence of SEQ ID NO:63 and each of said second polypeptides comprises the amino acid sequence of SEQ ID NO:64; or
(xix) each of said first polypeptides comprises the amino acid sequence of SEQ ID NO:65 and each of said second polypeptides comprises the amino acid sequence of SEQ ID NO:66; or
(xx) each of said first polypeptides comprises the amino acid sequence of SEQ ID NO:67 and each of said second polypeptides comprises the amino acid sequence of SEQ ID NO:68.

Other aspects of the disclosure relate to a compound comprising two first polypeptides and two second polypeptides; wherein said two first polypeptides are associated together via at least one disulfide bond and wherein each of said first polypeptide is associated to one said second polypeptide via at least one disulfide bond; and wherein (i) each of said first polypeptides comprises the amino acid sequence of SEQ ID NO:5 and each of said second polypeptides comprises the amino acid sequence of SEQ ID NO:6; or
(ii) each of said first polypeptides comprises the amino acid sequence of SEQ ID NO:7 and each of said second polypeptides comprises the amino acid sequence of SEQ ID NO:8; or
(iii) each of said first polypeptides comprises the amino acid sequence of SEQ ID NO:13 and each of said second polypeptides comprises the amino acid sequence of SEQ ID NO:14; or
(iv) each of said first polypeptides comprises the amino acid sequence of SEQ ID NO:15 and each of said second polypeptides comprises the amino acid sequence of SEQ ID NO:16; or
(v) each of said first polypeptides comprises the amino acid sequence of SEQ ID NO:21 and each of said second polypeptides comprises the amino acid sequence of SEQ ID NO:22; or
(vi) each of said first polypeptides comprises the amino acid sequence of SEQ ID NO:25 and each of said second polypeptides comprises the amino acid sequence of SEQ ID NO:26; or
(vii) each of said first polypeptides comprises the amino acid sequence of SEQ ID NO:29 and each of said second polypeptides comprises the amino acid sequence of SEQ ID NO:30; or
(viii) each of said first polypeptides comprises the amino acid sequence of SEQ ID NO:33 and each of said second polypeptides comprises the amino acid sequence of SEQ ID NO:34; or
(ix) each of said first polypeptides comprises the amino acid sequence of SEQ ID NO:37 and each of said second polypeptides comprises the amino acid sequence of SEQ ID NO:38; or
(x) each of said first polypeptides comprises the amino acid sequence of SEQ ID NO:41 and each of said second polypeptides comprises the amino acid sequence of SEQ ID NO:42; or
(xi) each of said first polypeptides comprises the amino acid sequence of SEQ ID NO:45 and each of said second polypeptides comprises the amino acid sequence of SEQ ID NO:46; or
(xii) each of said first polypeptides comprises the amino acid sequence of SEQ ID NO:49 and each of said second polypeptides comprises the amino acid sequence of SEQ ID NO:50; or
(xiii) each of said first polypeptides comprises the amino acid sequence of SEQ ID NO:53 and each of said second polypeptides comprises the amino acid sequence of SEQ ID NO:54; or
(xiv) each of said first polypeptides comprises the amino acid sequence of SEQ ID NO:55 and each of said second polypeptides comprises the amino acid sequence of SEQ ID NO:56; or
(xv) each of said first polypeptides comprises the amino acid sequence of SEQ ID NO:57 and each of said second polypeptides comprises the amino acid sequence of SEQ ID NO:58; or
(xvi) each of said first polypeptides comprises the amino acid sequence of SEQ ID NO:59 and each of said second polypeptides comprises the amino acid sequence of SEQ ID NO:60; or
(xvii) each of said first polypeptides comprises the amino acid sequence of SEQ ID NO:61 and each of said second polypeptides comprises the amino acid sequence of SEQ ID NO:62; or
(xviii) each of said first polypeptides comprises the amino acid sequence of SEQ ID NO:63 and each of said second polypeptides comprises the amino acid sequence of SEQ ID NO:64; or
(xix) each of said first polypeptides comprises the amino acid sequence of SEQ ID NO:65 and each of said second polypeptides comprises the amino acid sequence of SEQ ID NO:66; or
(xx) each of said first polypeptides comprises the amino acid sequence of SEQ ID NO:67 and each of said second polypeptides comprises the amino acid sequence of SEQ ID NO:68.

Other aspects of the disclosure relate to a compound comprising two first polypeptides and two second polypeptides;
wherein said two first polypeptides are associated together via at least one disulfide bond and wherein each of said first polypeptide is associated to one said second polypeptide via at least one disulfide bond;
wherein each of said first polypeptides comprises:
(iv) a light chain variable domain of a first immunoglobulin (VL1) specific for a first target protein;
(v) a heavy chain variable domain of a second immunoglobulin (VH2) specific for a second target protein;
(vi) a hinge region, a heavy chain constant region 2 (CH2) and a heavy chain constant region 3 (CH3); and wherein each of said second polypeptides comprises:
(i) a light chain variable domain of the second immunoglobulin (VL2) specific for said second target protein; and
(ii) a heavy chain variable domain of the first immunoglobulin (VH1) specific for said first target protein;
wherein the hinge, CH2 and CH3 of one of the first polypeptides associates with the hinge, CH2 and CH3 of the other of the first polypeptides and;
wherein
e) said VL1 and VH1 associate to form a binding site that binds said first target protein;
f) said VL2 and VH2 associate to form a binding site that binds said second target protein;
g) said heavy chain constant region 2 (CH2) comprises a tyrosine at position 252, a threonine at position 254 and a glutamic acid a position 256, numbered according to the EU index as in Kabat; and
h) said first target protein is BAFF and said second target protein is IL-23A or said first target protein is IL-23A and said second target protein is BAFF,
and wherein:
(i) said VL1 comprises SEQ ID NO:2, said VH1 comprises SEQ ID NO:1, said VL2 comprises SEQ ID NO:4 and said VH2 comprises SEQ ID NO:3; or
(ii) said VL1 comprises SEQ ID NO:4, said VH1 comprises SEQ ID NO:3, said VL2 comprises SEQ ID NO:2 and said VH2 comprises SEQ ID NO:1; or
(iii) said VL1 comprises SEQ ID NO:85, said VH1 comprises SEQ ID NO:84, said VL2 comprises SEQ ID NO:4 and said VH2 comprises SEQ ID NO:4; or
(iv) said VL1 comprises SEQ ID NO:4, said VH1 comprises SEQ ID NO:3, said VL2 comprises SEQ ID NO:85 and said VH2 comprises SEQ ID NO:84; or
(v) said VL1 comprises SEQ ID NO:87, said VH1 comprises SEQ ID NO:86, said VL2 comprises SEQ ID NO:4 and said VH2 comprises SEQ ID NO:3; or
(vi) said VL1 comprises SEQ ID NO:4, said VH1 comprises SEQ ID NO:3, said VL2 comprises SEQ ID NO:87 and said VH2 comprises SEQ ID NO:86; or
(vii) said VL1 comprises SEQ ID NO:89, said VH1 comprises SEQ ID NO:88, said VL2 comprises SEQ ID NO:4 and said VH2 comprises SEQ ID NO:3; or
(viii) said VL1 comprises SEQ ID NO:4, said VH1 comprises SEQ ID NO:3, said VL2 comprises SEQ ID NO:89 and said VH2 comprises SEQ ID NO:88; or
(ix) said VL1 comprises SEQ ID NO:91, said VH1 comprises SEQ ID NO:90, said VL2 comprises SEQ ID NO:4 and said VH2 comprises SEQ ID NO:3; or
(x) said VL1 comprises SEQ ID NO:4, said VH1 comprises SEQ ID NO:3, said VL2 comprises SEQ ID NO:91 and said VH2 comprises SEQ ID NO:90.

In some embodiments relating to the above aspect, each of said first polypeptides further comprises a first linker between said VL1 and said VH2, and each of said second polypeptides further comprises a second linker between said VL2 and said VH1. In some embodiments, said first linker or said second linker comprises the amino acid sequence GGGSGGGG (SEQ ID NO:69). In some embodiments, said first linker and said second linker comprise the amino acid sequence GGGSGGGG (SEQ ID NO:69). In some embodiments, each of said first polypeptides further comprises a third linker between said VH2 or said VL1 and said hinge region, and each of said second polypeptides further comprises a fourth linker at the C-terminal end of said VH1 or said VL2. In some embodiments, said third linker of said first polypeptide comprises the amino acid sequence GGCGGGEVAACEKEVAALEKEVAALEKEVAALEK (SEQ ID NO:82), and said fourth linker of said second polypeptide comprises the amino acid sequence GGCGGGKVAACKEKVAALKEKVAALKEKVAALKE (SEQ ID NO:83). In other embodiments, said third linker of said first polypeptide comprises the amino acid sequence GGCGGGKVAACKEKVAALKEKVAALKEKVAALKE (SEQ ID NO:83), and said fourth linker of said second polypeptide comprises the amino acid sequence GGCGGG-GEVAACEKEVAALEKEVAALEKEVAALEK (SEQ ID NO:82). In some embodiments, said third linker of said first polypeptide comprises the amino acid sequence GGCGGG-GEVAACEKEVAALEKEVAALEKEVAALEK (SEQ ID NO:82) or the amino acid sequence GGCGGGK-VAACKEKVAALKEKVAALKEKVAALKE (SEQ ID NO:83). In other embodiments, said forth linker of said second polypeptide comprises the amino acid sequence GGCGGGEVAACEKEVAALEKEVAALEKEVAALEK (SEQ ID NO:82) or the amino acid sequence GGCGGGK-VAACKEKVAALKEKVAALKEKVAALKE (SEQ ID NO:83). In some embodiments, said third linker comprises the amino acid sequence VEPKSC (SEQ ID NO:72) or the amino acid sequence FNRGEC (SEQ ID NO:71). In some embodiments, said fourth linker comprises the amino acid sequence FNRGEC (SEQ ID NO:71) or the amino acid sequence VEPKSC (SEQ ID NO:72). In some embodiments, said third linker comprises the amino acid sequence VEPKSC (SEQ ID NO:72) and said fourth linker comprises the amino acid sequence FNRGEC (SEQ ID NO:71). In some embodiments, said heavy chain constant region 2 (CH2) comprises an alanine at positions 234 and an alanine at position 235, numbered according to the EU index as in Kabat. In some embodiments, the amino acid sequence of said hinge region, said heavy chain constant region 2 (CH2) or said heavy chain constant region 3 (CH3) is derived from a IgG1 or from a IgG4. In some embodiments, said hinge region comprises the amino acid sequence EPKSCDKTH-TCPPCP (SEQ ID NO:76), the amino acid sequence LEP-KSSDKTHTCPPCP (SEQ ID NO:130) or the amino acid sequence ESKYGPPCPPCP (SEQ ID NO:134). In some embodiments, (i) each of said first polypeptides comprises the amino acid sequence of SEQ ID NO:9 and each of said second polypeptides comprises the amino acid sequence of SEQ ID NO:10; or
(ii) each of said first polypeptides comprises the amino acid sequence of SEQ ID NO:11 and each of said second polypeptides comprises the amino acid sequence of SEQ ID NO:12; or
(iii) each of said first polypeptides comprises the amino acid sequence of SEQ ID NO:17 and each of said second polypeptides comprises the amino acid sequence of SEQ ID NO:18; or
(iv) each of said first polypeptides comprises the amino acid sequence of SEQ ID NO:19 and each of said second polypeptides comprises the amino acid sequence of SEQ ID NO:20; or
(v) each of said first polypeptides comprises the amino acid sequence of SEQ ID NO:23 and each of said second polypeptides comprises the amino acid sequence of SEQ ID NO:24; or
(vi) each of said first polypeptides comprises the amino acid sequence of SEQ ID NO:27 and each of said second polypeptides comprises the amino acid sequence of SEQ ID NO:28; or (vii) each of said first polypeptides comprises the amino acid sequence of SEQ ID NO:31 and each of said second polypeptides comprises the amino acid sequence of SEQ ID NO:32; or
(viii) each of said first polypeptides comprises the amino acid sequence of SEQ ID NO:35 and each of said second polypeptides comprises the amino acid sequence of SEQ ID NO:36; or
(ix) each of said first polypeptides comprises the amino acid sequence of SEQ ID NO:39 and each of said second polypeptides comprises the amino acid sequence of SEQ ID NO:40; or
(x) each of said first polypeptides comprises the amino acid sequence of SEQ ID NO:43 and each of said second polypeptides comprises the amino acid sequence of SEQ ID NO:44; or
(xi) each of said first polypeptides comprises the amino acid sequence of SEQ ID NO:47 and each of said second polypeptides comprises the amino acid sequence of SEQ ID NO:48; or
(xii) each of said first polypeptides comprises the amino acid sequence of SEQ ID NO:51 and each of said second polypeptides comprises the amino acid sequence of SEQ ID NO:52.

Yet other aspects of the disclosure relate to a pharmaceutical composition comprising a compound described herein, such as a compound described above.

Other aspects of the disclosure relate to a method of treating an autoimmune or an inflammatory disease comprising administering a compound described herein, such as a compound described above, or a pharmaceutical composition comprising said compound to a subject.

Yet other aspects of the disclosure relate to a compound described herein, such as a compound described above, for use in medicine. In some embodiments, said use is the treatment of an autoimmune or an inflammatory disease.

Other aspects of the disclosure relate to a pharmaceutical composition comprising a compound described herein, such as a compound described above, for use in medicine. In some embodiments, said use is the treatment of an autoimmune or an inflammatory disease.

Yet other aspects of the disclosure relate to a nucleic acid comprising a nucleotide sequence encoding a polypeptide described herein, such as a polypeptide described above. Other aspects of the disclosure relate to a vector comprising said nucleic acid. In some embodiments, the vector comprises a promoter operably linked to said nucleic acid. Other aspects of the disclosure relate to a cell comprising said nucleic acid or said vector.

Other aspects of the disclosure relate to a method of producing a compound or polypeptide as described herein, such as a polypeptide described above, comprising obtaining a cell described herein, such a cell described above, and expressing a nucleic acid as described herein in said cell. In some embodiments, the method further comprises isolating and purifying said polypeptide or compound.

The details of one or more embodiments of the disclosure are set forth in the description below. Other features or advantages of the present disclosure will be apparent from the following drawings and detailed description of several embodiments, and also from the appending claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

DETAILED DESCRIPTION OF THE INVENTION

Figure 1A:
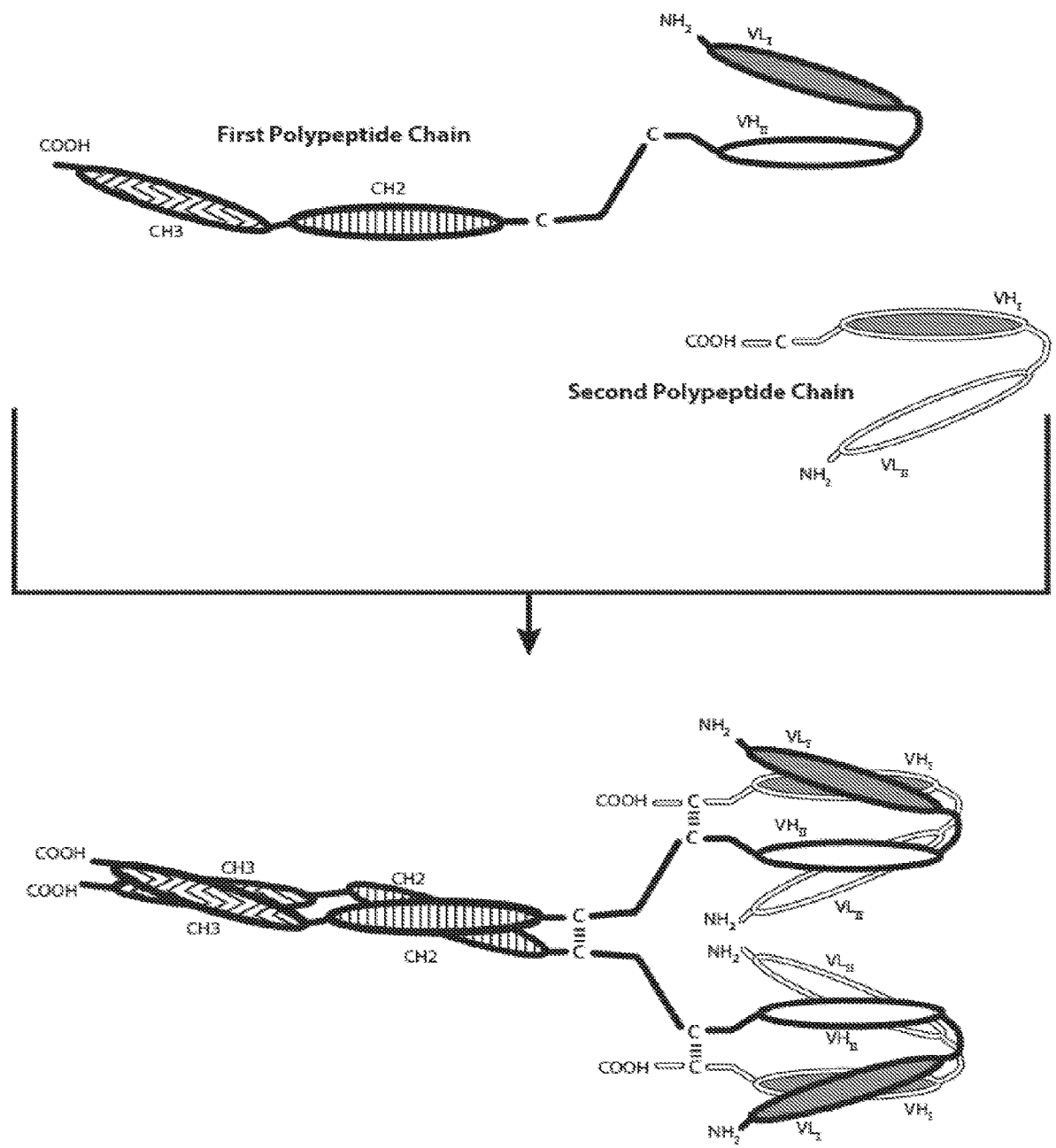
FIG. 1A is a diagram of an exemplary compound specific for BAFF and IL23A. The first polypeptide chain contains CH3, CH2, $VH_2$ ($VH_{II}$) and $VL_1$ ($VL_I$) domains. The second polypeptide chain contains $VH_1$ ($VH_I$) and $VL_2$($VL_{II}$) domains. $VL_1$ and $VH_1$ are specific for a first target protein (either BAFF or IL23A) and $VL_2$ and $VH_2$ are specific for a second target protein (either IL23A or BAFF). The upper panel shows each polypeptide chain separately. The lower panel shows a tetravalent compound (e.g., a monomer, a monomeric antibody as described in the Examples section) formed through association of the CH2 and CH3 domains of one first polypeptide with the CH2 and CH3 domains of another first polypeptide. The binding domains for the first and second target protein are formed through association of $VH_1$ and $VL_1$ and through association $VH_2$ and $VL_2$, respectively.

Described herein compounds that bind to both BAFF and IL-23A (also referred to as IL23p19 or IL23A). To date, there have been no approved compounds that target both BAFF and IL23A. There are limited studies with simultaneous neutralization of two/more key inflammatory mediators using biotherapeutics approach and these studies failed to show improvement in clinical outcomes that were measured for rheumatoid arthritis (RA). In addition, such combinations may increase side effects, such as the risk of infection (see, e.g., Genovese, M. C., Cohen, S., Moreland, L., Lium, D., Robbins, S., et al. (2004). *Arth. Rheum.* 50, 1412-9; Genovese, M. C., Cohen, S., Moreland, L., Lium, D., Robbins, S., et al. (2004). *Arth. Rheum.* 50, 1412-9; and Weinblatt, M., Schiff, M., Goldman, A. Kremer, J., Luggen, M., et al. (2007). *Ann. Rheum. Dis.* 66, 228-34). Further, such bi-specific compounds have been difficult to design, due to issues related to solubility (e.g., aggregation) and stability (e.g., poor pharmacokinetics).

Surprisingly, some of the compounds described herein that bind to BAFF and IL-23A have been found to have similar or improved properties compared to individual antibodies that target either IL-23A or BAFF. Some compounds were also found to have suitable pharmacokinetics and were soluble at suitable ranges for dosing purposes. Further, in some embodiments, there are advantages of single administration over multiple individual dose administration from the perspective of side effects of the individual therapies, and lower dosage. In addition, in some embodiments, the CMC properties of the compounds showed that some compounds had high melting temperatures (Tm) and low aggregation. In one aspect, one exemplary compound showed particularly low aggregation at high concentrations. The compounds described herein are believed to have one or more advantageous properties, e.g., decreased side effects, increased case and safety of administration, an increased half-life, increased binding affinity, or increased inhibitory activity, compared to standard antibody molecules, e.g., an IgG molecule or antigen-binding fragment (e.g., Fab).

Accordingly, aspects of the disclosure relate to compounds specific for both BAFF and IL-23A, as well as methods of use and production of such compounds. In one aspect, the subject technology relates to compositions with increased efficacy for treating and preventing autoimmune or inflammatory diseases, such as systemic lupus erythematosus (SLE), systemic lupus erythematosus with kidney involvement/Lupus Nephritis (LN), ANCA-associated vasculitis (AAV), primary Sjogren's syndrome (pSS), chronic graft versus host disease (cGVHD), systemic sclerosis (SSc), Rheumatoid Arthritis (RA), Psoriasis (Ps), Ankylosing Spondylitis (AS), and Psoriatic Arthritis (PA). A BAFF/IL23A dual antagonist will inhibit both autoantibody/immune complex and IL23 axis-mediated end organ damage, and may achieve superior induction and maintenance of clinical response than current Standard of Care for the treatment of SLE and LN. Compared to co-administration of a BAFF antibody and an IL-23 antibody to inhibit both pathways at the same time, a BAFF/IL23A dual antagonist is more convenient to patient that can lead to improved compliance and reduced pain. A BAFF/IL23A dual antagonist should allow for administration of reduced dosages, as well as lower costs associated with the treatment. In addition, a BAFF/IL23A antagonist may also be beneficial in the treatment of a cluster of diseases involving dysregulated B cells/autoantibody and IL23-mediated tissue damage including primary Sjogren's syndrome (pSS), chronic graft versus host disease (cGVHD), systemic sclerosis (SSc) and ANCA-associated vasculitis (AAV).

It is difficult to design a dual-targeting therapeutic molecule that brings two pharmacological entities together and maintains the functional potency of each component, while at the same time has biophysical properties suitable for large scale manufacture. Development of dual-targeting molecules has been hampered with many issues related to in vitro and in vivo stability, such as poor expression, aggregation, limited shelf-life, poor serum stability and poor pharmacokinetic properties in vivo (Demarest S J, Glaser S M. (2008). Curr Opin Drug Discov Devel. 11, 675-87).

Here we disclose a method to create dual-targeting molecules that inhibit both BAFF and IL23 function. The dual-targeting molecules of the subject technology have advantageous and surprising properties such as high melting temperatures (Tm), low aggregation at high concentrations, and predicted human PK properties that allows once every two weeks or less frequent s.c. administration.

Compounds

Aspects of the disclosure relate to a compound specific for both BAFF and IL23A. An exemplary protein sequence for BAFF and an exemplary protein sequence for IL23A are shown below.

```
>sp|Q9Y275|B-cell Activating Factor (BAFF)-
TN13B_HUMAN Tumor necrosis factor ligand
superfamily member 13B OS = Homo sapiens
GN = TNFSF13B PE = 1 SV = 1
                                   (SEQ ID NO: 80)
MDDSTEREQSRLTSCLKKREEMKLKECVSILPRKESPSVRSSKDGKLL

AATLLLALLSCCLTVVSFYQVAALQGDLASLRAELQGHHAEKLPAGAG

APKAGLEEAPAVTAGLKIFEPPAPGEGNSSQNSRNKRAVQGPEETVTQ

DCLQLIADSETPTIQKGSYTFVPWLLSFKRGSALEEKENKILVKETGY

FFIYGQVLYTDKTYAMGHLIQRKKVHVFGDELSLVTLFRCIQNMPETL

PNNSCYSAGIAKLEEGDELQLAIPRENAQISLDGDVTFFGALKLL

>NP_057668.1-IL23A [Homo sapiens]
                                   (SEQ ID NO: 81)
MLGSRAVMLLLLLPWTAQGRAVPGGSSPAWTQCQQLSQKLCTLAWSAHP

LVGHMDLREEGDEETTNDVPHIQCGDGCDPQGLRDNSQFGLQRIHQGLI

FYEKLLGSDIFTGEPSLLPDSPVGQLHASLLGLSQLLQPEGHHWETQQI

PSLSPSQPWQRLLLRFKILRSLQAFVAVAARVFAHGAATLSP
(amino acids 1-19 are a predicted signal sequence)
```

In some embodiments, the compound comprises a first polypeptide and a second polypeptide. In some embodiments, the first polypeptide comprises (i) a light chain variable domain of a first immunoglobulin (VL1) specific for a first target protein, (ii) a heavy chain variable domain of a second immunoglobulin (VH2) specific for a second target protein; and (iii) a hinge region, a heavy chain constant region 2 (CH2) and a heavy chain constant region 3 (CH3). In some embodiments, the first polypeptide further comprises a heavy chain constant region 1 (CH1). In some embodiments, the second polypeptide comprises: (i) a light chain variable domain of the second immunoglobulin (VL2) specific for the second target protein; (ii) a heavy chain variable domain of the first immunoglobulin (VH1) specific for the first target protein. In some embodiments, the second polypeptide further comprises a light chain constant region (CL).

It is to be understood that the variable domains and constant domains/regions of the first polypeptide can be in any order and that the variable domains and constant domains/regions (if any) of the second polypeptide can be in any order. Multiple exemplary configurations for the domains/regions on the first and second polypeptide from N-terminus to C-terminus are shown below.

Figure 1B:
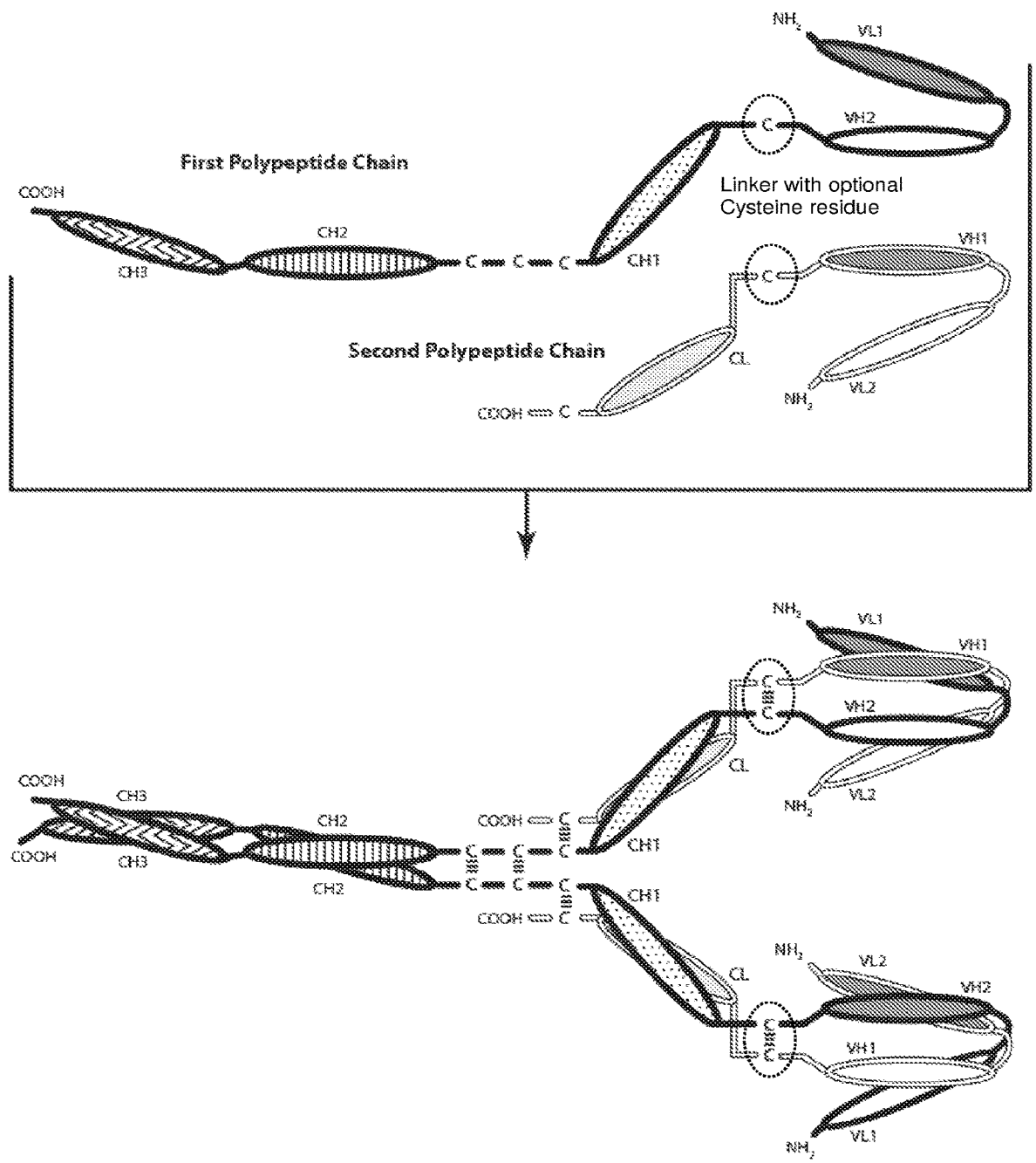
FIG. 1B is a diagram of another exemplary compound specific for BAFF and IL23A. The first polypeptide chain contains CH3, CH2, CH1, $VH_2$ ($VH_I$) and $VL_1$ ($VL_I$) domains. The second polypeptide chain contains CL, $VH_1$ ($VH_I$) and $VL_2$ ($VL_{II}$) domains. $VL_1$ and $VH_1$ are specific for a first target protein (either BAFF or IL23A) and $VL_2$ and $VH_2$ are specific for a second target protein (either IL23A or BAFF). The upper panel shows each polypeptide chain separately. The lower panel shows a tetravalent compound (e.g., a monomer, a monomeric antibody as described in the Examples section) formed through association of the CH2 and CH3 domains of one first polypeptide with the CH2 and CH3 domains of another first polypeptide. The binding domains for the first and second target protein are formed through association of $VH_1$ and $VL_1$ and through association $VH_2$ and $VL_2$, respectively. The compound is further associated through interactions between the CL and CH1 domains.

First polypeptide configuration 1: N-VL1-VH2-hinge-CH2-CH3-C
First polypeptide configuration 2: N-VH2-VL1-hinge-CH2-CH3-C
First polypeptide configuration 3: N-VL1-VH2-CH1-hinge-CH2-CH3-C
First polypeptide configuration 4: N-VH2-VL1-CH1-hinge-CH2-CH3-C
Second polypeptide configuration 1: N-VL2-VH1-C
Second polypeptide configuration 2: N-VH1-VL2-C
Second polypeptide configuration 3: N-VL2-VH1-CL-C
Second polypeptide configuration 4: N-VH1-VL2-CL-C Exemplary configurations of the compound are shown in FIGS. 1A and 1B.

In some embodiments, the variable regions of the first polypeptide and the second polypeptide associate with one another to form a binding site for the first target protein and a binding site for the second target protein. In some embodiments, the VL1 of the first polypeptide and the VH1 of the second polypeptide associate to form a binding site that binds the first target protein and the VL2 of the second polypeptide and the VH2 of the first polypeptide associate to form a binding site that binds the second target protein. In some embodiments, the first target protein is BAFF and the second target protein is IL23A. In other embodiments, the first target protein is IL23A and the second target protein is BAFF. It is to be understood that the terms "first" and "second" are not meant to imply a level of importance to either target protein.

Exemplary combinations of sequences for each of VL1, VH1, VL2, and VH2 are provided below in Table 1 and also in Table 2 in Example 1.

TABLE 1

Exemplary combinations of sequences for VL1, VH1, VL2, and VH2.

| Combination Number | VL1 sequence | VH1 sequence | VL2 sequence | VH2 sequence |
|---|---|---|---|---|
| 1 | SEQ ID NO: 2 | SEQ ID NO: 1 | SEQ ID NO: 4 | SEQ ID NO: 3 |
| 2 | SEQ ID NO: 4 | SEQ ID NO: 3 | SEQ ID NO: 2 | SEQ ID NO: 1 |
| 3 | SEQ ID NO: 85 | SEQ ID NO: 84 | SEQ ID NO: 4 | SEQ ID NO: 3 |
| 4 | SEQ ID NO: 4 | SEQ ID NO: 3 | SEQ ID NO: 85 | SEQ ID NO: 84 |
| 5 | SEQ ID NO: 87 | SEQ ID NO: 86 | SEQ ID NO: 4 | SEQ ID NO: 3 |
| 6 | SEQ ID NO: 4 | SEQ ID NO: 3 | SEQ ID NO: 87 | SEQ ID NO: 86 |
| 7 | SEQ ID NO: 89 | SEQ ID NO: 88 | SEQ ID NO: 4 | SEQ ID NO: 3 |
| 8 | SEQ ID NO: 4 | SEQ ID NO: 3 | SEQ ID NO: 89 | SEQ ID NO: 88 |
| 9 | SEQ ID NO: 91 | SEQ ID NO: 90 | SEQ ID NO: 4 | SEQ ID NO: 3 |
| 10 | SEQ ID NO: 4 | SEQ ID NO: 3 | SEQ ID NO: 91 | SEQ ID NO: 90 |

In some embodiments, the compound comprises a VL1 sequence comprising a first light chain CDR1, CDR2, and CDR3 and a VH1 sequence comprising a first heavy chain CDR1, CDR2, and CDR3, a VL2 sequence comprising a second light chain CDR1, CDR2 and CDR3, and a VH2 sequence comprising a second heavy chain CDR1, CDR2, and CDR3. In some embodiments, the CDRs are the CDRs of one or more VL1, VH1, VL2, and VH2 sequences provided in Table 1. Exemplary light chain and heavy chain CDR sequences for the VL1, VH1, VL2, and VH2 sequences provided in Table 1 are shown below:

```
SEQ ID NO: 1 CDRs:
                                        (SEQ ID NO: 92)
GGTFNNNAIN,
(CDR1)
                                        (SEQ ID NO: 93)
GIIPMFGTAKYSQNFQG,
(CDR2)
                                        (SEQ ID NO: 94)
SRDLLLFPHHALSP
(CDR3)

SEQ ID NO: 2 CDRs:
                                        (SEQ ID NO: 95)
QGDSLRSYYAS,
(CDR1)
                                        (SEQ ID NO: 96)
GKNNRPS,
(CDR2)
                                        (SEQ ID NO: 97)
SSRDSSGNHWV
(CDR3)

SEQ ID NO: 3 CDRs:
                                        (SEQ ID NO: 98)
GYTFTDQTIH,
(CDR1)
                                        (SEQ ID NO: 99)
YIYPRDDSPKYNENFKG,
(CDR2)
                                        (SEQ ID NO: 100)
PDRSGYAWFIY
(CDR3)

SEQ ID NO: 4 CDRs:
                                        (SEQ ID NO: 101)
KASRDVAIAVA,
(CDR1)
                                        (SEQ ID NO: 102)
WASTRHT,
(CDR2)
                                        (SEQ ID NO: 103)
HQYSSYPFT
(CDR3)

-continued
SEQ ID NO: 84 CDRs:
                                        (SEQ ID NO: 104)
DHIFSIHWMQ,
(CDR1)
                                        (SEQ ID NO: 105)
EIFPGSGTTDYNEKFKG,
(CDR2)
```

```
                                    -continued
GAFDY                               (SEQ ID NO: 106)
(CDR3)

SEQ ID NO: 85 CDRs:

RASQDIGNRLS                         (SEQ ID NO: 107)
(CDR1

ATSSLDS,                            (SEQ ID NO: 108)
(CDR2)

LQYASSPFT                           (SEQ ID NO: 109)
(CDR3)

SEQ ID NO: 86 CDRs:

DHIFSIHWMQ,                         (SEQ ID NO: 110)
(CDR1)

EIFPGSGTTDYNEKFKG,                  (SEQ ID NO: 111)
(CDR2)

GAFDY                               (SEQ ID NO: 112)
(CDR3)

SEQ ID NO: 87 CDRs:

RASQDIGNRLN                         (SEQ ID NO: 112)
(CDR1

ATSSLDS,                            (SEQ ID NO: 113)
(CDR2)

LQYASSPFT                           (SEQ ID NO: 114)
(CDR3)

SEQ ID NO: 88 CDRs:

GYSFSTFFIH,                         (SEQ ID NO: 115)
(CDR1)

RIDPNSGATKYNEKFES,                  (SEQ ID NO: 116)
(CDR2)

GEDLLIRTDALDY                       (SEQ ID NO: 117)
(CDR3)

SEQ ID NO: 89 CDRs:

KASQNAGIDVA,                        (SEQ ID NO: 118)
(CDR1)

SKSNRYT,                            (SEQ ID NO: 119)
(CDR2)

LQYRSYPRT                           (SEQ ID NO: 120)
(CDR3)

SEQ ID NO: 90 CDRs:

GYSFSTFFIH,                         (SEQ ID NO: 121)
(CDR1)

GRIDPNSGATKYNEKFES                  (SEQ ID NO: 122)
(CDR2),

GEDLLIRTDALDY                       (SEQ ID NO: 123)
(CDR3)

SEQ ID NO: 91 CDRs:

KASQNAGIDVA,                        (SEQ ID NO: 124)
(CDR1)

SKSNRYT,                            (SEQ ID NO: 125)
(CDR2)

LQYRSYPRT                           (SEQ ID NO: 126)
(CDR3)
```

In some embodiments, the compound comprises a VH1, VL1, VH2, and/or VL2 that comprises a sequence that is at least 80% (e.g., 85%, 90%, 95%, 96%, 97%, 98%, or 99%) identical (residue per residue for the entire length of the sequence) to a sequence described in Table 1. The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In some embodiments, the compound comprises a VH1, VL1, VH2, and/or VL2 that comprises a sequence comprising one or more (e.g., 1, 2, 3, 4, 5, 6, 7, 8, 9, 10 or more) mutations in a sequence described in Table 1. Such mutations can be conservative amino acid substitutions. As used herein, a "conservative amino acid substitution" refers to an amino acid substitution that does not alter the relative charge or size characteristics of the protein in which the amino acid substitution is made. Conservative substitutions of amino acids include, for example, substitutions made amongst amino acids within the following groups: (a) M, I, L, V; (b) F, Y, W; (c) K, R, H; (d) A, G; (e) S, T; (f) Q, N; and (g) E, D.

The amino acid sequences of the hinge region, CH2 and CH3 of the compound (and optionally the CH1 and CL, if the compound contains such regions) may be derived from any appropriate source, e.g., a constant region of an antibody such as an IgG1, IgG2, IgG3, or IgG4. Antibody heavy and light chain constant regions amino acid sequences are well known in the art, e.g., those provided in the IMGT database (www.imgt.org) or at www.vbase2.org/vbstat.php., both of which are incorporated by reference herein. Furthermore, in some expression systems the C-terminal lysine residue of the CH3 Domain may be post-translationally removed. Accordingly, the C-terminal lysine residue of the CH3 Domain is an optional amino acid residue. Specifically provided by the instant invention are molecules lacking the C-terminal lysine residue of the CH3 Domain. Also specifically encompassed by the instant invention are such constructs comprising the C-terminal lysine residue of the CH3 Domain. In some embodiments, the amino acid sequences of the CH2 and CH3 are derived from an IgG1 (e.g., SEQ ID NO:75) or an IgG4 (e.g., SEQ ID NO:73). In some embodiments, the CL comprises the amino acid sequence of a kappa CL or a lambda CL. In some embodiments, the hinge region comprises the amino acid sequence EPKSCDKTHTCPPCP (SEQ ID NO: 76). The hinge region of SEQ ID NO:76 is present in, for example, SEQ ID NO:5 polypeptide. In other embodiments, the hinge region comprises the amino acid sequence LEPKSSDKTHTCPPCP (SEQ ID NO:130). The hinge region of SEQ ID NO:130 is present in, for example, SEQ ID NO:9 polypeptide. The hinge region of SEQ ID NO:130 is also present at the beginning of the Fc domain of SEQ ID NO:129. In still other embodiments, the hinge region comprises the amino acid sequence ESKYGPPCPPCP (SEQ ID NO:134). The hinge region of SEQ ID NO:134 is present in, for example, SEQ ID NO:13 polypeptide. The hinge region of SEQ ID NO:134 is also present at the beginning of the Fc domain of SEQ ID NO:127.

In some embodiments, the CH2 and/or CH3 of the compound (and optionally the CH1 and CL, if the compound contains such regions) may comprise one or more amino acid substitutions that differ from a wild type CH2 or CH3, e.g., one or more amino acid substitutions in a wild type IgG1 CH2 or CH3 or one or more amino acid substitutions in a wild type IgG4 CH2 or CH3 (SEQ ID NO: 39 provides an exemplary wild-type IgG1). Such substitutions are known in the art (see, e.g., U.S. Pat. Nos. 7,704,497, 7,083,784, 6,821,505, 8,323,962, 6,737,056, and 7,416,727).

In some embodiments, the CH2 comprises an amino acid substitution at 234, 235, 252, 254, and/or 256, numbered according to the EU index as in Kabat for a conventional antibody (Kabat et al. Sequences of Proteins of Immunological Interest, U.S. Department of Health and Human Services, 1991, which is incorporated by reference herein in its entirety). It is to be understood that all amino acid positions described herein refer to the numbering of the EU index as in Kabat for a conventional antibody. In some embodiments, the CH2 comprises an amino acid substitution at position 252, 254, and/or 256. In some embodiments, the amino acid at position 252 is tyrosine, phenylalanine, serine, tryptophan, or threonine. In some embodiments, the amino acid at position 254 is threonine. In some embodiments, the amino acid at position 254 is serine, arginine, glutamine, glutamic acid, or aspartic acid. In some embodiments, the CH2 comprises a tyrosine at position 252, a threonine at position 254 and a glutamic acid a position 256 (referred to herein as a YTE mutant). In some embodiments, the CH2 comprises an amino acid substitution at position 234 and/or 235. In some embodiments, the CH2 comprises an alanine at position 234 and an alanine at position 235, also referred to herein as KO mutant. In some embodiments, the CH2 comprises a tyrosine at position 252, a threonine at position 254, a glutamic acid a position 256, an alanine at position 234 and an alanine at position 235, also referred to herein as KO-YTE mutant.

In some embodiments, one or more linkers may be used to connect domains/regions together on the first and/or second polypeptide. For example, the first polypeptide may comprise a linker between the VL1 and VH2. The first polypeptide further comprises a linker between the VL1 or VH2 (depending on the configuration as discussed above) and the hinge (e.g., –VL1-linker-hinge or -VH2-linker-hinge). If the first polypeptide comprises a CH1, e.g., first polypeptide may comprise a linker between the VL1 or VH2 (depending on the configuration as discussed above) and the CH1 (e.g., –VL1-linker-CH1 or -VH2-linker-CH1). In another example, the second polypeptide may comprise a linker between the VL2 and VH1. The second polypeptide may further comprise a linker after the VL2 or VH1 (depending on the configuration discussed above, e.g., –VL2-linker or -VH1-linker) at the C-terminal end of the polypeptide chain. If the second polypeptide further comprises a CL, the second polypeptide may further comprise a linker between the VL2 or VH1 (depending on the configuration as discussed above) and the CL (as in, e.g., –VL2-linker-CL or -VH1-linker-CL). It is to be understood that any number of linkers may be used to connect any domain or region to any other another domain or region on the first polypeptide and/or that any number of linkers may be used to connect any domain or region to any other another domain or region on the second polypeptide.

Any suitable linker known in the art is contemplated for use herein. In some embodiments, the linker is a peptide linker. In some embodiments, the peptide linker comprises at least two amino acids, e.g., 2, 3, 4, 5, 6, 7, 8, 9, 10 or more amino acids. In some embodiments, the peptide linker is no more than 50, 40, 30, 25, 20, 19, 18, 17, 16, 15, 14, 13, 12, 11, 10, 9, 8, 7, 6, 5, 4, 3, or 2 amino acids in length. In some embodiments, the peptide linker is between 2 and 50, 2 and 40, 2 and 30, 2 and 20, 2 and 10, 2 and 9, 2 and 8, 2 and 7, or 2 and 6 amino acids in length. In some embodiments, the peptide linker comprises the amino acid sequence GGGSGGGG (SEQ ID NO:69), LGGGSG (SEQ ID NO:70), FNRGEC (SEQ ID NO:71), VEPKSC (SEQ ID NO:72), GGCGGGEVAACEKEVAALEKEVAALEKEVAALEK (SEQ ID NO:82), GGCGGGKVAACKEKVAALKEKVAALKEKVAALKE (SEQ ID NO:83) or a combination thereof. In some embodiments, the peptide linker may comprise multiple copies of a linker sequence, e.g., multiple copies of the sequence GGGSGGGG (SEQ ID NO:69), LGGGSG (SEQ ID NO:70), FNRGEC (SEQ ID NO:71), VEPKSC (SEQ ID NO:72), or a combination thereof.

In some embodiments, the first and second polypeptides have the following configurations:
First polypeptide configuration 1: N-VL1-VH2-hinge-CH2-CH3-C,
First polypeptide configuration 2: N-VH2-VL1-hinge-CH2-CH3-C,
Second polypeptide configuration 1: N-VL2-VH1-C,
Second polypeptide configuration 2: N-VH1-VL2-C,
wherein the first linker between VL1 and VH2 of the first polypeptide or the second linker between VL2 and VH1 of the second polypeptide comprises the amino acid sequence GGGSGGGG (SEQ ID NO:69). In some embodiments, said first linker and said second linker comprise the amino acid sequence GGGSGGGG (SEQ ID NO:69). In some embodiments, the first polypeptide further comprises a third linker between the VH2 or VL2 and said hinge region and the second polypeptide further comprises a fourth linker after said VH1 or VL2 (at its C-terminus). In some embodiments, said third linker of said first polypeptide comprises the amino acid sequence GGCGGGEVAACEKEVAALEKEVAALEKEVAALEK (SEQ ID NO:82), and said fourth linker of said second polypeptide comprises the amino acid sequence GGCGGGKVAACKEKVAALKEKVAALKEKVAALKE (SEQ ID NO:83). In other embodiments, said third linker of said first polypeptide comprises the amino acid sequence GGCGGGKVAACKEKVAALKEKVAALKEKVAALKE (SEQ ID NO:83), and said fourth linker of said second polypeptide comprises the amino acid sequence GGCGGGEVAACEKEVAALEKEVAALEKEVAALEK (SEQ ID NO:82). In some embodiments, said third linker of said first polypeptide comprises the amino acid sequence GGCGGGEVAACEKEVAALEKEVAALEKEVAALEK (SEQ ID NO:82) or the amino acid sequence GGCGGGKVAACKEKVAALKEKVAALKEKVAALKE (SEQ ID NO:83). In other embodiments, said forth linker of said second polypeptide comprises the amino acid sequence GGCGGGEVAACEKEVAALEKEVAALEKEVAALEK (SEQ ID NO:82) or the amino acid sequence GGCGGGKVAACKEKVAALKEKVAALKEKVAALKE (SEQ ID NO:83). In some embodiments, said third linker comprises the amino acid sequence VEPKSC (SEQ ID NO:72) or the amino acid sequence FNRGEC (SEQ ID NO:71). In some embodiments, said fourth linker comprises the amino acid sequence FNRGEC (SEQ ID NO:71) or the amino acid sequence VEPKSC (SEQ ID NO:72). In some embodiments, said third linker comprises the amino acid sequence VEPKSC (SEQ ID NO:72) and said fourth linker comprises the amino acid sequence FNRGEC (SEQ ID NO:71). The amino acid sequence FNRGEC (SEQ ID NO:71) is the last six amino acid residues of the CL domain (SEQ ID NO:77) and the amino acid VEPKSC (SEQ ID NO: 72) includes the last amino acid of the CH1 and the first five amino acid residues of the hinge region of SEQ ID NO:76 (as in SEQ ID NO:5).

In some embodiments, the first and second polypeptides have the following configurations:
First polypeptide configuration 3: N-VL1-VH2-CH1-hinge-CH2-CH3-C,
First polypeptide configuration 4: N-VH2-VL1-CH1-hinge-CH2-CH3-C,
Second polypeptide configuration 3: N-VL2-VH1-CL-C,
Second polypeptide configuration 4: N-VH1-VL2-CL-C,
wherein the first linker between said VL1 and said VH2 of the first polypeptide or said second linker between said VL2 and said VH1 of the second polypeptide comprises the amino acid sequence GGGSGGGG (SEQ ID NO:69). In some embodiments, said first linker and said second linker comprise the amino acid sequence GGGSGGGG (SEQ ID NO:69). In some embodiments, said first polypeptide further comprises a third linker between said VH2 or VL1 and said CH1 and said second polypeptide further comprises a fourth linker between said VH1 or said VL2 and said CL. In some embodiments, said third linker or said fourth linker comprises the amino acid sequence LGGGSG (SEQ ID NO:70). In some embodiments, said third linker and said fourth linker comprise the amino acid sequence LGGGSG (SEQ ID NO:70). In some embodiments, said third linker and/or said fourth linker comprise an optional cysteine residue. In some embodiments, said third linker and/or said fourth linker comprise the amino acid sequence GGCGGG (SEQ ID NO:135) or LGGCGGGS (SEQ ID NO:136).

In some embodiments, said heavy chain constant region 2 (CH2) comprises an alanine at positions 234 and an alanine at position 235, numbered according to the EU index as in Kabat for a conventional antibody.

In some embodiments, the compound comprises two first polypeptides and two second polypeptides. In some embodiments, the hinge, CH2 and CH3 of one of the first polypeptides associates with the hinge, CH2 and CH3 of the other of the first polypeptides to form a tetravalent molecule (e.g., the two first polypeptides dimerize through associations between their respective hinge CH2 and CH3 domains to form a tetravalent molecule comprising two binding sites specific for the first target protein and two binding sites specific for the second target protein), a monomer or a monomeric antibody as described in the Examples section. If the first polypeptide further comprises a CH1 domain, and the second polypeptide further comprises a CL domain, the CH1 and CL domains may also participate in formation of a tetravalent molecule (e.g., the two first polypeptides dimerize through associations between their respective hinge, CH2 and CH3 domains and the CH1 of each said first polypeptides associates with the CL of one said second polypeptides to form a tetravalent molecule comprising two binding sites for the first target protein and two binding sites for the second target protein) a monomer, a monomeric antibody as described in the Examples section. In some embodiments, the two first polypeptides are associated together via at least one disulfide bond. In some embodiments, said compound comprises two said first polypeptides and two said second polypeptides, wherein each of said first polypeptides comprises a third linker, a hinge, a CH2 and a CH3, and each of said second polypeptides comprises a fourth linker and wherein the hinge, CH2 and CH3 of one of the first polypeptides associates with the hinge, CH2 and CH3 of the other of the first polypeptides and the third linker of each said first polypeptides associates with the fourth linker of one said second polypeptides to form a tetravalent molecule (e.g., a monomer, a monomeric antibody as described in the Examples section) (e.g., compounds U and T).

In some embodiments, the disclosure relates to a compound comprising two first polypeptides and two second polypeptides;
wherein said two first polypeptides are associated together via at least one disulfide bond and wherein each of said first polypeptide is associated to one said second polypeptide via at least one disulfide bond;
wherein each of said first polypeptides comprises:
(i) a light chain variable domain of a first immunoglobulin (VL1) specific for a first target protein;
(ii) a heavy chain variable domain of a second immunoglobulin (VH2) specific for a second target protein;
(iii) a heavy chain constant region 1 (CH1), a hinge region, a heavy chain constant region 2 (CH2) and a heavy chain constant region 3 (CH3); and
wherein each of said second polypeptides comprises:
(i) a light chain variable domain of the second immunoglobulin (VL2) specific for said second target protein;
(ii) a heavy chain variable domain of the first immunoglobulin (VH1) specific for said first target protein;
(iii) a light chain constant region domain (CL);
wherein the hinge, CH2 and CH3 of one of the first polypeptides associates with the hinge, CH2 and CH3 of the other of the first polypeptides and the CH1 of each said first polypeptides associates with the CL of said each second polypeptides to form a tetravalent molecule;
wherein
a) said VL1 and VH1 associate to form a binding site that binds said first target protein;
b) said VL2 and VH2 associate to form a binding site that binds said second target protein;
c) said heavy chain constant region 2 (CH2) comprises a tyrosine at position 252, a threonine at position 254 and a glutamic acid a position 256, numbered according to the EU index as in Kabat; and
d) said first target protein is BAFF and said second target protein is IL-23A or said first target protein is IL-23A and said second target protein is BAFF,
and wherein:
(i) said VL1 comprises SEQ ID NO:2, said VH1 comprises SEQ ID NO:1, said VL2 comprises SEQ ID NO:4 and said VH2 comprises SEQ ID NO:3; or
(ii) said VL1 comprises SEQ ID NO:4, said VH1 comprises SEQ ID NO:3, said VL2 comprises SEQ ID NO:2 and said VH2 comprises SEQ ID NO:1; or
(iii) said VL1 comprises SEQ ID NO:85, said VH1 comprises SEQ ID NO:84, said VL2 comprises SEQ ID NO:4 and said VH2 comprises SEQ ID NO:4; or
(iv) said VL1 comprises SEQ ID NO:4, said VH1 comprises SEQ ID NO:3, said VL2 comprises SEQ ID NO:85 and said VH2 comprises SEQ ID NO:84; or (v) said VL1 comprises SEQ ID NO:87, said VH1 comprises SEQ ID NO:86, said VL2 comprises SEQ ID NO:4 and said VH2 comprises SEQ ID NO:3; or
(vi) said VL1 comprises SEQ ID NO:4, said VH1 comprises SEQ ID NO:3, said VL2 comprises SEQ ID NO:87 and said VH2 comprises SEQ ID NO:86; or
(vii) said VL1 comprises SEQ ID NO:89, said VH1 comprises SEQ ID NO:88, said VL2 comprises SEQ ID NO:4 and said VH2 comprises SEQ ID NO:3; or
(viii) said VL1 comprises SEQ ID NO:4, said VH1 comprises SEQ ID NO:3, said VL2 comprises SEQ ID NO:89 and said VH2 comprises SEQ ID NO:88; or
(ix) said VL1 comprises SEQ ID NO:91, said VH1 comprises SEQ ID NO:90, said VL2 comprises SEQ ID NO:4 and said VH2 comprises SEQ ID NO:3; or
(x) said VL1 comprises SEQ ID NO:4, said VH1 comprises SEQ ID NO:3, said VL2 comprises SEQ ID NO:91 and said VH2 comprises SEQ ID NO:90.

In some embodiments relating to the above aspect, each of said first polypeptides further comprises a first linker between said VL1 and said VH2, and each of said second polypeptides further comprises a second linker between said VL2 and said VH1. In some embodiments, said first linker or said second linker comprises the amino acid sequence GGGSGGGG (SEQ ID NO:69). In some embodiments, said first linker and said second linker comprise the amino acid sequence GGGSGGGG (SEQ ID NO:69). In some embodiments, each of said first polypeptides further comprises a third linker between said VH2 or said VL1 and said CH1, and each of said second polypeptides further comprises a fourth linker between said VH1 or said VL2 and said CL. In some embodiments, said third linker or said fourth linker comprises the amino acid sequence LGGGSG (SEQ ID NO:70). In some embodiments, said third linker and said fourth linker comprise the amino acid sequence LGGGSG (SEQ ID NO:70). In some embodiments, said third linker and/or said fourth linker comprise an optional cysteine residue. In some embodiments, said third linker and/or said fourth linker comprise the amino acid sequence GGCGGG (SEQ ID NO:135) or LGGCGGGS (SEQ ID NO:136). In some embodiments, said heavy chain constant region 2 (CH2) comprises an alanine at positions 234 and an alanine at position 235, numbered according to the EU index as in Kabat. In some embodiments, the amino acid sequence of said hinge region, said heavy chain constant region 2 (CH2) or said heavy chain constant region 3 (CH3) is derived from a IgG1 or from a IgG4. In some embodiments, said hinge region comprises the amino acid sequence EPKSCDKTHTCPPCP (SEQ ID NO:76), the amino acid sequence LEPKSSDKTHTCPPCP (SEQ ID NO:130) or the amino acid sequence ESKYGPPCPPCP (SEQ ID NO:134). In some embodiments, (i) each of said first polypeptides comprises the amino acid sequence of SEQ ID NO:5 and each of said second polypeptides comprises the amino acid sequence of SEQ ID NO:6; or
  (ii) each of said first polypeptides comprises the amino acid sequence of SEQ ID NO:7 and each of said second polypeptides comprises the amino acid sequence of SEQ ID NO:8; or
  (iii) each of said first polypeptides comprises the amino acid sequence of SEQ ID NO:13 and each of said second polypeptides comprises the amino acid sequence of SEQ ID NO:14; or
  (iv) each of said first polypeptides comprises the amino acid sequence of SEQ ID NO:15 and each of said second polypeptides comprises the amino acid sequence of SEQ ID NO:16; or
(v) each of said first polypeptides comprises the amino acid sequence of SEQ ID NO:21 and each of said second polypeptides comprises the amino acid sequence of SEQ ID NO:22; or
(vi) each of said first polypeptides comprises the amino acid sequence of SEQ ID NO:25 and each of said second polypeptides comprises the amino acid sequence of SEQ ID NO:26; or
(vii) each of said first polypeptides comprises the amino acid sequence of SEQ ID NO:29 and each of said second polypeptides comprises the amino acid sequence of SEQ ID NO:30; or
(viii) each of said first polypeptides comprises the amino acid sequence of SEQ ID NO:33 and each of said second polypeptides comprises the amino acid sequence of SEQ ID NO:34; or
(ix) each of said first polypeptides comprises the amino acid sequence of SEQ ID NO:37 and each of said second polypeptides comprises the amino acid sequence of SEQ ID NO:38; or
(x) each of said first polypeptides comprises the amino acid sequence of SEQ ID NO:41 and each of said second polypeptides comprises the amino acid sequence of SEQ ID NO:42; or
(xi) each of said first polypeptides comprises the amino acid sequence of SEQ ID NO:45 and each of said second polypeptides comprises the amino acid sequence of SEQ ID NO:46; or
(xii) each of said first polypeptides comprises the amino acid sequence of SEQ ID NO:49 and each of said second polypeptides comprises the amino acid sequence of SEQ ID NO:50; or
(xiii) each of said first polypeptides comprises the amino acid sequence of SEQ ID NO:53 and each of said second polypeptides comprises the amino acid sequence of SEQ ID NO:54; or
(xiv) each of said first polypeptides comprises the amino acid sequence of SEQ ID NO:55 and each of said second polypeptides comprises the amino acid sequence of SEQ ID NO:56; or
(xv) each of said first polypeptides comprises the amino acid sequence of SEQ ID NO:57 and each of said second polypeptides comprises the amino acid sequence of SEQ ID NO:58; or
(xvi) each of said first polypeptides comprises the amino acid sequence of SEQ ID NO:59 and each of said second polypeptides comprises the amino acid sequence of SEQ ID NO:60; or
(xvii) each of said first polypeptides comprises the amino acid sequence of SEQ ID NO:61 and each of said second polypeptides comprises the amino acid sequence of SEQ ID NO:62; or
(xviii) each of said first polypeptides comprises the amino acid sequence of SEQ ID NO:63 and each of said second polypeptides comprises the amino acid sequence of SEQ ID NO:64; or
(xix) each of said first polypeptides comprises the amino acid sequence of SEQ ID NO:65 and each of said second polypeptides comprises the amino acid sequence of SEQ ID NO:66; or
(xx) each of said first polypeptides comprises the amino acid sequence of SEQ ID NO:67 and each of said second polypeptides comprises the amino acid sequence of SEQ ID NO:68.

Other aspects of the disclosure relate to a compound comprising two first polypeptides and two second polypeptides; wherein said two first polypeptides are associated together via at least one disulfide bond and wherein each of said first polypeptide is associated to one said second polypeptide via at least one disulfide bond; and wherein (i) each of said first polypeptides comprises the amino acid sequence of SEQ ID NO:5 and each of said second polypeptides comprises the amino acid sequence of SEQ ID NO:6; or (ii) each of said first polypeptides comprises the amino acid sequence of SEQ ID NO:7 and each of said second polypeptides comprises the amino acid sequence of SEQ ID NO:8; or (iii) each of said first polypeptides comprises the amino acid sequence of SEQ ID NO:13 and each of said second polypeptides comprises the amino acid sequence of SEQ ID NO:14; or (iv) each of said first polypeptides comprises the amino acid sequence of SEQ ID NO:15 and each of said second polypeptides comprises the amino acid sequence of SEQ ID NO:16; or (v) each of said first polypeptides comprises the amino acid sequence of SEQ ID NO:21 and each of said second polypeptides comprises the amino acid sequence of SEQ ID NO:22; or (vi) each of said first polypeptides comprises the amino acid sequence of SEQ ID NO:25 and each of said second polypeptides comprises the amino acid sequence of SEQ ID NO:26; or (vii) each of said first polypeptides comprises the amino acid sequence of SEQ ID NO:29 and each of said second polypeptides comprises the amino acid sequence of SEQ ID NO:30; or (viii) each of said first polypeptides comprises the amino acid sequence of SEQ ID NO:33 and each of said second polypeptides comprises the amino acid sequence of SEQ ID NO:34; or (ix) each of said first polypeptides comprises the amino acid sequence of SEQ ID NO:37 and each of said second polypeptides comprises the amino acid sequence of SEQ ID NO:38; or (x) each of said first polypeptides comprises the amino acid sequence of SEQ ID NO:41 and each of said second polypeptides comprises the amino acid sequence of SEQ ID NO:42; or (xi) each of said first polypeptides comprises the amino acid sequence of SEQ ID NO:45 and each of said second polypeptides comprises the amino acid sequence of SEQ ID NO:46; or (xii) each of said first polypeptides comprises the amino acid sequence of SEQ ID NO:49 and each of said second polypeptides comprises the amino acid sequence of SEQ ID NO:50; or (xiii) each of said first polypeptides comprises the amino acid sequence of SEQ ID NO:53 and each of said second polypeptides comprises the amino acid sequence of SEQ ID NO:54; or (xiv) each of said first polypeptides comprises the amino acid sequence of SEQ ID NO:55 and each of said second polypeptides comprises the amino acid sequence of SEQ ID NO:56; or (xv) each of said first polypeptides comprises the amino acid sequence of SEQ ID NO:57 and each of said second polypeptides comprises the amino acid sequence of SEQ ID NO:58; or (xvi) each of said first polypeptides comprises the amino acid sequence of SEQ ID NO:59 and each of said second polypeptides comprises the amino acid sequence of SEQ ID NO:60; or (xvii) each of said first polypeptides comprises the amino acid sequence of SEQ ID NO:61 and each of said second polypeptides comprises the amino acid sequence of SEQ ID NO:62; or (xviii) each of said first polypeptides comprises the amino acid sequence of SEQ ID NO:63 and each of said second polypeptides comprises the amino acid sequence of SEQ ID NO:64; or (xix) each of said first polypeptides comprises the amino acid sequence of SEQ ID NO:65 and each of said second polypeptides comprises the amino acid sequence of SEQ ID NO:66; or (xx) each of said first polypeptides comprises the amino acid sequence of SEQ ID NO:67 and each of said second polypeptides comprises the amino acid sequence of SEQ ID NO:68.

Also contemplated herein are other compounds that compete for binding with a compound as described herein, e.g., a test compound that competes with a compound as described herein for binding to BAFF and IL23A. In some embodiments, the test compound may have at least 80%, 85%, 90%, 95%, 96%, 97%, 98%, or 99% sequence identity (amino acid per amino acid over the entire length of the sequence) with a compound as described herein. Competitive binding may be determined using any assay known in the art, e.g., equilibrium binding, ELISA, surface plasmon resonance, or spectroscopy.

In some embodiments, the compound described herein specifically binds to both BAFF and IL23A. A compound that "specifically binds" to an antigen or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen than it does with alternative targets. A compound "specifically binds" to a target antigen or epitope if it binds with greater affinity, avidity, more readily, and/or with greater duration than it binds to other substances. For example, a compound that specifically (or preferentially) binds to an antigen (e.g., BAFF or IL23A) or an antigenic epitope therein is a compound that binds this target antigen with greater affinity, avidity, more readily, and/or with greater duration than it binds to other antigens or other epitopes in the same antigen. It is also understood by reading this definition that, for example, a compound that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding. In some examples, a compound that "specifically binds" to a target antigen or an epitope thereof may not bind to other antigens or other epitopes in the same antigen.

In some embodiments, a compound as described herein has a suitable binding affinity for BAFF and IL23 or antigenic epitopes thereof. As used herein, "binding affinity" refers to the apparent association constant or $K_A$. The $K_A$ is the reciprocal of the dissociation constant ($K_D$). The compound described herein may have a binding affinity ($K_D$) of at least $10^{-5}$, $10^{-6}$, $10^{-7}$, $10^{-8}$, $10^{-9}$, $10^{-10}$, $10^{-11}$, $10^{-12}$ M or lower for one or both of the target antigens or antigenic epitopes. An increased binding affinity corresponds to a decreased $K_D$. In some embodiments, the compound described herein has a binding affinity ($K_D$) of at least $10^{-11}$ M or lower for one or both of the target antigens or antigenic epitopes. Higher affinity binding of a compound for a first antigen and a second antigen relative to a third antigen can be indicated by a higher $K_A$ (or a smaller numerical value $K_D$) for binding the first antigen and second antigen than the $K_A$ (or numerical value $K_D$) for binding the third antigen. In such cases, the compound has specificity for the first antigen and second antigen (e.g., a first protein in a first conformation or mimic thereof and a second protein in a first conformation or mimic thereof) relative to the third antigen (e.g., the same first or second protein in a second conformation or mimic thereof; or a third protein). Differences in binding affinity (e.g., for specificity or other comparisons) can be at least 1.5, 2, 3, 4, 5, 10, 15, 20, 37.5, 50, 70, 80, 91, 100, 500, 1000, 10,000 or $10^5$ fold.

Binding affinity (or binding specificity) can be determined by a variety of methods including, equilibrium binding, ELISA, surface plasmon resonance, or spectroscopy (e.g., using a fluorescence assay). Exemplary conditions for evaluating binding affinity are in HBS-P buffer (10 mM HEPES pH 7.4, 150 mM NaCl, 0.005% (v/v) Surfactant P20). These techniques can be used to measure the concentration of bound binding protein as a function of target protein concentration. The concentration of bound binding protein ([Bound]) is related to the concentration of free target protein ([Free]) and the concentration of binding sites for the binding protein on the target where (N) is the number of binding sites per target molecule by the following equation:

$$[Bound]=[N][Free]/(Kd+[Free])$$

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

In some embodiments, the compound comprises a first polypeptide and a second polypeptide as defined in Table 2A. In some embodiments, the compound comprises:

(i) said first polypeptide comprises the amino acid sequence of SEQ ID NO:5 and said second polypeptide comprises the amino acid sequence of SEQ ID NO:6; or (ii) said first polypeptide comprises the amino acid sequence of SEQ ID NO:7 and said second polypeptide comprises the amino acid sequence of SEQ ID NO:8; or (iii) said first polypeptide comprises the amino acid sequence of SEQ ID NO:9 and said second polypeptide comprises the amino acid sequence of SEQ ID NO:10; or (iv) said first polypeptide comprises the amino acid sequence of SEQ ID NO:11 and said second polypeptide comprises the amino acid sequence of SEQ ID NO:12; or (v) said first polypeptide comprises the amino acid sequence of SEQ ID NO:13 and said second polypeptide comprises the amino acid sequence of SEQ ID NO:14; or (vi) said first polypeptide comprises the amino acid sequence of SEQ ID NO:15 and said second polypeptide comprises the amino acid sequence of SEQ ID NO:16; or (vii) said first polypeptide comprises the amino acid sequence of SEQ ID NO:17 and said second polypeptide comprises the amino acid sequence of SEQ ID NO:18; or (viii) said first polypeptide comprises the amino acid sequence of SEQ ID NO:19 and said second polypeptide comprises the amino acid sequence of SEQ ID NO:20; or (ix) said first polypeptide comprises the amino acid sequence of SEQ ID NO:21 and said second polypeptide comprises the amino acid sequence of SEQ ID NO:22; or (x) said first polypeptide comprises the amino acid sequence of SEQ ID NO:23 and said second polypeptide comprises the amino acid sequence of SEQ ID NO:24; or (xi) said first polypeptide comprises the amino acid sequence of SEQ ID NO:25 and said second polypeptide comprises the amino acid sequence of SEQ ID NO:26; or (xii) said first polypeptide comprises the amino acid sequence of SEQ ID NO:27 and said second polypeptide comprises the amino acid sequence of SEQ ID NO:28; or (xiii) said first polypeptide comprises the amino acid sequence of SEQ ID NO:29 and said second polypeptide comprises the amino acid sequence of SEQ ID NO:30; or (xiv) said first polypeptide comprises the amino acid sequence of SEQ ID NO:31 and said second polypeptide comprises the amino acid sequence of SEQ ID NO:32; or (xv) said first polypeptide comprises the amino acid sequence of SEQ ID NO:33 and said second polypeptide comprises the amino acid sequence of SEQ ID NO:34; or (xvi) said first polypeptide comprises the amino acid sequence of SEQ ID NO:35 and said second polypeptide comprises the amino acid sequence of SEQ ID NO:36; or (xvii) said first polypeptide comprises the amino acid sequence of SEQ ID NO:37 and said second polypeptide comprises the amino acid sequence of SEQ ID NO:38; or (xviii) said first polypeptide comprises the amino acid sequence of SEQ ID NO:39 and said second polypeptide comprises the amino acid sequence of SEQ ID NO:40; or (xix) said first polypeptide comprises the amino acid sequence of SEQ ID NO:41 and said second polypeptide comprises the amino acid sequence of SEQ ID NO:42; or (xx) said first polypeptide comprises the amino acid sequence of SEQ ID NO:43 and said second polypeptide comprises the amino acid sequence of SEQ ID NO:44; or (xxi) said first polypeptide comprises the amino acid sequence of SEQ ID NO:45 and said second polypeptide comprises the amino acid sequence of SEQ ID NO:46; or (xxii) said first polypeptide comprises the amino acid sequence of SEQ ID NO:47 and said second polypeptide comprises the amino acid sequence of SEQ ID NO:48; or
(xxiii) said first polypeptide comprises the amino acid sequence of SEQ ID NO:49 and said second polypeptide comprises the amino acid sequence of SEQ ID NO:50; or
(xxiv) said first polypeptide comprises the amino acid sequence of SEQ ID NO:51 and said second polypeptide comprises the amino acid sequence of SEQ ID NO:52; or
(xxv) said first polypeptide comprises the amino acid sequence of SEQ ID NO:53 and said second polypeptide comprises the amino acid sequence of SEQ ID NO:54; or
(xxvi) said first polypeptide comprises the amino acid sequence of SEQ ID NO:55 and said second polypeptide comprises the amino acid sequence of SEQ ID NO:56; or
(xxvii) said first polypeptide comprises the amino acid sequence of SEQ ID NO:57 and said second polypeptide comprises the amino acid sequence of SEQ ID NO:58; or
(xxviii) said first polypeptide comprises the amino acid sequence of SEQ ID NO:59 and said second polypeptide comprises the amino acid sequence of SEQ ID NO:60; or
(xxix) said first polypeptide comprises the amino acid sequence of SEQ ID NO:61 and said second polypeptide comprises the amino acid sequence of SEQ ID NO:62; or
(xxx) said first polypeptide comprises the amino acid sequence of SEQ ID NO:63 and said second polypeptide comprises the amino acid sequence of SEQ ID NO:64; or
(xxxi) said first polypeptide comprises the amino acid sequence of SEQ ID NO:65 and said second polypeptide comprises the amino acid sequence of SEQ ID NO:66; or
(xxxii) said first polypeptide comprises the amino acid sequence of SEQ ID NO:67 and said second polypeptide comprises the amino acid sequence of SEQ ID NO:68.

Methods of Producing Compounds, Nucleic Acids, Vectors, and Cells

Aspects of the disclosure also include nucleic acids that encode compounds described herein or polypeptides described herein (e.g., first or second polypeptides described herein), which may be encoded together or separately. The polynucleotides encoding the compounds described herein or polypeptides described herein may be obtained, and the nucleotide sequence of the polynucleotides determined, by any method known in the art.

In some embodiments, the nucleic acid is comprised within a vector, such as an expression vector. In some embodiments, the vector comprises a promoter operably linked to the nucleic acid.

A variety of promoters can be used for expression of the compounds described herein or polypeptides described herein, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter, and the herpes simplex tk virus promoter.

Regulatable promoters can also be used. Such regulatable promoters include those using the lac repressor from *E. coli* as a transcription modulator to regulate transcription from lac operator-bearing mammalian cell promoters [Brown, M. et al., Cell, 49:603-612 (1987)], those using the tetracycline repressor (tetR) [Gossen, M., and Bujard, H., Proc. Natl. Acad. Sci. USA 89:5547-5551 (1992); Yao, F. et al., Human Gene Therapy, 9:1939-1950 (1998); Shockelt, P., et al., Proc. Natl. Acad. Sci. USA, 92:6522-6526 (1995)]. Other systems include FK506 dimer, VP16 or p65 using astradiol, RU486, diphenol murislerone, or rapamycin. Inducible systems are available from Invitrogen, Clontech and Ariad.

Regulatable promoters that include a repressor with the operon can be used. In one embodiment, the lac repressor from *Escherichia coli* can function as a transcriptional modulator to regulate transcription from lac operator-bearing mammalian cell promoters [M. Brown et al., Cell, 49:603-612 (1987)]; Gossen and Bujard (1992); [M. Gossen et al., Natl. Acad. Sci. USA, 89:5547-5551 (1992)] combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. In one embodiment, a tetracycline inducible switch is used (Yao et al., Human Gene Therapy; Gossen et al., Natl. Acad. Sci. USA, 89:5547-5551 (1992); Shockett et al., Proc. Natl. Acad. Sci. USA, 92:6522-6526 (1995)).

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art.

An expression vector comprising the nucleic acid can be transferred to a host cell by conventional techniques (e.g., electroporation, liposomal transfection, and calcium phosphate precipitation) and the transfected cells are then cultured by conventional techniques to produce the compounds described herein. In some embodiments, the expression of the compounds described herein is regulated by a constitutive, an inducible or a tissue-specific promoter.

The host cells used to express the compounds described herein or polypeptides described herein may be either bacterial cells such as *Escherichia coli*, or, preferably, eukaryotic cells. In particular, mammalian cells, such as Chinese hamster ovary cells (CHO), in conjunction with a vector such as the major intermediate early gene promoter element from human cytomegalovirus is an effective expression system for immunoglobulins (Foccking et al. (1986) "Powerful And Versatile Enhancer-Promoter Unit For Mammalian Expression Vectors," Gene 45:101-106; Cockett et al. (1990) "High Level Expression Of Tissue Inhibitor Of Metalloproteinases In Chinese Hamster Ovary Cells Using Glutamine Synthetase Gene Amplification," Biotechnology 8:662-667).

A variety of host-expression vector systems may be utilized to express the compounds described herein or polypeptides described herein. Such host-expression systems represent vehicles by which the coding sequences of the compounds described herein or polypeptides described herein may be produced and subsequently purified, but also represent cells which may, when transformed or transfected with the appropriate nucleotide coding sequences, express the compounds described herein in situ. These include, but are not limited to, microorganisms such as bacteria (e.g., *E. coli* and *B. subtilis*) transformed with recombinant bacteriophage DNA, plasmid DNA or cosmid DNA expression vectors containing coding sequences for the compounds described herein; yeast (e.g., *Saccharomyces pichia*) transformed with recombinant yeast expression vectors containing sequences encoding the compounds described herein; insect cell systems infected with recombinant virus expression vectors (e.g., baclovirus) containing the sequences encoding the compounds described herein; plant cell systems infected with recombinant virus expression vectors (e.g., cauliflower mosaic virus (CaMV) and tobacco mosaic virus (TMV) or transformed with recombinant plasmid expression vectors (e.g., Ti plasmid) containing sequences encoding the molecules compounds described herein; or mammalian cell systems (e.g., COS, CHO, BHK, 293, 293T, 3T3 cells, lymphotic cells (see U.S. Pat. No. 5,807,715), Per C.6 cells (human retinal cells developed by Crucell) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the compound being expressed. For example, when a large quantity of such a protein is to be produced, for the generation of pharmaceutical compositions of compounds described herein, vectors which direct the expression of high levels of fusion protein products that are readily purified may be desirable. Such vectors include, but are not limited, to the *E. coli* expression vector pUR278 (Rüther et al. (1983) "Easy Identification Of cDNA Clones," EMBO J. 2:1791-1794), in which the coding sequence may be ligated individually into the vector in frame with the lac Z coding region so that a fusion protein is produced; pIN vectors (Inouye et al. (1985) "Up-Promoter Mutations In The 1pp Gene Of *Escherichia Coli*," Nucleic Acids Res. 13:3101-3110; Van Heeke et al. (1989) "Expression Of Human Asparagine Synthetase In *Escherichia Coli*," J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the immunoglobulin molecule in infected hosts (e.g., see Logan et al. (1984) "Adenovirus Tripartite Leader Sequence Enhances Translation Of mRNAs Late After Infection," Proc. Natl. Acad. Sci. USA 81:3655-3659). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al. (1987) "Expression And Secretion Vectors For Yeast," Methods in Enzymol. 153:516-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. For example, in certain embodiments, the compounds described herein may be expressed as a single gene product (e.g., as a single polypeptide chain, i.e., as a polyprotein precursor), requiring proteolytic cleavage by native or recombinant cellular mechanisms to form separate polypeptides of the compounds described herein. The disclosure thus encompasses engineering a nucleic acid sequence to encode a polyprotein precursor molecule comprising the polypeptides of the compounds described herein, which includes coding sequences capable of directing post translational cleavage of said polyprotein precursor. Post-translational cleavage of the polyprotein precursor results in the polypeptides of the compounds described herein. The post translational cleavage of the precursor molecule comprising the polypeptides of the compounds described herein may occur in vivo (i.e., within the host cell by native or recombinant cell systems/ mechanisms, e.g. furin cleavage at an appropriate site) or may occur in vitro (e.g. incubation of said polypeptide chain in a composition comprising proteases or peptidases of known activity and/or in a composition comprising conditions or reagents known to foster the desired proteolytic action). Purification and modification of recombinant proteins is well known in the art such that the design of the polyprotein precursor could include a number of embodiments readily appreciated by a skilled worker. Any known proteases or peptidases known in the art can be used for the described modification of the precursor molecule, e.g., thrombin or factor Xa (Nagai et al. (1985) "Oxygen Binding Properties Of Human Mutant Hemoglobins Synthesized In *Escherichia Coli*," Proc. Nat. Acad. Sci. USA 82:7252-7255, and reviewed in Jenny et al. (2003) "A Critical Review Of The Methods For Cleavage Of Fusion Proteins With Thrombin And Factor Xa," Protein Expr. Purif. 31:1-11, each of which is incorporated by reference herein in its entirety)), enterokinase (Collins-Racie et al. (1995) "Production Of Recombinant Bovine Enterokinase Catalytic Subunit In *Escherichia Coli* Using The Novel Secretory Fusion Partner DsbA," Biotechnology 13:982-987 hereby incorporated by reference herein in its entirety)), furin, and AcTEV (Parks et al. (1994) "Release Of Proteins And Peptides From Fusion Proteins Using A Recombinant Plant Virus Proteinase," Anal. Biochem. 216:413-417 hereby incorporated by reference herein in its entirety)) and the Foot and Mouth Disease Virus Protease C3.

Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 293T, 3T3, WI38, BT483, Hs578T, HTB2, BT20 and T47D, CRL7030 and Hs578Bst.

For long-term, high-yield production of recombinant proteins, stable expression is preferred. For example, cell lines which stably express compounds described herein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the compounds described herein. Such engineered cell lines may be particularly useful in screening and evaluation of compounds that interact directly or indirectly with the compounds described herein.

A number of selection systems may be used, including but not limited to the herpes simplex virus thymidine kinase (Wigler et al. (1977) "Transfer Of Purified Herpes Virus Thymidine Kinase Gene To Cultured Mouse Cells," Cell 11: 223-232), hypoxanthine-guanine phosphoribosyltransferase (Szybalska et al. (1992) "Use Of The HPRT Gene And The HAT Selection Technique In DNA-Mediated Transformation Of Mammalian Cells First Steps Toward Developing Hybridoma Techniques And Gene Therapy," Bioessays 14: 495-500), and adenine phosphoribosyltransferase (Lowy et al. (1980) "Isolation Of Transforming DNA: Cloning The Hamster aprt Gene," Cell 22: 817-823) genes can be employed in tk-, hgprt- or aprt-cells, respectively. Also, antimetabolite resistance can be used as the basis of selection for the following genes: dhfr, which confers resistance to methotrexate (Wigler et al. (1980) "Transformation Of Mammalian Cells With An Amplifiable Dominant-Acting Gene," Proc. Natl. Acad. Sci. USA 77:3567-3570; O'Hare et al. (1981) "Transformation Of Mouse Fibroblasts To Methotrexate Resistance By A Recombinant Plasmid Expressing A Prokaryotic Dihydrofolate Reductase," Proc. Natl. Acad. Sci. USA 78: 1527-1531); gpt, which confers resistance to mycophenolic acid (Mulligan et al. (1981) "Selection For Animal Cells That Express The *Escherichia coli* Gene Coding For Xanthine-Guanine Phosphoribosyltransferase," Proc. Natl. Acad. Sci. USA 78: 2072-2076); neo, which confers resistance to the aminoglycoside G-418 (Tolstoshev (1993) "Gene Therapy, Concepts, Current Trials And Future Directions," Ann. Rev. Pharmacol. Toxicol. 32:573-596; Mulligan (1993) "The Basic Science Of Gene Therapy," Science 260:926-932; and Morgan et al. (1993) "Human Gene Therapy," Ann. Rev. Biochem. 62:191-217) and hygro, which confers resistance to hygromycin (Santerre et al. (1984) "Expression Of Prokaryotic Genes For Hygromycin B And G418 Resistance As Dominant-Selection Markers In Mouse L Cells," Gene 30:147-156). Methods commonly known in the art of recombinant DNA technology which can be used are described in Ausubel et al. (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al. (1981) "A New Dominant Hybrid Selective Marker For Higher Eukaryotic Cells," J. Mol. Biol. 150:1-14.

The expression levels of compounds described herein or polypeptides described herein can be increased by vector amplification (for a review, see Bebbington and Hentschel, The use of vectors based on gene amplification for the expression of cloned genes in mammalian cells in DNA cloning, Vol. 3 (Academic Press, New York, 1987). When a marker in the vector system expressing a compound described herein is amplifiable, increase in the level of inhibitor present in culture of host cell will increase the number of copies of the marker gene. Since the amplified region is associated with the nucleotide sequence of a compound described herein or a polypeptide described herein, production of the polypeptide will also increase (Crouse et al. (1983) "Expression And Amplification Of Engineered Mouse Dihydrofolate Reductase Minigenes," Mol. Cell. Biol. 3:257-266).

The host cell may be co-transfected with two expression vectors, the first vector encoding the first polypeptide of a compound described herein and the second vector encoding the second polypeptide of a compound described herein. The two vectors may contain identical selectable markers which enable equal expression of both polypeptides. Alternatively, a single vector may be used which encodes both polypeptides. The coding sequences for the polypeptides of compounds described herein may comprise cDNA or genomic DNA.

Once a compound described herein or polypeptide described herein has been recombinantly expressed, it may be purified by any method known in the art for purification of polypeptides, polyproteins or antibodies (e.g., analogous to antibody purification schemes based on antigen selectivity) for example, by chromatography (e.g., ion exchange, affinity, particularly by affinity for the specific antigen (optionally after Protein A selection where the compound comprises an Fc domain (or portion thereof)), and sizing column chromatography), centrifugation, differential solubility, or by any other standard technique for the purification of polypeptides or antibodies.

Other aspects of the disclosure relate to a cell comprising a nucleic acid described herein or a vector described herein. The cell may be a prokaryotic or eukaryotic cell. In some embodiments, the cell in a mammalian cell. Exemplary cell types are described herein.

Yet other aspects of the disclosure relate to a method of producing a compound described herein or a polypeptide described herein (e.g., a first polypeptide or a second polypeptide), the method comprising obtaining a cell described herein and expressing nucleic acid described herein in said cell. In some embodiments, the method further comprises isolating and purifying a compound described herein or a polypeptide described herein.

Methods of Treatment and Compositions for Use in Medicine

Other aspects of the disclosure relate to methods of treatment and compositions for use in medicine. Non-limiting examples of compounds for use in such methods and composition are those that comprise:
  (i) said first polypeptide comprises the amino acid sequence of SEQ ID NO:5 and said second polypeptide comprises the amino acid sequence of SEQ ID NO:6; or
  (ii) said first polypeptide comprises the amino acid sequence of SEQ ID NO:7 and said second polypeptide comprises the amino acid sequence of SEQ ID NO:8; or
  (iii) said first polypeptide comprises the amino acid sequence of SEQ ID NO:9 and said second polypeptide comprises the amino acid sequence of SEQ ID NO:10; or
  (iv) said first polypeptide comprises the amino acid sequence of SEQ ID NO:11 and said second polypeptide comprises the amino acid sequence of SEQ ID NO:12; or
  (v) said first polypeptide comprises the amino acid sequence of SEQ ID NO:13 and said second polypeptide comprises the amino acid sequence of SEQ ID NO:14; or
  (vi) said first polypeptide comprises the amino acid sequence of SEQ ID NO:15 and said second polypeptide comprises the amino acid sequence of SEQ ID NO:16; or
  (vii) said first polypeptide comprises the amino acid sequence of SEQ ID NO:17 and said second polypeptide comprises the amino acid sequence of SEQ ID NO:18; or
  (viii) said first polypeptide comprises the amino acid sequence of SEQ ID NO:19 and said second polypeptide comprises the amino acid sequence of SEQ ID NO:20; or
  (ix) said first polypeptide comprises the amino acid sequence of SEQ ID NO:21 and said second polypeptide comprises the amino acid sequence of SEQ ID NO:22; or
  (x) said first polypeptide comprises the amino acid sequence of SEQ ID NO:23 and said second polypeptide comprises the amino acid sequence of SEQ ID NO:24; or
  (xi) said first polypeptide comprises the amino acid sequence of SEQ ID NO:25 and said second polypeptide comprises the amino acid sequence of SEQ ID NO:26; or
  (xii) said first polypeptide comprises the amino acid sequence of SEQ ID NO:27 and said second polypeptide comprises the amino acid sequence of SEQ ID NO:28; or
  (xiii) said first polypeptide comprises the amino acid sequence of SEQ ID NO:29 and said second polypeptide comprises the amino acid sequence of SEQ ID NO:30; or
  (xiv) said first polypeptide comprises the amino acid sequence of SEQ ID NO:31 and said second polypeptide comprises the amino acid sequence of SEQ ID NO:32; or
  (xv) said first polypeptide comprises the amino acid sequence of SEQ ID NO:33 and said second polypeptide comprises the amino acid sequence of SEQ ID NO:34; or
  (xvi) said first polypeptide comprises the amino acid sequence of SEQ ID NO:35 and said second polypeptide comprises the amino acid sequence of SEQ ID NO:36; or
  (xvii) said first polypeptide comprises the amino acid sequence of SEQ ID NO:37 and said second polypeptide comprises the amino acid sequence of SEQ ID NO:38; or
  (xviii) said first polypeptide comprises the amino acid sequence of SEQ ID NO:39 and said second polypeptide comprises the amino acid sequence of SEQ ID NO:40; or
  (xix) said first polypeptide comprises the amino acid sequence of SEQ ID NO:41 and said second polypeptide comprises the amino acid sequence of SEQ ID NO:42; or
  (xx) said first polypeptide comprises the amino acid sequence of SEQ ID NO:43 and said second polypeptide comprises the amino acid sequence of SEQ ID NO:44; or
  (xxi) said first polypeptide comprises the amino acid sequence of SEQ ID NO:45 and said second polypeptide comprises the amino acid sequence of SEQ ID NO:46; or
  (xxii) said first polypeptide comprises the amino acid sequence of SEQ ID NO:47 and said second polypeptide comprises the amino acid sequence of SEQ ID NO:48; or
  (xxiii) said first polypeptide comprises the amino acid sequence of SEQ ID NO:49 and said second polypeptide comprises the amino acid sequence of SEQ ID NO:50; or
  (xxiv) said first polypeptide comprises the amino acid sequence of SEQ ID NO:51 and said second polypeptide comprises the amino acid sequence of SEQ ID NO:52; or
  (xxv) said first polypeptide comprises the amino acid sequence of SEQ ID NO:53 and said second polypeptide comprises the amino acid sequence of SEQ ID NO:54; or
  (xxvi) said first polypeptide comprises the amino acid sequence of SEQ ID NO:55 and said second polypeptide comprises the amino acid sequence of SEQ ID NO:56; or
  (xxvii) said first polypeptide comprises the amino acid sequence of SEQ ID NO:57 and said second polypeptide comprises the amino acid sequence of SEQ ID NO:58; or
  (xxviii) said first polypeptide comprises the amino acid sequence of SEQ ID NO:59 and said second polypeptide comprises the amino acid sequence of SEQ ID NO:60; or
  (xxix) said first polypeptide comprises the amino acid sequence of SEQ ID NO:61 and said second polypeptide comprises the amino acid sequence of SEQ ID NO:62; or
  (xxx) said first polypeptide comprises the amino acid sequence of SEQ ID NO:63 and said second polypeptide comprises the amino acid sequence of SEQ ID NO:64; or
  (xxxi) said first polypeptide comprises the amino acid sequence of SEQ ID NO:65 and said second polypeptide comprises the amino acid sequence of SEQ ID NO:66; or (xxxii) said first polypeptide comprises the amino acid sequence of SEQ ID NO:67 and said second polypeptide comprises the amino acid sequence of SEQ ID NO:68.

In some embodiments, the method of treatment or the use is a method of treating an autoimmune or an inflammatory disease or use in such a method. In some embodiments, the method comprises administering a compound described herein or a pharmaceutical composition comprising said compound to a subject, e.g., a subject having or at risk for having an autoimmune or an inflammatory disease.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human subject having, at risk for, or suspected of having a disease. A subject having a disease can be identified by routine medical examination, e.g., a physical examination, a laboratory test, an organ functional test, a CT scan, or an ultrasound. A subject suspected of having any of such a disease might show one or more symptoms of the disease. Signs and symptoms for diseases, e.g., autoimmune and inflammatory diseases, are well known to those of ordinary skill in the art. A subject at risk for the disease can be a subject having one or more of the risk factors for that disease.

Non-limiting examples of autoimmune diseases include lupus nephritis (LN) (systemic lupus erythematosus (SLE) with kidney involvement), systemic lupus erythematosus (SLE), primary Sjogren's syndrome (pSS), Sjogren's disease, graft versus host disease (GVHD) (e.g., chronic graft versus host disease (cGVHD)), systemic sclerosis (SSc), Anti-Neutrophil Cytoplasmic Autoantibody (ANCA)-associated vasculitis (AAV), rheumatoid arthritis, psoriasis, type 1 diabetes, systemic lupus erythematosus, transplant rejection, autoimmune thyroid disease (Hashimoto's disease), sarcoidosis, scleroderma, granulomatous vasculitis, Crohn's disease, ulcerative colitis, Sjogren's disease, ankylosing spondylitis, psoriatic arthritis, polymyositis dermatomyositis, polyarteritis nodosa, immunologically mediated blistering skin diseases, Behcet's syndrome, multiple sclerosis, Goodpasture's disease or immune mediated glomerulonephritis.

Non-limiting examples of inflammatory diseases include including rheumatoid arthritis, systemic lupus erythematosus, alopecia areata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (ALPS), autoimmune thrombocytopenic purpura (ATP), Behcet's disease, bullous pemphigoid, cardiomyopathy, celiac sprue-dermatitis, chronic fatigue syndrome immune deficiency syndrome (CFIDS), chronic inflammatory demyelinating polyneuropathy, cicatricial pemphigoid, cold agglutinin disease, Crest syndrome, Crohn's disease, Dego's disease, dermatomyasitis, dermatomyositis—juvenile, discoid lupus, essential mixed cryoglobulinemia, fibromyalgia—fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type 1), juvenile arthritis, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis. In some embodiments, the autoimmune or inflammatory disease is Crohn's disease, ankylosing spondylitis, or psoriatic arthritis.

To practice a method disclosed herein, an effective amount of a compound or pharmaceutical composition described herein can be administered to a subject (e.g., a human) in need of the treatment. Various delivery systems are known and can be used to administer the compounds of the subject technology. Methods of administration include, but are not limited to, intradermal, intramuscular, intraperitoneal, intravenous, subcutaneous, intranasal, epidural, and oral routes. The compounds of the subject technology can be administered, for example by infusion, bolus or injection, and can be administered together with other biologically active agents such as anti-inflammatory agents. Administration can be systemic or local. In preferred embodiments, the administration is by subcutaneous injection. Formulations for such injections may be prepared in, for example, prefilled syringes that may be administered once every other week.

"An effective amount" as used herein refers to the amount of each compound required to confer therapeutic effect on the subject, either alone or in combination with one or more other compounds. Effective amounts vary, as recognized by those skilled in the art, depending on the particular condition being treated, the severity of the condition, the individual subject parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a subject may insist upon a lower dose or tolerable dose for medical reasons, psychological reasons or for virtually any other reasons.

Empirical considerations, such as the half-life, generally will contribute to the determination of the dosage. For example, compounds that are compatible with the human immune system, such as compounds comprising regions from humanized antibodies or fully human antibodies, may be used to prolong half-life of the compound and to prevent the compound being attacked by the host's immune system. Frequency of administration may be determined and adjusted over the course of therapy, and is generally, but not necessarily, based on treatment and/or suppression and/or amelioration and/or delay of a disease. Alternatively, sustained continuous release formulations of a compound may be appropriate. Various formulations and devices for achieving sustained release are known in the art.

In some embodiments, dosage is daily, every other day, every three days, every four days, every five days, or every six days. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the compound used) can vary over time.

In some embodiments, for an adult subject of normal weight, doses ranging from about 0.01 to 1000 mg/kg may be administered. In some embodiments, the dose is between 1 to 200 mg. The particular dosage regimen, i.e., dose, timing and repetition, will depend on the particular subject and that subject's medical history, as well as the properties of the compound (such as the half-life of the compound, and other considerations well known in the art).

For the purpose of the present disclosure, the appropriate dosage of a compound as described herein will depend on the specific compound (or compositions thereof) employed, the formulation and route of administration, the type and severity of the disease, whether the compound is administered for preventive or therapeutic purposes, previous therapy, the subject's clinical history and response to the antagonist, and the discretion of the attending physician. Typically the clinician will administer a compound until a dosage is reached that achieves the desired result. Administration of one or more compounds can be continuous or intermittent, depending, for example, upon the recipient's physiological condition, whether the purpose of the administration is therapeutic or prophylactic, and other factors known to skilled practitioners. The administration of a compound may be essentially continuous over a preselected period of time or may be in a series of spaced dose, e.g., either before, during, or after developing a disease.

As used herein, the term "treating" refers to the application or administration of a compound or composition including the compound to a subject, who has a disease, a symptom of the disease, or a predisposition toward the disease, with the purpose to cure, heal, alleviate, relieve, alter, remedy, ameliorate, improve, or affect the disease, the symptom of the disease, or the predisposition toward the disease.

Alleviating a disease includes delaying the development or progression of the disease, or reducing disease severity. Alleviating the disease does not necessarily require curative results. As used therein, "delaying" the development of a disease means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a disease includes initial onset and/or recurrence.

In some embodiments, the compound described herein is administered to a subject in need of the treatment at an amount sufficient to inhibit the activity of one or both of BAFF or IL23A by at least 20% (e.g., 30%, 40%, 50%, 60%, 70%, 80%, 90% or greater) in vivo or in vitro. Methods for determining the inhibitory capability of a compound are known in the art. Exemplary BAFF and IL23A inhibition assays are provided in the Examples.

Conventional methods, known to those of ordinary skill in the art of medicine, can be used to administer the compound or pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Pharmaceutical Compositions

Yet other aspects of the disclosure relate to pharmaceutical compositions comprising a compound described herein. A composition comprising a compound of the subject technology (e.g., compounds specific for both BAFF and IL23A) can be administered to a subject having or at risk of having an autoimmune or an inflammatory disease. The subject technology further provides for the use of a compound of the subject technology in the manufacture of a medicament for treatment of an autoimmune or an inflammatory disease. The compounds can be administered either alone or in combination with other compositions in the prevention or treatment of an autoimmune or an inflammatory disease. Non-limiting examples of compounds of the subject technology for use in such pharmaceutical compositions are those that comprise:

(i) said first polypeptide comprises the amino acid sequence of SEQ ID NO:5 and said second polypeptide comprises the amino acid sequence of SEQ ID NO:6; or (ii) said first polypeptide comprises the amino acid sequence of SEQ ID NO:7 and said second polypeptide comprises the amino acid sequence of SEQ ID NO:8; or (iii) said first polypeptide comprises the amino acid sequence of SEQ ID NO:9 and said second polypeptide comprises the amino acid sequence of SEQ ID NO:10; or (iv) said first polypeptide comprises the amino acid sequence of SEQ ID NO:11 and said second polypeptide comprises the amino acid sequence of SEQ ID NO:12; or (v) said first polypeptide comprises the amino acid sequence of SEQ ID NO:13 and said second polypeptide comprises the amino acid sequence of SEQ ID NO:14; or (vi) said first polypeptide comprises the amino acid sequence of SEQ ID NO:15 and said second polypeptide comprises the amino acid sequence of SEQ ID NO:16; or (vii) said first polypeptide comprises the amino acid sequence of SEQ ID NO:17 and said second polypeptide comprises the amino acid sequence of SEQ ID NO:18; or (viii) said first polypeptide comprises the amino acid sequence of SEQ ID NO:19 and said second polypeptide comprises the amino acid sequence of SEQ ID NO:20; or (ix) said first polypeptide comprises the amino acid sequence of SEQ ID NO:21 and said second polypeptide comprises the amino acid sequence of SEQ ID NO:22; or (x) said first polypeptide comprises the amino acid sequence of SEQ ID NO:23 and said second polypeptide comprises the amino acid sequence of SEQ ID NO:24; or (xi) said first polypeptide comprises the amino acid sequence of SEQ ID NO:25 and said second polypeptide comprises the amino acid sequence of SEQ ID NO:26; or (xii) said first polypeptide comprises the amino acid sequence of SEQ ID NO:27 and said second polypeptide comprises the amino acid sequence of SEQ ID NO:28; or (xiii) said first polypeptide comprises the amino acid sequence of SEQ ID NO:29 and said second polypeptide comprises the amino acid sequence of SEQ ID NO:30; or (xiv) said first polypeptide comprises the amino acid sequence of SEQ ID NO:31 and said second polypeptide comprises the amino acid sequence of SEQ ID NO:32; or (xv) said first polypeptide comprises the amino acid sequence of SEQ ID NO:33 and said second polypeptide comprises the amino acid sequence of SEQ ID NO:34; or (xvi) said first polypeptide comprises the amino acid sequence of SEQ ID NO:35 and said second polypeptide comprises the amino acid sequence of SEQ ID NO:36; or (xvii) said first polypeptide comprises the amino acid sequence of SEQ ID NO:37 and said second polypeptide comprises the amino acid sequence of SEQ ID NO:38; or (xviii) said first polypeptide comprises the amino acid sequence of SEQ TD NO:39 and said second polypeptide comprises the amino acid sequence of SEQ ID NO:40; or (xix) said first polypeptide comprises the amino acid sequence of SEQ ID NO:41 and said second polypeptide comprises the amino acid sequence of SEQ ID NO:42; or (xx) said first polypeptide comprises the amino acid sequence of SEQ ID NO:43 and said second polypeptide comprises the amino acid sequence of SEQ ID NO:44; or (xxi) said first polypeptide comprises the amino acid sequence of SEQ ID NO:45 and said second polypeptide comprises the amino acid sequence of SEQ ID NO:46; or (xxii) said first polypeptide comprises the amino acid sequence of SEQ ID NO:47 and said second polypeptide comprises the amino acid sequence of SEQ ID NO:48; or (xxiii) said first polypeptide comprises the amino acid sequence of SEQ ID NO:49 and said second polypeptide comprises the amino acid sequence of SEQ ID NO:50; or (xxiv) said first polypeptide comprises the amino acid sequence of SEQ ID NO:51 and said second polypeptide comprises the amino acid sequence of SEQ ID NO:52; or (xxv) said first polypeptide comprises the amino acid sequence of SEQ ID NO:53 and said second polypeptide comprises the amino acid sequence of SEQ ID NO:54; or (xxvi) said first polypeptide comprises the amino acid sequence of SEQ ID NO:55 and said second polypeptide comprises the amino acid sequence of SEQ ID NO:56; or (xxvii) said first polypeptide comprises the amino acid sequence of SEQ ID NO:57 and said second polypeptide comprises the amino acid sequence of SEQ ID NO:58; or (xxviii) said first polypeptide comprises the amino acid sequence of SEQ ID NO:59 and said second polypeptide comprises the amino acid sequence of SEQ ID NO:60; or (xxix) said first polypeptide comprises the amino acid sequence of SEQ ID NO:61 and said second polypeptide comprises the amino acid sequence of SEQ ID NO:62; or (xxx) said first polypeptide comprises the amino acid sequence of SEQ ID NO:63 and said second polypeptide comprises the amino acid sequence of SEQ ID NO:64; or (xxxi) said first polypeptide comprises the amino acid sequence of SEQ ID NO:65 and said second polypeptide comprises the amino acid sequence of SEQ ID NO:66; or (xxxii) said first polypeptide comprises the amino acid sequence of SEQ ID NO:67 and said second polypeptide comprises the amino acid sequence of SEQ ID NO:68.

As used herein, the term "pharmaceutical composition" refers to the formulation of a compound described herein in combination with a pharmaceutically acceptable carrier. The pharmaceutical composition can further comprise additional agents (e.g. for specific delivery, increasing half-life, or other therapeutic compounds).

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the compound from one site (e.g., the delivery site) of the body, to another site (e.g., organ, tissue or portion of the body). A pharmaceutically acceptable carrier is "acceptable" in the sense of being compatible with the other ingredients of the formulation and not injurious to the tissue of the subject (e.g., physiologically compatible, sterile, physiologic pH, etc.). Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

In some embodiments, a compound of the subject technology in a composition is administered by injection, by means of a catheter, by means of a suppository, or by means of an implant, the implant being of a porous, non-porous, or gelatinous material, including a membrane, such as a sialastic membrane, or a fiber. Typically, when administering the composition, materials to which the compound of the subject technology does not absorb are used.

In other embodiments, the compounds of the subject technology are delivered in a controlled release system. In one embodiment, a pump may be used (see, e.g., Langer, 1990, Science 249:1527-1533; Sefton, 1989, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used. (See, e.g., Medical Applications of Controlled Release (Langer and Wise eds., CRC Press, Boca Raton, Fla., 1974); Controlled Drug Bioavailability, Drug Product Design and Performance (Smolen and Ball eds., Wiley, New York, 1984); Ranger and Peppas, 1983, Macromol. Sci. Rev. Macromol. Chem. 23:61. See also Levy et al., 1985, Science 228:190; During et al., 1989, Ann. Neurol. 25:351; Howard et al., 1989, J. Neurosurg. 71:105.) Other controlled release systems are discussed, for example, in Langer, supra.

Compounds of the subject technology can be administered as pharmaceutical compositions comprising a therapeutically effective amount of a binding agent and one or more pharmaceutically compatible ingredients.

In typical embodiments, the pharmaceutical composition is formulated in accordance with routine procedures as a pharmaceutical composition adapted for intravenous or subcutaneous administration to a subject, e.g., a human being. Typically, compositions for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

A pharmaceutical composition for systemic administration may be a liquid, e.g., sterile saline, lactated Ringer's or Hank's solution. In addition, the pharmaceutical composition can be in solid forms and re-dissolved or suspended immediately prior to use. Lyophilized forms are also contemplated.

The pharmaceutical composition can be contained within a lipid particle or vesicle, such as a liposome or microcrystal, which is also suitable for parenteral administration. The particles can be of any suitable structure, such as unilamellar or plurilamellar, so long as compositions are contained therein. Compounds can be entrapped in 'stabilized plasmid-lipid particles' (SPLP) containing the fusogenic lipid dioleoylphosphatidylethanolamine (DOPE), low levels (5-10 mol %) of cationic lipid, and stabilized by a polyethyleneglycol (PEG) coating (Zhang Y. P. et al., Gene Ther. 1999, 6:1438-47). Positively charged lipids such as N-[1-(2,3-dioleoyloxi)propyl]-N,N,N-trimethyl-amoniummethyl-sulfate, or "DOTAP," are particularly preferred for such particles and vesicles. The preparation of such lipid particles is well known. See, e.g., U.S. Pat. Nos. 4,880,635; 4,906,477; 4,911,928; 4,917,951; 4,920,016; and 4,921,757.

The pharmaceutical compositions of this disclosure may be administered or packaged as a unit dose, for example. The term "unit dose" when used in reference to a pharmaceutical composition of the present disclosure refers to physically discrete units suitable as unitary dosage for the subject, each unit containing a predetermined quantity of active material calculated to produce the desired therapeutic effect in association with the required diluent; i.e., carrier, or vehicle.

In some embodiments, a compound described herein may be conjugated to a therapeutic moiety, e.g., an anti-inflammatory agent. Techniques for conjugating such therapeutic moieties to polypeptides, including e.g., Fc domains, are well known; see, e.g., Amon et al., "Monoclonal Antibodies For Immunotargeting Of Drugs In Cancer Therapy", in Monoclonal Antibodies And Cancer Therapy, Reisfeld et al. (eds.), 1985, pp. 243-56, Alan R. Liss, Inc.); Hellstrom et al., "Antibodies For Drug Delivery", in Controlled Drug Delivery (2nd Ed.), Robinson et al. (eds.), 1987, pp. 623-53, Marcel Dekker, Inc.); Thorpe, "Antibody Carriers Of Cytotoxic Agents In Cancer Therapy: A Review", in Monoclonal Antibodies '84: Biological And Clinical Applications, Pinchera et al. (eds.), 1985, pp. 475-506); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), 1985, pp. 303-16, Academic Press; and Thorpe et al. (1982) "The Preparation And Cytotoxic Properties Of Antibody-Toxin Conjugates," Immunol. Rev., 62:119-158.

Further, the pharmaceutical composition can be provided as a pharmaceutical kit comprising (a) a container containing a compound of the subject technology in lyophilized form and (b) a second container containing a pharmaceutically acceptable diluent (e.g., sterile water) for injection. The pharmaceutically acceptable diluent can be used for reconstitution or dilution of the lyophilized compound of the subject technology. Optionally associated with such container(s) can be a notice in the form prescribed by a governmental agency regulating the manufacture, use or sale of pharmaceuticals or biological products, which notice reflects approval by the agency of manufacture, use or sale for human administration.

In another aspect, an article of manufacture containing materials useful for the treatment of the diseases described above is included. In some embodiments, the article of manufacture comprises a container and a label. Suitable containers include, for example, bottles, vials, syringes, and test tubes. The containers may be formed from a variety of materials such as glass or plastic. In some embodiments, the container holds a composition that is effective for treating a disease described herein and may have a sterile access port. For example, the container may be an intravenous solution bag or a vial having a stopper pierceable by a hypodermic injection needle. The active agent in the composition is a compound of the subject technology. In some embodiments, the label on or associated with the container indicates that the composition is used for treating the disease of choice. The article of manufacture may further comprise a second container comprising a pharmaceutically-acceptable buffer, such as phosphate-buffered saline, Ringer's solution, or dextrose solution. It may further include other materials desirable from a commercial and user standpoint, including other buffers, diluents, filters, needles, syringes, and package inserts with instructions for use.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1. Construction of Exemplary Compounds Targeting IL23A and BAFF

The compounds of the subject technology were produced by recombinant methods known in the art (see, e.g., PCT Publications WO 2006/113665, WO 2008/157379, and WO 2010/080538, the contents of all of which are incorporated herein by reference). Table 2A provides exemplary compounds that bind to both IL23A and BAFF utilized in the Examples below. Briefly, plasmids encoding the first and second polypeptide for each compound were transfected together into CHO-S cells using FreeStyle MAX Reagent (CHO). The cells were cultured for 13-14 days and the compounds produced by the cells were purified using Protein-A chromatography. The compounds were further purified using a size exclusion chromatography.

| Compound ID | Large Chain vL | Large Chain vH | Small Chain vL | Small Chain vH | $3^{rd}$ and/or $4^{th}$ Linker types | Constant Domain Isotype | SEQ ID NO: ($1^{st}/2^{nd}$) poly peptides) |
|---|---|---|---|---|---|---|---|
| Compound E | BAFF(1) VL (SEQ ID NO: 2) | IL23A(1) VH (SEQ ID NO: 3) | IL23A(1) VL (SEQ ID NO: 4) | BAFF(1) VH (SEQ ID NO: 1) | LGGGSG (SEQ ID NO: 70) | IgG1 KO-YTE (SEQ ID NO: 128) | 5/6 |
| Compound V | IL23A(1) VL (SEQ ID NO: 4) | BAFF(1) VH (SEQ ID NO: 1) | BAFF(1) VL (SEQ ID NO: 2) | IL23A(1) VH (SEQ ID NO: 3) | LGGGSG (SEQ ID NO: 70) | IgG1 KO-YTE (SEQ ID NO: 128) | 7/8 |
| Compound U | BAFF(1) VL (SEQ ID NO: 2) | IL23A(1) VH (SEQ ID NO: 3) | IL23A(1) VL (SEQ ID NO: 4) | BAFF(1) VH (SEQ ID NO: 1) | E(C-1) (SEQ ID NO: 82), K-coil (C-1) (SEQ ID NO: 83) | Fc-IgG1 KO-YTE (SEQ ID NO: 129) | 9/10 |
| Compound T | IL23A(1) VL (SEQ ID NO: 4) | BAFF(1) VH (SEQ ID NO: 1) | BAFF(1) VL (SEQ ID NO: 2) | IL23A(1) VH (SEQ ID NO: 3) | E(C-1) (SEQ ID NO: 82), K-coil (C-1) (SEQ ID NO: 83) | Fc-IgG1 KO-YTE (SEQ ID NO: 129) | 11/12 |
| Compound X | BAFF(1) VL (SEQ ID NO: 2) | IL23A(1) VH (SEQ ID NO: 3) | IL23A(1) VL (SEQ ID NO: 4) | BAFF(1) VH (SEQ ID NO: 1) | LGGGS G (SEQ ID NO: 70) | Fc-IgG4-Pro-YTE (SEQ ID NO: 127) | 13/14 |
| Compound F | IL23A(1) VL (SEQ ID NO: 4) | BAFF(1) VH (SEQ ID NO: 1) | BAFF(1) VL (SEQ ID NO: 2) | IL23A(1) VH (SEQ ID NO: 3) | LGGGS G (SEQ ID NO: 70) | Fc-IgG4-Pro-YTE (SEQ ID NO: 127) | 15/16 |
| Compound W | BAFF(1) VL (SEQ ID NO: 2) | IL23A(1) VH (SEQ ID NO: 3) | IL23A(1) VL (SEQ ID NO: 4) | BAFF(1) VH (SEQ ID NO: 1) | E(C-1) (SEQ ID NO: 82), K-coil (C-1) (SEQ ID NO: 83) | Fc-IgG4-Pro-YTE (SEQ ID NO: 127) | 17/18 |
| Compound S | IL23A(1) VL (SEQ ID NO: 4) | BAFF(1) VH (SEQ ID NO: 1) | BAFF(1) VL (SEQ ID NO: 2) | IL23A(1) VH (SEQ ID NO: 3) | E(C-1) (SEQ ID NO: 82), K-coil (C-1) (SEQ ID NO: 83) | Fc-IgG4-Pro-YTE (SEQ ID NO: 127) | 19/20 |

-continued

| Compound ID | Large Chain vL | Large Chain vH | Small Chain vL | Small Chain vH | 3rd and/or 4th Linker types | Constant Domain Isotype | SEQ ID NO: (1st/2nd) poly peptides) |
|---|---|---|---|---|---|---|---|
| Compound G | IL23A(1) VL (SEQ ID NO: 4) | BAFF(4) VH (SEQ ID NO: 84) | BAFF(4) VL (SEQ ID NO: 85) | IL23A(1) VH (SEQ ID NO: 3) | LGGGSG (SEQ ID NO: 70) | IgG1 KO-YTE (SEQ ID NO: 128) | 21/22 |
| Compound AA | IL23A(1) VL (SEQ ID NO: 4) | BAFF (4) VH (SEQ ID NO: 84) | BAFF(4) VL (SEQ ID NO: 85) | iL23A(1) VH (SEQ ID NO: 3) | E(C-1) (SEQ ID NO: 82), K-coil (C-1) (SEQ ID NO: 83) | Fc-IgG1 KO-YTE (SEQ ID NO: 129) | 23/24 |
| Compound I | IL23A(1) VL (SEQ ID NO: 4) | BAFF(4) VH (SEQ ID NO: 84) | BAFF(4) VL (SEQ ID NO: 85) | IL23A(1) VH (SEQ ID NO: 3) | LGGGSG (SEQ ID NO: 70) | IgG4-Pro-YTE (SEQ ID NO: 74) | 25/26 |
| Compound AB | IL23A(1) VL (SEQ ID NO: 4) | BAFF (4) VH (SEQ ID NO: 84) | BAFF (4) VL (SEQ ID NO: 85) | IL23A(1) VH (SEQ ID NO: 3) | E(C-1) (SEQ ID NO: 82), K-coil (C-1) (SEQ ID NO: 83) | Fc-IgG1 KO-YTE (SEQ ID NO: 129) | 27/28 |
| Compound K | IL23A(1) VL (SEQ ID NO: 4) | BAFF (5) VH (SEQ ID NO: 86) | BAFF (5) VL (SEQ ID NO: 87) | IL23A(1) VH (SEQ ID NO: 3) | LGGGSG (SEQ ID NO: 70) | IgG1KO-YTE (SEQ ID NO: 128) | 29/30 |
| Compound AC | IL23A(1) VL (SEQ ID NO: 4) | BAFF (5) VH (SEQ ID NO: 86) | BAFF (5) VL (SEQ ID NO: 87) | IL23A(1) VH (SEQ ID NO: 3) | E(C-1) (SEQ ID NO: 82), K-coil (C-1) (SEQ ID NO: 83) | Fc-IgG1 KO-YTE (SEQ ID NO: 129) | 31/32 |
| Compound M | IL23A(1) VL (SEQ ID NO: 4) | BAFF(5) VH (SEQ ID NO: 86) | BAFF (5) VL (SEQ ID NO: 87) | IL23A(1) VH (SEQ ID NO: 3) | LGGGSG (SEQ ID NO: 70) | IgG4-Pro-YTE (SEQ ID NO: 74) | 33/34 |
| Compound AD | IL23A(1) VL (SEQ ID NO: 4) | BAFF(5) VH (SEQ ID NO: 86) | BAFF (5) VL (SEQ ID NO: 87) | IL23A(1) VH (SEQ ID NO: 3) | E(C-1) (SEQ ID NO: 82), K-coil (C-1) (SEQ ID NO: 83) | Fc-IgG4-Pro-YTE (SEQ ID NO: 127) | 35/36 |
| Compound C | IL23A(1) VL (SEQ ID NO: 4) | BAFF (6) VH (SEQ ID NO: 88) | BAFF (6) VL (SEQ ID NO: 89) | IL23A(1) VH (SEQ ID NO: 3) | LGGGSG (SEQ ID NO: 70) | IgG1 KO-YTE (SEQ ID NO: 128) | 37/38 |
| Compound AE | IL23A(1) VL (SEQ ID NO: 4) | BAFF (6) VH (SEQ ID NO: 88) | BAFF (6) VL (SEQ ID NO: 89) | iL23A(1) VH (SEQ ID NO: 3) | E(C-1) (SEQ ID NO: 82), K-coil (C-1) (SEQ ID NO: 83) | Fc-IgG1 KO-YTE (SEQ ID NO: 129) | 39/40 |
| Compound D | IL23A(1) VL (SF.Q ID NO: 4) | BAFF (6) VH (SEQ ID NO: 88) | BAFF (6) VL (SF.Q ID NO: 89) | IL23A(1) VH (SEQ ID NO: 3) | LGGGSG (SEQ ID NO: 70) | IgG4-Pro-YTE (SEQ ID NO: 74) | 41/42 |

-continued

| Compound ID | Large Chain vL | Large Chain vH | Small Chain vL | Small Chain vH | 3rd and/or 4th Linker types | Constant Domain Isotype | SEQ ID NO: (1st/2nd) poly peptides) |
|---|---|---|---|---|---|---|---|
| Compound AF | IL23A(1) VL (SEQ ID NO: 4) | BAFF(6) VH (SEQ ID NO: 88) | BAFF (6) VL (SEQ ID NO: 89) | IL23A(1) VH (SEQ ID NO: 3) | E(C-1) (SEQ ID NO: 82), K-coil (C-1) (SEQ ID NO: 83) | Fc-IgG4-Pro-YTE (SEQ ID NO: 127) | 43/44 |
| Compound A | IL23A(1) VL (SEQ ID NO: 4) | BAFF (7) VH (SF.Q ID NO: 90) | BAFF(7) VL (SEQ ID NO: 91) | IL23A(1) VH (SEQ ID NO: 3) | LGGGS G (SEQ ID NO: 70) | IgG1 KO-YTE (SEQ ID NO: 128) | 45/46 |
| Compound AG | IL23A(1) VL (SEQ ID NO: 4) | BAFF (7) VH (SEQ ID NO: 90) | BAFF (7) VL (SEQ ID NO: 91) | IL23A(1) VH (SEQ ID NO: 3) | E(C-1) (SEQ ID NO: 82), K-coil (C-1) (SEQ ID NO: 83) | Fc-IgG1 KO-YTE (SEQ ID NO: 129) | 47/48 |
| Compound B | IL23A(1) VL (SEQ ID NO: 4) | BAFF (7) VH (SEQ ID NO: 90) | BAFF (7) VL (SEQ ID NO: 91) | IL23A(1) VH (SEQ ID NO: 3) | LGGGS G (SEQ ID NO: 70) | IgG4-Pro-YTE (SEQ ID NO: 74) | 49/50 |
| Compound AH | IL23A(1) VL (SEQ ID NO: 4) | BAFF (7) VH (SEQ ID NO: 90) | BAFF (7) VL (SEQ ID NO: 91) | IL23A(1) VH (SEQ ID NO: 3) | E(C-1) (SEQ ID NO: 82), K-coil (C-1) (SEQ ID NO: 83) | Fc-IgG4-Pro-YTE (SEQ ID NO: 127) | 51/52 |
| Compound H | BAFF (4) VL (SEQ ID NO: 85) | IL23A(1) VH (SEQ ID NO: 3) | IL23A(1) VL (SEQ ID NO: 4) | BAFF (4) VH (SEQ ID NO: 84) | LGGGS G (SEQ ID NO: 70) | IgG1 KO-YTE (SEQ ID NO: 128) | 53/54 |
| Compound J | BAFF (4) VL (SEQ ID NO: 85) | IL23A(1) VH (SEQ ID NO: 3) | IL23A(1) VL (SEQ ID NO: 4) | BAFF (4) VH (SEQ ID NO: 84) | LGGGS G (SEQ ID NO: 70) | IgG4-Pro-YTE (SEQ ID NO: 74) | 55/56 |
| Compound L | BAFF (5) VL (SEQ ID NO: 87) | IL23A(1) VH (SEQ ID NO: 3) | IL23A(1) VL (SEQ ID NO: 4) | BAFF (5) VH (SEQ ID NO: 86) | LGGGS G (SEQ ID NO: 70) | IgG1 KO-YTE (SEQ ID NO: 128) | 57/58 |
| Compound N | BAFF (5) VL (SEQ ID NO: 87) | IL23A(1) VH (SEQ ID NO: 3) | IL23A(1) VL (SEQ ID NO: 4) | BAFF (5) VH (SEQ ID NO: 86) | LGGGS G (SEQ ID NO: 70) | IgG4-Pro-YTE (SEQ ID NO: 74) | 59/60 |
| Compound O | BAFF (6) VL (SEQ ID NO: 89) | IL23A(1) VH (SEQ ID NO: 3) | IL23A(1) VL (SEQ ID NO: 4) | BAFF (6) VH (SEQ ID NO: 88) | LGGGS G (SEQ ID NO: 70) | IgG1 KO-YTE (SEQ ID NO: 128) | 61/62 |
| Compound F | BAFF (6) VL (SEQ ID NO: 89) | IL23A(1) VH (SEQ ID NO: 3) | IL23A(1) VL (SEQ ID NO: 4) | BAFF (6) VH (SEQ ID NO: 88) | LGGGS G (SEQ ID NO: 70) | IgG4-Pro-YTE (SEQ ID NO: 74) | 63/64 |
| Compound Q | BAFF 7) VL (SEQ ID NO: 91) | IL23A(1) VH (SEQ ID NO: 3) | IL23A(1) VL (SEQ ID NO: 4) | BAFF (7) VH (SEQ ID NO: 90) | LGGGS G (SEQ ID NO: 70) | IgG1 KO-YTE (SEQ ID NO: 128) | 65/66 |

-continued

| Compound ID | Large Chain vL | Large Chain vH | Small Chain vL | Small Chain vH | 3rd and/or 4th Linker types | Constant Domain Isotype | SEQ ID NO: (1st/2nd) poly peptides) |
|---|---|---|---|---|---|---|---|
| Compound R | BAFF (7) VL (SEQ ID NO: 91) | IL23A(1) VH (SEQ ID NO: 3) | IL23A(1) VL (SEQ ID NO: 4) | BAFF (7) VH (SEQ ID NO: 90) | LGGGS G (SEQ ID NO: 70) | IgG4-Pro-YTE (SEQ ID NO: 74) | 67/68 |

VL = variable domain light chain, VH = variable domain heavy chain, each chain comprises the linker GGGSGGG (SEQ ID NO: 69) between the VL and VH.

Control antibodies were also used for comparison purposes. The controls were monoclonal antibodies that targeted either BAFF or IL23.

TABLE 2B

Control antibodies/antagonist

| Control compounds | Sequence | |
|---|---|---|
| Control Antibody 1 (anti-BAFF monoclonal antibody) (BAFF (1)) | BAFF(1) VH (SEQ ID NO: 1) | BAFF(1) VL (SEQ ID NO: 2) |
| Control Fusion Protein Antagonist 2 (non-antibody BAFF selective antagonist) (BAFF (2)) | BAFF(2) (SEQ ID NO: 131) | |
| Control Antibody 3 (anti-BAFF monoclonal antibody) (BAFF (3)) | BAFF(3) VH (SEQ ID NO: 132) | BAFF(3) VL (SEQ ID NO: 133) |
| Control Antibody 4 (anti-IL-23A monoclonal antibody) (IL-23A (1)) | IL23A(1) VH (SEQ ID NO: 3) | IL23A(1) VL (SEQ ID NO: 4) |

Example 2: Thermal Stability of Compounds

Methods

Thermal unfolding and aggregation of 2 mg/ml solutions of the compounds in phosphate buffer were monitored from 20° C. to 110° C. at a scan rate of 60° C./hr via an automated capillary DSC (MicroCal, LLC, Boston). Two scans with the corresponding buffer were performed to establish instrument thermal history and to obtain the instrument baseline for each sample, with the average of these scans subtracted from the subsequent protein thermogram to obtain the apparent heat capacity. Normalized scans were then analyzed with Origin 7.0. Pre-transition baselines were subtracted from each resulting heat capacity thermogram, to give the resulting excess heat capacity (Cp,ex) as a function of temperature. Reported values of transition temperatures (Tm) represent positions of peak maxima determined by visual inspection of the experimental thermograms.

Results

The results are shown in Table 3. The data show that exemplary compounds targeting IL23A and BAFF have a range of transition temperatures for the first peak ($T_{m1}$), ranging from 51.59 to 71.25° C. The results are surprising because the exemplary compounds all had the same overall structure and contained the same VH and VL gene sequences targeting IL-23A. Compounds with higher transition temperatures are more stable and predicted to have a long shelf-life.

TABLE 3

Thermal unfolding transition temperatures for compounds

| Compound ID | $T_{m1}$ (° C.) | $T_{m2}$ (° C.) |
|---|---|---|
| Compound A | 69.35 | 83.63 |
| Compound B | 65.87 | — |
| Compound C | 67.89 | 82.36 |
| Compound D | 64.93 | — |
| Compound E | 51.59 | 68.8 |
| Compound F | 52.75 | 64.48 |
| Compound G | 70.88 | 83.21 |
| Compound H | 71.25 | 83.62 |
| Compound I | 67.83 | — |
| Compound J | 68.26 | — |
| Compound K | 68.33 | 83.23 |
| Compound L | 68.3 | 82.58 |
| Compound M | 64.98 | — |
| Compound N | 65.52 | — |
| Compound O | 67.79 | 83.85 |
| Compound P | 65.09 | — |
| Compound Q | 69.19 | 81.9 |
| Compound R | 65.97 | — |
| Compound X | 52.36 | 64.53 |

Example 3. Surface Plasma Resonance (SPR) Affinity of Exemplary Compounds

Test compounds were analyzed by SPR to determine affinity for BAFF and IL23A.

Materials and Methods:

SPR experiments were performed on a ProteOn XPR36 instrument (Bio Rad). A GLM chip was preconditioned with sequential injections of 60 sec of 0.5% SDS, 50 mM NaOH, and 100 mM HCl at a flow rate of 30 µl/min both vertical and horizontal directions.

The preconditioned GLM chip was then activated by an injection of EDC (76.7 mg/ml) and sulfo-NHS (21.7 mg/ml) mixture with ratio of 1:1 in 6 horizontal channels. Goat-anti-human IgG (GAHA) Fc gamma (Invitrogen) at a concentration of 30 μg/ml in 10 mM, pH 5.0 sodium acetate buffer was immobilized to 8,000 resonance units on the activated GLM chip in 6 horizontal channels. The chip was finally deactivated with 1 M ethanolamine HCl in 6 horizontal channels. The prepared GAHA chip was rotated to vertical direction to capture test compounds, over 5 vertical channels and the last channel was used as a column reference.

The captured chip was then rotated again to the horizontal direction for binding. Linked human IL-23 (Boehringer Ingelheim Pharmaceuticals, Inc.) with five concentrations, 10.0 nM, 5.00 nM, 2.50 nM, 1.25 nM and 0.625 nM, were injected horizontally over the test compound surfaces for 10 minutes at a flow rate of 40 μl/min in the following running buffer (Bio Rad): phosphate buffer saline (pH 7.4), 0.005% Tween 20. The dissociation was allowed for 2 hour. The GAHA surface was regenerated using short pulse injection (18 seconds) of 0.85% phosphoric acid (Bio Rad) at a flow rate of 100 μl/min both horizontal and vertical directions after 10 min association and 2 hr dissociation. The regenerated GAHA was ready for another binding cycle. Binding of compounds to cynomolgus IL23, human BAFF or cynomolgus BAFF was done in similar way but the titration concentrations for binding to human BAFF or cynomolgus BAFF are 6.25 nM, 3.12 nM, 1.56 nM, 0.78 nM, and 0.39 nM.

Results:

The results in Table 4 show that both compounds tested were able to bind BAFF and IL23 with a dissociation constant (KD) in the picomolar range.

TABLE 4

Affinity of compounds binding to BAFF and IL23

| Compound ID | KD to human BAFF (pM) | KD to cynomolgus BAFF (pM) | KD to human IL23 (pM) | KD to cynomolgus IL23 (pM) |
|---|---|---|---|---|
| Compound A | <15 | <15 | <15 | <15 |
| Compound B | <15 | <15 | <15 | <15 |
| Compound C | <15 | <15 | <15 | <15 |
| Compound D | <15 | <15 | <15 | <15 |
| Compound E | <15 | <15 | <15 | <15 |
| Compound F | <15 | <15 | <15 | <15 |

Example 4. Inhibition of Human and Cynomolgus BAFF Trimer-Induced NFkB Activation in BAFFR-CHO Luciferase Reporter Cells Materials/Methods:

Briefly, human BAFFR CHO NFkB luciferase reporter cells were harvested, washed, counted and resuspended at a concentration of $1.6 \times 10^6$ cells per ml in assay medium (AM) of (v/v) 1% Penicillin/Streptomycin in X-VIVO15, a chemically defined serum-free media (Lonza). Recombinant human or cynomolgus BAFF trimer (Boehringer Ingelheim Pharmaceuticals, Inc.) was prepared at a single concentration (52 pM) in AM and pre-incubated with AM alone or with serial titrations of test compound for 30 minutes at 37° C., 5% CO2 in a humidified incubator. After pre-incubation of BAFF+test compound, 50 ul of the mixture(s) was added to 50 ul of cells and the test plate was further incubated at 37° C. (as described) for 24 hours. Control samples received either AM (unstimulated controls) or recombinant BAFF trimer diluted in AM (stimulated controls). After 24 hour incubation, the cell suspension was treated with 100 ul STEADY-Glo reagent (Promega), following manufacturer's instruction, and assayed for luciferase expression. Resulting Relative Luminesence Units (RLU) were plotted versus Log 10 nanamolar concentration of the test compound, where $IC_{50}$ & $IC_{90}$ values were calculated using a 4 Parameter Logistic Model, supported by Excel add-in Xlfit (ID Business Solutions Limited). The test compound $IC_{50}$ & $IC_{90}$ values were calculated as described above and Geomeans were calculated across multiple experiments and shown in Table 5 and Table 6.

Results:

The test compounds dose-dependently inhibited human and cynomolgus BAFF trimer-induced NFkB activation in BAFFR-CHO luciferase reporter cells. The results illustrated in Table 5 and 6 indicate that the $IC_{50}$ & $IC_{90}$ geomean values for the test compounds were comparable or more potent than control BAFF antagonists.

TABLE 5

$IC_{50}$ and $IC_{90}$ Geomean values for inhibiting human BAFF trimer in BAFFR-CHO report cells

| Compound ID | $IC_{50}$ (pM) | $IC_{90}$ (pM) |
|---|---|---|
| Compound A | 43 | 180 |
| Compound B | 39 | 256 |
| Compound C | 35 | 110 |
| Compound D | 34 | 172 |
| Compound F | 72 | 293 |
| Compound O | 27 | 119 |
| Compound P | 19 | 88 |
| Compound Q | 26 | 108 |
| Compound R | 30 | 139 |
| Compound X | 106 | 361 |
| Control Antibody 1 (BAFF (1)) | 232 | 743 |
| Control Fusion Protein Antagonist 2 (BAFF (2)) | 173 | 914 |
| Control Antibody 3 (BAFF (3)) | 70 | 417 |

TABLE 6

$IC_{50}$ and $IC_{90}$ Geomean values for inhibiting cynomolgus BAFF trimer BAFFR-CHO report cells

| Compound ID | IC50 Geomean pM | IC90 Geomean pM |
|---|---|---|
| Compound A | 132 | 191 |
| Compound B | 132 | 295 |
| Compound D | 118 | 248 |
| Control Antibody 1 (BAFF (1)) | 288 | 635 |
| Control Fusion Protein Antagonist 2 (BAFF (2)) | 602 | 1089 |
| Control Antibody 3 (BAFF (3)) | 257 | 588 |

Example 5. Inhibition of Human BAFF Trimer-Induced NFkB Activation in TACI-CHO Luciferase Reporter Cells Materials/Methods:

Briefly, human TACI CHO NFkB luciferase reporter cells were harvested, washed, counted and resuspended at a concentration of $1.6 \times 10^6$ cells per ml in assay medium (AM) of (v/v) 1% Penicillin/Streptomycin in X-VIVO15, a chemically defined serum-free media (Lonza). Recombinant human BAFF trimer (Boehringer Ingelheim Pharmaceuticals, Inc.) was prepared at a single concentration (222 pM) in AM and pre-incubated with AM alone or with serial titrations of test compound for 30 minutes at 37° C., 5% $CO2$ in a humidified incubator. After pre-incubation of BAFF+test compound, 50 ul of the mixture(s) was added to 50 ul of cells and the test plate was further incubated at 37° C. (as described) for 24 hours. Control samples received either AM (unstimulated controls) or recombinant human BAFF trimer diluted in AM (stimulated controls). After 24 hour incubation, the cell suspension was treated with 100 ul STEADY-Glo reagent (Promega), following manufacturer's instruction, and assayed for luciferase expression. Resulting Relative Luminesence Units (RLU) were plotted versus Log 10 nanamolar concentration of the test compound, where $IC_{50}$ & $IC_{90}$ values were calculated using a 4 Parameter Logistic Model, supported by Excel add-in Xlfit (ID Business Solutions Limited). The test compound $IC_{50}$ & $IC_{90}$ values were calculated as described above and Geomeans were calculated across multiple experiments and shown in Table 7.

Results:

The test compounds dose-dependently inhibited human BAFF trimer-induced NFkB activation in TACI-CHO luciferase reporter cells. The results illustrated in Table 7 indicate that the $IC_{50}$ & $IC_{90}$ Geomean values for the test compound were comparable to or more potent than control BAFF antagonists.

TABLE 7

$IC_{50}$ and $IC_{90}$ Geomean values for inhibiting human BAFF trimer in TACI-CHO report cells

| Compound ID | IC50 Geomean pM | IC90 Geomean pM |
|---|---|---|
| Compound A | 159 | 417 |
| Compound B | 159 | 510 |
| Compound D | 163 | 436 |
| Control Antibody 1 (BAFF (1)) | 273 | 576 |
| Control Fusion Protein Antagonist 2 (BAFF (2)) | 829 | 1945 |
| Control Antibody 3 (BAFF (3)) | 241 | 618 |

Example 6. Inhibition of BAFF 60 Mer-Induced NFkB Activation in BAFFR-CHO Luciferase Reporter Cells Materials/Methods:

Briefly, human BAFFR CHO NFkB luciferase reporter cells were harvested, washed, counted and resuspended at a concentration of $1.6 \times 10^6$ cells per ml in assay medium (AM) of (v/v) 1% Penicillin/Streptomycin in X-VIVO15, a chemically defined serum-free media (Lonza). Recombinant human BAFF 60 mer (Boehringer Ingelheim Pharmaceuticals, Inc.) was prepared at a single concentration (4.2 pM) in AM and pre-incubated with AM alone or with serial titrations of test compound for 30 minutes at 37° C., 5% $CO2$ in a humidified incubator. After pre-incubation of BAFF+test compound, 50 ul of the mixture(s) was added to 50 ul of cells and the test plate was further incubated at 37° C. (as described) for 24 hours. Control samples received either AM (unstimulated controls) or recombinant human BAFF 60 mer diluted in AM (stimulated controls). After 24 hour incubation, the cell suspension was treated with 100 ul STEADY-Glo reagent (Promega), following manufacturer's instruction, and assayed for luciferase expression. Resulting Relative Luminesence Units (RLU) were plotted versus Log 10 nanamolar concentration of the test compound, where $IC_{50}$ & $IC_{90}$ values were calculated using a 4 Parameter Logistic Model, supported by Excel add-in Xlfit (ID Business Solutions Limited). The test compound $IC_{50}$ & $IC_{90}$ values were calculated as described above and Geomeans were calculated across multiple experiments and shown in Table 8.

Results:

The test compounds dose-dependently inhibited human BAFF 60 mer-induced NFkB activation in BAFFR-CHO luciferase reporter cells. The results illustrated in Table 8 indicate that the $IC_{50}$ & $IC_{90}$ Geomean values for the test compounds A, B, C, D, O, P, Q and R were more potent than all three control BAFF antagonists.

TABLE 8

$IC_{50}$ and $IC_{90}$ Geomean values for inhibiting human BAFF 60mer in BAFFR-CHO reporter cells

| Compound ID | $IC_{50}$ (pM) | $IC_{90}$ (pM) |
|---|---|---|
| Compound A | 6 | 19 |
| Compound B | 6 | 17 |
| Compound C | 6 | 14 |
| Compound D | 4 | 12 |
| Compound F | 1300 | 7388 |
| Compound O | 5 | 6 |
| Compound P | 2 | 9 |
| Compound Q | 5 | 13 |
| Compound R | 5 | 16 |
| Compound X | 1555 | 6839 |
| Control Antibody 1 (BAFF (1)) | 24075 | 180053 |
| Control Fusion Protein Antagonist 2 (BAFF (2)) | 43 | 107 |
| Control Antibody 3 (BAFF (3)) | 15 | 38 |

Example 7: Neutralization of Membrane Bound BAFF-Induced NFkB Activation in BAFFR-CHO Luciferase Reporter Cells Materials/Methods CHO-K1 cells expressing human BAFF were counted and resuspended at a concentration of $2 \times 10^6$ cells per ml in standard growth medium. To stop cleavage of membrane-bound BAFF, cells were treated with 0.125% paraformaldehyde (Electron Microscopy) and incubated at room temperature for one hour. The fixed human BAFF CHO-K1 cells were then washed and resuspended at $2 \times 10^6$ cells per ml in standard growth media and incubated overnight at 37° C., 5% $CO_2$. The fixed human BAFF CHO-K1 cells were then harvested and resuspended at a concentration of $3.2 \times 10^6$ cells per ml in X-VIVO15, a chemically defined serum-free (Lonza) assay medium (AM) containing 1% Penicillin/Streptomycin (v/v).

Human BAFFR CHO NFkB luciferase reporter cells were harvested, washed, and resuspended at a concentration of $1.6 \times 10^6$ cells per ml in assay medium. Fixed human BAFF CHO-K1 cells prepared at $3.2 \times 10^6$ cells per ml in AM and pre-incubated with serial titrations of test compounds for 30 minutes were then added to 50 ul of human BAFFR CHO NFkB luciferase reporter cells and further incubated at 37° C. for 24 hours. Control reporter cells received either only AM (unstimulated controls) or fixed human BAFF CHO-K1 cells diluted in AM (stimulated controls). After 24 hour incubation, samples were treated with 100 ul STEADY-Glo reagent (Promega), and assayed for luciferase expression. Relative Luminescence Units (RLU) were plotted versus $Log_{10}$ nanamolar concentrations of the test compounds, where $IC_{50}$ and $IC_{90}$ values were calculated using a 4 Parameter Logistic Model, supported by Excel add-in XIfit (ID Business Solutions Limited). The test compounds $IC_{50}$ and $IC_{90}$ values were calculated as described above and Geomeans were calculated across multiple experiments and shown in Table 9.

Results

The test compounds dose-dependently inhibited membrane-bound human BAFF-induced NFkB activation in BAFFR-CHO luciferase reporter cells. The results illustrated in Table 9 indicate that the $IC_{50}$ and $IC_{90}$ values for the test compounds were more potent than all three control BAFF antagonists.

TABLE 9

$IC_{50}$ and $IC_{90}$ Geomean Values for inhibiting mbBAFF in BAFFR-CHO reporter cells

| Compound ID | $IC_{50}$ (pM) | $IC_{90}$ (pM) |
| --- | --- | --- |
| Compound A | 118 | 1015 |
| Compound B | 125 | 1139 |
| Compound D | 104 | 938 |
| Control Antibody 1 (BAFF (1)) | 553 | 10116 |
| Control Fusion Protein Antagonist 2 (BAFF (2)) | 581 | 3678 |
| Control Antibody 3 (BAFF (3)) | 250 | 2916 |

Example 8: Inhibition of Human IL-23 Activity in Lymphoblast B Cells (DB Cells) with STAT5-Luciferase Reporter Materials/Methods Lymphoblast B cells (DB cells; ATCC catalog #CRL-2289) were stable transduced with a lenti-viral STAT-3/luciferase reporter gene (Qiagen). Transduced cells were kept under selection using puromycin (Life Technologies). The complete culture medium was RPMI-1640 medium (Life Technologies) supplemented with 10% FBS (Hyclone) and 2 µg/mL puromycin (Life Technologies). The assay medium was RPMI-1640 medium (Life Technologies) supplemented with 10% FBS (Hyclone).

Engineered DB-STAT3 cells were seeded at 20,000 cells/well in a white, flat-bottom 96-well plate at 80 µL/well in assay medium. Test compounds (10x) were prepared in polypropylene, round-bottom 96-well plates in assay medium, and diluted accordingly to create dose ranges from 1 µg/mL to 10 pg/mL. 10 µL of diluted test molecules or assay medium (for control wells) were added to each well in triplicate. 10 µL of 10× human IL-23 (to a final concentration of 75 ng/mL per plate) were added to each well. Alternatively, 10 µL of media was added to the control wells. The IL-23 dose selected for use in the assay represents the $EC_{60}$ stimulant dose of human IL-23 for DB engineered cells as determined in prior studies. The plates were incubated overnight at 37° C. in 5% $CO_2$. The ONE-Glo™ luciferase assay reagent (Promega) was prepared and 100 µL was added to each well and mixed. The luminescence was measured on an Envision plate reader and then plotted (y-axis) against antibody concentration (x-axis). $IC_{50}$ values of compounds were determined by applying the data to a 4-parmeter sigmoidal dose-response function using Graph-Pad Prism 6 software. $IC_{90}$ values were determined by calculating the data with Find ECanything with GraphPad Prism 6 software. Geomeans were calculated across multiple experiments and shown in Table 10.

Results

The results showed that the tested compounds were able to inhibit human IL-23 activity in DB cells with STAT3-luciferase reporter.

TABLE 10

$IC_{50}$ and $IC_{90}$ Geomean values for inhibiting human IL-23 in lymphoblast B cells

| Compound ID | $IC_{50}$ (pM) | $IC_{90}$ (pM) |
| --- | --- | --- |
| Compound A | 145 | 1229 |
| Compound B | 161 | 1101 |
| Compound C | 189 | 2330 |
| Compound D | 128 | 3087 |
| Control Antibody 4 (IL-23A (1)) | 79 | 634 |

Example 9: Inhibition of Human and Cynomolgus IL-23 Activity in Mouse Splenocytes Materials and Methods Mononuclear cells from mouse spleens (female C57BL/6 less than 13 weeks of age; Jackson Laboratories) were isolated washed, counted, and resuspended to $4\times10^6$ cells/ml in a standard T cell media (TCM). One hundred microliters of the mIL-2/splenocyte suspension was added to 96 well microtiter plates. Recombinant human IL-23 (Boehringer Ingelheim Pharmaceuticals, Inc.) or recombinant cynomolgus IL-23 (Boehringer Ingelheim Pharmaceuticals, Inc.) was diluted in TCM and pre-incubated for 2 hours at 37° C. with TCM alone or with titrations of test samples. After the pre-incubation of test sample+IL-23, 100 ul of the mixture was added to the cells and the test plates were incubated at 37° C. with 5% $CO_2$-humidified air for 48 hours. Control samples received either TCM (unstimulated controls) or recombinant IL-23 diluted in TCM (stimulated controls). After the incubation, mouse IL-17 levels were determined from the supernatant using the Quantikine® Mouse IL-17 Immunoassay according to the manufacturer's instructions (R&D Systems). Interpolated mIL-17 pg/ml values were determined for each sample and converted to percent of control (POC). The POC was plotted versus concentration of the test sample and $IC_{90}$ values were calculated using a 4 Parameter Logistic Model enabled by the Excel add-in XLfit (Activity Base software, ID Business Solutions, Ltd.). Test compounds were analyzed with respect to the $IC_{50}$ and $IC_{90}$ as described above, and Geomeans were calculated across multiple experiments for each test compound and shown in Table 11.

Results

The results showed that the tested compounds were able to inhibit both human and cynomolgus-IL23 induced mouse splenocyte release of mouse IL-17.

TABLE 11

IC$_{50}$ and IC$_{90}$ Geomean values for inhibiting human and cynomolgus IL-23 in mouse splenocytes

|  | Human IL23 | | Cyno IL23 | |
| --- | --- | --- | --- | --- |
| Compound ID | IC$_{50}$ (pM) | IC$_{90}$ (pM) | IC$_{50}$ (pM) | IC$_{90}$ (pM) |
| Compound A | 146 | 1647 | 155 | 1309 |
| Compound B | 202 | 1360 | 200 | 1480 |
| Compound C | 133 | 761 | 110 | 880 |
| Compound D | 105 | 1700 | 97 | 1554 |
| Control Antibody 4 (IL-23A (1)) | 84 | 366 | 64 | 331 |

Example 10. Pharmacokinetics of Compounds in Cynomolgus Monkeys

Materials and Methods:

Single intravenous (IV) dose PK studies for test Compounds A, B, C, and D were conducted in male cynomolgus monkeys (n=2 per molecule). Doses were administered as a slow 1 mg/kg IV bolus injection. Whole blood samples were collected pre-dose and 0.25, 2 and 6 h post-dose on the day of dosing and 1, 2, 3, 4, 7, 10, 14, 21, and 28 days post-dose.

Serum concentrations of dosed molecules were measured by an MSD-based ligand binding assay.

Calibration standard curve and quality control (QC) samples were prepared in 100% pooled cynomolgus monkey serum. Each standard curve consisted of seven non-zero points starting at 512 ng/mL then serially diluted three-fold. A blank sample (matrix without analyte) was also included. Five QC samples at low, medium, and high ranges were prepared starting at 256 ng/mL, then serially diluted four-fold to 8 ng/mL, then a 2-fold dilution was used to prepare the lowest QC at 4 ng/mL. Standard curve and QC samples were included in duplicate during each analytical run. Lower and upper limits of quantification were defined as the lowest and highest QC points having reproducible back-calculated concentrations not exceeding 30 percent (%) of nominal concentrations. Acceptance criterion for standard curve points was 30 percent (%) of nominal concentrations.

To measure active drug concentration in serum samples a master mix was prepared, combining 0.5 µg/mL biotinylated recombinant human BAFF and 0.5 µg/mL sulfo-labeled goat anti-human IgG detection in binding buffer (5% BSA in 1×PBS with 0.05% Tween 20). Master mix was added to a 96-well non-binding and light-blocking plate at 50 µL per well. Twenty-five µL of standards and QCs (stock diluted 1:20 in binding buffer) were added per well in duplicate to the non-binding plate containing the master mix. Unknown serum samples were diluted 1:20 in binding buffer and 1:400 in binding buffer containing 5% serum. Twenty-five µL of diluted samples were added per well to non-binding plates containing master mix. Non-binding plates were incubated at room temperature on a plate shaker (500 rpm, 1.5 h). In parallel, an MSD streptavidin gold plate was blocked using 150 µL blocking buffer (5% BSA with 1×PBS with 0.05% Tween 20) and incubated at room temperature on a plate shaker (500 rpm, 1.5 h). After incubation, MSD plates were washed three times with 300 µL per well of wash buffer (0.05% Tween 20 in 1×PBS). Fifty µL of sample from non-binding plates were added to MSD plates and incubated at room temperature (1.5 h, 600 rpm). After incubation, plates were washed three times with wash buffer, and 150 µL of 2× Read Buffer T was added to each well and read immediately on an MSD Sector Imager 2400. Standard curves were fitted to a four-parameter logistics equation using MSD Discovery Workbench software. Pharmacokinetic parameters were calculated using non-compartmental analysis in Phoenix WinNonlin 6.3 (Certara, MD, USA).

Figure 2:
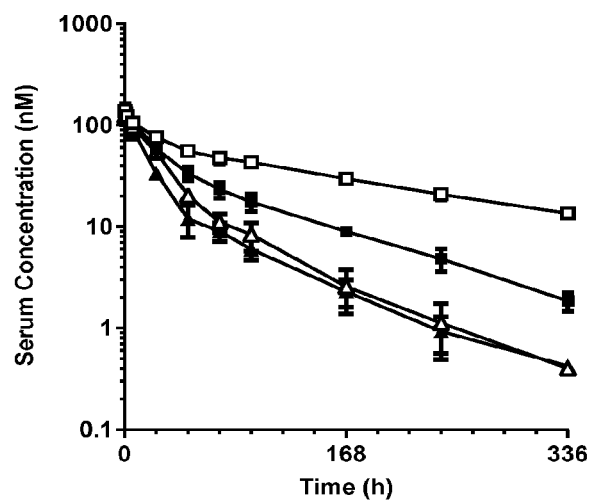
FIG. 2 is a graph showing the serum concentrations (mean±SD) for Compound A (closed squares), Compound B (open squares), Compound C (closed triangles) and Compound D (open triangles) in male cynomolgus monkeys following a single 1 mg/kg intravenous dose, as described in Example 10.

Results:

Mean (SD) serum concentration vs. time profiles for test compounds are illustrated in FIG. 2. Mean (SD) pharmacokinetic parameters for test compounds are summarized in Table 12. Serum samples displaying a precipitous drop in drug concentration over time that were confirmed to be anti-drug antibody positive were excluded from pharmacokinetic parameter calculations.

TABLE 12

Mean (SD) pharmacokinetic parameters of test compounds in male cynomolgus monkeys following a single 1 mg/kg intravenous dose

| Compound ID | AUC$_{0-last}$ (µg*d/mL) | AUC$_{0-inf}$ (µg*d/mL) | CL (mL/day/kg) | Vss (mL/kg) | T$_{1/2}$ (days) |
| --- | --- | --- | --- | --- | --- |
| Compound A | 52.5 (6.6) | 54.2 (7.1) | 18.6 (2.4) | 61.6 (4.3) | 3.1 (0.3) |
| Compound B | 102.7 (1.8) | 127.0 (3.6) | 7.9 (0.2) | 64.4 (6.6) | 6.2 (0.7) |
| Compound C | 26.6 (1.4) | 27.0 (1.3) | 37.1 (1.8) | 66.9 (13.2) | 2.3 (0.4) |
| Compound D | 33.8 (1.3) | 34.5 (1.8) | 29.0 (1.5) | 55.7 (5.5) | 2.8 (0.8) |

Example 11. Predicting Human PK and Human Dose of an Exemplary Compound

Figure 3:
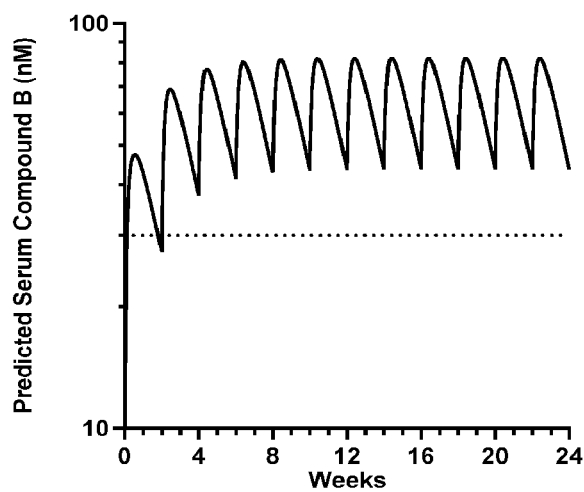
FIG. 3. Shows the predicted human serum concentration-time profile of Compound B, following a 100 mg s.c. dose administered once every two-weeks, as described in Example 11. The dotted line represents the targeted $C_{min}$ (30 nM).

Elementary Dedrick scaling was used to scale mean monkey serum concentrations of Compound B to human, using an allometric exponent of 1.0 for volume of distribution and 0.85 for clearance. The predicted human i.v. serum concentration-time profile was fitted to a linear two-compartment model. The human s.c. serum concentration-time profile was predicted by combining parameters from the two-compartment i.v. model with the mean s.c. absorption rate and bioavailability observed for marketed therapeutic mAbs. The clearance and terminal half-life are predicted to be 0.34 L/d and 9.9 d in healthy humans, respectively. The predicted human serum concentration-time profile of Compound B, following a 100 mg s.c. dose administered once every two-weeks, was shown in FIG. 3.

The predicted human efficacious dose is 1 mg/kg delivered s.c. once every two weeks. This dose regimen is predicted to maintain a Cmin≥30 nM (6 µg/mL) with biweekly or less frequent s.c. administration. The predicted efficacious dose may be based on concentration-PD biomarker responses observed for belimumab (Benlysta®), tabalumab and blisibimod in SLE and RA patients. In these studies, maximal inhibition of BAFF-related biomarkers was associated with a 30-40 nM steady-state Cmin. The concentration required to neutralize IL23 is much lower than that required to neutralize BAFF, and therefore does not impact the overall required Cmin for the dual antagonist.

Example 12. Purification of Compounds

Methods:

Compounds were purified using Mab Select SuRe as an affinity purification step. Elution was performed using Sodium Acetate buffer pH 3.5. Following Mab Select SuRe purification the sample was neutralized and applied to a Poros 50 HS resin and eluted using a Sodium Chloride gradient in Sodium Citrate Buffer. Monomer peak elutes at 20 mM NaCitrate and 120 mM NaCl pH 6.0. Following ion exchange chromatography, the sample was consistently >95% monomer.

Sedimentation velocity (SV) experiment via Analytical ultracentrifugation (AUC) was used to provide information on sample purity and aggregation states. Samples were centrifuged in an optima XL-I (Beckman Coulter, Fullerton, CA) at 20° C. using an An60Ti four-hole rotor running at 40,000 rpm. The sedimentation process was monitored by ultraviolet absorbance at 280 nm, using corresponding dilution buffer as reference buffer. The variation in the concentration distribution in the ultracentrifuge cell with time was collected using XL-I operating software and was analyzed using the continuous c(S) distribution model in the SEDFIT software (version 14.1) to give the distribution of sedimentation coefficient. Monomer percentage was calculated based on the integrated peak area.

Results:

The results of purification of the compounds are shown in Table 13. The data show that the compounds have high purity and homogeneity, indicating good stability.

TABLE 13

| Parameter Name | Compounds A, B, C, D |
|---|---|
| Percent Monomer (sedimentation velocity) | 99% monomer 1% aggregate |

Example 13: Mass Spectrometry Profile of Compounds

Methods:
Native Sample

This procedure yielded the intact mass of the compound or protein. 0.15 ul of sample was injected onto an Agilent PoroShell 300SB-C3 column, 5 um, (30×1.0 mm). The column temperature was 80° C. and flow rate was 150 ul/min. The compound or protein was eluted off the column with a gradient from 10% B at 0 minutes to 85% B at 6 minutes. Mobile phase A was Water/Acetonitrile/Formic Acid/Ammonium Acetate (99/1/0.1/2 mM) and Mobile phase B was n-Propanol/Acetonitrile/Water/Formic Acid (70/20/10/0.1). The effluent was directed to an Agilent 6224 TOF mass spectrometer, which was scanned from mass 600 to mass 3200. The raw data was deconvoluted with the program MassHunter.

Reduced Sample

This procedure yielded the mass of the protein or the light chain and the mass of the heavy chain. 5 ul of sample was added to 5 uL of a 20:1 mixture of 8M Guanadine HCL:TCEP and incubated for 15 minutes at room temperature. 0.15 ul of this sample was injected as above, with the following differences: the compound or protein was eluted off the column with a gradient from 5% B at 0 minutes to 85% B at 6 minutes, the column temperature was 60° C. and the mass range was 600-2000.

Deglycosylated Sample

This procedure yielded the deglycosylated mass of the protein or the light chain and the heavy chain. 7.5 ul of sample was added to 3.2 uL of a 20:1 mixture of 400 mM Ammonium Bicarbonate:PNGase F and incubated for 3 hours at 37° C. Then, 10 ul of a 20:1 mixture of 8M Guanadine HCL:TCEP was added to the sample and incubated for 15 minutes at room temperature. This sample was injected as above for reduced sample.

Peptide Mapping by Mass Spectrometry

Samples were diluted into a denaturing buffer consisting of 6M GdHCl, 250 mM Tris-HCL pH 7.5 and 10 mM DTT and then incubated at 37° C. for 30 minutes. Samples were then alkylated with iodoacetamide, and incubated in the dark at room temperature for 30 minutes. The reaction mixtures were purified and buffer exchanged into 100 mM Tris-HCL pH 7.5 using Sephadex G-25 Superfine cartridges. Samples were then digested with trypsin during a 4 hour incubation at 37° C. The digested reaction mixtures were subsequently quenched by adding TFA.

The obtained tryptic digest was injected onto a Phenomenex Jupiter C18 reversed phase column via the autosampler of a Dionex Ultimate 3000 HPLC. A gradient solvent system consisting of solvent A: 0.1% Formic acid/99% water/1% acetonitrile and solvent B: 0.1% Formic acid/5% water/95% acetonitrile was utilized. The percentage of solvent B was increased from 0% to 38% over 140 minutes. The chromatographic separation took place at room temperature at a flow rate of 100 µl/min. Sample storage in the autosampler was at 4° C. After chromatographic separation the sample entered a Thermo Scientific Orbitrap Fusion mass spectrometer operated in positive electrospray ionization mode. The employed method included activation types of CID utilizing a resolution of 30,000, a minimum signal of 10,000, an isolation width of 1.0 and a normalized collision energy of 35.0V. The S-lens RF level was set at 20%. The data collection type is profile for the full MS scan and centroid for the CID MS/MS data. Data is collected over a mass range of 250-2000 Da at an acquisition rate of 1 spectra/second.

Collected raw LC-MS and LC-MS/MS fragmentation data from the enzymatic digest were analyzed utilizing Proteome Discover 1.4 (Thermo Scientific) against the given sequence. Identified peptides containing a consensus of N-X-S/T (X is not P) were then analyzed by manually extracting EIC for the glycosylated peptides. The MS intensities of the glycosylated peptides across the EIC were used to estimate their percentages of the total abundance of glycoforms.

Results:

The results are shown in Table 14. The data indicate the intended amino acid sequence and structure has been expressed and recovered without unexpected heterogeneity. The glycosylation pattern is typical of a conventional antibody expressed in CHO cells and does not show any atypical structures.

TABLE 14

| Parameter | Compound B |
|---|---|
| Mass Spectrometry: Intact Molecular Weight Profile | Intact/Matches Sequence |
| Mass Spectrometry: Glycosylation Profile | Similar to CHO expressed IgG |

Example 14: Monomer Content at High Concentration

The purpose of this process description is to assess the inherent properties of compound B by evaluating aggregation with increased concentration. A standard buffer of 20 mM NaCitrate 120 mM NaCl pH 6 is used without formulation assessment to understand the molecules propensity to aggregate.

Methods:

The compound B was concentrated gradually to a concentration as high as possible without precipitation observed using Amicon Ultra centrifugal filter with cut-off molecular weight of 50,000 Dalton (Millipore, Billerica). The concentrated protein solutions were then subjected to analytical sec analysis to provide information on sample purity and aggregation states. Chromatography was run using an Agilent 1200 series HPLC system. The system was run at 1.0 ml/min for 23 minutes. ~30 ug of material was injected into a Tosoh Biosciences TSKgel G3000SWXL column (5 um 250a 7.8×30 cm) and results were read at 280 nm. Running buffer used was 50 mM NaPhosphate, 0.2 M L-arginine pH 6.8.

Figure 4:
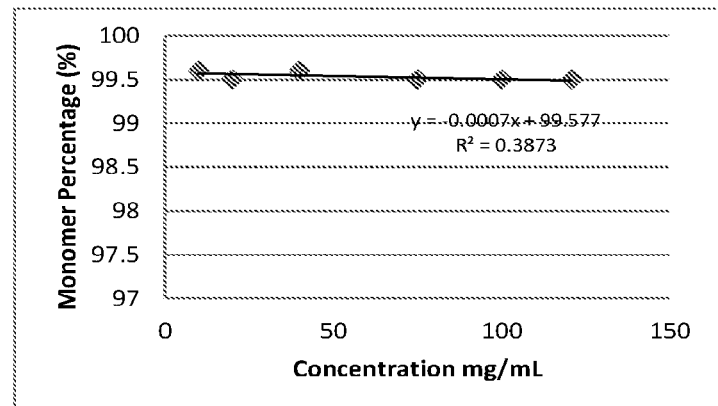
FIG. 4 shows graphical summary of monomer percentage vs. concentration for Compound B, as described in Example 14.

Results:

Summary of Analytical SEC data for compound B during concentration process is listed in Table 15 and FIG. 4. Data showing aggregation and sample purity at increasing concentration is presented which demonstrates that compound B does not have a propensity to aggregate with increased concentration.

TABLE 15

Summary of Analytical SEC data for compound B during concentration process

| Compound B concentration (mg/ml) | Analytical SEC data |
|---|---|
| 10 | 99.6% monomer, 0.4% aggregate |
| 20 | 99.5% monomer, 0.5% aggregate |
| 40 | 99.6% monomer, 0.4% aggregate |
| 75 | 99.5% monomer, 0.5% aggregate |
| 100 | 99.5% monomer, 0.5% aggregate |
| 121 | 99.5% monomer, 0.5% aggregate |

M = monomer,
A = aggregate

Example 15: Valence of Compounds

Methods:

Analytical Membrane-Confined Electrophoresis was used to measure the valence of compounds which had previously been dialyzed into 10 mM Acetate 50 mM KCl pH 5.0 buffer overnight. In the experimental setup, 20 µL of sample at 1 mg/mL was loaded into a 2×2×4 mm3 quartz cuvette which both ends were sealed by 10 MWCO semi-permeable regenerated cellulose BioTech grade membranes. These membranes trap the macromolecule while allowing water and solvent components through. A 1 mA electric current was then applied through the cuvette, establishing an electric field along its length in which the charged macromolecule moved in the electric field with a continuous flow of fresh buffer. The real-time moving concentration boundary was detected using a linear photodiode array (LPDA) that provides intensity readings spaced along the cuvette. The velocity of the concentration boundary was used to calculate the electrophoretic mobility and subsequently the effective valence. Additional information such as the Stokes Radius (obtained from the sedimentation velocity run in the AUC), counterion radius (0.122 nm for chloride ion), buffer conductance (6.35 mS) and ionic strength (0.05 M) were then used to reveal the underlying valence of the macromolecule.

Results:

The valence data (see Table 16) indicate colloidal stability of the compounds in solution, i.e. net interaction of protein and protein in solution. The compounds with valence greater than 15 have strong net repulsive interaction and high potential to be formulated at high concentration.

TABLE 16

Valence data for compounds

| Compound ID | Valence at pH 5.0 |
|---|---|
| Compound A | 24.4 ± 0.2 |
| Compound B | 21.5 ± 0.3 |
| Compound D | 21.8 ± 0.2 |

Example 16: Whole Blood Stability of Compounds

Methods

A whole blood interference assay was developed on an Octet RED96 to detect the effects of non-specific binding or off-target binding for compounds in the presence of whole blood (WB). The compound solutions in whole blood and 1× kinetic running buffer (1×kb) were incubated at a temperature of 37° C. for 48 hours. Kinetic measurements for the incubated compound samples were performed with an Octet RED96 equipped with streptavidin (SA) biosensor tips (ForteBio, Menlo Park, CA) at 27° C. The ratio of the on-rates/binding signals in buffer and whole blood were reported. A ratio <2 was considered to show no interference.

Results

The results are shown in Table 17. No whole blood interference was observed for test compounds.

TABLE 17

Whole blood binding results for compounds

| Parameters | Ratio of binding signal in WB/kinetic buffer to hu BAFF | Ratio of binding signal in WB/kinetic buffer to hu IL23 |
|---|---|---|
| Compound A | 1.2 | 1.1 |
| Compound B | 1.2 | 1.5 |
| Compound C | 1.1 | 1.3 |
| Compound D | 1.3 | 1.7 |
| Compound E | 1.0 | 1.1 |
| Compound F | 1.0 | 1.2 |

Example 17: Prediction of in Silico Immunogenicity

Methods

Immunogenicity of protein therapeutics was predicted in silico by utilizing a computational tool, EpiMatrix that was developed by EpiVax, Inc. (Providence, RI). EpiMatrix incorporates the prediction of T-helper epitope as well as the T-reg epitope, of which the former is to provoke an immune response while the latter is inhibitory. Briefly, the protein sequence was first parsed into overlapping 9-mer peptide frames that has been proven the core of class II HLA binding. The binding potential of 9-mer peptides to each of eight common class II HLA alleles are evaluated based on experimental data or computational prediction. A score is generated to reflect the binding potential of the 9-mer peptide to each HLA allele and normalization is performed to make it possible to compare any 9-mer across multiple HLA alleles and enable immunogenicity prediction on a global scale. In the end the program generates an overall 'immunogenicity score', tReg Adjusted Epx Score, that likelihood that the compounds will provoke an immune response in vivo.

Results

The results are shown in Table 18. The overall immunogenicity scores for test compounds are low and predict that these compounds are not likely to illicit a strong immune response in vivo.

TABLE 18

EpiVax Scores

| Parameter | EpiVax (Chain 1, Chain 2) |
|---|---|
| Compound A | −46.13, −28.39 |
| Compound B | −45.77, −28.39 |
| Compound C | −41.40, −28.42 |
| Compound D | −41.01, −28.42 |
| Compound E | −39.81, −41.43 |
| Compound F | −42.15, −36.94 |
| Compound G | −43.75, −29.30 |
| Compound H | −35.19, −43.44 |
| Compound I | −43.38, −29.30 |
| Compound J | −34.78, −43.44 |
| Compound K | −43.75, −33.61 |
| Compound L | −37.80, −43.44 |
| Compound M | −43.38, −33.61 |
| Compound N | −37.40, −43.44 |
| Compound O | −34.66, −39.56 |
| Compound P | −34.24, −39.56 |
| Compound Q | −34.64, −47.37 |
| Compound R | −34.22, −47.37 |
| Compound S | −40.96, −40.09 |
| Compound T | −43.91, −40.09 |
| Compound U | −41.31, −44.98 |
| Compound V | −42.53, −36.94 |
| Compound W | −38.33, −44.98 |
| Compound X | −39.42, −41.43 |

Example 18: Inhibition of Human BAFF in Primary Human B-Cell Proliferation Assay Materials and Methods The normal healthy blood samples (n=3 donors) used in this study were purchased from Biological Specialty Corporation, Philadelphia, PA The complete culture medium was IMDM (Life Technologies) supplemented with 10% FBS (Life Technologies) plus Pen/Strep (Life Technologies). The B-cell isolation buffer consisted of sterile $Mg^{++}$ and $Ca^{++}$ free DPBS (Life Technologies) plus 2% FBS plus 2 mM EDTA (Life Technologies).

Isolation of Human B Cells from Healthy Human Whole Blood

Four hundred mL of heparinized whole blood was transferred to a 1000 mL sterile polystyrene bottle and an equal volume of DPBS was added. Thirty-five 35 mL of PBS-diluted blood was placed on the top of a 15 mL Ficoll-Paque™ Plus (GE Healthcare) gradient preloaded in a 50 mL polystyrene round-bottom tube. The tubes were centrifuged at 2000 rpm at room temperature for 20 minutes without brake. Next, two-thirds of the top supernatant was aspirated, and the middle gray layer containing peripheral blood mononuclear cells (PBMC) was transferred to a 50 mL conical tube. DPBS (Ca++ and Mg++ free)+2% FBS was added, up to a volume of 50 mL. The tubes were spun down at 1200 rpm for 10 minutes. The resulting cell pellet was resuspended with DPBS (Ca++ and Mg++ free)+2% FBS (wash buffer), and the centrifugation step (1200 rpm for 10 minutes) was repeated. The cell pellet was again resuspended in wash buffer up to 50 mL. Cell viability and cell concentration were measured at this point.

The tube was then spun down at 1200 rpm for 10 minutes, and the supernatant was discarded. The cell pellet was resuspended with complete culture medium and the cell concentration was adjusted to $5 \times 10^6$ cells/mL. The suspended cells were placed into a 75 $cm^2$ tissue culture flask and incubated in a 5% $CO_2$ incubator (at 37° C.) overnight. The B cells were then isolated by using Dynabeads® Untouched™ Human B Cells Kit (Life Technologies) following the manufacturer's protocol. The cell concentration was adjusted to be suitable for the downstream procedure after measuring cell concentration and viability.

Evaluation of B-Cell Proliferation Using $^3$H-Thymidine Incorporation Assay

B cells were seeded in a Falcon tissue culture 96-well, round-bottom plate ($1 \times 10^5$ cells/100 µL culture medium per well). Then, test articles were prepared at 4× serial concentrations ranging from 0.028 to 20 nM and B cell stimuli (anti-IgM antibody and human BAFF) at 4× concentrations (8 µg/mL and 20 ng/mL, respectively) with complete culture medium. 50 µL of prediluted test articles were added to the respective wells (0.007 to 5 nM, final concentration). Then, 50 µL of prediluted goat anti-human IgM (2 µg/mL, final concentration) and hBAFF (5 ng/mL or 98 pM, final concentration) were added to the corresponding wells (see FIG. 6). The B cells were cultivated in a 5% $CO_2$ 37° C. humidified incubator for 72 hours. Eighteen hours prior to the end of the incubation, 20 µL of 1 µCi $^3$H-thymidine (Pelkin Elmer) was added to each well. A cell harvester was used to transfer $^3$H-thymidine incorporated DNA/well to a microfiber glass filter plate, where 30 µL scintillation enhancer was added to the wells after air-drying the plate for at least 4 hours. The counts per minute (cpm) value of each well was measured using a MicroBeta Topcount, and the cpm value (y-axis) versus concentration of test articles (x-axis) was plotted.

Statistical Analyses $IC_{50}$ and $IC_{90}$ were determined by curve fitting the data to a 4-parmeter sigmoidal dose-response function using Graph-Pad Prism 6 software. Geomeans were calculated across three experiments and shown in Table 19.

Results

The results showed that Compound B appeared to be approximately 2-fold more potent as compared to Control Antibody 3 when comparing $IC_{50}$ and $IC_{90}$ values.

TABLE 19

IC50 and IC90 Geomean values for inhibiting human BAFF in primary human B-cell proliferation assay

| Compound ID | $IC_{50}$ (pM) | $IC_{90}$ (pM) |
|---|---|---|
| Compound B | 33.7 | 160.2 |
| Control Antibody 3 (BAFF (3)) | 87.3 | 370.8 |

Example 19. Inhibition of B220+ B Cell Numbers Induced by Human BAFF Overexpression in B10.RIII Mice Materials and Methods Briefly, on day 1 B10.RIII female mice (6-8 weeks old, Jackson Laboratory) were randomly divided into 10 groups, 10 animals/group and given a 100 µl intraperiotoneal injection of either citrate buffer (20 mM NaCitrate, 115 mM NaCl, pH 6.0) or test compounds at equivalent molar dose of 1.3, 0.4 and 0.13 mg/kg vs. 1, 3 and 0.1 mg/kg respectively. Naïve untreated mice were an additional control. Immediately following treatment day 1, mice were administered a single 3 mg dose (1.5 mg/mL) of human BAFF minicircle DNA (System Biosciences) via hydrodynamic injection versus empty vector (EV) control group. Intraperiotoneal treatment with either citrate buffer or test compounds was repeated every 72 hours on days 3, 6, 9 and 12.

Figure 5:
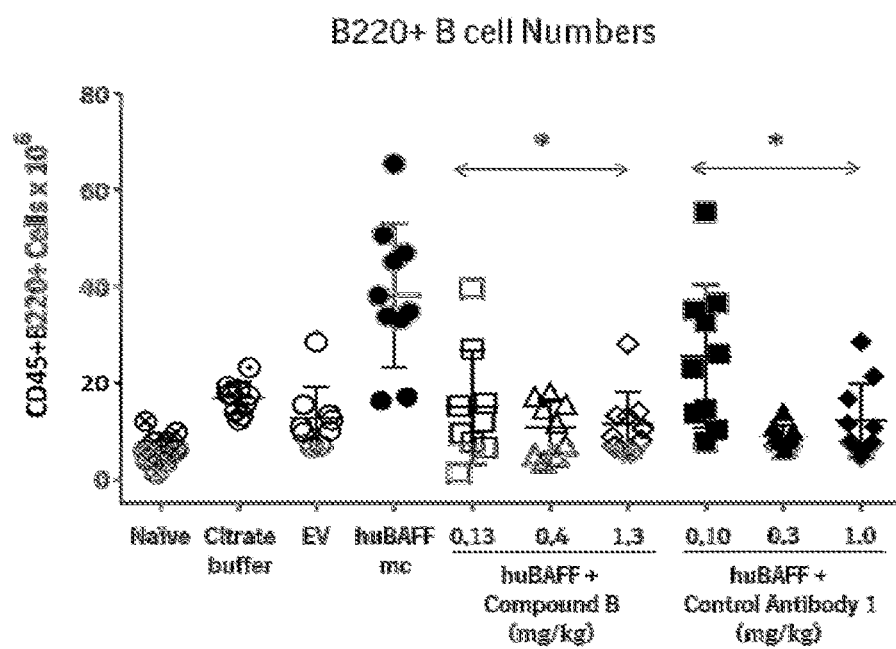
FIG. 5 shows that Compound B maintains functional potency vs. anti-BAFF in vivo. Mice were dosed equimolar with either anti-BAFF or Compound B and challenged with human BAFF minicircle to induce B cell expansion. On day 14 spleens were collected and analyzed by flow cytometry for mouse B220+ B cells as a measure of functional blockade of BAFF.

On day 14 mice were anesthetized via isoflurane (Butler Schein) and sacrificed via cervical dislocation. Spleens were removed and a cell suspension analyzed by flow cytometry for B220+ B cells. The mean numbers for each treatment group were determined and significance compared to control calculated using the One-way ANOVA followed by Dunnett's multiple comparisons test. Results are shown in FIG. 5.

Results

The results showed that treatment for 14 days with Compound B was able to significantly inhibit the expansion of B220+ B cells induced by human BAFF minicircle DNA.

Example 20. Inhibition of Human IL23 Induced Mouse IL17A and IL22 Release in C57/B16 Mice Materials and Methods Briefly, C57BL/6 female mice (7-10 weeks old, Charles River) were randomly divided into 8 groups, 8 animals/group and given a 100 µl intraperiotoneal injection of either citrate buffer (20 mM NaCitrate, 115 mM NaCl, pH 6.0) or test compounds at equivalent molar dose of 1.3, 0.4 and 0.13 mg/kg vs. 1, 3 and 0.1 mg/kg respectively.

One hour after test compound dosing mice were anesthetized via isoflurane (Butler Schein) and given a 20µl intradermal injection of either 0.1% BSA (Sigma) control or 15 µg/ml (0.3 µg) rhIL23 (generated in-house) diluted in saline (Invitrogen) to both ears. Intradermal challenges were repeated daily for 2 consecutive days. Twenty-four hours after the second challenge the mice were sacrificed via cervical dislocation and each ear was removed. Ear tissue was homogenized in 1 ml of homogenization buffer (HBSS (Gibco); 0.4% Triton X-100 (Sigma); 1× SigmaFast Protease Inhibitor (Sigma)) using a MP Biomedicals Fast-Prep 24 homogenizer. Homogenized samples are centrifuged at 4 C for 10 min and supernatant collected. Supernatants were assayed for the presence of mouse IL17A and IL22, using the Quantikine® Mouse IL-17 and mouse IL-22 Immunoassays according to the manufacturer's instructions (R&D Systems). Interpolated cytokine pg/ml values were determined for each sample. The mean pg/ml levels for each treatment group were determined and significance compared to control calculated using the One-way ANOVA followed by Dunnett's multiple comparisons test.

Results

Figure 6:
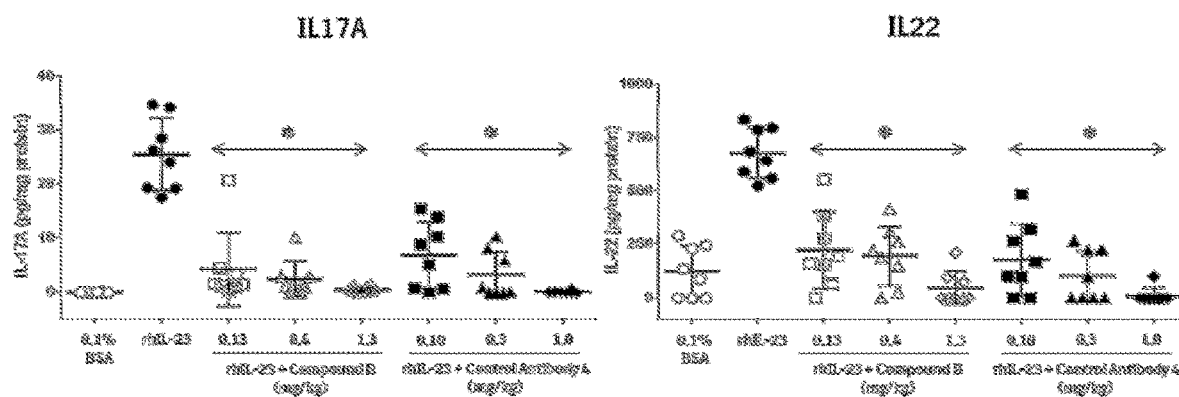
FIG. 6 shows that Compound B maintains functional potency vs. Anti-IL23 in vivo. Evaluation of Compound B in the IL23 induced cytokine assay. Mice were dosed equimolar with either anti-IL23 or compound B and challenged with human IL23 twice to induce ear inflammation. Twenty four hours after the final injection, ears were collected and analyzed for mouse IL17A and mouse IL22 as a measure of functional blockade of IL23.

The results in FIG. 6 showed that treatment with a single intraperitoneal dose of Compound B was able to significantly inhibit the release of mouse IL17 and IL22 in the skin induced by two daily consecutive intra dermal injections of recombinant human IL23.

SEQUENCES

| SEQ ID NO | Sequence |
|---|---|
| 1 | QVQLQQSGAEVKKPGSSVRVSCKASGGTFNNNAINWVRQAPGQGLEWMGGIIP MFGTAKYSQNFQGRVAITADESTGTASMELSSLRSEDTAVYYCARSRDLLLFPHH ALSPWGRGTMVTVSS |
| 2 | SSELTQDPAVSVALGQTVRVTCQGDSLRSYYASWYQQKPGQAPVLVIYGKNNRP SGIPDRFSGSSSGNTASLTITGAQAEDEADYYCSSRDSSGNHWVFGGGTELTVL |
| 3 | QVQLVQSGAEVKKPGSSVKVSCKASGYTFTDQTIHWMRQAPGQGLEWIGYIYPR DDSPKYNENFKGKVTITADKSTSTAYMELSSLRSEDTAVYYCAIPDRSGYAWFIY WGQGTLVTVSS |
| 4 | DIQMTQSPSSLSASVGDRVTITCKASRDVAIAVAWYQQKPGKVPKLLIYWASTRH TGVPSRFSGSGSRTDFTLTISSLQPEDVADYFCHQYSSYPFTEGSGTKLEIK |
| 5 | SSELTQDPAVSVALGQTVRVTCQGDSLRSYYASWYQQKPGQAPVLVIYGKNNRP SGIPDRFSGSSSGNTASLTITGAQAEDEADYYCSSRDSSGNHWVFGGGTELTVLG GGSGGGGQVQLVQSGAEVKKPGSSVKVSCKASGYTFTDQTIHWMRQAPGQGLE WIGYIYPRDDSPKYNENFKGKVTITADKSTSTAYMELSSLRSEDTAVYYCAIPDRS GYAWFIYWGQGTLVTVSSLGGGSGASTKGPSVFPLAPSSKSTSGGTAALGCLVK DYFPEPVTVSWNSGALTSGVHTFPAVLQSSGLYSLSSVVTVPSSSLGTQTYICNVN HKPSNTKVDKRVEPKSCDKTHTCPPCPAPEAAGGPSVFLFPPKPKDTLYITREPEV TCVVVDVSHEDPEVKFNWYVDGVEVHNAKTKPREEQYNSTYRVVSVLTVLHQD WLNGKEYKCKVSNKALPAPIEKTISKAKGQPREPQVYTLPPSREEMTKNQVSLTC LVKGFYPSDIAVEWESNGQPENNYKTTPPVLDSDGSFFLYSKLTVDKSRWQQGN VFSCSVMHEALHNHYTQKSLSLSPG |

SEQUENCES

| SEQ ID NO | Sequence |
|---|---|
| 6 | DIQMTQSPSSLSASVGDRVTITCKASRDVAIAVAWYQQKPGKVPKLLIYWASTRH<br>TGVPSRFSGSGSRTDFTLTISSLQPEDVADYFCHQYSSYPFTFGSGTKLEIKGGGSG<br>GGGQVQLQQSGAEVKKPGSSVRVSCKASGGTFNNNAINWVRQAPGQGLEWMG<br>GIIPMFGTAKYSQNFQGRVAITADESTGTASMELSSLRSEDTAVYYCARSRDLLLF<br>PHHALSPWGRGTMVTVSSLGGGSGRTVAAPSVFIFPPSDEQLKSGTASVVCLLNN<br>FYPREAKVQWKVDNALQSGNSQESVTEQDSKDSTYSLSSTLTLSKADYEKHKVY<br>ACEVTHQGLSSPVTKSFNRGEC |
| 7 | DIQMTQSPSSLSASVGDRVTITCKASRDVAIAVAWYQQKPGKVPKLLIYWASTRH<br>TGVPSRFSGSGSRTDFTLTISSLQPEDVADYFCHQYSSYPFTFGSGTKLEIKGGGSG<br>GGGQVQLQQSGAEVKKPGSSVRVSCKASGGTFNNNAINWVRQAPGQGLEWMG<br>GIIPMFGTAKYSQNFQGRVAITADESTGTASMELSSLRSEDTAVYYCARSRDLLLF<br>PHHALSPWGRGTMVTVSSLGGGSGASTKGPSVFPLAPSSKSTSGGTAALGCLVKD<br>YFPEPVTVSWNSGALTSGVHTFPAVLQSSGLYSLSSVVTVPSSSLGTQTYICNVNH<br>KPSNTKVDKRVEPKSCDKTHTCPPCPAPEAAGGPSVFLEPPKPKDTLYITREPEVT<br>CVVVDVSHEDPEVKFNWYVDGVEVHNAKTKPREEQYNSTYRVVSVLTVLHQD<br>WLNGKEYKCKVSNKALPAPIEKTISKAKGQPREPQVYTLPPSREEMTKNQVSLTC<br>LVKGFYPSDIAVEWESNGQPENNYKTTPPVLDSDGSFFLYSKLTVDKSRWQQGN<br>VFSCSVMHEALHNHYTQKSLSLSPG |
| 8 | SSELTQDPAVSVALGQTVRVTCQGDSLRSYYASWYQQKPGQAPVLVIYGKNNRP<br>SGIPDRFSGSSSGNTASLTITGAQAEDEADYYCSSRDSSGNHWVFGGGTELTVLG<br>GGSGGGGQVQLVQSGAEVKKPGSSVKVSCKASGYTFTDQTIHWMRQAPGQGLE<br>WIGYIYPRDDSPKYNENFKGKVTITADKSTSTAYMELSSLRSEDTAVYYCAIPDRS<br>GYAWFIYWGQGTLVTVSSLGGGSGRTVAAPSVFIFPPSDEQLKSGTASVVCLLNN<br>FYPREAKVQWKVDNALQSGNSQESVTEQDSKDSTYSLSSTLTLSKADYEKHKVY<br>ACEVTHQGLSSPVTKSFNRGEC |
| 9 | SSELTQDPAVSVALGQTVRVTCQGDSLRSYYASWYQQKPGQAPVLVIYGKNNRP<br>SGTPDRFSGSSSGNTASLTITGAQAEDEADYYCSSRDSSGNHWVFGGGTELTVLG<br>GGSGGGGQVQLVQSGAEVKKPGSSVKVSCKASGYTFTDQTIHWMRQAPGQGLE<br>WIGYIYPRDDSPKYNENFKGKVTITADKSTSTAYMELSSLRSEDTAVYYCAIPDRS<br>GYAWFIYWGQGTLVTVSSGGCGGGEVAACEKEVAALEKEVAALEKEVAALEKL<br>EPKSSDKTHTCPPCPAPEAAGGPSVFLEPPKPKDTLYITREPEVTCVVVDVSHEDP<br>EVKFNWYVDGVEVHNAKTKPREEQYNSTYRVVSVLTVLHQDWLNGKEYKCKV<br>SNKALPAPIEKTISKAKGQPREPQVYTLPPSREEMTKNQVSLTCLVKGFYPSDIAV<br>EWESNGQPENNYKTTPPVLDSDGSFFLYSKLTVDKSRWQQGNVFSCSVMHEALH<br>NHYTQKSLSLSPG |
| 10 | DIQMTQSPSSLSASVGDRVTITCKASRDVAIAVAWYQQKPGKVPKLLIYWASTRH<br>TGVPSRFSGSGSRTDFTLTISSLQPEDVADYFCHQYSSYPFTFGSGTKLEIKGGGSG<br>GGGQVQLQQSGAEVKKPGSSVRVSCKASGGTENNNATNWVRQAPGQGLEWMG<br>GIIPMFGTAKYSQNFQGRVAITADESTGTASMELSSLRSEDTAVYYCARSRDLLLF<br>PHHALSPWGRGTMVTVSSGGCGGGKVAACEKEVAALKEKVAALEKEVAALKE |
| 11 | DIQMTQSPSSLSASVGDRVTITCKASRDVAIAVAWYQQKPGKVPKLLIYWASTRH<br>TGVPSRFSGSGSRTDFTLTISSLQPEDVADYFCHQYSSYPFTEGSGTKLEIKGGGSG<br>GGGQVQLQQSGAEVKKPGSSVRVSCKASGGTFNNNAINWVRQAPGQGLEWMG<br>GIIPMFGTAKYSQNFQGRVAITADESTGTASMELSSLRSEDTAVYYCARSRDLLLF<br>PHHALSPWGRGTMVTVSSGGCGGGEVAACEKEVAALEKEVAALEKEVAALEKL<br>EPKSSDKTHTCPPCPAPEAAGGPSVFLFPPKPKDTLYTTREPEVTCVVVDVSHEDP<br>EVKFNWYVDGVEVHNAKTKPREPQYNSTYRVVSVLTVLHQDWLNGKEYKCKV<br>SNKALPAPIEKTISKAKGQPREPQVYTLPPSREEMTKNQVSLTCLVKGFYPSDIAV<br>EWESNGQPENNYKTTPPVLDSDGSFFLYSKLTVDKSRWQQGNVFSCSVMHEALH<br>NHYTQKSLSLSPG |
| 12 | SSELTQDPAVSVALGQTVRVTCQGDSLRSYYASWYQQKPGQAPVLVIYGKNNRP<br>SGIPDRFSGSSSGNTASLTITGAQAEDEADYYCSSRDSSGNHWVFGGGTELTVLG<br>GGSGGGGQVQLVQSGAEVKKPGSSVKVSCKASGYTFTDQTIHWMRQAPGQGLE<br>WIGYIYPRDDSPKYNENFKGKVTITADKSTSTAYMELSSLRSEDTAVYYCAIPDRS<br>GYAWFIYWGQGTLVTVSSGGCGGGKVAACEKEVAALKEKVAALKEKVAALKE |
| 13 | SSELTQDPAVSVALGQTVRVTCQGDSLRSYYASWYQQKPGQAPVLVIYGKNNRP<br>SGIPDRFSGSSSGNTASLTITGAQAEDEADYYCSSRDSSGNHWVFGGGTELTVLG<br>GGSGGGGQVQLVQSGAEVKKPGSSVKVSCKASGYTFTDQTIHWMRQAPGQGLE<br>WIGYIYPRDDSPKYNENFKGKVTITADKSTSTAYMELSSLRSEDTAVYYCAIPDRS<br>GYAWFIYWGQGTLVTVSSLGGGSGASTKGPSVFPLAPCSRSTSESTAALGCLVKD<br>YFPEPVTVSWNSGALTSGVHTFPAVLQSSGLYSLSSVVTVPSSSLGTKTYTCNVD<br>HKPSNTKVDKRVESKYGPPCPPCPAPEFLGGPSVFLFPPKPKDTLYITREPEVTCV<br>VVDVSQEDPEVQFNWYVDGVEVHNAKTKPREEQFNSTYRVVSVLTVLHQDWLN<br>GKEYKCKVSNKGLPSSTEKTTSKAKGQPREPQVYTLPPSQEEMTKNQVSLTCLVK<br>GFYPSDIAVEWESNGQPENNYKTTPPVLDSDGSFFLYSRLTVDKSRWQEGNVFSC<br>SVMHEALHNHYTQKSLSLSLG |

| SEQ ID NO | Sequence |
|---|---|
| 14 | DIQMTQSPSSLSASVGDRVTITCKASRDVAIAVAWYQQKPGKVPKLLIYWASTRH TGVPSRFSGSGSRTDFTLTISSLQPEDVADYFCHQYSSYPFTFGSGTKLEIKGGGSG GGGQVQLQQSGAEVKKPGSSVRVSCKASGGTFNNNAINWVRQAPGQGLEWMG GIIPMFGTAKYSQNFQGRVAITADESTGTASMELSSLRSEDTAVYYCARSRDLLLF PHHALSPWGRGTMVTVSSLGGGSGRTVAAPSVFIFPPSDEQLKSGTASVVCLLNN FYPREAKVQWKVDNALQSGNSQESVTEQDSKDSTYSLSSTLTLSKADYEKHKVY ACEVTHQGLSSPVTKSFNRGEC |
| 15 | DIQMTQSPSSLSASVGDRVTITCKASRDVAIAVAWYQQKPGKVPKLLIYWASTRH TGVPSRFSGSGSRTDFTLTISSLQPEDVADYFCHQYSSYPFTFGSGTKLEIKGGGSG GGGQVQLQQSGAEVKKPGSSVRVSCKASGGTFNNNAINWVRQAPGQGLEWMG GIIPMFGTAKYSQNFQGRVAITADESTGTASMELSSLRSEDTAVYYCARSRDLLLF PHHALSPWGRGTMVTVSSLGGGSGASTKGPSVFPLAPCSRSTSESTAALGCLVKD YFPEPVTVSWNSGALTSGVHTFPAVLQSSGLYSLSSVVTVPSSSLGTKTYTCNVD HKPSNTKVDKRVESKYGPPCPPCPAPEFLGGPSVFLFPPKPKDTLYITREPEVTCV VVDVSQEDPEVQFNWYVDGVEVHNAKTKPREEQFNSTYRVVSVLTVLHQDWLN GKEYKCKVSNKGLPSSIEKTISKAKGQPREPQVYTLPPSQEEMTKNQVSLTCLVK GFYPSDTAVEWESNGQPENNYKTTPPVLDSDGSFFLYSRLTVDKSRWQEGNVFSC SVMHEALHNHYTQKSLSLSLG |
| 16 | SSELTQDPAVSVALGQTVRVTCQGDSLRSYYASWYQQKPGQAPVLVIYGKNNRP SGIPDRFSGSSSGNTASLTITGAQAEDEADYYCSSRDSSGNHWVFGGGTELTVLG GGSGGGGQVQLVQSGAEVKKPGSSVKVSCKASGYTFTDQTIHWMRQAPGQGLE WIGYIYPRDDSPKYNENFKGKVTITADKSTSTAYMELSSLRSEDTAVYYCAIPDRS GYAWFIYWGQGTLVTVSSLGGGSGRTVAAPSVFIFPPSDEQLKSGTASVVCLLNN FYPREAKVQWKVDNALQSGNSQESVTEQDSKDSTYSLSSTLTLSKADYEKHKVY ACEVTHQGLSSPVTKSFNRGEC |
| 17 | SSELTQDPAVSVALGQTVRVTCQGDSLRSYYASWYQQKPGQAPVLVIYGKNNRP SGIPDRFSGSSSGNTASLTITGAQAEDEADYYCSSRDSSGNHWVFGGGTELTVLG GGSGGGGQVQLVQSGAEVKKPGSSVKVSCKASGYTFTDQTIHWMRQAPGQGLE WIGYIYPRDDSPKYNENFKGKVTITADKSTSTAYMELSSLRSEDTAVYYCAIPDRS GYAWFIYWGQGTLVTVSSGGCGGGEVAACEKEVAALEKEVAALEKEVAALEKE SKYGPPCPPCPAPEFLGGPSVFLFPPKPKDTLYITREPEVTCVVVDVSQEDPEVQFN WYVDGVEVHNAKTKPREEQFNSTYRVVSVLTVLHQDWLNGKEYKCKVSNKGL PSSIEKTISKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEALHNHYTQ KSLSLSLG |
| 18 | DIQMTQSPSSLSASVGDRVTITCKASRDVAIAVAWYQQKPGKVPKLLIYWASTRH TGVPSRFSGSGSRTDFTLTISSLQPEDVADYFCHQYSSYPFTFGSGTKLEIKGGGSG GGGQVQLQQSGAEVKKPGSSVRVSCKASGGTFNNNAINWVRQAPGQGLEWMG GIIPMFGTAKYSQNFQGRVAITADESTGTASMELSSLRSEDTAVYYCARSRDLLLF PHHALSPWGRGTMVTVSSGGCGGGKVAACEKEVAALKEKVAALKEKVAALKE |
| 19 | DIQMTQSPSSLSASVGDRVTITCKASRDVAIAVAWYQQKPGKVPKLLIYWASTRH TGVPSRFSGSGSRTDFTLTISSLQPEDVADYFCHQYSSYPFTFGSGTKLEIKGGGSG GGGQVQLQQSGAEVKKPGSSVRVSCKASGGTFNNNAINWVRQAPGQGLEWMG GIIPMFGTAKYSQNFQGRVAITADESTGTASMELSSLRSEDTAVYYCARSRDLLLF PHHALSPWGRGTMVTVSSGGCGGGEVAACEKEVAALEKEVAALEKEVAALEKE SKYGPPCPPCPAPEFLGGPSVFLFPPKPKDTLYITREPEVTCVVVDVSQEDPEVQFN WYVDGVEVHNAKTKPREEQFNSTYRVVSVLTVLHQDWLNGKEYKCKVSNKGL PSSIEKTISKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEALHNHYTQ KSLSLSLG |
| 20 | SSELTQDPAVSVALGQTVRVTCQGDSLRSYYASWYQQKPGQAPVLVIYGKNNRP SGIPDRFSGSSSGNTASLTITGAQAEDEADYYCSSRDSSGNHWVFGGGTELTVLG GGSGGGGQVQLVQSGAEVKKPGSSVKVSCKASGYTFTDQTIHWMRQAPGQGLE WIGYIYPRDDSPKYNENFKGKVTITADKSTSTAYMELSSLRSEDTAVYYCATPDRS GYAWFIYWGQGTLVTVSSGGCGGGKVAACEKEVAALKEKVAALKEKVAALKE |
| 21 | DIQMTQSPSSLSASVGDRVTITCKASRDVAIAVAWYQQKPGKVPKLLIYWASTRH TGVPSRFSGSGSRTDFTLTISSLQPEDVADYFCHQYSSYPFTFGSGTKLEIKGGGSG GGGQVQLVQSGAEVKKPGSSVKVSCKAPDHIFSIHWMQWVRQAPGQGLEWMG EIFPGSGTTDYNEKFKGKVTITVDKSTSTAYMELSSLRSEDTAVYYCASGAFDYW GQGTTVTVSSLGGGSGASTKGPSVFPLAPSSKSTSGGTAALGCLVKDYFPEPVTVS WNSGALTSGVHTFPAVLQSSGLYSLSSVVTVPSSSLGTQTYICNVNHKPSNTKVD KRVEPKSCDKTHTCPPCPAPEAAGGPSVFLFPPKPKDTLYITREPEVTCVVVDVSH EDPEVKFNWYVDGVEVHNAKTKPREEQYNSTYRVVSVLTVLHQDWLNGKEYK CKVSNKALPAPIEKTISKAKGQPREPQVYTLPPSREEMTKNQVSLTCLVKGFYPSD IAVEWESNGQPENNYKTTPPVLDSDGSFFLYSKLTVDKSRWQQGNVFSCSVMHE ALHNHYTQKSLSLSPG |

| SEQ ID NO | Sequence |
|---|---|
| 22 | DIQMTQSPSSLSASVGDRVTITCRASQDIGNRLSWLQQEPGKAPKRLIYATSSLDS GVPSRFSGSRSGTEFTLTISSLQPEDFVTYYCLQYASSPFTFGQGTKLEIKGGGSGG GGGQVQLVQSGAEVKKPGSSVKVSCKASGYTFTDQTIHWMRQAPGQGLEWIGYIY PRDDSPKYNENFKGKVTITADKSTSTAYMELSSLRSEDTAVYYCAIPDRSGYAWF IYWGQGTLVTVSSLGGGSGRTVAAPSVFIFPPSDEQLKSGTASVVCLLNNFYPREA KVQWKVDNALQSGNSQESVTEQDSKDSTYSLSSTLTLSKADYEKHKVYACEVTH QGLSSPVTKSFNRGEC |
| 23 | DIQMTQSPSSLSASVGDRVTITCKASRDVAIAVAWYQQKPGKVPKLLIYWASTRH TGVPSRFSGSGSRTDFTLTISSLQPEDVADYFCHQYSSYPFTFGSGTKLEIKGGGSG GGGQVQLVQSGAEVKKPGSSVKVSCKAPDHIFSIHWMQWVRQAPGQGLEWMG EIFPGSGTTDYNEKFKGKVTITVDKSTSTAYMELSSLRSEDTAVYYCASGAFDYW GQGTTVTVSSGGCGGGEVAACEKEVAALEKEVAALEKEVAALEKLEPKSSDKTH TCPPCPAPEAAGGPSVFLFPPKPKDTLYITREPEVTCVVVDVSHEDPEVKFNWYV DGVEVHNAKTKPREEQYNSTYRVVSVLTVLHQDWLNGKEYKCKVSNKALPAPI EKTISKAKGQPREPQVYTLPPSREEMTKNQVSLTCLVKGFYPSDIAVEWESNGQP ENNYKTTPPVLDSDGSFFLYSKLTVDKSRWQQGNVFSCSVMHEALHNHYTQKSL SLSPG |
| 24 | DIQMTQSPSSLSASVGDRVTITCRASQDIGNRLSWLQQEPGKAPKRLIYATSSLDS GVPSRFSGSRSGTEFTLTISSLQPEDFVTYYCLQYASSPFTFGQGTKLEIKGGGSGG GGGQVQLVQSGAEVKKPGSSVKVSCKASGYTFTDQTIHWMRQAPGQGLEWIGYIY PRDDSPKYNENFKGKVTITADKSTSTAYMELSSLRSEDTAVYYCAIPDRSGYAWF IYWGQGTLVTVSSGGCGGGKVAACKEKVAALKEKVAALKEKVAALKE |
| 25 | DIQMTQSPSSLSASVGDRVTITCKASRDVAIAVAWYQQKPGKVPKLLIYWASTRH TGVPSRFSGSGSRTDFTLTISSLQPEDVADYFCHQYSSYPFTFGSGTKLEIKGGGSG GGGQVQLVQSGAEVKKPGSSVKVSCKAPDHIFSTHWMQWVRQAPGQGLEWMG EIFPGSGTTDYNEKFKGKVTITVDKSTSTAYMELSSLRSEDTAVYYCASGAFDYW GQGTTVTVSSLGGGSGASTKGPSVFPLAPCSRSTSESTAALGCLVKDYFPEPVTVS WNSGALTSGVHTFPAVLQSSGLYSLSSVVTVPSSSLGTKTYTCNVDHKPSNTKVD KRVESKYGPPCPPCPAPEFLGGPSVFLFPPKPKDTLYITREPEVTCVVVDVSQEDPE VQFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIAVE WESNGQPENNYKTTPPVLDSDGSFFLYSRLTVDKSRWQEGNVFSCSVMHEALHN HYTQKSLSLSLG |
| 26 | DIQMTQSPSSLSASVGDRVTITCRASQDIGNRLSWLQQEPGKAPKRLIYATSSLDS GVPSRFSGSRSGTEFTLTISSLQPEDFVTYYCLQYASSPFTFGQGTKLEIKGGGSGG GGGQVQLVQSGAEVKKPGSSVKVSCKASGYTFTDQTIHWMRQAPGQGLEWIGYIY PRDDSPKYNENFKGKVTITADKSTSTAYMELSSLRSEDTAVYYCAIPDRSGYAWF IYWGQGTLVTVSSLGGGSGRTVAAPSVFIFPPSDEQLKSGTASVVCLLNNFYPREA KVQWKVDNALQSGNSQESVTEQDSKDSTYSLSSTLTLSKADYEKHKVYACEVTH QGLSSPVTKSFNRGEC |
| 27 | DIQMTQSPSSLSASVGDRVTITCKASRDVAIAVAWYQQKPGKVPKLLIYWASTRH TGVPSRFSGSGSRTDFTLTISSLQPEDVADYFCHQYSSYPFTFGSGTKLEIKGGGSG GGGQVQLVQSGAEVKKPGSSVKVSCKAPDHIFSIHWMQWVRQAPGQGLEWMG EIFPGSGTTDYNEKFKGKVTITVDKSTSTAYMELSSLRSEDTAVYYCASGAFDYW GQGTTVTVSSGGCGGGEVAACEKEVAALEKEVAALEKEVAALEKESKYGPPCPP CPAPEFLGGPSVFLFPPKPKDTLYITREPEVTCVVVDVSQEDPEVQFNWYVDGVE VHNAKTKPREEQFNSTYRVVSVLTVLHQDWLNGKEYKCKVSNKGLPSSIEKTISK AKGQPREPQVYTLPPSQEEMTKNQVSLTCLVKGFYPSDIAVEWESNGQPENNYK TTPPVLDSDGSFFALYSRLTVDKSRWQEGNVFSCSVMHEALHNHYTQKSLSLSLG |
| 28 | DIQMTQSPSSLSASVGDRVTITCRASQDIGNRLSWLQQEPGKAPKRLIYATSSLDS GVPSRFSGSRSGTEFTLTISSLQPEDFVTYYCLQYASSPFTFGQGTKLEIKGGGSGG GGGQVQLVQSGAEVKKPGSSVKVSCKASGYTFTDQTIHWMRQAPGQGLEWIGYIY PRDDSPKYNENFKGKVTITADKSTSTAYMELSSLRSEDTAVYYCAIPDRSGYAWF TYWGQGTLVTVSSGGCGGGKVAACKEKVAALKEKVAALKEKVAALKE |
| 29 | DIQMTQSPSSLSASVGDRVTITCKASRDVAIAVAWYQQKPGKVPKLLIYWASTRH TGVPSRFSGSGSRTDFTLTISSLQPEDVADYFCHQYSSYPFTFGSGTKLEIKGGGSG GGGQVQLVQSGAEVKKPGSSVKVSCKAPDHIFSIHWMQWVRQAPGQGLEWMG EIFPGSGTTDYNEKFKGKVTITVDKSTSTAYMELSSLRSEDTAVYYCASGAFDYW GQGTTVTVSSLGGGSGASTKGPSVFPLAPSSKSTSGGTAALGCLVKDYFPEPVTVS WNSGALTSGVHTFPAVLQSSGLYSLSSVVTVPSSSLGTQTYICNVNHKPSNTKVD KRVEPKSCDKTHTCPPCPAPEAAGGPSVFLFPPKPKDTLYITREPEVTCVVVDVSH EDPEVKFNWYVDGVEVHNAKTKPREEQYNSTYRVVSVLTVLHQDWLNGKEYK CKVSNKALPAPIEKTISKAKGQPREPQVYTLPPSREEMTKNQVSLTCLVKGFYPSD IAVEWESNGQPENNYKTTPPVLDSDGSFFLYSKLTVDKSRWQQGNVFSCSVMHE ALHNHYTQKSLSLSPG |

-continued

SEQUENCES

| SEQ ID NO | Sequence |
|---|---|
| 30 | DIQMTQSPSSLSASVGDRVTITCRASQDIGNRLNWYQQKPGKAPKRLIYATSSLDS<br>GVPSRFSGSRSGTEFTLTISSLQPEDFVTYYCLQYASSPFTFGQGTKLEIKGGGSGG<br>GGGVQLVQSGAEVKKPGSSVKVSCKASGYTFTDQTIHWMRQAPGQGLEWIGYIY<br>PRDDSPKYNENFKGKVTITADKSTSTAYMELSSLRSEDTAVYYCAIPDRSGYAWF<br>IYWGQGTLVTVSSLGGGSGRTVAAPSVFIFPPSDEQLKSGTASVVCLLNNFYPREA<br>KVQWKVDNALQSGNSQESVTEQDSKDSTYSLSSTLTLSKADYEKHKVYACEVTH<br>QGLSSPVTKSFNRGEC |
| 31 | DIQMTQSPSSLSASVGDRVTITCKASRDVAIAVAWYQQKPGKVPKLLIYWASTRH<br>TGVPSRFSGSGSRTDFTLTISSLQPEDVADYFCHQYSSYPFTFGSGTKLEIKGGGSG<br>GGGGQVQLVQSGAEVKKPGSSVKVSCKAPDHIFSIHWMQWVRQAPGQGLEWMG<br>EIFPGSGTTDYNEKFKGKVTITVDKSTSTAYMELSSLRSEDTAVYYCASGAFDYW<br>GQGTTVTVSSGCGGGEVAACEKEVAALEKEVAALEKEVAALEKLEPKSSDKTH<br>TCPPCPAPEAAGGPSVFLFPPKPKDTLYITREPEVTCVVVDVSHEDPEVKFNWYV<br>DGVEVHNAKTKPREEQYNSTYRVVSVLTVLHQDWLNGKEYKCKVSNKALPAPI<br>EKTISKAKGQPREPQVYTLPPSREEMTKNQVSLTCLVKGFYPSDTAVEWESNGQP<br>ENNYKTTPPVLDSDGSFFLYSKLTVDKSRWQQGNVFSCSVMHEALHNHYTQKSL<br>SLSPG |
| 32 | DIQMTQSPSSLSASVGDRVTITCRASQDIGNRLNWYQQKPGKAPKRLIYATSSLDS<br>GVPSRFSGSRSGTEFTLTISSLQPEDFVTYYCLQYASSPFTFGQGTKLEIKGGGSGG<br>GGGVQLVQSGAEVKKPGSSVKVSCKASGYTFTDQTIHWMRQAPGQGLEWIGYIY<br>PRDDSPKYNENFKGKVTITADKSTSTAYMELSSLRSEDTAVYYCAIPDRSGYAWF<br>IYWGQGTLVTVSSGGCGGGKVAACKEKVAALKEKVAALKEKVAALKE |
| 33 | DIQMTQSPSSLSASVGDRVTITCKASRDVAIAVAWYQQKPGKVPKLLIYWASTRH<br>TGVPSRFSGSGSRTDFTLTISSLQPEDVADYFCHQYSSYPFTFGSGTKLEIKGGGSG<br>GGGGQVQLVQSGAEVKKPGSSVKVSCKAPDHIFSIHWMQWVRQAPGQGLEWMG<br>EIFPGSGTTDYNEKFKGKVTITVDKSTSTAYMELSSLRSEDTAVYYCASGAFDYW<br>GQGTTVTVSSLGGGSGASTKGPSVFPLAPCSRSTSESTAALGCLVKDYFPEPVTVS<br>WNSGALTSGVHTFPAVLQSSGLYSLSSVVTVPSSSLGTKTYTCNVDHKPSNTKVD<br>KRVESKYGPPCPPCPAPEFLGGPSVFLFPPKPKDTLYITREPEVTCVVVDVSQEDPE<br>VQFNWYVDGVEVHNAKTKPREEQFNSTYRVVSVLTVLHQDWLNGKEYKCKVS<br>NKGLPSSIEKTISKAKGQPREPQVYTLPPSQEEMTKNQVSLTCLVKGFYPSDIAVE<br>WESNGQPENNYKTTPPVLDSDGSFFLYSRLTVDKSRWQEGNVFSCSVMHEALHN<br>HYTQKSLSLSLG |
| 34 | DTQMTQSPSSLSASVGDRVTITCRASQDIGNRLNWYQQKPGKAPKRLIYATSSLDS<br>GVPSRFSGSRSGTEFTLTISSLQPEDFVTYYCLQYASSPFTFGQGTKLEIKGGGSGG<br>GGGVQLVQSGAEVKKPGSSVKVSCKASGYTFTDQTIHWMRQAPGQGLEWIGYIY<br>PRDDSPKYNENFKGKVTITADKSTSTAYMELSSLRSEDTAVYYCAIPDRSGYAWF<br>IYWGQGTLVTVSSLGGGSGRTVAAPSVFIFPPSDEQLKSGTASVVCLLNNFYPREA<br>KVQWKVDNALQSGNSQESVTEQDSKDSTYSLSSTLTLSKADYEKHKVYACEVTH<br>QGLSSPVTKSFNRGEC |
| 35 | DIQMTQSPSSLSASVGDRVTITCKASRDVAIAVAWYQQKPGKVPKLLIYWASTRH<br>TGVPSRFSGSGSRTDFTLTISSLQPEDVADYFCHQYSSYPFTFGSGTKLEIKGGGSG<br>GGGGQVQLVQSGAEVKKPGSSVKVSCKAPDHIFSIHWMQWVRQAPGQGLEWMG<br>EIFPGSGTTDYNEKFKGKVTITVDKSTSTAYMELSSLRSEDTAVYYCASGAFDYW<br>GQGTTVTVSSGGCGGGEVAACEKEVAALEKEVAALEKEVAALEKESKYGPPCPP<br>CPAPEFLGGPSVFLFPPKPKDTLYITREPEVTCVVVDVSQEDPEVQFNWYVDGVE<br>VHNAKTKPREEQFNSTYRVVSVLTVLHQDWLNGKEYKCKVSNKGLPSSIEKTISK<br>AKGQPREPQVYTLPPSQEEMTKNQVSLTCLVKGFYPSDIAVEWESNGQPENNYK<br>TTPPVLDSDGSFFLYSRLTVDKSRWQEGNVFSCSVMHEALHNHYTQKSLSLSLG |
| 36 | DIQMTQSPSSLSASVGDRVTITCRASQDIGNRLNWYQQKPGKAPKRLIYATSSLDS<br>GVPSRFSGSRSGTEFTLTISSLQPEDFVTYYCLQYASSPFTFGQGTKLEIKGGGSGG<br>GGGVQLVQSGAEVKKPGSSVKVSCKASGYTFTDQTTHWMRQAPGQGLEWTGYTY<br>PRDDSPKYNENFKGKVTITADKSTSTAYMELSSLRSEDTAVYYCAIPDRSGYAWF<br>IYWGQGTLVTVSSGGCGGGKVAACKEKVAALKEKVAALKEKVAALKE |
| 37 | DIQMTQSPSSLSASVGDRVTITCKASRDVAIAVAWYQQKPGKVPKLLIYWASTRH<br>TGVPSRFSGSGSRTDFTLTISSLQPEDVADYFCHQYSSYPFTFGSGTKLEIKGGGSG<br>GGGGQVQLVQSGAEVKKPGASVKVSCKASGYSFSTFFIHWVRQRPGQGLEWIGRI<br>DPNSGATKYNEKFESKVTLTRDTSISTAYMELSRLRSDDTAVYYCARGEDLLIRT<br>DALDYWGQGTSVTVSSLGGGSGASTKGPSVFPLAPSSKSTSGGTAALGCLVKDY<br>FPEPVTVSWNSGALTSGVHTFPAVLQSSGLYSLSSVVTVPSSSLGTQTYICNVNHK<br>PSNTKVDKRVEPKSCDKTHTCPPCPAPEAAGGPSVFLFPPKPKDTLYITREPEVTC<br>VVVDVSHEDPEVKFNWYVDGVEVHNAKTKPREEQYNSTYRVVSVLTVLHQDW<br>LNGKEYKCKVSNKALPAPTEKTISKAKGQPREPQVYTLPPSREEMTKNQVSLTCL<br>VKGFYPSDIAVEWESNGQPENNYKTTPPVLDSDGSFFLYSKLTVDKSRWQQGNV<br>FSCSVMHEALHNHYTQKSLSLSPG |

SEQUENCES

| SEQ ID NO | Sequence |
| --- | --- |
| 38 | DIQMTQSPSSLSASVGDRVSITCKASQNAGIDVAWFQQKPGKAPKLLIYSKSNRY<br>TGVPSRFSGSGSGTDFTLTISSLQPEDFADYYCLQYRSYPRTFGGGTKLEIKGGGS<br>GGGGQVQLVQSGAEVKKPGSSVKVSCKASGYTFTDQTIHWMRQAPGQGLEWIG<br>YIYPRDDSPKYNENFKGKVTITADKSTSTAYMELSSLRSEDTAVYYCAIPDRSGY<br>AWFIYWGQGTLVTVSSLGGGSGRTVAAPSVFIFPPSDEQLKSGTASVVCLLNNFY<br>PREAKVQWKVDNALQSGNSQESVTEQDSKDSTYSLSSTLTLSKADYEKHKVYAC<br>EVTHQGLSSPVTKSFNRGEC |
| 39 | DIQMTQSPSSLSASVGDRVTITCKASRDVAIAVAWYQQKPGKVPKLLIYWASTRH<br>TGVPSRFSGSGSRTDFTLTISSLQPEDVADYFCHQYSSYPFTFGSGTKLEIKGGGSG<br>GGGGQVQLVQSGAEVKKPGASVKVSCKASGYSFSTFFIHWVRQRPGQGLEWIGRI<br>DPNSGATKYNEKFESKVTLTRDTSISTAYMELSRLRSDDTAVYYCARGEDLLIRT<br>DALDYWGQGTSVTVSSGGCGGGEVAACEKEVAALEKEVAALEKEVAALEKLEP<br>KSSDKTHTCPPCPAPEAAGGPSVFLFPPKPKDTLYITREPEVTCVVVDVSHEDPEV<br>KFNWYVDGVEVHNAKTKPREEQYNSTYRVVSVLTVLHQDWLNGKEYKCKVSN<br>KALPAPIEKTISKAKGQPREPQVYTLPPSREEMTKNQVSLTCLVKGFYPSDIAVEW<br>ESNGQPENNYKTTPPVLDSDGSFFLYSKLTVDKSRWQQGNVFSCSVMHEALHNH<br>YTQKSLSLSPG |
| 40 | DIQMTQSPSSLSASVGDRVSITCKASQNAGIDVAWFQQKPGKAPKLLIYSKSNRY<br>TGVPSRFSGSGSGTDFTLTISSLQPEDFADYYCLQYRSYPRTFGGGTKLEIKGGGS<br>GGGGQVQLVQSGAEVKKPGSSVKVSCKASGYTFTDQTIHWMRQAPGQGLEWIG<br>YIYPRDDSPKYNENFKGKVTITADKSTSTAYMELSSLRSEDTAVYYCAIPDRSGY<br>AWFIYWGQGTLVTVSSGGCGGGKVAACKEKVAALKEKVAALKEKVAALKE |
| 41 | DIQMTQSPSSLSASVGDRVTITCKASRDVAIAVAWYQQKPGKVPKLLIYWASTRH<br>TGVPSRFSGSGSRTDFTLTISSLQPEDVADYFCHQYSSYPFTEGSGTKLEIKGGGSG<br>GGGGQVQLVQSGAEVKKPGASVKVSCKASGYSFSTFFIHWVRQRPGQGLEWIGRI<br>DPNSGATKYNEKFESKVTLTRDTSISTAYMELSRLRSDDTAVYYCARGEDLLIRT<br>DALDYWGQGTSVTVSSLGGGSGASTKGPSVFPLAPCSRSTSESTAALGCLVKDYF<br>PEPVTVSWNSGALTSGVHTFPAVLQSSGLYSLSSVVTVPSSSLGTKTYTCNVDHK<br>PSNTKVDKRVESKYGPPCPPCPAPEFLGGPSVFLFPPKPKDTLYITREPEVTCVVV<br>DVSQEDPEVQFNWYVDGVEVHNAKTKPREEQFNSTYRVVSVLTVLHQDWLNGK<br>EYKCKVSNKGLPSSIEKTISKAKGQPREPQVYTLPPSQEEMTKNQVSLTCLVKGFY<br>PSDIAVEWESNGQPENNYKTTPPVLDSDGSFFLYSRLTVDKSRWQEGNVFSCSVM<br>HEALHNHYTQKSLSLSLG |
| 42 | DIQMTQSPSSLSASVGDRVSITCKASQNAGIDVAWFQQKPGKAPKLLIYSKSNRY<br>TGVPSRFSGSGSGTDFTLTISSLQPEDFADYYCLQYRSYPRTFGGGTKLEIKGGGS<br>GGGGQVQLVQSGAEVKKPGSSVKVSCKASGYTFTDQTIHWMRQAPGQGLEWIG<br>YIYPRDDSPKYNENFKGKVTITADKSTSTAYMELSSLRSEDTAVYYCAIPDRSGY<br>AWFIYWGQGTLVTVSSLGGGSGRTVAAPSVFIFPPSDEQLKSGTASVVCLLNNFY<br>PREAKVQWKVDNALQSGNSQESVTEQDSKDSTYSLSSTLTLSKADYEKHKVYAC<br>EVTHQGLSSPVTKSFNRGEC |
| 43 | DIQMTQSPSSLSASVGDRVTITCKASRDVAIAVAWYQQKPGKVPKLLIYWASTRH<br>TGVPSRFSGSGSRTDFTLTISSLQPEDVADYFCHQYSSYPFTEGSGTKLEIKGGGSG<br>GGGGQVQLVQSGAEVKKPGASVKVSCKASGYSFSTFFTHWVRQRPGQGLEWTGRI<br>DPNSGATKYNEKFESKVTLTRDTSISTAYMELSRLRSDDTAVYYCARGEDLLIRT<br>DALDYWGQGTSVTVSSGGCGGGEVAACEKEVAALEKLVAALLKEVAALEKESK<br>YGPPCPPCPAPEFLGGPSVFLFPPKPKDTLYITREPEVTCVVVDVSQEDPEVQFNW<br>YVDGVEVHNAKTKPREEQFNSTYRVVSVLTVLHQDWLNGKEYKCKVSNKGLPS<br>SIEKTISKAKGQPREPQVYTLPPSQEEMTKNQVSLTCLVKGFYPSDIAVEWESNGQ<br>PENNYKTTPPVLDSDGSFFLYSRLTVDKSRWQEGNVFSCSVMHEALHNHYTQKS<br>LSLSLG |
| 44 | DIQMTQSPSSLSASVGDRVSITCKASQNAGIDVAWFQQKPGKAPKLLIYSKSNRY<br>TGVPSRFSGSGSGTDFTLTISSLQPEDFADYYCLQYRSYPRTFGGGTKLEIKGGGS<br>GGGGQVQLVQSGAEVKKPGSSVKVSCKASGYTFTDQTIHWMRQAPGQGLEWIG<br>YIYPRDDSPKYNENFKGKVTITADKSTSTAYMELSSLRSEDTAVYYCAIPDRSGY<br>AWFIYWGQGTLVTVSSGGCGGGKVAACKEKVAALKEKVAALKEKVAALKE |
| 45 | DIQMTQSPSSLSASVGDRVTITCKASRDVAIAVAWYQQKPGKVPKLLIYWASTRH<br>TGVPSRFSGSGSRTDFTLTISSLQPEDVADYFCHQYSSYPFTFGSGTKLEIKGGGSG<br>GGGGQVQLVQSGAEVKKPGASVKVSCKASGYSFSTFFIHWVRQAPGQGLEWIGRI<br>DPNSGATKYNEKFESRVTMTRDTSISTAYMELSRLRSDDTAVYYCARGEDLLIRT<br>DALDYWGQGTSVTVSSLGGGSGASTKGPSVFPLAPSSKSTSGGTAALGCLVKDY<br>FPEPVTVSWNSGALTSGVHTFPAVLQSSGLYSLSSVVTVPSSSLGTQTYTCNVNHK<br>PSNTKVDKRVEPKSCDKTHTCPPCPAPEAAGGPSVFLFPPKPKDTLYITREPEVTC<br>VVVDVSHEDPEVKIANWYVDGVEVHNAKTKPREEQYNSTYRVVSVLTVLHQDW<br>LNGKEYKCKVSNKALPAPIEKTISKAKGQPREPQVYTLPPSREEMTKNQVSLTCL<br>VKGFYPSDIAVEWESNGQPENNYKTTPPVLDSDGSFFLYSKLTVDKSRWQQGNV<br>FSCSVMHEALHNHYTQKSLSLSPG |

| SEQ ID NO | Sequence |
|---|---|
| 46 | DIQMTQSPSSLSASVGDRVSITCKASQNAGIDVAWFQQKPGKAPKLLIYSKSNRY TGVPSRFSGSGSGTDFTLTISSLQPEDFATYYCLQYRSYPRTFGQGTKLEIKGGGSG GGGQVQLVQSGAEVKKPGSSVKVSCKASGYTFTDQTIHWMRQAPGQGLEWIGYI YPRDDSPKYNENFKGKVTITADKSTSTAYMELSSLRSEDTAVYYCAIPDRSGYAW FIYWGQGTLVTVSSLGGGSGRTVAAPSVFIFPPSDEQLKSGTASVVCLLNNFYPRE AKVQWKVDNALQSGNSQESVTEQDSKDSTYSLSSTLTLSKADYEKHKVYACEVT HQGLSSPVTKSFNRGEC |
| 47 | DIQMTQSPSSLSASVGDRVTITCKASRDVAIAVAWYQQKPGKVPKLLIYWASTRH TGVPSRFSGSGSRTDFTLTISSLQPEDVADYFCHQYSSYPFTFGSGTKLEIKGGGSG GGGQVQLVQSGAEVKKPGASVKVSCKASGYSFSTFFIHWVRQAPGQGLEWIGRI DPNSGATKYNEKFESRVTMTRDTSISTAYMELSRLRSDDTAVYYCARGEDLLIRT DALDYWGQGTSVTVSSGGCGGGEVAACEKEVAALEKEVAALEKEVAALEKLEP KSSDKTHTCPPCPAPEAAGGPSVFLFPPKPKDTLYITREPEVTCVVVDVSHEDPEV KFNWYVDGVEVHNAKTKPREEQYNSTYRVVSVLTVLHQDWLNGKEYKCKVSN KALPAPIEKTISKAKGQPREPQVYTLPPSREEMTKNQVSLTCLVKGFYPSDIAVEW ESNGQPENNYKTTPPVLDSDGSFFLYSKLTVDKSRWQQGNVFSCSVMHEALHNH YTQKSLSLSPG |
| 48 | DIQMTQSPSSLSASVGDRVSITCKASQNAGIDVAWFQQKPGKAPKLLIYSKSNRY TGVPSRFSGSGSGTDFTLTISSLQPEDFATYYCLQYRSYPRTFGQGTKLEIKGGGSG GGGQVQLVQSGAEVKKPGSSVKVSCKASGYTFTDQTIHWMRQAPGQGLEWIGYI YPRDDSPKYNENFKGKVTITADKSTSTAYMELSSLRSEDTAVYYCAIPDRSGYAW FIYWGQGTLVTVSSGGCGGGKVAACKEKVAALKEKVAALKEKVAALKE |
| 49 | DIQMTQSPSSLSASVGDRVTITCKASRDVAIAVAWYQQKPGKVPKLLIYWASTRH TGVPSRFSGSGSRTDFTLTISSLQPEDVADYFCHQYSSYPFTFGSGTKLEIKGGGSG GGGQVQLVQSGAEVKKPGASVKVSCKASGYSFSTFFIHWVRQAPGQGLEWIGRI DPNSGATKYNEKFESRVTMTRDTSISTAYMELSRLRSDDTAVYYCARGEDLLIRT DALDYWGQGTSVTVSSLGGGSGASTKGPSVFPLAPCSRSTSESTAALGCLVKDYF PEPVTVSWNSGALTSGVHTFPAVLQSSGLYSLSSVVTVPSSSLGTKTYTCNVDHK PSNTKVDKRVESKYGPPCPPCPAPEFLGGPSVFLFPPKPKDTLYITREPEVTCVVV DVSQEDPEVQFNWYVDGVEVHNAKTKPREEQFNSTYRVVSVLTVLHQDWLNGK EYKCKVSNKGLPSSIEKTISKAKGQPREPQVYTLPPSQEEMTKNQVSLTCLVKGFY PSDIAVEWESNGQPENNYKTTPPVLDSDGSFFLYSRLTVDKSRWQEGNVFSCSVM HEALHNHYTQKSLSLSLG |
| 50 | DIQMTQSPSSLSASVGDRVSITCKASQNAGIDVAWFQQKPGKAPKLLIYSKSNRY TGVPSRFSGSGSGTDFTLTISSLQPEDFATYYCLQYRSYPRTFGQGTKLEIKGGGSG GGGQVQLVQSGAEVKKPGSSVKVSCKASGYTFTDQTIHWMRQAPGQGLEWIGYI YPRDDSPKYNENFKGKVTITADKSTSTAYMELSSLRSEDTAVYYCAIPDRSGYAW FIYWGQGTLVTVSSLGGGSGRTVAAPSVFIFPPSDEQLKSGTASVVCLLNNFYPRE AKVQWKVDNALQSGNSQESVTEQDSKDSTYSLSSTLTLSKADYEKHKVYACEVT HQGLSSPVTKSFNRGEC |
| 51 | DIQMTQSPSSLSASVGDRVTITCKASRDVAIAVAWYQQKPGKVPKLLIYWASTRH TGVPSRFSGSGSRTDFTLTISSLQPEDVADYFCHQYSSYPFTFGSGTKLEIKGGGSG GGGQVQLVQSGAEVKKPGASVKVSCKASGYSFSTFFIHWVRQAPGQGLEWIGRI DPNSGATKYNEKFESRVTMTRDTSISTAYMELSRLRSDDTAVYYCARGEDLLIRT DALDYWGQGTSVTVSSGGCGGGEVAACEKEVAALEKEVAALEKEVAALEKESK YGPPCPPCPAPEFLGGPSVFLFPPKPKDTLYITREPEVTCVVVDVSQEDPEVQFNW YVDGVEVHNAKTKPREEQFNSTYRVVSVLTVLHQDWLNGKEYKCKVSNKGLPS SIEKTISKAKGQPREPQVYTLPPSQEEMTKNQVSLTCLVKGFYPSDIAVEWESNGQ PENNYKTTPPVLDSDGSFFLYSRLTVDKSRWQEGNVFSCSVMHEALHNHYTQKS LSLSLG |
| 52 | DIQMTQSPSSLSASVGDRVSITCKASQNAGTDVAWFQQKPGKAPKLLTYSKSNRY TGVPSRFSGSGSGTDFTLTISSLQPEDFATYYCLQYRSYPRTFGQGTKLEIKGGGSG GGGQVQLVQSGAEVKKPGSSVKVSCKASGYTFTDQTIHWMRQAPGQGLEWIGYI YPRDDSPKYNENFKGKVTITADKSTSTAYMELSSLRSEDTAVYYCAIPDRSGYAW FIYWGQGTLVTVSSGGCGGGKVAACKEKVAALKEKVAALKEKVAALKE |
| 53 | DIQMTQSPSSLSASVGDRVTITCRASQDIGNRLSWLQQEPGKAPKRLIYATSSLDS GVPSRFSGSRSGTEFTLTISSLQPEDFVTYYCLQYASSPFTFGQGTKLEIKGGGSGG GGQVQLVQSGAEVKKPGSSVKVSCKASGYTFTDQTIHWMRQAPGQGLEWIGYIY PRDDSPKYNENFKGKVTITADKSTSTAYMELSSLRSEDTAVYYCAIPDRSGYAWF IYWGQGTLVTVSSLGGGSGASTKGPSVFPLAPSSKSTSGGTAALGCLVKDYFPEP VTVSWNSGALTSGVHTFPAVLQSSGLYSLSSVVTVPSSSLGTQTYICNVNHKPSNT KVDKRVEPKSCDKTHTCPPCPAPEAAGGPSVFLFPPKPKDTLYITREPEVTCVVVD VSHEDPEVKFNWYVDGVEVHNAKTKPREEQYNSTYRVVSVLTVLHQDWLNGK EYKCKVSNKALPAPIEKTISKAKGQPREPQVYTLPPSREEMTKNQVSLTCLVKGF YPSDIAVEWESNGQPENNYKTTPPVLDSDGSFELYSKLTVDKSRWQQGNVESCSV MHEALHNHYTQKSLSLSPG |

| SEQ ID NO | Sequence |
|---|---|
| 54 | DIQMTQSPSSLSASVGDRVTITCKASRDVAIAVAWYQQKPGKVPKLLIYWASTRH TGVPSRFSGSGSRTDFTLTISSLQPEDVADYFCHQYSSYPFTFGSGTKLEIKGGGSG GGGQVQLVQSGAEVKKPGSSVKVSCKAPDHIFSTHWMQWVRQAPGQGLEWMG EIFPGSGTTDYNEKFKGKVTITVDKSTSTAYMELSSLRSEDTAVYYCASGAFDYW GQGTTVTVSSLGGGSGRTVAAPSVFIFPPSDEQLKSGTASVVCLLNNFYPREAKV QWKVDNALQSGNSQESVTEQDSKDSTYSLSSTLTLSKADYEKHKVYACEVTHQG LSSPVTKSFNRGEC |
| 55 | DIQMTQSPSSLSASVGDRVTITCRASQDIGNRLSWLQQEPGKAPKRLIYATSSLDS GVPSRFSGSRSGTEFTLTISSLQPEDFVTYYCLQYASSPFTFGQGTKLEIKGGGSGG GGGQVQLVQSGAEVKKPGSSVKVSCKASGYTFTDQTIHWMRQAPGQGLEWIGYIY PRDDSPKYNENFKGKVTITADKSTSTAYMELSSLRSEDTAVYYCAIPDRSGYAWF IYWGQGTLVTVSSLGGGSGASTKGPSVFPLAPCSRSTSESTAALGCLVKDYFPEPV TVSWNSGALTSGVHTFPAVLQSSGLYSLSSVVTVPSSSLGTKTYTCNVDHKPSNT KVDKRVESKYGPPCPPCPAPEFLGGPSVFLFPPKPKDTLYTTREPEVTCVVVDVSQ EDPEVQFNWYVDGVEVHNAKTKPREEQFNSTYRVVSVLTVLHQDWLNGKEYKC KVSNKGLPSSIEKTISKAKGQPREPQVYTLPPSQEEMTKNQVSLTCLVKGEYPSDI AVEWESNGQPENNYKTTPPVLDSDGSFFLYSRLTVDKSRWQEGNVFSCSVMHEA LHNHYTQKSLSLSLG |
| 56 | DIQMTQSPSSLSASVGDRVTITCKASRDVAIAVAWYQQKPGKVPKLLIYWASTRH TGVPSRFSGSGSRTDFTLTISSLQPEDVADYFCHQYSSYPFTFGSGTKLEIKGGGSG GGGQVQLVQSGAEVKKPGSSVKVSCKAPDHIFSIHWMQWVRQAPGQGLEWMG EIFPGSGTTDYNEKFKGKVTITVDKSTSTAYMELSSLRSEDTAVYYCASGAFDYW GQGTTVTVSSLGGGSGRTVAAPSVFIFPPSDEQLKSGTASVVCLLNNFYPREAKV QWKVDNALQSGNSQESVTEQDSKDSTYSLSSTLTLSKADYEKHKVYACEVTHQG LSSPVTKSFNRGEC |
| 57 | DIQMTQSPSSLSASVGDRVTITCRASQDIGNRLNWYQQKPGKAPKRLIYATSSLDS GVPSRFSGSRSGTEFTLTISSLQPEDFVTYYCLQYASSPFTFGQGTKLEIKGGGSGG GGGQVQLVQSGAEVKKPGSSVKVSCKASGYTFTDQTIHWMRQAPGQGLEWIGYIY PRDDSPKYNENFKGKVTITADKSTSTAYMELSSLRSEDTAVYYCAIPDRSGYAWF IYWGQGTLVTVSSLGGGSGASTKGPSVFPLAPSSKSTSGGTAALGCLVKDYFPEP VTVSWNSGALTSGVHTFPAVLQSSGLYSLSSVVTVPSSSLGTQTYICNVNHKPSNT KVDKRVEPKSCDKTHTCPPCPAPEAAGGPSVFLFPPKPKDTLYITREPEVTCVVVD VSHEDPEVKFNWYVDGVEVHNAKTKPREEQYNSTYRVVSVLTVLHQDWLNGK EYKCKVSNKALPAPIEKTISKAKGQPREPQVYTLPPSREEMTKNQVSLTCLVKGF YPSDIAVEWESNGQPENNYKTTPPVLDSDGSFFLYSKLTVDKSRWQQGNVFSCSV MHEALHNHYTQKSLSLSPG |
| 58 | DIQMTQSPSSLSASVGDRVTITCKASRDVAIAVAWYQQKPGKVPKLLIYWASTRH TGVPSRFSGSGSRTDFTLTISSLQPEDVADYFCHQYSSYPFTFGSGTKLEIKGGGSG GGGQVQLVQSGAEVKKPGSSVKVSCKAPDHIFSIHWMQWVRQAPGQGLEWMG ETFPGSGTTDYNEKFKGKVTITVDKSTSTAYMELSSLRSEDTAVYYCASGAFDYW GQGTTVTVSSLGGGSGRTVAAPSVFIFPPSDEQLKSGTASVVCLLNNFYPREAKV QWKVDNALQSGNSQESVTEQDSKDSTYSLSSTLTLSKADYEKHKVYACEVTHQG LSSPVTKSFNRGEC |
| 59 | DIQMTQSPSSLSASVGDRVTITCRASQDIGNRLNWYQQKPGKAPKRLIYATSSLDS GVPSRFSGSRSGTEFTLTISSLQPEDFVTYYCLQYASSPFTFGQGTKLEIKGGGSGG GGGQVQLVQSGAEVKKPGSSVKVSCKASGYTFTDQTIHWMRQAPGQGLEWIGYIY PRDDSPKYNENFKGKVTITADKSTSTAYMELSSLRSEDTAVYYCAIPDRSGYAWF IYWGQGTLVTVSSLGGGSGASTKGPSVFPLAPCSRSTSESTAALGCLVKDYFPEPV TVSWNSGALTSGVHTFPAVLQSSGLYSLSSVVTVPSSSLGTKTYTCNVDHKPSNT KVDKRVESKYGPPCPPCPAPEFLGGPSVFLFPPKPKDTLYITREPEVTCVVVDVSQ EDPEVQFNWYVDGVEVHNAKTKPREEQFNSTYRVVSVLTVLHQDWLNGKEYKC KVSNKGLPSSIEKTISKAKGQPREPQVYTLPPSQEEMTKNQVSLTCLVKGFYPSDI AVEWESNGQPENNYKTTPPVLDSDGSFELYSRLTVDKSRWQEGNVFSCSVMHEA LHNHYTQKSLSLSLG |
| 60 | DIQMTQSPSSLSASVGDRVTITCKASRDVAIAVAWYQQKPGKVPKLLIYWASTRH TGVPSRFSGSGSRTDFTLTISSLQPEDVADYFCHQYSSYPFTFGSGTKLEIKGGGSG GGGQVQLVQSGAEVKKPGSSVKVSCKAPDHIFSIHWMQWVRQAPGQGLEWMG EIFPGSGTTDYNEKFKGKVTITVDKSTSTAYMELSSLRSEDTAVYYCASGAFDYW GQGTTVTVSSLGGGSGRTVAAPSVFTFPPSDEQLKSGTASVVCLLNNFYPREAKV QWKVDNALQSGNSQESVTEQDSKDSTYSLSSTLTLSKADYEKHKVYACEVTHQG LSSPVTKSFNRGEC |
| 61 | DIQMTQSPSSLSASVGDRVSITCKASQNAGIDVAWFQQKPGKAPKLLIYSKSNRY TGVPSRFSGSGSTDFTLTISSLQPEDFADYCLQYRSYPRTFGGGTKLEIKGGGS GGGGQVQLVQSGAEVKKPGSSVKVSCKASGYTFTDQTIHWMRQAPGQGLEWIG YIYPRDDSPKYNENFKGKVTITADKSTSTAYMELSSLRSEDTAVYYCAIPDRSGY AWFIYWGQGTLVTVSSLGGGSGASTKGPSVFPLAPSSKSTSGGTAALGCLVKDYF |

| SEQ ID NO | Sequence |
|---|---|
| | PEPVTVSWNSGALTSGVHTFPAVLQSSGLYSLSSVVTVPSSSLGTQTYICNVNHKP SNTKVDKRVEPKSCDKTHTCPPCPAPEAAGGPSVFLFPPKPKDTLYITREPEVTCV VVDVSHEDPEVKFNWYVDGVEVHNAKTKPREEQYNSTYRVVSVLTVLHQDWL NGKEYKCKVSNKALPAPIEKTISKAKGQPREPQVYTLPPSREEMTKNQVSLTCLV KGFYPSDIAVEWESNGQPENNYKTTPPVLDSDGSFFLYSKLTVDKSRWQQGNVFS CSVMHEALHNHYTQKSLSLSPG |
| 62 | DIQMTQSPSSLSASVGDRVTITCKASRDVAIAVAWYQQKPGKVPKLLIYWASTRH TGVPSRFSGSGSRTDFTLTISSLQPEDVADYFCHQYSSYPFTFGSGTKLEIKGGGSG GGGQVQLVQSGAEVKKPGASVKVSCKASGYSFSTFFIHWVRQRPGQGLEWIGRI DPNSGATKYNEKFESKVTLTRDTSISTAYMELSRLRSDDTAVYYCARGEDLLIRT DALDYWGQGTSVTVSSLGGGSGRTVAAPSVFTFPPSDEQLKSGTASVVCLLNNFY PREAKVQWKVDNALQSGNSQESVTEQDSKDSTYSLSSTLTLSKADYEKHKVYAC EVTHQGLSSPVTKSFNRGEC |
| 63 | DIQMTQSPSSLSASVGDRVSITCKASQNAGIDVAWFQQKPGKAPKLLIYSKSNRY TGVPSRFSGSGSGTDFTLTISSLQPEDFADYYCLQYRSYPTFGGGTKLEIKGGGS GGGGQVQLVQSGAEVKKPGSSVKVSCKASGYTFTDQTIHWMRQAPGQGLEWIG YIYPRDDSPKYNENFKGKVTITADKSTSTAYMELSSLRSEDTAVYYCAIPDRSGY AWFIYWGQGTLVTVSSLGGGSGASTKGPSVFPLAPCSRSTSESTAALGCLVKDYF PEPVTVSWNSGALTSGVHTFPAVLQSSGLYSLSSVVTVPSSSLGTKTYTCNVDHK PSNTKVDKRVESKYGPPCPPCPAPEFLGGPSVFLFPPKPKDTLYITREPEVTCVVV DVSQEDPEVQFNWYVDGVEVHNAKTKPREEQFNSTYRVVSVLTVLHQDWLNGK EYKCKVSNKGLPSSTEKTTSKAKGQPREPQVYTLPPSQEEMTKNQVSLTCLVKGFY PSDIAVEWESNGQPENNYKTTPPVLDSDGSFFLYSRLTVDKSRWQEGNVFSCSVM HEALHNHYTQKSLSLSLG |
| 64 | DIQMTQSPSSLSASVGDRVTITCKASRDVAIAVAWYQQKPGKVPKLLIYWASTRH TGVPSRFSGSGSRTDFTLTISSLQPEDVADYFCHQYSSYPFTFGSGTKLEIKGGGS GGGGQVQLVQSGAEVKKPGASVKVSCKASGYSFSTFFIHWVRQRPGQGLEWIGRI DPNSGATKYNEKFESKVTLTRDTSISTAYMELSRLRSDDTAVYYCARGEDLLIRT DALDYWGQGTSVTVSSLGGGSGRTVAAPSVFIFPPSDEQLKSGTASVVCLLNNFY PREAKVQWKVDNALQSGNSQESVTEQDSKDSTYSLSSTLTLSKADYEKHKVYAC EVTHQGLSSPVTKSFNRGEC |
| 65 | DIQMTQSPSSLSASVGDRVSITCKASQNAGIDVAWFQQKPGKAPKLLIYSKSNRY TGVPSRFSGSGSGTDFTLTISSLQPEDFATYYCLQYRSYPRTFGQGTKLEIKGGGS GGGGQVQLVQSGAEVKKPGSSVKVSCKASGYTFTDQTIHWMRQAPGQGLEWIGYI YPRDDSPKYNENFKGKVTITADKSTSTAYMELSSLRSEDTAVYYCAIPDRSGYAW FIYWGQGTLVTVSSLGGGSGASTKGPSVFPLAPSSKSTSGGTAALGCLVKDYFPEP VTVSWNSGALTSGVHTFPAVLQSSGLYSLSSVVTVPSSSLGTQTYICNVNHKPSNT KVDKRVEPKSCDKTHTCPPCPAPEAAGGPSVFLFPPKPKDTLYITREPEVTCVVVD VSHEDPEVKFNWYVDGVEVHNAKTKPREEQYNSTYRVVSVLTVLHQDWLNGK EYKCKVSNKALPAPIEKTISKAKGQPREPQVYTLPPSREEMTKNQVSLTCLVKGF YPSDIAVEWESNGQPENNYKTTPPVLDSDGSFFLYSKLTVDKSRWQQGNVFSCSV MHEALHNHYTQKSLSLSPG |
| 66 | DIQMTQSPSSLSASVGDRVTITCKASRDVAIAVAWYQQKPGKVPKLLIYWASTRH TGVPSRFSGSGSRTDFTLTISSLQPEDVADYFCHQYSSYPFTFGSGTKLEIKGGGSG GGGQVQLVQSGAEVKKPGASVKVSCKASGYSFSTFFIHWVRQAPGQGLEWIGRI DPNSGATKYNEKFESRVTMTRDTSISTAYMELSRLRSDDTAVYYCARGEDLLIRT DALDYWGQGTSVTVSSLGGGSGRTVAAPSVFIFPPSDEQLKSGTASVVCLLNNFY PREAKVQWKVDNALQSGNSQESVTEQDSKDSTYSLSSTLTLSKADYEKHKVYAC EVTHQGLSSPVTKSFNRGEC |
| 67 | DIQMTQSPSSLSASVGDRVSITCKASQNAGIDVAWFQQKPGKAPKLLIYSKSNRY TGVPSRFSGSGSGTDFTLTISSLQPEDFATYYCLQYRSYPRTFGQGTKLEIKGGGSG GGGQVQLVQSGAEVKKPGSSVKVSCKASGYTFTDQTIHWMRQAPGQGLEWIGYI YPRDDSPKYNENFKGKVTITADKSTSTAYMELSRLRSEDTAVYYCAIPDRSGYAW FIYWGQGTLVTVSSLGGGSGASTKGPSVFPLAPCSRSTSESTAALGCLVKDYFPEP VTVSWNSGALTSGVHTFPAVLQSSGLYSLSSVVTVPSSSLGTKTYTCNVDHKPSN TKVDKRVESKYGPPCPPCPAPEFLGGPSVFLFPPKPKDTLYITREPEVTCVVVDVS QEDPEVQFNWYVDGVEVHNAKTKPREEQFNSTYRVVSVLTVLHQDWLNGKEY KCKVSNKGLPSSIEKTISKAKGQPREPQVYTLPPSQEEMTKNQVSLTCLVKGFYPS DTAVEWESNGQPENNYKTTPPVLDSDGSFFLYSRLTVDKSRWQEGNVFSCSVMH EALHNHYTQKSLSLSLG |
| 68 | DIQMTQSPSSLSASVGDRVTITCKASRDVAIAVAWYQQKPGKVPKLLIYWASTRH TGVPSRFSGSGSRTDFTLTISSLQPEDVADYFCHQYSSYPFTFGSGTKLEIKGGGSG GGGQVQLVQSGAEVKKPGASVKVSCKASGYSFSTFFIHWVRQAPGQGLEWIGRI DPNSGATKYNEKFESRVTMTRDTSISTAYMELSRLRSDDTAVYYCARGEDLLIRT DALDYWGQGTSVTVSSLGGGSGRTVAAPSVFIFPPSDEQLKSGTASVVCLLNNFY PREAKVQWKVDNALQSGNSQESVTEQDSKDSTYSLSSTLTLSKADYEKHKVYAC EVTHQGLSSPVTKSFNRGEC |

| SEQ ID NO | Sequence |
|---|---|
| 69 | GGGSGGGG |
| 70 | LGGGSG |
| 71 | FNRGEC |
| 72 | VEPKSC |
| 73 | ASTKGPSVFPLAPCSRSTSESTAALGCLVKDYFPEPVTVSWNSGALTSGVHTFPAV<br>LQSSGLYSLSSVVTVPSSSLGTKTYTCNVDHKPSNTKVDKRVESKYGPPCPPCPAP<br>EFLGGPSVFLFPPKPKDTLMISRTPEVTCVVVDVSQEDPEVQFNWYVDGVEVHNA<br>KTKPREEQFNSTYRVVSVLTVLHQDWLNGKEYKCKVSNKGLPSSIEKTISKAKGQ<br>PREPQVYTLPPSQEEMTKNQVSLTCLVKGFYPSDIAVEWESNGQPENNYKTTPPV<br>LDSDGSFFLYSRLTVDKSRWQEGNVFSCSVMHEALHNHYTQKSLSLSLG |
| 74 | ASTKGPSVFPLAPCSRSTSESTAALGCLVKDYFPEPVTVSWNSGALTSGVHTFPAV<br>LQSSGLYSLSSVVTVPSSSLGTKTYTCNVDHKPSNTKVDKRVESKYGPPCPPCPAP<br>EFLGGPSVFLFPPKPKDTLYITREPEVTCVVVDVSQEDPEVQFNWYVDGVEVHNA<br>KTKPREEQFNSTYRVVSVLTVLHQDWLNGKEYKCKVSNKGLPSSIEKTISKAKGQ<br>PREPQVYTLPPSQEEMTKNQVSLTCLVKGFYPSDIAVEWESNGQPENNYKTTPPV<br>LDSDGSFFLYSRLTVDKSRWQEGNVFSCSVMHEALHNHYTQKSLSLSLG |
| 75 | ASTKGPSVFPLAPSSKSTSGGTAALGCLVKDYFPEPVTVSWNSGALTSGVHTFPA<br>VLQSSGLYSLSSVVTVPSSSLGTQTYICNVNHKPSNTKVDKRVEPKSCDKTHTCPP<br>CPAPELLGGPSVFLFPPKPKDTLMISRTPEVTCVVVDVSHEDPEVKFNWYVDGVE<br>VHNAKTKPREEQYNSTYRVVSVLTVLHQDWLNGKEYKCKVSNKALPAPIEKTIS<br>KAKGQPREPQVYTLPPSREEMTKNQVSLTCLVKGFYPSDIAVEWESNGQPENNY<br>KTTPPVLDSDGSFFLYSKLTVDKSRWQQGNVFSCSVMHEALHNHYTQKSLSLSP<br>G |
| 76 | EPKSCDKTHTCPPCP |
| 77 | RTVAAPSVFIFPPSDEQLKSGTASVVCLLNNFYPREAKVQWKVDNALQSGNSQES<br>VTEQDSKDSTYSLSSTLTLSKADYEKHKVYACEVTHQGLSSPVTKSFNRGEC |
| 78 | ASTKGPSVFPLAPSSKSTSGGTAALGCLVKDYFPEPVTVSWNSGALTSGVHTFPA<br>VLQSSGLYSLSSVVTVPSSSLGTQTYICNVNHKPSNTKVDKRVEPKSCDKTHTCPP<br>CPAPEAAGGPSVFLFPPKPKDTLYITREPEVTCVVVDVSHEDPEVKFNWYVDGVE<br>VHNAKTKPREEQYNSTYRVVSVLTVLHQDWLNGKEYKCKVSNKALPAPIEKTIS<br>KAKGQPREPQVYTLPPSREEMTKNQVSLTCLVKGFYPSDIAVEWESNGQPENNY<br>KTTPPVLDSDGSFFLYSKLTVDKSRWQQGNVFSCSVMHEALHNHYTQKSLSLSP<br>GK |
| 79 | ASTKGPSVFPLAPSSKSTSGGTAALGCLVKDYFPEPVTVSWNSGALTSGVHTFPA<br>VLQSSGLYSLSSVVTVPSSSLGTQTYICNVNHKPSNTKVDKRVEPKSCDKTHTCPP<br>CPAPEAAGGPSVFLFPPKPKDTLMISRTPEVTCVVVDVSHEDPEVKFNWYVDGVE<br>VHNAKTKPREEQYNSTYRVVSVLTVLHQDWLNGKEYKCKVSNKALPAPTEKTTS<br>KAKGQPREPQVYTLPPSREEMTKNQVSLTCLVKGFYPSDIAVEWESNGQPENNY<br>KTTPPVLDSDGSFFLYSKETVDKSRWQQGNVFSCSVMHEALHNHYTQKSLSLSP<br>G |
| 80 | MDDSTEREQSRLTSCLKKREEMKLKECVSILPRKESPSVRSSKDGKLLAATLLLAL<br>LSCCLTVVSFYQVAALQGDLASLRAELQGHHAEKLPAGAGAPKAGLEEAPAVTA<br>GLKIFEPPAPGEGNSSQNSRNKRAVQGPEETVTQDCLQLIADSETPTIQKGSYTFVP<br>WLLSFKRGSALEEKENKILVKETGYFFIYGQVLYTDKTYAMGHLIQRKKVHVFG<br>DELSLVTLFRCIQNMPETLPNNSCYSAGIAKLEEGDELQLAIPRENAQISLDGDVTF<br>FGALKLL |
| 81 | MLGSRAVMLLLLLPWTAQGRAVPGGSSPAWTQCQQLSQKLCTLAWSAHPLVGH<br>MDLREEGDEETTNDVPHIQCGDGCDPQGLRDNSQFCLQRIHQGLIFYEKLLGSDIF<br>TGEPSLLPDSPVGQLHASLLGLSQLLQPEGHHWETQQIPSLSPSQPWQRLLLRFKIL<br>RSLQAFVAVAARVFAHGAATLSP |
| 82 | GGCGGGEVAACEKEVAALEKEVAALEKEVAALEK |
| 83 | GGCGGGKVAACKEKVAALKEKVAALKEKVAALKE |
| 84 | QVQLVQSGAEVKKPGSSVKVSCKAPDHIFSIHWMQWVRQAPGQGLEWMGEIFP<br>GSGTTDYNEKFKGKVTITVDKSTSTAYMELSSLRSEDTAVYYCASGAFDYWGQG<br>TTVTVSS |
| 85 | DIQMTQSPSSLSASVGDRVTITCRASQDIGNRLSWLQQEPGKAPKRLIYATSSLDS<br>GVPSRFSGSRSGTEFTLTISSLQPEDFVTYYCLQYASSPFTFGQGTKLETK |

SEQUENCES

| SEQ ID NO | Sequence |
|---|---|
| 86 | QVQLVQSGAEVKKPGSSVKVSCKAPDHIFSIHWMQWVRQAPGQGLEWMGEIFPGSGTTDYNEKFKGKVTITVDKSTSTAYMELSSLRSEDTAVYYCASGAFDYWGQGTTVTVSS |
| 87 | DIQMTQSPSSLSASVGDRVTITCRASQDIGNRLNWYQQKPGKAPKRLIYATSSLDSGVPSRFSGSRSGTEFTLTISSLQPEDFVTYYCLQYASSPFTFGQGTKLEIK |
| 88 | QVQLVQSGAEVKKPGASVKVSCKASGYSFSTFFIHWVRQRPGQGLEWIGRIDPNSGATKYNEKFESKVTLTRDTSISTAYMELSRLRSDDTAVYYCARGEDLLIRTDALDYWGQGTSVTVSS |
| 89 | DIQMTQSPSSLSASVGDRVSITCKASQNAGIDVAWFQQKPGKAPKLLIYSKSNRYTGVPSRFSGSGSGTDFTLTISSLQPEDFADYYCLQYRSYPRTFGGGTKLEIK |
| 90 | QVQLVQSGAEVKKPGASVKVSCKASGYSFSTFFIHWVRQAPGQGLEWIGRIDPNSGATKYNEKFESRVTMTRDTSISTAYMELSRLRSDDTAVYYCARGEDLLIRTDALDYWGQGTSVTVSS |
| 91 | DIQMTQSPSSLSASVGDRVSITCKASQNAGIDVAWFQQKPGKAPKLLIYSKSNRYTGVPSRFSGSGSGTDFTLTISSLQPEDFATYYCLQYRSYPRTFGQGTKLEIK |
| 92 | GGTFNNNAIN |
| 93 | GIIPMFGTAKYSQNFQG |
| 94 | SRDLLLFPHHALSP |
| 95 | QGDSLRSYYAS |
| 96 | GKNNRPS |
| 97 | SSRDSSGNHWV |
| 98 | GYTFTDQTIH |
| 99 | YIYPRDDSPKYNENFKG |
| 100 | PDRSGYAWFIY |
| 101 | KASRDVAIAVA |
| 102 | WASTRHT |
| 103 | HQYSSYPFT |
| 104 | DHIFSIHWMQ |
| 105 | EIFPGSGTTDYNEKFKG |
| 106 | GAFDY |
| 107 | RASQDIGNRLS |
| 108 | ATSSLDS |
| 109 | LQYASSPFT |
| 110 | DHIFSIHWMQ |
| 111 | EIFPGSGTTDYNEKFKG |
| 112 | GAFDY |
| 113 | RASQDIGNRLN |
| 114 | ATSSLDS |
| 115 | GYSFSTFFIH |
| 116 | RIDPNSGATKYNEKFES |
| 117 | GEDLLIRTDALDY |

| SEQ ID NO | Sequence |
|---|---|
| 118 | KASQNAGIDVA |
| 119 | SKSNRYT |
| 120 | LQYRSYPRT |
| 121 | GYSFSTFFIH |
| 122 | GRIDPNSGATKYNEKFES |
| 123 | GEDLLIRTDALDY |
| 124 | KASQNAGTDVA |
| 125 | SKSNRYT |
| 126 | LQYRSYPRT |
| 127 | ESKYGPPCPPCPAPEFLGGPSVFLFPPKPKDTLYITREPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLG |
| 128 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPEAAGGPSVFLEPPKPKDTLYITREPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 129 | LEPKSSDKTHTCPPCPAPEAAGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 130 | LEPKSSDKTHTCPPCP |
| 131 | GCKWDLLIKQWVCDPLGSGSATGGSGSTASSGSGSATHMLPGCKWDLLIKQWVCDPLGGGGVDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 132 | QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARGYYDILTGYYYYFDYWGQGTLVTVSS |
| 133 | EIVLTQSPATLSLSPGERATLSCRASQSVSRYLAWYQQKPGQAPRLLIYDASNRATGIPARESGSGSGTDSTLTISSLEPEDEAVIYCQQRSNWPRTFAGQGTKVEIK |
| 134 | ESKYGPPCPPCP |
| 135 | GGCGGG |
| 136 | LGGCGGGS |

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

The invention claimed is:

1. A method of suppressing an inflammatory response in in a subject in need thereof comprising administering a compound comprising a first polypeptide and a second polypeptide, wherein:
  (A) said first polypeptide comprises:
    (i) a light chain variable domain of a first immunoglobulin (VL1) specific for a first target protein;
    (ii) a heavy chain variable domain of a second immunoglobulin (VH2) specific for a second target protein; and
    (iii) a hinge region, a heavy chain constant region 2 (CH2) and a heavy chain constant region 3 (CH3); and
  (B) said second polypeptide comprises:
    (i) a light chain variable domain of the second immunoglobulin (VL2) specific for said second target protein;
    (ii) a heavy chain variable domain of the first immunoglobulin (VH1) specific for said first target protein; wherein:
      a) said VL1 and VH1 associate to form a binding site that binds said first target protein;
      b) said VL2 and VH2 associate to form a binding site that binds said second target protein;
      c) said heavy chain constant region 2 (CH2) comprises a tyrosine at position 252, a threonine at position 254 and a glutamic acid a position 256, numbered according to the EU index as in Kabat for the CH2 of a conventional antibody; and
      d) said first target protein is B-cell activating factor ("BAFF") and said second target protein is Interleukin-23A ("IL-23A"); or
      e) said first target protein is IL-23A and said second target protein is BAFF, and
  wherein:
    (i) said VL1 comprises the amino acid sequence of SEQ ID NO:2, said VH1 comprises the amino acid sequence of SEQ ID NO:1, said VL2 comprises the amino acid sequence of SEQ ID NO:4 and said VH2 comprises the amino acid sequence of SEQ ID NO:3; or
    (ii) said VL1 comprises the amino acid sequence of SEQ ID NO:4, said VH1 comprises the amino acid sequence of SEQ ID NO:3, said VL2 comprises the amino acid sequence of SEQ ID NO:2 and said VH2 comprises the amino acid sequence of SEQ ID NO:1; or
    (iii) said VL1 comprises the amino acid sequence of SEQ ID NO:89, said VH1 comprises the amino acid sequence of SEQ ID NO:88, said VL2 comprises the amino acid sequence of SEQ ID NO:4 and said VH2 comprises the amino acid sequence of SEQ ID NO:3; or
    (iv) said VL1 comprises the amino acid sequence of SEQ ID NO:4, said VH1 comprises the amino acid sequence of SEQ ID NO:3, said VL2 comprises the amino acid sequence of SEQ ID NO:89 and said VH2 comprises the amino acid sequence of SEQ ID NO:88; or
    (v) said VL1 comprises the amino acid sequence of SEQ ID NO:91, said VH1 comprises the amino acid sequence of SEQ ID NO:90, said VL2 comprises the amino acid sequence of SEQ ID NO:4 and said VH2 comprises the amino acid sequence of SEQ ID NO:3; or
    (vi) said VL1 comprises the amino acid sequence of SEQ ID NO:4, said VH1 comprises the amino acid sequence of SEQ ID NO:3, said VL2 comprises the amino acid sequence of SEQ ID NO:91 and said VH2 comprises the amino acid sequence of SEQ ID NO:90.

2. The method according to claim 1, wherein said first polypeptide further comprises a first linker between said VL1 and said VH2 and said second polypeptide further comprises a second linker between said VL2 and said VH1.

3. The method according to claim 2, wherein said first linker or said second linker comprises the amino acid sequence of GGGSGGGG (SEQ ID NO:69).

4. The method according to claim 2, wherein said first linker and said second linker comprise the amino acid sequence of GGGSGGGG (SEQ ID NO:69).

5. The method according to claim 1, wherein said first polypeptide further comprises a heavy chain constant region 1 domain (CH1) and said second polypeptide further comprises a light chain constant region domain (CL), wherein said CL and said CH1 are associated together via a disulfide bond to form a CI domain.

6. The method according to claim 5, wherein said first polypeptide further comprises a third linker between said VH2 and said CH1 and said second polypeptide further comprises a fourth linker between said VH1 and said CL.

7. The method according to claim 6, wherein said third linker or said fourth linker comprises the amino acid sequence of LGGGSG (SEQ ID NO:70).

8. The method according to claim 6, wherein said third linker and said fourth linker comprise the amino acid sequence of LGGGSG (SEQ ID NO:70).

9. The method according to claim 1, wherein said heavy chain constant region 2 (CH2) comprises an alanine at positions 234 and an alanine at position 235, numbered according to the EU index as in Kabat for the CH2 of a conventional antibody.

10. The method according to claim 1, wherein the amino acid sequence of said hinge region, said heavy chain constant region 2 (CH2) or said heavy chain constant region 3 (CH3) is derived from an IgG1 or from an IgG4.

11. The method according to claim 1, wherein said hinge region comprises the amino acid sequence of EPKSCDKTHTCPPCP (SEQ ID NO:76), the amino acid sequence of LEPKSSDKTHTCPPCP (SEQ ID NO:130) or the amino acid sequence of ESKYGPPCPPCP (SEQ ID NO:134).

12. The method according to claim 1,
wherein:
(i) said first polypeptide comprises the amino acid sequence of SEQ ID NO:5 and said second polypeptide comprises the amino acid sequence of SEQ ID NO:6; or
(ii) said first polypeptide comprises the amino acid sequence of SEQ ID NO:7 and said second polypeptide comprises the amino acid sequence of SEQ ID NO:8; or
(iii) said first polypeptide comprises the amino acid sequence of SEQ ID NO:9 and said second polypeptide comprises the amino acid sequence of SEQ ID NO:10; or
(iv) said first polypeptide comprises the amino acid sequence of SEQ ID NO:11 and said second polypeptide comprises the amino acid sequence of SEQ ID NO:12; or
(v) said first polypeptide comprises the amino acid sequence of SEQ ID NO:13 and said second polypeptide comprises the amino acid sequence of SEQ ID NO:14; or
(vi) said first polypeptide comprises the amino acid sequence of SEQ ID NO:15 and said second polypeptide comprises the amino acid sequence of SEQ ID NO:16; or
(vii) said first polypeptide comprises the amino acid sequence of SEQ ID NO:17 and said second polypeptide comprises the amino acid sequence of SEQ ID NO:18; or
(viii) said first polypeptide comprises the amino acid sequence of SEQ ID NO:19 and said second polypeptide comprises the amino acid sequence of SEQ ID NO:20; or
(ix) said first polypeptide comprises the amino acid sequence of SEQ ID NO:37 and said second polypeptide comprises the amino acid sequence of SEQ ID NO:38; or
(x) said first polypeptide comprises the amino acid sequence of SEQ ID NO:39 and said second polypeptide comprises the amino acid sequence of SEQ ID NO:40; or
(xi) said first polypeptide comprises the amino acid sequence of SEQ ID NO:41 and said second polypeptide comprises the amino acid sequence of SEQ ID NO:42; or (xii) said first polypeptide comprises the amino acid sequence of SEQ ID NO:43 and said second polypeptide comprises the amino acid sequence of SEQ ID NO:44; or (xiii) said first polypeptide comprises the amino acid sequence of SEQ ID NO:45 and said second polypeptide comprises the amino acid sequence of SEQ ID NO:46; or (xiv) said first polypeptide comprises the amino acid sequence of SEQ ID NO:47 and said second polypeptide comprises the amino acid sequence of SEQ ID NO:48; or (xv) said first polypeptide comprises the amino acid sequence of SEQ ID NO:49 and said second polypeptide comprises the amino acid sequence of SEQ ID NO:50; or (xvi) said first polypeptide comprises the amino acid sequence of SEQ ID NO:51 and said second polypeptide comprises the amino acid sequence of SEQ ID NO:52; or (xvii) said first polypeptide comprises the amino acid sequence of SEQ ID NO:61 and said second polypeptide comprises the amino acid sequence of SEQ ID NO:62; or (xviii) said first polypeptide comprises the amino acid sequence of SEQ ID NO:63 and said second polypeptide comprises the amino acid sequence of SEQ ID NO:64; or (xix) said first polypeptide comprises the amino acid sequence of SEQ ID NO:65 and said second polypeptide comprises the amino acid sequence of SEQ ID NO:66; or
(xx) said first polypeptide comprises the amino acid sequence of SEQ ID NO:67 and said second polypeptide comprises the amino acid sequence of SEQ ID NO:68.

13. The method according to claim 1 wherein said compound comprises two first polypeptides and two second polypeptides; wherein said two first polypeptides are associated together via at least one disulfide bond and wherein each of said first polypeptide is associated to one said second polypeptide via at least one disulfide bond; wherein each of said first polypeptides comprises: (i) a light chain variable domain of a first immunoglobulin (VL1) specific for a first target protein; (ii) a heavy chain variable domain of a second immunoglobulin (VH2) specific for a second target protein; (iii) a heavy chain constant region 1 (CH1), a hinge region, a heavy chain constant region 2 (CH2) and a heavy chain constant region 3 (CH3); and wherein each of said second polypeptide comprises: (i) a light chain variable domain of the second immunoglobulin (VL2) specific for said second target protein; (ii) a heavy chain variable domain of the first immunoglobulin (VH1) specific for said first target protein; (iii) a light chain constant region domain (CL); wherein the hinge, CH2 and CH3 of one of the first polypeptides associates with the hinge, CH2 and CH3 of the other of the first polypeptides and the CH1 of each said first polypeptides associates with the CL of said each second polypeptides to form a tetravalent molecule; wherein a) said VL1 and VH1 associate to form a binding site that binds said first target protein; b) said VL2 and VH2 associate to form a binding site that binds said second target protein; c) said heavy chain constant region 2 (CH2) comprises a tyrosine at position 252, a threonine at position 254 and a glutamic acid a position 256, numbered according to the EU index as in Kabat for the CH2 of a conventional antibody; and d) said first target protein is B-cell activating factor ("BAFF") and said second target protein is Interleukin-23A ("IL-23") or said first target protein is IL-23A and said second target protein is BAFF, and wherein: (i) said VL1 comprises the amino acid sequence of SEQ ID NO:2, said VH1 comprises the amino acid sequence of SEQ ID NO:1, said VL2 comprises the amino acid sequence of SEQ ID NO:4 and said VH2 comprises the amino acid sequence of SEQ ID NO:3; or (ii) said VL1 comprises the amino acid sequence of SEQ ID NO:4, said VH1 comprises the amino acid sequence of SEQ ID NO:3, said VL2 comprises the amino acid sequence of SEQ ID NO:2 and said VH2 comprises the amino acid sequence of SEQ ID NO:1; or (iii) said VL1 comprises the amino acid sequence of SEQ ID NO:89, said VH1 comprises the amino acid sequence of SEQ ID NO:88, said VL2 comprises the amino acid sequence of SEQ ID NO:4 and said VH2 comprises the amino acid sequence of SEQ ID NO:3; or (iv) said VL1 comprises the amino acid sequence of SEQ ID NO:4, said VH1 comprises the amino acid sequence of SEQ ID NO:3, said VL2 comprises the amino acid sequence of SEQ ID NO:89 and said VH2 comprises the amino acid sequence of SEQ ID NO:88; or (v) said VL1 comprises the amino acid sequence of SEQ ID NO:91, said VH1 comprises the amino acid sequence of SEQ ID NO:90, said VL2 comprises the amino acid sequence of SEQ ID NO:4 and said VH2 comprises the amino acid sequence of SEQ ID NO:3; or (vi) said VL1 comprises the amino acid sequence of SEQ ID NO:4, said VH1 comprises the amino acid sequence of SEQ ID NO:3, said VL2 comprises the amino acid sequence of SEQ ID NO:91 and said VH2 comprises the amino acid sequence of SEQ ID NO:90.

14. A method of suppressing an inflammatory response in in a subject in need thereof according to claim 1, wherein the administered compound comprises a first polypeptide and a second polypeptide, wherein: (A) said first polypeptide comprises: (i) a light chain variable domain of a first immunoglobulin (VL1) specific for a first target protein; (ii) a heavy chain variable domain of a second immunoglobulin (VH2) specific for a second target protein; and (iii) a hinge region, a heavy chain constant region 2 (CH2) and a heavy chain constant region 3 (CH3); and (B) said second polypeptide comprises: (i) a light chain variable domain of the second immunoglobulin (VL2) specific for said second target protein; (ii) a heavy chain variable domain of the first immunoglobulin (VH1) specific for said first target protein; wherein: a) said VL1 and VH1 associate to form a binding site that binds said first target protein; b) said VL2 and VH2 associate to form a binding site that binds said second target protein; c) said heavy chain constant region 2 (CH2) comprises a tyrosine at position 252, a threonine at position 254 and a glutamic acid a position 256, numbered according to the EU index as in Kabat for the CH2 of a conventional antibody; and d) said first target protein is B-cell activating factor ("BAFF") and said second target protein is Interleukin-23A ("IL-23A") or said first target protein is IL-23A and said second target protein is BAFF, and wherein: (i) said first polypeptide comprises the amino acid sequence of SEQ ID NO:61 and said second polypeptide comprises the amino acid sequence of SEQ ID NO:62.

15. A method of suppressing an inflammatory response in in a subject in need thereof according to claim 1, wherein the administered compound comprises a first polypeptide and a second polypeptide, wherein: (A) said first polypeptide comprises: (i) a light chain variable domain of a first immunoglobulin (VL1) specific for a first target protein; (ii) a heavy chain variable domain of a second immunoglobulin (VH2) specific for a second target protein; and (iii) a hinge region, a heavy chain constant region 2 (CH2) and a heavy chain constant region 3 (CH3); and (B) said second polypeptide comprises: (i) a light chain variable domain of the second immunoglobulin (VL2) specific for said second target protein; (ii) a heavy chain variable domain of the first immunoglobulin (VH1) specific for said first target protein; wherein: a) said VL1 and VH1 associate to form a binding site that binds said first target protein; b) said VL2 and VH2 associate to form a binding site that binds said second target protein; c) said heavy chain constant region 2 (CH2) comprises a tyrosine at position 252, a threonine at position 254 and a glutamic acid a position 256, numbered according to the EU index as in Kabat for the CH2 of a conventional antibody; and d) said first target protein is B-cell activating factor ("BAFF") and said second target protein is Interleukin-23A ("IL-23A") or said first target protein is IL-23A and said second target protein is BAFF, and wherein: (i) said first polypeptide comprises the amino acid sequence of SEQ ID NO:49 and said second polypeptide comprises the amino acid sequence of SEQ ID NO:50.

16. A method of suppressing an inflammatory response in in a subject in need thereof according to claim 1, wherein the administered compound comprises a first polypeptide and a second polypeptide, wherein: (A) said first polypeptide comprises: (i) a light chain variable domain of a first immunoglobulin (VL1) specific for a first target protein; (ii) a heavy chain variable domain of a second immunoglobulin (VH2) specific for a second target protein; and (iii) a hinge region, a heavy chain constant region 2 (CH2) and a heavy chain constant region 3 (CH3); and (B) said second polypeptide comprises: (i) a light chain variable domain of the second immunoglobulin (VL2) specific for said second target protein; (ii) a heavy chain variable domain of the first immunoglobulin (VH1) specific for said first target protein; wherein: a) said VL1 and VH1 associate to form a binding site that binds said first target protein; b) said VL2 and VH2 associate to form a binding site that binds said second target protein; c) said heavy chain constant region 2 (CH2) comprises a tyrosine at position 252, a threonine at position 254 and a glutamic acid a position 256, numbered according to the EU index as in Kabat for the CH2 of a conventional antibody; and d) said first target protein is B-cell activating factor ("BAFF") and said second target protein is Interleukin-23A ("IL-23A") or said first target protein is IL-23A and said second target protein is BAFF, and wherein: (i) said VL1 comprises the amino acid sequence of SEQ ID NO:4, said VH1 comprises the amino acid sequence of SEQ ID NO:3, said VL2 comprises the amino acid sequence of SEQ ID NO:91 and said VH2 comprises the amino acid sequence of SEQ ID NO:90.

17. A method of suppressing an inflammatory response in in a subject in need thereof according to claim 1, wherein the administered compound comprises a first polypeptide and a second polypeptide, wherein: (A) said first polypeptide comprises: (i) a light chain variable domain of a first immunoglobulin (VL1) specific for a first target protein; (ii) a heavy chain variable domain of a second immunoglobulin (VH2) specific for a second target protein; and (iii) a hinge region, a heavy chain constant region 2 (CH2) and a heavy chain constant region 3 (CH3); and (B) said second polypeptide comprises: (i) a light chain variable domain of the second immunoglobulin (VL2) specific for said second target protein; (ii) a heavy chain variable domain of the first immunoglobulin (VH1) specific for said first target protein; wherein: a) said VL1 and VH1 associate to form a binding site that binds said first target protein; b) said VL2 and VH2 associate to form a binding site that binds said second target protein; c) said heavy chain constant region 2 (CH2) comprises a tyrosine at position 252, a threonine at position 254 and a glutamic acid a position 256, numbered according to the EU index as in Kabat for the CH2 of a conventional antibody; and d) said first target protein is B-cell activating factor ("BAFF") and said second target protein is Interleukin-23A ("IL-23A") or said first target protein is IL-23A and said second target protein is BAFF, and wherein: (i) said first polypeptide comprises the amino acid sequence of SEQ ID NO:11 and said second polypeptide comprises the amino acid sequence of SEQ ID NO:12.

18. The method of claim 1, wherein the subject has an inflammatory condition.

19. The method of claim 1, wherein the subject has an autoimmune condition.

20. The method of claim 1, wherein the subject has an inflammatory or autoimmune condition selected from systemic lupus erythematosus (SLE), systemic lupus erythematosus with kidney involvement/Lupus Nephritis (LN), ANCA-associated vasculitis (AAV), primary Sjogren's syndrome (pSS), chronic graft versus host disease (cGVHD), systemic sclerosis (SSc), Rheumatoid Arthritis (RA), Psoriasis (Ps), Ankylosing Spondylitis (AS) and Psoriatic Arthritis (PA).

\* \* \* \* \*

SEQUENCE LISTING

<160> NUMBER OF SEQ ID NOS: 136

<210> SEQ ID NO 1
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 1

Gln Val Gln Leu Gln Gln Ser Gly Ala Glu Val Lys Lys Pro Gly Ser
1               5                   10                  15

Ser Val Arg Val Ser Cys Lys Ala Ser Gly Gly Thr Phe Asn Asn Asn
                20                  25                  30

Ala Ile Asn Trp Val Arg Gln Ala Pro Gly Gln Gly Leu Glu Trp Met
            35                  40                  45

Gly Gly Ile Ile Pro Met Phe Gly Thr Ala Lys Tyr Ser Gln Asn Phe
    50                  55                  60

Gln Gly Arg Val Ala Ile Thr Ala Asp Glu Ser Thr Gly Thr Ala Ser
65                  70                  75                  80

Met Glu Leu Ser Ser Leu Arg Ser Glu Asp Thr Ala Val Tyr Tyr Cys
                85                  90                  95

Ala Arg Ser Arg Asp Leu Leu Leu Phe Pro His His Ala Leu Ser Pro
            100                 105                 110

Trp Gly Arg Gly Thr Met Val Thr Val Ser Ser
        115                 120

<210> SEQ ID NO 2
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 2

Ser Ser Glu Leu Thr Gln Asp Pro Ala Val Ser Val Ala Leu Gly Gln
1               5                   10                  15

Thr Val Arg Val Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Ser Ser Arg Asp Ser Ser Gly Asn His
                85                  90                  95

Trp Val Phe Gly Gly Gly Thr Glu Leu Thr Val Leu
            100                 105

<210> SEQ ID NO 3
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 3

Gln Val Gln Leu Val Gln Ser Gly Ala Glu Val Lys Lys Pro Gly Ser
1               5                   10                  15

```
Ser Val Lys Val Ser Cys Lys Ala Ser Gly Tyr Thr Phe Thr Asp Gln
            20                  25                  30

Thr Ile His Trp Met Arg Gln Ala Pro Gly Gln Gly Leu Glu Trp Ile
        35                  40                  45

Gly Tyr Ile Tyr Pro Arg Asp Asp Ser Pro Lys Tyr Asn Glu Asn Phe
 50                  55                  60

Lys Gly Lys Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Ile Pro Asp Arg Ser Gly Tyr Ala Trp Phe Ile Tyr Trp Gly Gln
            100                 105                 110

Gly Thr Leu Val Thr Val Ser Ser
        115                 120

<210> SEQ ID NO 4
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
 50                  55                  60

Ser Gly Ser Arg Thr Asp Phe Thr Leu Thr Ile Ser Ser Leu Gln Pro
 65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys
            100                 105

<210> SEQ ID NO 5
<211> LENGTH: 571
<212> TYPE: PRT
<213> ORGANISM: Artificial Sequence
<220> FEATURE:
<223> OTHER INFORMATION: Synthetic Polypeptide

<400> SEQUENCE: 5

Ser Ser Glu Leu Thr Gln Asp Pro Ala Val Ser Val Ala Leu Gly Gln
1               5                   10                  15

Thr Val Arg Val Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Ser Ser Arg Asp Ser Ser Gly Asn His
```

```
              85                  90                  95
Trp Val Phe Gly Gly Gly Thr Glu Leu Thr Val Leu Gly Gly Gly Ser
                100                 105                 110

Gly Gly Gly Gly Gln Val Gln Leu Val Gln Ser Gly Ala Glu Val Lys
                115                 120                 125

Lys Pro Gly Ser Ser Val Lys Val Ser Cys Lys Ala Ser Gly Tyr Thr
            130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
                180                 185                 190

Ser Thr Ala Tyr Met Glu Leu Ser Ser Leu Arg Ser Glu Asp Thr Ala
            195                 200                 205

Val Tyr Tyr Cys Ala Ile Pro Asp Arg Ser Gly Tyr Ala Trp Phe Ile
            210                 215                 220

Tyr Trp Gly Gln Gly Thr Leu Val Thr Val Ser Ser Leu Gly Gly Gly
225                 230                 235                 240

Ser Gly Ala Ser Thr Lys Gly Pro Ser Val Phe Pro Leu Ala Pro Ser
                245                 250                 255

Ser Lys Ser Thr Ser Gly Gly Thr Ala Ala Leu Gly Cys Leu Val Lys
            260                 265                 270

Asp Tyr Phe Pro Glu Pro Val Thr Val Ser Trp Asn Ser Gly Ala Leu
            275                 280                 285

Thr Ser Gly Val His Thr Phe Pro Ala Val Leu Gln Ser Ser Gly Leu
        290                 295                 300

Tyr Ser Leu Ser Ser Val Val Thr Val Pro Ser Ser Ser Leu Gly Thr
305                 310                 315                 320

Gln Thr Tyr Ile Cys Asn Val Asn His Lys Pro Ser Asn Thr Lys Val
                325                 330                 335

Asp Lys Arg Val Glu Pro Lys Ser Cys Asp Lys Thr His Thr Cys Pro
            340                 345                 350

Pro Cys Pro Ala Pro Glu Ala Ala Gly Gly Pro Ser Val Phe Leu Phe
        355                 360                 365

Pro Pro Lys Pro Lys Asp Thr Leu Tyr Ile Thr Arg Glu Pro Glu Val
        370                 375                 380

Thr Cys Val Val Val Asp Val Ser His Glu Asp Pro Glu Val Lys Phe
385                 390                 395                 400

Asn Trp Tyr Val Asp Gly Val Glu Val His Asn Ala Lys Thr Lys Pro
                405                 410                 415

Arg Glu Glu Gln Tyr Asn Ser Thr Tyr Arg Val Val Ser Val Leu Thr
            420                 425                 430

Val Leu His Gln Asp Trp Leu Asn Gly Lys Glu Tyr Lys Cys Lys Val
            435                 440                 445

Ser Asn Lys Ala Leu Pro Ala Pro Ile Glu Lys Thr Ile Ser Lys Ala
        450                 455                 460

Lys Gly Gln Pro Arg Glu Pro Gln Val Tyr Thr Leu Pro Pro Ser Arg
465                 470                 475                 480

Glu Glu Met Thr Lys Asn Gln Val Ser Leu Thr Cys Leu Val Lys Gly
                485                 490                 495

Phe Tyr Pro Ser Asp Ile Ala Val Glu Trp Glu Ser Asn Gly Gln Pro
            500                 505                 510
```

Glu Asn Asn Tyr Lys Thr Thr Pro Pro Val Leu Asp Ser Asp Gly Ser
            515                 520                 525

Phe Phe Leu Tyr Ser Lys Leu Thr Val Asp Lys Ser Arg Trp Gln Gln
            530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly
                565                 570

<210> SEQ ID NO 6
<211> LENGTH: 351
<212> TYPE: PRT
<213> ORGANISM: Artificial Sequence
<220> FEATURE:
<223> OTHER INFORMATION: Synthetic Polypeptide

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Gln Gln Ser Gly Ala Glu Val Lys Lys
        115                 120                 125

Pro Gly Ser Ser Val Arg Val Ser Cys Lys Ala Ser Gly Gly Thr Phe
    130                 135                 140

Asn Asn Asn Ala Ile Asn Trp Val Arg Gln Ala Pro Gly Gln Gly Leu
145                 150                 155                 160

Glu Trp Met Gly Gly Ile Ile Pro Met Phe Gly Thr Ala Lys Tyr Ser
                165                 170                 175

Gln Asn Phe Gln Gly Arg Val Ala Ile Thr Ala Asp Glu Ser Thr Gly
            180                 185                 190

Thr Ala Ser Met Glu Leu Ser Ser Leu Arg Ser Glu Asp Thr Ala Val
        195                 200                 205

Tyr Tyr Cys Ala Arg Ser Arg Asp Leu Leu Phe Pro His His Ala
    210                 215                 220

Leu Ser Pro Trp Gly Arg Gly Thr Met Val Thr Val Ser Ser Leu Gly
225                 230                 235                 240

Gly Gly Ser Gly Arg Thr Val Ala Ala Pro Ser Val Phe Ile Phe Pro
                245                 250                 255

Pro Ser Asp Glu Gln Leu Lys Ser Gly Thr Ala Ser Val Val Cys Leu
            260                 265                 270

Leu Asn Asn Phe Tyr Pro Arg Glu Ala Lys Val Gln Trp Lys Val Asp
        275                 280                 285

Asn Ala Leu Gln Ser Gly Asn Ser Gln Glu Ser Val Thr Glu Gln Asp
    290                 295                 300

```
Ser Lys Asp Ser Thr Tyr Ser Leu Ser Ser Thr Leu Thr Leu Ser Lys
305                 310                 315                 320

Ala Asp Tyr Glu Lys His Lys Val Tyr Ala Cys Glu Val Thr His Gln
            325                 330                 335

Gly Leu Ser Ser Pro Val Thr Lys Ser Phe Asn Arg Gly Glu Cys
        340                 345                 350

<210> SEQ ID NO 7
<211> LENGTH: 573
<212> TYPE: PRT
<213> ORGANISM: Artificial Sequence
<220> FEATURE:
<223> OTHER INFORMATION: Synthetic Polypeptide

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Gln Gln Ser Gly Ala Glu Val Lys Lys
        115                 120                 125

Pro Gly Ser Ser Val Arg Val Ser Cys Lys Ala Ser Gly Gly Thr Phe
    130                 135                 140

Asn Asn Asn Ala Ile Asn Trp Val Arg Gln Ala Pro Gly Gln Gly Leu
145                 150                 155                 160

Glu Trp Met Gly Gly Ile Ile Pro Met Phe Gly Thr Ala Lys Tyr Ser
                165                 170                 175

Gln Asn Phe Gln Gly Arg Val Ala Ile Thr Ala Asp Glu Ser Thr Gly
            180                 185                 190

Thr Ala Ser Met Glu Leu Ser Ser Leu Arg Ser Glu Asp Thr Ala Val
        195                 200                 205

Tyr Tyr Cys Ala Arg Ser Arg Asp Leu Leu Leu Phe Pro His His Ala
    210                 215                 220

Leu Ser Pro Trp Gly Arg Gly Thr Met Val Thr Val Ser Ser Leu Gly
225                 230                 235                 240

Gly Gly Ser Gly Ala Ser Thr Lys Gly Pro Ser Val Phe Pro Leu Ala
                245                 250                 255

Pro Ser Ser Lys Ser Thr Ser Gly Gly Thr Ala Ala Leu Gly Cys Leu
            260                 265                 270

Val Lys Asp Tyr Phe Pro Glu Pro Val Thr Val Ser Trp Asn Ser Gly
        275                 280                 285

Ala Leu Thr Ser Gly Val His Thr Phe Pro Ala Val Leu Gln Ser Ser
    290                 295                 300

Gly Leu Tyr Ser Leu Ser Ser Val Val Thr Val Pro Ser Ser Ser Leu
305                 310                 315                 320
```

Gly Thr Gln Thr Tyr Ile Cys Asn Val Asn His Lys Pro Ser Asn Thr
            325                 330                 335

Lys Val Asp Lys Arg Val Glu Pro Lys Ser Cys Asp Lys Thr His Thr
        340                 345                 350

Cys Pro Pro Cys Pro Ala Pro Glu Ala Ala Gly Gly Pro Ser Val Phe
    355                 360                 365

Leu Phe Pro Pro Lys Pro Lys Asp Thr Leu Tyr Ile Thr Arg Glu Pro
370                 375                 380

Glu Val Thr Cys Val Val Val Asp Val Ser His Glu Asp Pro Glu Val
385                 390                 395                 400

Lys Phe Asn Trp Tyr Val Asp Gly Val Glu Val His Asn Ala Lys Thr
                405                 410                 415

Lys Pro Arg Glu Glu Gln Tyr Asn Ser Thr Tyr Arg Val Val Ser Val
            420                 425                 430

Leu Thr Val Leu His Gln Asp Trp Leu Asn Gly Lys Glu Tyr Lys Cys
        435                 440                 445

Lys Val Ser Asn Lys Ala Leu Pro Ala Pro Ile Glu Lys Thr Ile Ser
    450                 455                 460

Lys Ala Lys Gly Gln Pro Arg Glu Pro Gln Val Tyr Thr Leu Pro Pro
465                 470                 475                 480

Ser Arg Glu Glu Met Thr Lys Asn Gln Val Ser Leu Thr Cys Leu Val
                485                 490                 495

Lys Gly Phe Tyr Pro Ser Asp Ile Ala Val Glu Trp Glu Ser Asn Gly
            500                 505                 510

Gln Pro Glu Asn Asn Tyr Lys Thr Thr Pro Pro Val Leu Asp Ser Asp
        515                 520                 525

Gly Ser Phe Phe Leu Tyr Ser Lys Leu Thr Val Asp Lys Ser Arg Trp
    530                 535                 540

Gln Gln Gly Asn Val Phe Ser Cys Ser Val Met His Glu Ala Leu His
545                 550                 555                 560

Asn His Tyr Thr Gln Lys Ser Leu Ser Leu Ser Pro Gly
                565                 570

<210> SEQ ID NO 8
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 8

Ser Ser Glu Leu Thr Gln Asp Pro Ala Val Ser Val Ala Leu Gly Gln
1               5                   10                  15

Thr Val Arg Val Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Ser Ser Arg Asp Ser Ser Gly Asn His
                85                  90                  95

Trp Val Phe Gly Gly Gly Thr Glu Leu Thr Val Leu Gly Gly Gly Ser
            100                 105                 110

Gly Gly Gly Gly Gln Val Gln Leu Val Gln Ser Gly Ala Glu Val Lys
            115                 120                 125

Lys Pro Gly Ser Ser Val Lys Val Ser Cys Lys Ala Ser Gly Tyr Thr
130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
210                 215                 220

Tyr Trp Gly Gln Gly Thr Leu Val Thr Val Ser Ser Leu Gly Gly Gly
225                 230                 235                 240

Ser Gly Arg Thr Val Ala Ala Pro Ser Val Phe Ile Phe Pro Pro Ser
                245                 250                 255

Asp Glu Gln Leu Lys Ser Gly Thr Ala Ser Val Val Cys Leu Leu Asn
            260                 265                 270

Asn Phe Tyr Pro Arg Glu Ala Lys Val Gln Trp Lys Val Asp Asn Ala
        275                 280                 285

Leu Gln Ser Gly Asn Ser Gln Glu Ser Val Thr Glu Gln Asp Ser Lys
290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
            340                 345

<210> SEQ ID NO 9
<211> LENGTH: 502
<212> TYPE: PRT
<213> ORGANISM: Artificial Sequence
<220> FEATURE:
<223> OTHER INFORMATION: Synthetic Polypeptide

<400> SEQUENCE: 9

Ser Ser Glu Leu Thr Gln Asp Pro Ala Val Ser Val Ala Leu Gly Gln
1               5                   10                  15

Thr Val Arg Val Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Ser Ser Arg Asp Ser Ser Gly Asn His
                85                  90                  95

Trp Val Phe Gly Gly Gly Thr Glu Leu Thr Val Leu Gly Gly Gly Ser
            100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
            130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
210                 215                 220

Tyr Trp Gly Gln Gly Thr Leu Val Thr Val Ser Ser Gly Gly Cys Gly
225                 230                 235                 240

Gly Gly Glu Val Ala Ala Cys Glu Lys Glu Val Ala Ala Leu Glu Lys
            245                 250                 255

Glu Val Ala Ala Leu Glu Lys Glu Val Ala Ala Leu Glu Lys Leu Glu
            260                 265                 270

Pro Lys Ser Ser Asp Lys Thr His Thr Cys Pro Pro Cys Pro Ala Pro
        275                 280                 285

Glu Ala Ala Gly Gly Pro Ser Val Phe Leu Phe Pro Pro Lys Pro Lys
290                 295                 300

Asp Thr Leu Tyr Ile Thr Arg Glu Pro Glu Val Thr Cys Val Val Val
305                 310                 315                 320

Asp Val Ser His Glu Asp Pro Glu Val Lys Phe Asn Trp Tyr Val Asp
                325                 330                 335

Gly Val Glu Val His Asn Ala Lys Thr Lys Pro Arg Glu Glu Gln Tyr
            340                 345                 350

Asn Ser Thr Tyr Arg Val Val Ser Val Leu Thr Val Leu His Gln Asp
        355                 360                 365

Trp Leu Asn Gly Lys Glu Tyr Lys Cys Lys Val Ser Asn Lys Ala Leu
370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Ser Arg Glu Glu Met Thr Lys
                405                 410                 415

Asn Gln Val Ser Leu Thr Cys Leu Val Lys Gly Phe Tyr Pro Ser Asp
            420                 425                 430

Ile Ala Val Glu Trp Glu Ser Asn Gly Gln Pro Glu Asn Asn Tyr Lys
        435                 440                 445

Thr Thr Pro Pro Val Leu Asp Ser Asp Gly Ser Phe Phe Leu Tyr Ser
450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly
            500

<210> SEQ ID NO 10
<211> LENGTH: 272
<212> TYPE: PRT
<213> ORGANISM: Artificial Sequence
<220> FEATURE:

<223> OTHER INFORMATION: Synthetic Polypeptide

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Gln Gln Ser Gly Ala Glu Val Lys Lys
        115                 120                 125

Pro Gly Ser Ser Val Arg Val Ser Cys Lys Ala Ser Gly Gly Thr Phe
130                 135                 140

Asn Asn Asn Ala Ile Asn Trp Val Arg Gln Ala Pro Gly Gln Gly Leu
145                 150                 155                 160

Glu Trp Met Gly Gly Ile Ile Pro Met Phe Gly Thr Ala Lys Tyr Ser
                165                 170                 175

Gln Asn Phe Gln Gly Arg Val Ala Ile Thr Ala Asp Glu Ser Thr Gly
            180                 185                 190

Thr Ala Ser Met Glu Leu Ser Ser Leu Arg Ser Glu Asp Thr Ala Val
        195                 200                 205

Tyr Tyr Cys Ala Arg Ser Arg Asp Leu Leu Leu Phe Pro His His Ala
210                 215                 220

Leu Ser Pro Trp Gly Arg Gly Thr Met Val Thr Val Ser Ser Gly Gly
225                 230                 235                 240

Cys Gly Gly Gly Lys Val Ala Ala Cys Lys Glu Lys Val Ala Ala Leu
                245                 250                 255

Lys Glu Lys Val Ala Ala Leu Lys Glu Lys Val Ala Ala Leu Lys Glu
            260                 265                 270

<210> SEQ ID NO 11
<211> LENGTH: 504
<212> TYPE: PRT
<213> ORGANISM: Artificial Sequence
<220> FEATURE:
<223> OTHER INFORMATION: Synthetic Polypeptide

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
                100                 105                 110

Gly Gly Gly Gln Val Gln Leu Gln Gln Ser Gly Ala Glu Val Lys Lys
                115                 120                 125

Pro Gly Ser Ser Val Arg Val Ser Cys Lys Ala Ser Gly Gly Thr Phe
            130                 135                 140

Asn Asn Asn Ala Ile Asn Trp Val Arg Gln Ala Pro Gly Gln Gly Leu
145                 150                 155                 160

Glu Trp Met Gly Gly Ile Ile Pro Met Phe Gly Thr Ala Lys Tyr Ser
                165                 170                 175

Gln Asn Phe Gln Gly Arg Val Ala Ile Thr Ala Asp Glu Ser Thr Gly
                180                 185                 190

Thr Ala Ser Met Glu Leu Ser Ser Leu Arg Ser Glu Asp Thr Ala Val
            195                 200                 205

Tyr Tyr Cys Ala Arg Ser Arg Asp Leu Leu Leu Phe Pro His His Ala
            210                 215                 220

Leu Ser Pro Trp Gly Arg Gly Thr Met Val Thr Val Ser Ser Gly Gly
225                 230                 235                 240

Cys Gly Gly Gly Glu Val Ala Ala Cys Glu Lys Glu Val Ala Ala Leu
                245                 250                 255

Glu Lys Glu Val Ala Ala Leu Glu Lys Glu Val Ala Ala Leu Glu Lys
                260                 265                 270

Leu Glu Pro Lys Ser Ser Asp Lys Thr His Thr Cys Pro Pro Cys Pro
            275                 280                 285

Ala Pro Glu Ala Ala Gly Gly Pro Ser Val Phe Leu Phe Pro Pro Lys
            290                 295                 300

Pro Lys Asp Thr Leu Tyr Ile Thr Arg Glu Pro Glu Val Thr Cys Val
305                 310                 315                 320

Val Val Asp Val Ser His Glu Asp Pro Glu Val Lys Phe Asn Trp Tyr
                325                 330                 335

Val Asp Gly Val Glu Val His Asn Ala Lys Thr Lys Pro Arg Glu Glu
            340                 345                 350

Gln Tyr Asn Ser Thr Tyr Arg Val Val Ser Val Leu Thr Val Leu His
            355                 360                 365

Gln Asp Trp Leu Asn Gly Lys Glu Tyr Lys Cys Lys Val Ser Asn Lys
            370                 375                 380

Ala Leu Pro Ala Pro Ile Glu Lys Thr Ile Ser Lys Ala Lys Gly Gln
385                 390                 395                 400

Pro Arg Glu Pro Gln Val Tyr Thr Leu Pro Pro Ser Arg Glu Glu Met
                405                 410                 415

Thr Lys Asn Gln Val Ser Leu Thr Cys Leu Val Lys Gly Phe Tyr Pro
            420                 425                 430

Ser Asp Ile Ala Val Glu Trp Glu Ser Asn Gly Gln Pro Glu Asn Asn
            435                 440                 445

Tyr Lys Thr Thr Pro Pro Val Leu Asp Ser Asp Gly Ser Phe Phe Leu
            450                 455                 460

Tyr Ser Lys Leu Thr Val Asp Lys Ser Arg Trp Gln Gln Gly Asn Val
465                 470                 475                 480

Phe Ser Cys Ser Val Met His Glu Ala Leu His Asn His Tyr Thr Gln
                485                 490                 495

```
Lys Ser Leu Ser Leu Ser Pro Gly
            500

<210> SEQ ID NO 12
<211> LENGTH: 270
<212> TYPE: PRT
<213> ORGANISM: Artificial Sequence
<220> FEATURE:
<223> OTHER INFORMATION: Synthetic Polypeptide

<400> SEQUENCE: 12

Ser Ser Glu Leu Thr Gln Asp Pro Ala Val Ser Val Ala Leu Gly Gln
1               5                   10                  15

Thr Val Arg Val Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Ser Ser Arg Asp Ser Ser Gly Asn His
                85                  90                  95

Trp Val Phe Gly Gly Gly Thr Glu Leu Thr Val Leu Gly Gly Gly Ser
            100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
    130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
    210                 215                 220

Tyr Trp Gly Gln Gly Thr Leu Val Thr Val Ser Ser Gly Gly Cys Gly
225                 230                 235                 240

Gly Gly Lys Val Ala Ala Cys Lys Glu Lys Val Ala Ala Leu Lys Glu
                245                 250                 255

Lys Val Ala Ala Leu Lys Glu Lys Val Ala Ala Leu Lys Glu
            260                 265                 270

<210> SEQ ID NO 13
<211> LENGTH: 568
<212> TYPE: PRT
<213> ORGANISM: Artificial Sequence
<220> FEATURE:
<223> OTHER INFORMATION: Synthetic Polypeptide

<400> SEQUENCE: 13

Ser Ser Glu Leu Thr Gln Asp Pro Ala Val Ser Val Ala Leu Gly Gln
1               5                   10                  15

Thr Val Arg Val Thr Cys Gln Gly Asp Ser Leu Arg Ser Tyr Tyr Ala
            20                  25                  30
```

```
Ser Trp Tyr Gln Gln Lys Pro Gly Gln Ala Pro Val Leu Val Ile Tyr
             35                  40                  45

Gly Lys Asn Asn Arg Pro Ser Gly Ile Pro Asp Arg Phe Ser Gly Ser
         50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Ser Ser Arg Asp Ser Ser Gly Asn His
                 85                  90                  95

Trp Val Phe Gly Gly Gly Thr Glu Leu Thr Val Leu Gly Gly Gly Ser
             100                 105                 110

Gly Gly Gly Gly Gln Val Gln Leu Val Gln Ser Gly Ala Glu Val Lys
             115                 120                 125

Lys Pro Gly Ser Ser Val Lys Val Ser Cys Lys Ala Ser Gly Tyr Thr
             130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Ser Pro Lys Tyr
                 165                 170                 175

Asn Glu Asn Phe Lys Gly Lys Val Thr Ile Thr Ala Asp Lys Ser Thr
             180                 185                 190

Ser Thr Ala Tyr Met Glu Leu Ser Ser Leu Arg Ser Glu Asp Thr Ala
             195                 200                 205

Val Tyr Tyr Cys Ala Ile Pro Asp Arg Ser Gly Tyr Ala Trp Phe Ile
             210                 215                 220

Tyr Trp Gly Gln Gly Thr Leu Val Thr Val Ser Ser Leu Gly Gly Gly
225                 230                 235                 240

Ser Gly Ala Ser Thr Lys Gly Pro Ser Val Phe Pro Leu Ala Pro Cys
             245                 250                 255

Ser Arg Ser Thr Ser Glu Ser Thr Ala Ala Leu Gly Cys Leu Val Lys
             260                 265                 270

Asp Tyr Phe Pro Glu Pro Val Thr Val Ser Trp Asn Ser Gly Ala Leu
             275                 280                 285

Thr Ser Gly Val His Thr Phe Pro Ala Val Leu Gln Ser Ser Gly Leu
             290                 295                 300

Tyr Ser Leu Ser Ser Val Val Thr Val Pro Ser Ser Ser Leu Gly Thr
305                 310                 315                 320

Lys Thr Tyr Thr Cys Asn Val Asp His Lys Pro Ser Asn Thr Lys Val
                 325                 330                 335

Asp Lys Arg Val Glu Ser Lys Tyr Gly Pro Pro Cys Pro Pro Cys Pro
             340                 345                 350

Ala Pro Glu Phe Leu Gly Gly Pro Ser Val Phe Leu Phe Pro Pro Lys
             355                 360                 365

Pro Lys Asp Thr Leu Tyr Ile Thr Arg Glu Pro Glu Val Thr Cys Val
370                 375                 380

Val Val Asp Val Ser Gln Glu Asp Pro Glu Val Gln Phe Asn Trp Tyr
385                 390                 395                 400

Val Asp Gly Val Glu Val His Asn Ala Lys Thr Lys Pro Arg Glu Glu
                 405                 410                 415

Gln Phe Asn Ser Thr Tyr Arg Val Val Ser Val Leu Thr Val Leu His
                 420                 425                 430

Gln Asp Trp Leu Asn Gly Lys Glu Tyr Lys Cys Lys Val Ser Asn Lys
             435                 440                 445
```

```
Gly Leu Pro Ser Ser Ile Glu Lys Thr Ile Ser Lys Ala Lys Gly Gln
        450                 455                 460

Pro Arg Glu Pro Gln Val Tyr Thr Leu Pro Pro Ser Gln Glu Glu Met
465                 470                 475                 480

Thr Lys Asn Gln Val Ser Leu Thr Cys Leu Val Lys Gly Phe Tyr Pro
                485                 490                 495

Ser Asp Ile Ala Val Glu Trp Glu Ser Asn Gly Gln Pro Glu Asn Asn
                500                 505                 510

Tyr Lys Thr Thr Pro Pro Val Leu Asp Ser Asp Gly Ser Phe Phe Leu
                515                 520                 525

Tyr Ser Arg Leu Thr Val Asp Lys Ser Arg Trp Gln Glu Gly Asn Val
        530                 535                 540

Phe Ser Cys Ser Val Met His Glu Ala Leu His Asn His Tyr Thr Gln
545                 550                 555                 560

Lys Ser Leu Ser Leu Ser Leu Gly
                565

<210> SEQ ID NO 14
<211> LENGTH: 351
<212> TYPE: PRT
<213> ORGANISM: Artificial Sequence
<220> FEATURE:
<223> OTHER INFORMATION: Synthetic Polypeptide

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
                20                  25                  30

Val Ala Trp Tyr Gln Gln Lys Pro Gly Lys Val Pro Lys Leu Leu Ile
            35                  40                  45

Tyr Trp Ala Ser Thr Arg His Thr Gly Val Pro Ser Arg Phe Ser Gly
        50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
                100                 105                 110

Gly Gly Gly Gln Val Gln Leu Gln Gln Ser Gly Ala Glu Val Lys Lys
            115                 120                 125

Pro Gly Ser Ser Val Arg Val Ser Cys Lys Ala Ser Gly Gly Thr Phe
130                 135                 140

Asn Asn Asn Ala Ile Asn Trp Val Arg Gln Ala Pro Gly Gln Gly Leu
145                 150                 155                 160

Glu Trp Met Gly Gly Ile Ile Pro Met Phe Gly Thr Ala Lys Tyr Ser
                165                 170                 175

Gln Asn Phe Gln Gly Arg Val Ala Ile Thr Ala Asp Glu Ser Thr Gly
                180                 185                 190

Thr Ala Ser Met Glu Leu Ser Ser Leu Arg Ser Glu Asp Thr Ala Val
            195                 200                 205

Tyr Tyr Cys Ala Arg Ser Arg Asp Leu Leu Leu Phe Pro His His Ala
        210                 215                 220

Leu Ser Pro Trp Gly Arg Gly Thr Met Val Thr Val Ser Ser Leu Gly
225                 230                 235                 240
```

```
Gly Gly Ser Gly Arg Thr Val Ala Ala Pro Ser Val Phe Ile Phe Pro
                245                 250                 255

Pro Ser Asp Glu Gln Leu Lys Ser Gly Thr Ala Ser Val Val Cys Leu
            260                 265                 270

Leu Asn Asn Phe Tyr Pro Arg Glu Ala Lys Val Gln Trp Lys Val Asp
        275                 280                 285

Asn Ala Leu Gln Ser Gly Asn Ser Gln Glu Ser Val Thr Glu Gln Asp
    290                 295                 300

Ser Lys Asp Ser Thr Tyr Ser Leu Ser Ser Thr Leu Thr Leu Ser Lys
305                 310                 315                 320

Ala Asp Tyr Glu Lys His Lys Val Tyr Ala Cys Glu Val Thr His Gln
                325                 330                 335

Gly Leu Ser Ser Pro Val Thr Lys Ser Phe Asn Arg Gly Glu Cys
            340                 345                 350

<210> SEQ ID NO 15
<211> LENGTH: 570
<212> TYPE: PRT
<213> ORGANISM: Artificial Sequence
<220> FEATURE:
<223> OTHER INFORMATION: Synthetic Polypeptide

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Gln Gln Ser Gly Ala Glu Val Lys Lys
        115                 120                 125

Pro Gly Ser Ser Val Arg Val Ser Cys Lys Ala Ser Gly Gly Thr Phe
    130                 135                 140

Asn Asn Asn Ala Ile Asn Trp Val Arg Gln Ala Pro Gly Gln Gly Leu
145                 150                 155                 160

Glu Trp Met Gly Gly Ile Ile Pro Met Phe Gly Thr Ala Lys Tyr Ser
                165                 170                 175

Gln Asn Phe Gln Gly Arg Val Ala Ile Thr Ala Asp Glu Ser Thr Gly
            180                 185                 190

Thr Ala Ser Met Glu Leu Ser Ser Leu Arg Ser Glu Asp Thr Ala Val
        195                 200                 205

Tyr Tyr Cys Ala Arg Ser Arg Asp Leu Leu Leu Phe Pro His His Ala
    210                 215                 220

Leu Ser Pro Trp Gly Arg Gly Thr Met Val Thr Val Ser Ser Leu Gly
225                 230                 235                 240

Gly Gly Ser Gly Ala Ser Thr Lys Gly Pro Ser Val Phe Pro Leu Ala
                245                 250                 255
```

```
Pro Cys Ser Arg Ser Thr Ser Glu Ser Thr Ala Ala Leu Gly Cys Leu
            260                 265                 270

Val Lys Asp Tyr Phe Pro Glu Pro Val Thr Val Ser Trp Asn Ser Gly
        275                 280                 285

Ala Leu Thr Ser Gly Val His Thr Phe Pro Ala Val Leu Gln Ser Ser
    290                 295                 300

Gly Leu Tyr Ser Leu Ser Ser Val Val Thr Val Pro Ser Ser Ser Leu
305                 310                 315                 320

Gly Thr Lys Thr Tyr Thr Cys Asn Val Asp His Lys Pro Ser Asn Thr
            325                 330                 335

Lys Val Asp Lys Arg Val Glu Ser Lys Tyr Gly Pro Pro Cys Pro Pro
        340                 345                 350

Cys Pro Ala Pro Glu Phe Leu Gly Gly Pro Ser Val Phe Leu Phe Pro
    355                 360                 365

Pro Lys Pro Lys Asp Thr Leu Tyr Ile Thr Arg Glu Pro Glu Val Thr
370                 375                 380

Cys Val Val Val Asp Val Ser Gln Glu Asp Pro Glu Val Gln Phe Asn
385                 390                 395                 400

Trp Tyr Val Asp Gly Val Glu Val His Asn Ala Lys Thr Lys Pro Arg
            405                 410                 415

Glu Glu Gln Phe Asn Ser Thr Tyr Arg Val Val Ser Val Leu Thr Val
        420                 425                 430

Leu His Gln Asp Trp Leu Asn Gly Lys Glu Tyr Lys Cys Lys Val Ser
    435                 440                 445

Asn Lys Gly Leu Pro Ser Ser Ile Glu Lys Thr Ile Ser Lys Ala Lys
450                 455                 460

Gly Gln Pro Arg Glu Pro Gln Val Tyr Thr Leu Pro Pro Ser Gln Glu
465                 470                 475                 480

Glu Met Thr Lys Asn Gln Val Ser Leu Thr Cys Leu Val Lys Gly Phe
            485                 490                 495

Tyr Pro Ser Asp Ile Ala Val Glu Trp Glu Ser Asn Gly Gln Pro Glu
        500                 505                 510

Asn Asn Tyr Lys Thr Thr Pro Pro Val Leu Asp Ser Asp Gly Ser Phe
    515                 520                 525

Phe Leu Tyr Ser Arg Leu Thr Val Asp Lys Ser Arg Trp Gln Glu Gly
530                 535                 540

Asn Val Phe Ser Cys Ser Val Met His Glu Ala Leu His Asn His Tyr
545                 550                 555                 560

Thr Gln Lys Ser Leu Ser Leu Ser Leu Gly
            565                 570

<210> SEQ ID NO 16
<211> LENGTH: 349
<212> TYPE: PRT
<213> ORGANISM: Artificial Sequence
<220> FEATURE:
<223> OTHER INFORMATION: Synthetic Polypeptide

<400> SEQUENCE: 16

Ser Ser Glu Leu Thr Gln Asp Pro Ala Val Ser Val Ala Leu Gly Gln
1               5                   10                  15

Thr Val Arg Val Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45
```

Gly Lys Asn Asn Arg Pro Ser Gly Ile Pro Asp Arg Phe Ser Gly Ser
            50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Ser Ser Arg Asp Ser Ser Gly Asn His
                85                  90                  95

Trp Val Phe Gly Gly Gly Thr Glu Leu Thr Val Leu Gly Gly Gly Ser
            100                 105                 110

Gly Gly Gly Gly Gln Val Gln Leu Val Gln Ser Gly Ala Glu Val Lys
            115                 120                 125

Lys Pro Gly Ser Ser Val Lys Val Ser Cys Lys Ala Ser Gly Tyr Thr
130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
            195                 200                 205

Val Tyr Tyr Cys Ala Ile Pro Asp Arg Ser Gly Tyr Ala Trp Phe Ile
210                 215                 220

Tyr Trp Gly Gln Gly Thr Leu Val Thr Val Ser Ser Leu Gly Gly Gly
225                 230                 235                 240

Ser Gly Arg Thr Val Ala Ala Pro Ser Val Phe Ile Phe Pro Pro Ser
                245                 250                 255

Asp Glu Gln Leu Lys Ser Gly Thr Ala Ser Val Val Cys Leu Leu Asn
            260                 265                 270

Asn Phe Tyr Pro Arg Glu Ala Lys Val Gln Trp Lys Val Asp Asn Ala
            275                 280                 285

Leu Gln Ser Gly Asn Ser Gln Glu Ser Val Thr Glu Gln Asp Ser Lys
290                 295                 300

Asp Ser Thr Tyr Ser Leu Ser Ser Thr Leu Thr Leu Ser Lys Ala Asp
305                 310                 315                 320

Tyr Glu Lys His Lys Val Tyr Ala Cys Glu Val Thr His Gln Gly Leu
                325                 330                 335

Ser Ser Pro Val Thr Lys Ser Phe Asn Arg Gly Glu Cys
            340                 345

<210> SEQ ID NO 17
<211> LENGTH: 498
<212> TYPE: PRT
<213> ORGANISM: Artificial Sequence
<220> FEATURE:
<223> OTHER INFORMATION: Synthetic Polypeptide

<400> SEQUENCE: 17

Ser Ser Glu Leu Thr Gln Asp Pro Ala Val Ser Val Ala Leu Gly Gln
1               5                   10                  15

Thr Val Arg Val Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

```
Ser Ser Gly Asn Thr Ala Ser Leu Thr Ile Thr Gly Ala Gln Ala Glu
 65                  70                  75                  80

Asp Glu Ala Asp Tyr Tyr Cys Ser Ser Arg Asp Ser Ser Gly Asn His
                 85                  90                  95

Trp Val Phe Gly Gly Gly Thr Glu Leu Thr Val Leu Gly Gly Gly Ser
            100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
    130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
    210                 215                 220

Tyr Trp Gly Gln Gly Thr Leu Val Thr Val Ser Ser Gly Gly Cys Gly
225                 230                 235                 240

Gly Gly Glu Val Ala Ala Cys Glu Lys Glu Val Ala Ala Leu Glu Lys
                245                 250                 255

Glu Val Ala Ala Leu Glu Lys Glu Val Ala Ala Leu Glu Lys Glu Ser
            260                 265                 270

Lys Tyr Gly Pro Pro Cys Pro Pro Cys Pro Ala Pro Glu Phe Leu Gly
        275                 280                 285

Gly Pro Ser Val Phe Leu Phe Pro Pro Lys Pro Lys Asp Thr Leu Tyr
    290                 295                 300

Ile Thr Arg Glu Pro Glu Val Thr Cys Val Val Val Asp Val Ser Gln
305                 310                 315                 320

Glu Asp Pro Glu Val Gln Phe Asn Trp Tyr Val Asp Gly Val Glu Val
                325                 330                 335

His Asn Ala Lys Thr Lys Pro Arg Glu Glu Gln Phe Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Gly Leu Pro Ser Ser Ile
    370                 375                 380

Glu Lys Thr Ile Ser Lys Ala Lys Gly Gln Pro Arg Glu Pro Gln Val
385                 390                 395                 400

Tyr Thr Leu Pro Pro Ser Gln Glu Glu Met Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Arg Leu Thr Val
    450                 455                 460

Asp Lys Ser Arg Trp Gln Glu Gly Asn Val Phe Ser Cys Ser Val Met
465                 470                 475                 480

His Glu Ala Leu His Asn His Tyr Thr Gln Lys Ser Leu Ser Leu Ser
```

-continued

```
                485                 490                 495

Leu Gly

<210> SEQ ID NO 18
<211> LENGTH: 272
<212> TYPE: PRT
<213> ORGANISM: Artificial Sequence
<220> FEATURE:
<223> OTHER INFORMATION: Synthetic Polypeptide

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Gln Gln Ser Gly Ala Glu Val Lys Lys
        115                 120                 125

Pro Gly Ser Ser Val Arg Val Ser Cys Lys Ala Ser Gly Gly Thr Phe
130                 135                 140

Asn Asn Asn Ala Ile Asn Trp Val Arg Gln Ala Pro Gly Gln Gly Leu
145                 150                 155                 160

Glu Trp Met Gly Gly Ile Ile Pro Met Phe Gly Thr Ala Lys Tyr Ser
                165                 170                 175

Gln Asn Phe Gln Gly Arg Val Ala Ile Thr Ala Asp Glu Ser Thr Gly
            180                 185                 190

Thr Ala Ser Met Glu Leu Ser Ser Leu Arg Ser Glu Asp Thr Ala Val
        195                 200                 205

Tyr Tyr Cys Ala Arg Ser Arg Asp Leu Leu Phe Pro His His Ala
    210                 215                 220

Leu Ser Pro Trp Gly Arg Gly Thr Met Val Thr Val Ser Ser Gly Gly
225                 230                 235                 240

Cys Gly Gly Lys Val Ala Ala Cys Lys Glu Lys Val Ala Ala Leu
                245                 250                 255

Lys Glu Lys Val Ala Ala Leu Lys Glu Lys Val Ala Ala Leu Lys Glu
            260                 265                 270

<210> SEQ ID NO 19
<211> LENGTH: 500
<212> TYPE: PRT
<213> ORGANISM: Artificial Sequence
<220> FEATURE:
<223> OTHER INFORMATION: Synthetic Polypeptide

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
```

-continued

```
                20                  25                  30
Val Ala Trp Tyr Gln Gln Lys Pro Gly Lys Val Pro Lys Leu Leu Ile
            35                  40                  45
Tyr Trp Ala Ser Thr Arg His Thr Gly Val Pro Ser Arg Phe Ser Gly
 50                  55                  60
Ser Gly Ser Arg Thr Asp Phe Thr Leu Thr Ile Ser Ser Leu Gln Pro
 65                  70                  75                  80
Glu Asp Val Ala Asp Tyr Phe Cys His Gln Tyr Ser Ser Tyr Pro Phe
                85                  90                  95
Thr Phe Gly Ser Gly Thr Lys Leu Glu Ile Lys Gly Gly Ser Gly
            100                 105                 110
Gly Gly Gly Gln Val Gln Leu Gln Gln Ser Gly Ala Glu Val Lys Lys
            115                 120                 125
Pro Gly Ser Ser Val Arg Val Ser Cys Lys Ala Ser Gly Gly Thr Phe
            130                 135                 140
Asn Asn Asn Ala Ile Asn Trp Val Arg Gln Ala Pro Gly Gln Gly Leu
145                 150                 155                 160
Glu Trp Met Gly Gly Ile Ile Pro Met Phe Gly Thr Ala Lys Tyr Ser
                165                 170                 175
Gln Asn Phe Gln Gly Arg Val Ala Ile Thr Ala Asp Glu Ser Thr Gly
            180                 185                 190
Thr Ala Ser Met Glu Leu Ser Ser Leu Arg Ser Glu Asp Thr Ala Val
            195                 200                 205
Tyr Tyr Cys Ala Arg Ser Arg Asp Leu Leu Leu Phe Pro His His Ala
            210                 215                 220
Leu Ser Pro Trp Gly Arg Gly Thr Met Val Thr Val Ser Ser Gly Gly
225                 230                 235                 240
Cys Gly Gly Gly Glu Val Ala Ala Cys Glu Lys Glu Val Ala Ala Leu
                245                 250                 255
Glu Lys Glu Val Ala Ala Leu Glu Lys Glu Val Ala Ala Leu Glu Lys
            260                 265                 270
Glu Ser Lys Tyr Gly Pro Pro Cys Pro Pro Cys Pro Ala Pro Glu Phe
            275                 280                 285
Leu Gly Gly Pro Ser Val Phe Leu Phe Pro Pro Lys Pro Lys Asp Thr
            290                 295                 300
Leu Tyr Ile Thr Arg Glu Pro Glu Val Thr Cys Val Val Val Asp Val
305                 310                 315                 320
Ser Gln Glu Asp Pro Glu Val Gln Phe Asn Trp Tyr Val Asp Gly Val
                325                 330                 335
Glu Val His Asn Ala Lys Thr Lys Pro Arg Glu Glu Gln Phe Asn Ser
                340                 345                 350
Thr Tyr Arg Val Val Ser Val Leu Thr Val Leu His Gln Asp Trp Leu
                355                 360                 365
Asn Gly Lys Glu Tyr Lys Cys Lys Val Ser Asn Lys Gly Leu Pro Ser
            370                 375                 380
Ser Ile Glu Lys Thr Ile Ser Lys Ala Lys Gly Gln Pro Arg Glu Pro
385                 390                 395                 400
Gln Val Tyr Thr Leu Pro Pro Ser Gln Glu Glu Met Thr Lys Asn Gln
                405                 410                 415
Val Ser Leu Thr Cys Leu Val Lys Gly Phe Tyr Pro Ser Asp Ile Ala
                420                 425                 430
Val Glu Trp Glu Ser Asn Gly Gln Pro Glu Asn Asn Tyr Lys Thr Thr
            435                 440                 445
```

Pro Pro Val Leu Asp Ser Asp Gly Ser Phe Phe Leu Tyr Ser Arg Leu
    450                 455                 460

Thr Val Asp Lys Ser Arg Trp Gln Glu Gly Asn Val Phe Ser Cys Ser
465                 470                 475                 480

Val Met His Glu Ala Leu His Asn His Tyr Thr Gln Lys Ser Leu Ser
                485                 490                 495

Leu Ser Leu Gly
            500

<210> SEQ ID NO 20
<211> LENGTH: 270
<212> TYPE: PRT
<213> ORGANISM: Artificial Sequence
<220> FEATURE:
<223> OTHER INFORMATION: Synthetic Polypeptide

<400> SEQUENCE: 20

Ser Ser Glu Leu Thr Gln Asp Pro Ala Val Ser Val Ala Leu Gly Gln
1               5                   10                  15

Thr Val Arg Val Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Ser Ser Arg Asp Ser Ser Gly Asn His
                85                  90                  95

Trp Val Phe Gly Gly Gly Thr Glu Leu Thr Val Leu Gly Gly Gly Ser
            100                 105                 110

Gly Gly Gly Gly Gln Val Gln Leu Val Gln Ser Gly Ala Glu Val Lys
        115                 120                 125

Lys Pro Gly Ser Ser Val Lys Val Ser Cys Lys Ala Ser Gly Tyr Thr
130                 135                 140

Phe Thr Asp Gln Thr Ile His Trp Met Arg Gln Ala Pro Gly Gln Gly
145                 150                 155                 160

Leu Glu Trp Ile Gly Tyr Ile Tyr Pro Arg Asp Asp Ser Pro Lys Tyr
                165                 170                 175

Asn Glu Asn Phe Lys Gly Lys Val Thr Ile Thr Ala Asp Lys Ser Thr
            180                 185                 190

Ser Thr Ala Tyr Met Glu Leu Ser Ser Leu Arg Ser Glu Asp Thr Ala
        195                 200                 205

Val Tyr Tyr Cys Ala Ile Pro Asp Arg Ser Gly Tyr Ala Trp Phe Ile
210                 215                 220

Tyr Trp Gly Gln Gly Thr Leu Val Thr Val Ser Ser Gly Gly Cys Gly
225                 230                 235                 240

Gly Gly Lys Val Ala Ala Cys Lys Glu Lys Val Ala Ala Leu Lys Glu
                245                 250                 255

Lys Val Ala Ala Leu Lys Glu Lys Val Ala Ala Leu Lys Glu
            260                 265                 270

<210> SEQ ID NO 21
<211> LENGTH: 564
<212> TYPE: PRT
<213> ORGANISM: Artificial Sequence
<220> FEATURE:
<223> OTHER INFORMATION: Synthetic Polypeptide

<400> SEQUENCE: 21

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Pro Asp His Ile Phe
130                 135                 140

Ser Ile His Trp Met Gln Trp Val Arg Gln Ala Pro Gly Gln Gly Leu
145                 150                 155                 160

Glu Trp Met Gly Glu Ile Phe Pro Gly Ser Gly Thr Thr Asp Tyr Asn
                165                 170                 175

Glu Lys Phe Lys Gly Lys Val Thr Ile Thr Val Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ser Gly Ala Phe Asp Tyr Trp Gly Gln Gly Thr Thr
    210                 215                 220

Val Thr Val Ser Ser Leu Gly Gly Gly Ser Gly Ala Ser Thr Lys Gly
225                 230                 235                 240

Pro Ser Val Phe Pro Leu Ala Pro Ser Ser Lys Ser Thr Ser Gly Gly
                245                 250                 255

Thr Ala Ala Leu Gly Cys Leu Val Lys Asp Tyr Phe Pro Glu Pro Val
            260                 265                 270

Thr Val Ser Trp Asn Ser Gly Ala Leu Thr Ser Gly Val His Thr Phe
        275                 280                 285

Pro Ala Val Leu Gln Ser Ser Gly Leu Tyr Ser Leu Ser Ser Val Val
    290                 295                 300

Thr Val Pro Ser Ser Ser Leu Gly Thr Gln Thr Tyr Ile Cys Asn Val
305                 310                 315                 320

Asn His Lys Pro Ser Asn Thr Lys Val Asp Lys Arg Val Glu Pro Lys
                325                 330                 335

Ser Cys Asp Lys Thr His Thr Cys Pro Pro Cys Pro Ala Pro Glu Ala
            340                 345                 350

Ala Gly Gly Pro Ser Val Phe Leu Phe Pro Pro Lys Pro Lys Asp Thr
        355                 360                 365

Leu Tyr Ile Thr Arg Glu Pro Glu Val Thr Cys Val Val Val Asp Val
    370                 375                 380

Ser His Glu Asp Pro Glu Val Lys Phe Asn Trp Tyr Val Asp Gly Val
385                 390                 395                 400
```

```
Glu Val His Asn Ala Lys Thr Lys Pro Arg Glu Gln Tyr Asn Ser
                405                 410                 415

Thr Tyr Arg Val Val Ser Val Leu Thr Val Leu His Gln Asp Trp Leu
            420                 425                 430

Asn Gly Lys Glu Tyr Lys Cys Lys Val Ser Asn Lys Ala Leu Pro Ala
                435                 440                 445

Pro Ile Glu Lys Thr Ile Ser Lys Ala Lys Gly Gln Pro Arg Glu Pro
            450                 455                 460

Gln Val Tyr Thr Leu Pro Pro Ser Arg Glu Glu Met Thr Lys Asn Gln
465                 470                 475                 480

Val Ser Leu Thr Cys Leu Val Lys Gly Phe Tyr Pro Ser Asp Ile Ala
                485                 490                 495

Val Glu Trp Glu Ser Asn Gly Gln Pro Glu Asn Asn Tyr Lys Thr Thr
            500                 505                 510

Pro Pro Val Leu Asp Ser Asp Gly Ser Phe Phe Leu Tyr Ser Lys Leu
                515                 520                 525

Thr Val Asp Lys Ser Arg Trp Gln Gln Gly Asn Val Phe Ser Cys Ser
530                 535                 540

Val Met His Glu Ala Leu His Asn His Tyr Thr Gln Lys Ser Leu Ser
545                 550                 555                 560

Leu Ser Pro Gly

<210> SEQ ID NO 22
<211> LENGTH: 348
<212> TYPE: PRT
<213> ORGANISM: Artificial Sequence
<220> FEATURE:
<223> OTHER INFORMATION: Synthetic Polypeptide

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Arg
            20                  25                  30

Leu Ser Trp Leu Gln Gln Glu Pro Gly Lys Ala Pro Lys Arg Leu Ile
        35                  40                  45

Tyr Ala Thr Ser Ser Leu Asp Ser Gly Val Pro Ser Arg Phe Ser Gly
    50                  55                  60

Ser Arg Ser Gly Thr Glu Phe Thr Leu Thr Ile Ser Ser Leu Gln Pro
65                  70                  75                  80

Glu Asp Phe Val Thr Tyr Tyr Cys Leu Gln Tyr Ala Ser Ser Pro Phe
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
    130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190
```

```
Thr Ala Tyr Met Glu Leu Ser Ser Leu Arg Ser Glu Asp Thr Ala Val
            195                 200                 205

Tyr Tyr Cys Ala Ile Pro Asp Arg Ser Gly Tyr Ala Trp Phe Ile Tyr
210                 215                 220

Trp Gly Gln Gly Thr Leu Val Thr Val Ser Ser Leu Gly Gly Gly Ser
225                 230                 235                 240

Gly Arg Thr Val Ala Ala Pro Ser Val Phe Ile Phe Pro Pro Ser Asp
                245                 250                 255

Glu Gln Leu Lys Ser Gly Thr Ala Ser Val Val Cys Leu Leu Asn Asn
            260                 265                 270

Phe Tyr Pro Arg Glu Ala Lys Val Gln Trp Lys Val Asp Asn Ala Leu
        275                 280                 285

Gln Ser Gly Asn Ser Gln Glu Ser Val Thr Glu Gln Asp Ser Lys Asp
    290                 295                 300

Ser Thr Tyr Ser Leu Ser Ser Thr Leu Thr Leu Ser Lys Ala Asp Tyr
305                 310                 315                 320

Glu Lys His Lys Val Tyr Ala Cys Glu Val Thr His Gln Gly Leu Ser
                325                 330                 335

Ser Pro Val Thr Lys Ser Phe Asn Arg Gly Glu Cys
            340                 345

<210> SEQ ID NO 23
<211> LENGTH: 495
<212> TYPE: PRT
<213> ORGANISM: Artificial Sequence
<220> FEATURE:
<223> OTHER INFORMATION: Synthetic Polypeptide

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Pro Asp His Ile Phe
    130                 135                 140

Ser Ile His Trp Met Gln Trp Val Arg Gln Ala Pro Gly Gln Gly Leu
145                 150                 155                 160

Glu Trp Met Gly Glu Ile Phe Pro Gly Ser Gly Thr Thr Asp Tyr Asn
                165                 170                 175

Glu Lys Phe Lys Gly Lys Val Thr Ile Thr Val Asp Lys Ser Thr Ser
            180                 185                 190

Thr Ala Tyr Met Glu Leu Ser Ser Leu Arg Ser Glu Asp Thr Ala Val
        195                 200                 205
```

Tyr Tyr Cys Ala Ser Gly Ala Phe Asp Tyr Trp Gly Gln Gly Thr Thr
            210                 215                 220

Val Thr Val Ser Ser Gly Gly Cys Gly Gly Gly Glu Val Ala Ala Cys
225                 230                 235                 240

Glu Lys Glu Val Ala Ala Leu Glu Lys Glu Val Ala Ala Leu Glu Lys
                    245                 250                 255

Glu Val Ala Ala Leu Glu Lys Leu Glu Pro Lys Ser Ser Asp Lys Thr
            260                 265                 270

His Thr Cys Pro Pro Cys Pro Ala Pro Glu Ala Ala Gly Gly Pro Ser
            275                 280                 285

Val Phe Leu Phe Pro Pro Lys Pro Lys Asp Thr Leu Tyr Ile Thr Arg
290                 295                 300

Glu Pro Glu Val Thr Cys Val Val Asp Val Ser His Glu Asp Pro
305                 310                 315                 320

Glu Val Lys Phe Asn Trp Tyr Val Asp Gly Val Glu Val His Asn Ala
                    325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
            355                 360                 365

Lys Cys Lys Val Ser Asn Lys Ala Leu Pro Ala Pro Ile Glu Lys Thr
370                 375                 380

Ile Ser Lys Ala Lys Gly Gln Pro Arg Glu Pro Gln Val Tyr Thr Leu
385                 390                 395                 400

Pro Pro Ser Arg Glu Glu Met Thr Lys Asn Gln Val Ser Leu Thr Cys
                    405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
            435                 440                 445

Ser Asp Gly Ser Phe Phe Leu Tyr Ser Lys Leu Thr Val Asp Lys Ser
450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly
                    485                 490                 495

<210> SEQ ID NO 24
<211> LENGTH: 269
<212> TYPE: PRT
<213> ORGANISM: Artificial Sequence
<220> FEATURE:
<223> OTHER INFORMATION: Synthetic Polypeptide

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Arg
            20                  25                  30

Leu Ser Trp Leu Gln Gln Glu Pro Gly Lys Ala Pro Lys Arg Leu Ile
        35                  40                  45

Tyr Ala Thr Ser Ser Leu Asp Ser Gly Val Pro Ser Arg Phe Ser Gly
    50                  55                  60

Ser Arg Ser Gly Thr Glu Phe Thr Leu Thr Ile Ser Ser Leu Gln Pro
65                  70                  75                  80

```
Glu Asp Phe Val Thr Tyr Tyr Cys Leu Gln Tyr Ala Ser Ser Pro Phe
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
            115                 120                 125

Pro Gly Ser Ser Val Lys Val Ser Cys Lys Ala Ser Gly Tyr Thr Phe
            130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
            195                 200                 205

Tyr Tyr Cys Ala Ile Pro Asp Arg Ser Gly Tyr Ala Trp Phe Ile Tyr
            210                 215                 220

Trp Gly Gln Gly Thr Leu Val Thr Val Ser Ser Gly Gly Cys Gly Gly
225                 230                 235                 240

Gly Lys Val Ala Ala Cys Lys Glu Lys Val Ala Ala Leu Lys Glu Lys
                245                 250                 255

Val Ala Ala Leu Lys Glu Lys Val Ala Ala Leu Lys Glu
            260                 265

<210> SEQ ID NO 25
<211> LENGTH: 561
<212> TYPE: PRT
<213> ORGANISM: Artificial Sequence
<220> FEATURE:
<223> OTHER INFORMATION: Synthetic Polypeptide

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
            35                  40                  45

Tyr Trp Ala Ser Thr Arg His Thr Gly Val Pro Ser Arg Phe Ser Gly
        50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
            115                 120                 125

Pro Gly Ser Ser Val Lys Val Ser Cys Lys Ala Pro Asp His Ile Phe
            130                 135                 140

Ser Ile His Trp Met Gln Trp Val Arg Gln Ala Pro Gly Gln Gly Leu
145                 150                 155                 160

Glu Trp Met Gly Glu Ile Phe Pro Gly Ser Gly Thr Thr Asp Tyr Asn
                165                 170                 175
```

```
Glu Lys Phe Lys Gly Lys Val Thr Ile Thr Val Asp Lys Ser Thr Ser
                180                 185                 190

Thr Ala Tyr Met Glu Leu Ser Ser Leu Arg Ser Glu Asp Thr Ala Val
            195                 200                 205

Tyr Tyr Cys Ala Ser Gly Ala Phe Asp Tyr Trp Gly Gln Gly Thr Thr
210                 215                 220

Val Thr Val Ser Ser Leu Gly Gly Gly Ser Ala Ser Thr Lys Gly
225                 230                 235                 240

Pro Ser Val Phe Pro Leu Ala Pro Cys Ser Arg Ser Thr Ser Glu Ser
                245                 250                 255

Thr Ala Ala Leu Gly Cys Leu Val Lys Asp Tyr Phe Pro Glu Pro Val
            260                 265                 270

Thr Val Ser Trp Asn Ser Gly Ala Leu Thr Ser Gly Val His Thr Phe
        275                 280                 285

Pro Ala Val Leu Gln Ser Ser Gly Leu Tyr Ser Leu Ser Ser Val Val
    290                 295                 300

Thr Val Pro Ser Ser Ser Leu Gly Thr Lys Thr Tyr Thr Cys Asn Val
305                 310                 315                 320

Asp His Lys Pro Ser Asn Thr Lys Val Asp Lys Arg Val Glu Ser Lys
                325                 330                 335

Tyr Gly Pro Pro Cys Pro Pro Cys Pro Ala Pro Glu Phe Leu Gly Gly
            340                 345                 350

Pro Ser Val Phe Leu Phe Pro Pro Lys Pro Lys Asp Thr Leu Tyr Ile
        355                 360                 365

Thr Arg Glu Pro Glu Val Thr Cys Val Val Val Asp Val Ser Gln Glu
    370                 375                 380

Asp Pro Glu Val Gln Phe Asn Trp Tyr Val Asp Gly Val Glu Val His
385                 390                 395                 400

Asn Ala Lys Thr Lys Pro Arg Glu Glu Gln Phe Asn Ser Thr Tyr Arg
                405                 410                 415

Val Val Ser Val Leu Thr Val Leu His Gln Asp Trp Leu Asn Gly Lys
            420                 425                 430

Glu Tyr Lys Cys Lys Val Ser Asn Lys Gly Leu Pro Ser Ser Ile Glu
        435                 440                 445

Lys Thr Ile Ser Lys Ala Lys Gly Gln Pro Arg Glu Pro Gln Val Tyr
    450                 455                 460

Thr Leu Pro Pro Ser Gln Glu Glu Met Thr Lys Asn Gln Val Ser Leu
465                 470                 475                 480

Thr Cys Leu Val Lys Gly Phe Tyr Pro Ser Asp Ile Ala Val Glu Trp
                485                 490                 495

Glu Ser Asn Gly Gln Pro Glu Asn Asn Tyr Lys Thr Thr Pro Pro Val
            500                 505                 510

Leu Asp Ser Asp Gly Ser Phe Phe Leu Tyr Ser Arg Leu Thr Val Asp
        515                 520                 525

Lys Ser Arg Trp Gln Glu Gly Asn Val Phe Ser Cys Ser Val Met His
    530                 535                 540

Glu Ala Leu His Asn His Tyr Thr Gln Lys Ser Leu Ser Leu Ser Leu
545                 550                 555                 560

Gly

<210> SEQ ID NO 26
<211> LENGTH: 348
<212> TYPE: PRT
<213> ORGANISM: Artificial Sequence
```

<220> FEATURE:
<223> OTHER INFORMATION: Synthetic Polypeptide

<400> SEQUENCE: 26

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Arg
            20                  25                  30

Leu Ser Trp Leu Gln Gln Glu Pro Gly Lys Ala Pro Lys Arg Leu Ile
        35                  40                  45

Tyr Ala Thr Ser Ser Leu Asp Ser Gly Val Pro Ser Arg Phe Ser Gly
    50                  55                  60

Ser Arg Ser Gly Thr Glu Phe Thr Leu Thr Ile Ser Ser Leu Gln Pro
65                  70                  75                  80

Glu Asp Phe Val Thr Tyr Tyr Cys Leu Gln Tyr Ala Ser Ser Pro Phe
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
    210                 215                 220

Trp Gly Gln Gly Thr Leu Val Thr Val Ser Ser Leu Gly Gly Gly Ser
225                 230                 235                 240

Gly Arg Thr Val Ala Ala Pro Ser Val Phe Ile Phe Pro Pro Ser Asp
                245                 250                 255

Glu Gln Leu Lys Ser Gly Thr Ala Ser Val Val Cys Leu Leu Asn Asn
            260                 265                 270

Phe Tyr Pro Arg Glu Ala Lys Val Gln Trp Lys Val Asp Asn Ala Leu
        275                 280                 285

Gln Ser Gly Asn Ser Gln Glu Ser Val Thr Glu Gln Asp Ser Lys Asp
    290                 295                 300

Ser Thr Tyr Ser Leu Ser Ser Thr Leu Thr Leu Ser Lys Ala Asp Tyr
305                 310                 315                 320

Glu Lys His Lys Val Tyr Ala Cys Glu Val Thr His Gln Gly Leu Ser
                325                 330                 335

Ser Pro Val Thr Lys Ser Phe Asn Arg Gly Glu Cys
            340                 345
```

<210> SEQ ID NO 27
<211> LENGTH: 491
<212> TYPE: PRT
<213> ORGANISM: Artificial Sequence
<220> FEATURE:
<223> OTHER INFORMATION: Synthetic Polypeptide

<400> SEQUENCE: 27

```
Asp Ile Gln Met Thr Gln Ser Pro Ser Ser Leu Ser Ala Ser Val Gly
 1               5                   10                  15
Asp Arg Val Thr Ile Thr Cys Lys Ala Ser Arg Asp Val Ala Ile Ala
             20                  25                  30
Val Ala Trp Tyr Gln Gln Lys Pro Gly Lys Val Pro Lys Leu Leu Ile
         35                  40                  45
Tyr Trp Ala Ser Thr Arg His Thr Gly Val Pro Ser Arg Phe Ser Gly
 50                  55                  60
Ser Gly Ser Arg Thr Asp Phe Thr Leu Thr Ile Ser Ser Leu Gln Pro
 65                  70                  75                  80
Glu Asp Val Ala Asp Tyr Phe Cys His Gln Tyr Ser Ser Tyr Pro Phe
                 85                  90                  95
Thr Phe Gly Ser Gly Thr Lys Leu Glu Ile Lys Gly Gly Gly Ser Gly
            100                 105                 110
Gly Gly Gly Gln Val Gln Leu Val Gln Ser Gly Ala Glu Val Lys Lys
        115                 120                 125
Pro Gly Ser Ser Val Lys Val Ser Cys Lys Ala Pro Asp His Ile Phe
    130                 135                 140
Ser Ile His Trp Met Gln Trp Val Arg Gln Ala Pro Gly Gln Gly Leu
145                 150                 155                 160
Glu Trp Met Gly Glu Ile Phe Pro Gly Ser Gly Thr Thr Asp Tyr Asn
                165                 170                 175
Glu Lys Phe Lys Gly Lys Val Thr Ile Thr Val Asp Lys Ser Thr Ser
            180                 185                 190
Thr Ala Tyr Met Glu Leu Ser Ser Leu Arg Ser Glu Asp Thr Ala Val
        195                 200                 205
Tyr Tyr Cys Ala Ser Gly Ala Phe Asp Tyr Trp Gly Gln Gly Thr Thr
    210                 215                 220
Val Thr Val Ser Ser Gly Gly Cys Gly Gly Gly Glu Val Ala Ala Cys
225                 230                 235                 240
Glu Lys Glu Val Ala Ala Leu Glu Lys Glu Val Ala Ala Leu Glu Lys
                245                 250                 255
Glu Val Ala Ala Leu Glu Lys Glu Ser Lys Tyr Gly Pro Pro Cys Pro
            260                 265                 270
Pro Cys Pro Ala Pro Glu Phe Leu Gly Gly Pro Ser Val Phe Leu Phe
        275                 280                 285
Pro Pro Lys Pro Lys Asp Thr Leu Tyr Ile Thr Arg Glu Pro Glu Val
    290                 295                 300
Thr Cys Val Val Val Asp Val Ser Gln Glu Asp Pro Glu Val Gln Phe
305                 310                 315                 320
Asn Trp Tyr Val Asp Gly Val Glu Val His Asn Ala Lys Thr Lys Pro
                325                 330                 335
Arg Glu Glu Gln Phe Asn Ser Thr Tyr Arg Val Val Ser Val Leu Thr
            340                 345                 350
Val Leu His Gln Asp Trp Leu Asn Gly Lys Glu Tyr Lys Cys Lys Val
        355                 360                 365
Ser Asn Lys Gly Leu Pro Ser Ser Ile Glu Lys Thr Ile Ser Lys Ala
    370                 375                 380
Lys Gly Gln Pro Arg Glu Pro Gln Val Tyr Thr Leu Pro Pro Ser Gln
385                 390                 395                 400
Glu Glu Met Thr Lys Asn Gln Val Ser Leu Thr Cys Leu Val Lys Gly
                405                 410                 415
```

```
Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
            435                 440                 445

Phe Phe Leu Tyr Ser Arg Leu Thr Val Asp Lys Ser Arg Trp Gln Glu
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Leu Gly
                485                 490

<210> SEQ ID NO 28
<211> LENGTH: 269
<212> TYPE: PRT
<213> ORGANISM: Artificial Sequence
<220> FEATURE:
<223> OTHER INFORMATION: Synthetic Polypeptide

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Arg
            20                  25                  30

Leu Ser Trp Leu Gln Gln Glu Pro Gly Lys Ala Pro Lys Arg Leu Ile
        35                  40                  45

Tyr Ala Thr Ser Ser Leu Asp Ser Gly Val Pro Ser Arg Phe Ser Gly
    50                  55                  60

Ser Arg Ser Gly Thr Glu Phe Thr Leu Thr Ile Ser Ser Leu Gln Pro
65                  70                  75                  80

Glu Asp Phe Val Thr Tyr Tyr Cys Leu Gln Tyr Ala Ser Ser Pro Phe
                85                  90                  95

Thr Phe Gly Gln Gly Thr Lys Leu Glu Ile Lys Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
    210                 215                 220

Trp Gly Gln Gly Thr Leu Val Thr Val Ser Ser Gly Gly Cys Gly Gly
225                 230                 235                 240

Gly Lys Val Ala Ala Cys Lys Glu Lys Val Ala Ala Leu Lys Glu Lys
                245                 250                 255

Val Ala Ala Leu Lys Glu Lys Val Ala Ala Leu Lys Glu
            260                 265

<210> SEQ ID NO 29
```

<211> LENGTH: 564
<212> TYPE: PRT
<213> ORGANISM: Artificial Sequence
<220> FEATURE:
<223> OTHER INFORMATION: Synthetic Polypeptide

<400> SEQUENCE: 29

```
Asp Ile Gln Met Thr Gln Ser Pro Ser Ser Leu Ser Ala Ser Val Gly
1               5                   10                  15
Asp Arg Val Thr Ile Thr Cys Lys Ala Ser Arg Asp Val Ala Ile Ala
            20                  25                  30
Val Ala Trp Tyr Gln Gln Lys Pro Gly Lys Val Pro Lys Leu Leu Ile
        35                  40                  45
Tyr Trp Ala Ser Thr Arg His Thr Gly Val Pro Ser Arg Phe Ser Gly
    50                  55                  60
Ser Gly Ser Arg Thr Asp Phe Thr Leu Thr Ile Ser Ser Leu Gln Pro
65                  70                  75                  80
Glu Asp Val Ala Asp Tyr Phe Cys His Gln Tyr Ser Ser Tyr Pro Phe
                85                  90                  95
Thr Phe Gly Ser Gly Thr Lys Leu Glu Ile Lys Gly Gly Gly Ser Gly
            100                 105                 110
Gly Gly Gly Gln Val Gln Leu Val Gln Ser Gly Ala Glu Val Lys Lys
        115                 120                 125
Pro Gly Ser Ser Val Lys Val Ser Cys Lys Ala Pro Asp His Ile Phe
130                 135                 140
Ser Ile His Trp Met Gln Trp Val Arg Gln Ala Pro Gly Gln Gly Leu
145                 150                 155                 160
Glu Trp Met Gly Glu Ile Phe Pro Gly Ser Gly Thr Thr Asp Tyr Asn
                165                 170                 175
Glu Lys Phe Lys Gly Lys Val Thr Ile Thr Val Asp Lys Ser Thr Ser
            180                 185                 190
Thr Ala Tyr Met Glu Leu Ser Ser Leu Arg Ser Glu Asp Thr Ala Val
        195                 200                 205
Tyr Tyr Cys Ala Ser Gly Ala Phe Asp Tyr Trp Gly Gln Gly Thr Thr
    210                 215                 220
Val Thr Val Ser Ser Leu Gly Gly Gly Ser Gly Ala Ser Thr Lys Gly
225                 230                 235                 240
Pro Ser Val Phe Pro Leu Ala Pro Ser Ser Lys Ser Thr Ser Gly Gly
                245                 250                 255
Thr Ala Ala Leu Gly Cys Leu Val Lys Asp Tyr Phe Pro Glu Pro Val
            260                 265                 270
Thr Val Ser Trp Asn Ser Gly Ala Leu Thr Ser Gly Val His Thr Phe
        275                 280                 285
Pro Ala Val Leu Gln Ser Ser Gly Leu Tyr Ser Leu Ser Ser Val Val
    290                 295                 300
Thr Val Pro Ser Ser Ser Leu Gly Thr Gln Thr Tyr Ile Cys Asn Val
305                 310                 315                 320
Asn His Lys Pro Ser Asn Thr Lys Val Asp Lys Arg Val Glu Pro Lys
                325                 330                 335
Ser Cys Asp Lys Thr His Thr Cys Pro Pro Cys Pro Ala Pro Glu Ala
            340                 345                 350
Ala Gly Gly Pro Ser Val Phe Leu Phe Pro Pro Lys Pro Lys Asp Thr
        355                 360                 365
Leu Tyr Ile Thr Arg Glu Pro Glu Val Thr Cys Val Val Val Asp Val
    370                 375                 380
```

```
Ser His Glu Asp Pro Glu Val Lys Phe Asn Trp Tyr Val Asp Gly Val
385                 390                 395                 400

Glu Val His Asn Ala Lys Thr Lys Pro Arg Glu Glu Gln Tyr Asn Ser
            405                 410                 415

Thr Tyr Arg Val Val Ser Val Leu Thr Val Leu His Gln Asp Trp Leu
        420                 425                 430

Asn Gly Lys Glu Tyr Lys Cys Lys Val Ser Asn Lys Ala Leu Pro Ala
            435                 440                 445

Pro Ile Glu Lys Thr Ile Ser Lys Ala Lys Gly Gln Pro Arg Glu Pro
450                 455                 460

Gln Val Tyr Thr Leu Pro Pro Ser Arg Glu Glu Met Thr Lys Asn Gln
465                 470                 475                 480

Val Ser Leu Thr Cys Leu Val Lys Gly Phe Tyr Pro Ser Asp Ile Ala
            485                 490                 495

Val Glu Trp Glu Ser Asn Gly Gln Pro Glu Asn Asn Tyr Lys Thr Thr
            500                 505                 510

Pro Pro Val Leu Asp Ser Asp Gly Ser Phe Phe Leu Tyr Ser Lys Leu
        515                 520                 525

Thr Val Asp Lys Ser Arg Trp Gln Gln Gly Asn Val Phe Ser Cys Ser
530                 535                 540

Val Met His Glu Ala Leu His Asn His Tyr Thr Gln Lys Ser Leu Ser
545                 550                 555                 560

Leu Ser Pro Gly

<210> SEQ ID NO 30
<211> LENGTH: 348
<212> TYPE: PRT
<213> ORGANISM: Artificial Sequence
<220> FEATURE:
<223> OTHER INFORMATION: Synthetic Polypeptide

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Arg
            20                  25                  30

Leu Asn Trp Tyr Gln Gln Lys Pro Gly Lys Ala Pro Lys Arg Leu Ile
        35                  40                  45

Tyr Ala Thr Ser Ser Leu Asp Ser Gly Val Pro Ser Arg Phe Ser Gly
    50                  55                  60

Ser Arg Ser Gly Thr Glu Phe Thr Leu Thr Ile Ser Ser Leu Gln Pro
65                  70                  75                  80

Glu Asp Phe Val Thr Tyr Tyr Cys Leu Gln Tyr Ala Ser Ser Pro Phe
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175
```

```
Glu Asn Phe Lys Gly Lys Val Thr Ile Thr Ala Asp Lys Ser Thr Ser
                180                 185                 190

Thr Ala Tyr Met Glu Leu Ser Ser Leu Arg Ser Glu Asp Thr Ala Val
            195                 200                 205

Tyr Tyr Cys Ala Ile Pro Asp Arg Ser Gly Tyr Ala Trp Phe Ile Tyr
        210                 215                 220

Trp Gly Gln Gly Thr Leu Val Thr Val Ser Ser Leu Gly Gly Gly Ser
225                 230                 235                 240

Gly Arg Thr Val Ala Ala Pro Ser Val Phe Ile Phe Pro Pro Ser Asp
                245                 250                 255

Glu Gln Leu Lys Ser Gly Thr Ala Ser Val Val Cys Leu Leu Asn Asn
            260                 265                 270

Phe Tyr Pro Arg Glu Ala Lys Val Gln Trp Lys Val Asp Asn Ala Leu
        275                 280                 285

Gln Ser Gly Asn Ser Gln Glu Ser Val Thr Glu Gln Asp Ser Lys Asp
    290                 295                 300

Ser Thr Tyr Ser Leu Ser Ser Thr Leu Thr Leu Ser Lys Ala Asp Tyr
305                 310                 315                 320

Glu Lys His Lys Val Tyr Ala Cys Glu Val Thr His Gln Gly Leu Ser
                325                 330                 335

Ser Pro Val Thr Lys Ser Phe Asn Arg Gly Glu Cys
            340                 345

<210> SEQ ID NO 31
<211> LENGTH: 495
<212> TYPE: PRT
<213> ORGANISM: Artificial Sequence
<220> FEATURE:
<223> OTHER INFORMATION: Synthetic Polypeptide

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
                20                  25                  30

Val Ala Trp Tyr Gln Gln Lys Pro Gly Lys Val Pro Lys Leu Leu Ile
            35                  40                  45

Tyr Trp Ala Ser Thr Arg His Thr Gly Val Pro Ser Arg Phe Ser Gly
50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Pro Asp His Ile Phe
    130                 135                 140

Ser Ile His Trp Met Gln Trp Val Arg Gln Ala Pro Gly Gln Gly Leu
145                 150                 155                 160

Glu Trp Met Gly Glu Ile Phe Pro Gly Ser Gly Thr Asp Tyr Asn
                165                 170                 175

Glu Lys Phe Lys Gly Lys Val Thr Ile Thr Val Asp Lys Ser Thr Ser
                180                 185                 190
```

```
Thr Ala Tyr Met Glu Leu Ser Ser Leu Arg Ser Glu Asp Thr Ala Val
            195                 200                 205

Tyr Tyr Cys Ala Ser Gly Ala Phe Asp Tyr Trp Gly Gln Gly Thr Thr
210                 215                 220

Val Thr Val Ser Ser Gly Gly Cys Gly Gly Gly Glu Val Ala Ala Cys
225                 230                 235                 240

Glu Lys Glu Val Ala Ala Leu Glu Lys Glu Val Ala Ala Leu Glu Lys
            245                 250                 255

Glu Val Ala Ala Leu Glu Lys Leu Glu Pro Lys Ser Ser Asp Lys Thr
            260                 265                 270

His Thr Cys Pro Pro Cys Pro Ala Pro Glu Ala Ala Gly Gly Pro Ser
            275                 280                 285

Val Phe Leu Phe Pro Pro Lys Pro Lys Asp Thr Leu Tyr Ile Thr Arg
290                 295                 300

Glu Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
            325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
            355                 360                 365

Lys Cys Lys Val Ser Asn Lys Ala Leu Pro Ala Pro Ile Glu Lys Thr
            370                 375                 380

Ile Ser Lys Ala Lys Gly Gln Pro Arg Glu Pro Gln Val Tyr Thr Leu
385                 390                 395                 400

Pro Pro Ser Arg Glu Glu Met Thr Lys Asn Gln Val Ser Leu Thr Cys
            405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
            435                 440                 445

Ser Asp Gly Ser Phe Phe Leu Tyr Ser Lys Leu Thr Val Asp Lys Ser
450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly
            485                 490                 495

<210> SEQ ID NO 32
<211> LENGTH: 269
<212> TYPE: PRT
<213> ORGANISM: Artificial Sequence
<220> FEATURE:
<223> OTHER INFORMATION: Synthetic Polypeptide

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Arg
            20                  25                  30

Leu Asn Trp Tyr Gln Gln Lys Pro Gly Lys Ala Pro Lys Arg Leu Ile
        35                  40                  45

Tyr Ala Thr Ser Ser Leu Asp Ser Gly Val Pro Ser Arg Phe Ser Gly
    50                  55                  60
```

```
Ser Arg Ser Gly Thr Glu Phe Thr Leu Thr Ile Ser Ser Leu Gln Pro
 65                  70                  75                  80

Glu Asp Phe Val Thr Tyr Tyr Cys Leu Gln Tyr Ala Ser Ser Pro Phe
                 85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
            115                 120                 125

Pro Gly Ser Ser Val Lys Val Ser Cys Lys Ala Ser Gly Tyr Thr Phe
        130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Ser Pro Lys Tyr Asn
                165                 170                 175

Glu Asn Phe Lys Gly Lys Val Thr Ile Thr Ala Asp Lys Ser Thr Ser
                180                 185                 190

Thr Ala Tyr Met Glu Leu Ser Ser Leu Arg Ser Glu Asp Thr Ala Val
            195                 200                 205

Tyr Tyr Cys Ala Ile Pro Asp Arg Ser Gly Tyr Ala Trp Phe Ile Tyr
210                 215                 220

Trp Gly Gln Gly Thr Leu Val Thr Val Ser Ser Gly Gly Cys Gly Gly
225                 230                 235                 240

Gly Lys Val Ala Ala Cys Lys Glu Lys Val Ala Ala Leu Lys Glu Lys
                245                 250                 255

Val Ala Ala Leu Lys Glu Lys Val Ala Ala Leu Lys Glu
            260                 265

<210> SEQ ID NO 33
<211> LENGTH: 561
<212> TYPE: PRT
<213> ORGANISM: Artificial Sequence
<220> FEATURE:
<223> OTHER INFORMATION: Synthetic Polypeptide

<400> SEQUENCE: 33

Asp Ile Gln Met Thr Gln Ser Pro Ser Ser Leu Ser Ala Ser Val Gly
  1               5                  10                  15

Asp Arg Val Thr Ile Thr Cys Lys Ala Ser Arg Asp Val Ala Ile Ala
                 20                  25                  30

Val Ala Trp Tyr Gln Gln Lys Pro Gly Lys Val Pro Lys Leu Leu Ile
             35                  40                  45

Tyr Trp Ala Ser Thr Arg His Thr Gly Val Pro Ser Arg Phe Ser Gly
         50                  55                  60

Ser Gly Ser Arg Thr Asp Phe Thr Leu Thr Ile Ser Ser Leu Gln Pro
 65                  70                  75                  80

Glu Asp Val Ala Asp Tyr Phe Cys His Gln Tyr Ser Ser Tyr Pro Phe
                 85                  90                  95

Thr Phe Gly Ser Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
            115                 120                 125

Pro Gly Ser Ser Val Lys Val Ser Cys Lys Ala Pro Asp His Ile Phe
        130                 135                 140

Ser Ile His Trp Met Gln Trp Val Arg Gln Ala Pro Gly Gln Gly Leu
145                 150                 155                 160
```

```
Glu Trp Met Gly Glu Ile Phe Pro Gly Ser Gly Thr Thr Asp Tyr Asn
                165                 170                 175
Glu Lys Phe Lys Gly Lys Val Thr Ile Thr Val Asp Lys Ser Thr Ser
            180                 185                 190
Thr Ala Tyr Met Glu Leu Ser Ser Leu Arg Ser Glu Asp Thr Ala Val
        195                 200                 205
Tyr Tyr Cys Ala Ser Gly Ala Phe Asp Tyr Trp Gly Gln Gly Thr Thr
    210                 215                 220
Val Thr Val Ser Ser Leu Gly Gly Gly Ser Gly Ala Ser Thr Lys Gly
225                 230                 235                 240
Pro Ser Val Phe Pro Leu Ala Pro Cys Ser Arg Ser Thr Ser Glu Ser
                245                 250                 255
Thr Ala Ala Leu Gly Cys Leu Val Lys Asp Tyr Phe Pro Glu Pro Val
            260                 265                 270
Thr Val Ser Trp Asn Ser Gly Ala Leu Thr Ser Gly Val His Thr Phe
        275                 280                 285
Pro Ala Val Leu Gln Ser Ser Gly Leu Tyr Ser Leu Ser Ser Val Val
    290                 295                 300
Thr Val Pro Ser Ser Ser Leu Gly Thr Lys Thr Tyr Thr Cys Asn Val
305                 310                 315                 320
Asp His Lys Pro Ser Asn Thr Lys Val Asp Lys Arg Val Glu Ser Lys
                325                 330                 335
Tyr Gly Pro Pro Cys Pro Pro Cys Pro Ala Pro Glu Phe Leu Gly Gly
            340                 345                 350
Pro Ser Val Phe Leu Phe Pro Pro Lys Pro Lys Asp Thr Leu Tyr Ile
        355                 360                 365
Thr Arg Glu Pro Glu Val Thr Cys Val Val Val Asp Val Ser Gln Glu
    370                 375                 380
Asp Pro Glu Val Gln Phe Asn Trp Tyr Val Asp Gly Val Glu Val His
385                 390                 395                 400
Asn Ala Lys Thr Lys Pro Arg Glu Glu Gln Phe Asn Ser Thr Tyr Arg
                405                 410                 415
Val Val Ser Val Leu Thr Val Leu His Gln Asp Trp Leu Asn Gly Lys
            420                 425                 430
Glu Tyr Lys Cys Lys Val Ser Asn Lys Gly Leu Pro Ser Ser Ile Glu
        435                 440                 445
Lys Thr Ile Ser Lys Ala Lys Gly Gln Pro Arg Glu Pro Gln Val Tyr
    450                 455                 460
Thr Leu Pro Pro Ser Gln Glu Glu Met Thr Lys Asn Gln Val Ser Leu
465                 470                 475                 480
Thr Cys Leu Val Lys Gly Phe Tyr Pro Ser Asp Ile Ala Val Glu Trp
                485                 490                 495
Glu Ser Asn Gly Gln Pro Glu Asn Asn Tyr Lys Thr Thr Pro Pro Val
            500                 505                 510
Leu Asp Ser Asp Gly Ser Phe Phe Leu Tyr Ser Arg Leu Thr Val Asp
        515                 520                 525
Lys Ser Arg Trp Gln Glu Gly Asn Val Phe Ser Cys Ser Val Met His
    530                 535                 540
Glu Ala Leu His Asn His Tyr Thr Gln Lys Ser Leu Ser Leu Ser Leu
545                 550                 555                 560
Gly

<210> SEQ ID NO 34
```

<211> LENGTH: 348
<212> TYPE: PRT
<213> ORGANISM: Artificial Sequence
<220> FEATURE:
<223> OTHER INFORMATION: Synthetic Polypeptide

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Arg
            20                  25                  30

Leu Asn Trp Tyr Gln Gln Lys Pro Gly Lys Ala Pro Lys Arg Leu Ile
        35                  40                  45

Tyr Ala Thr Ser Ser Leu Asp Ser Gly Val Pro Ser Arg Phe Ser Gly
50                  55                  60

Ser Arg Ser Gly Thr Glu Phe Thr Leu Thr Ile Ser Ser Leu Gln Pro
65                  70                  75                  80

Glu Asp Phe Val Thr Tyr Tyr Cys Leu Gln Tyr Ala Ser Ser Pro Phe
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
210                 215                 220

Trp Gly Gln Gly Thr Leu Val Thr Val Ser Ser Leu Gly Gly Gly Ser
225                 230                 235                 240

Gly Arg Thr Val Ala Ala Pro Ser Val Phe Ile Phe Pro Pro Ser Asp
                245                 250                 255

Glu Gln Leu Lys Ser Gly Thr Ala Ser Val Val Cys Leu Leu Asn Asn
            260                 265                 270

Phe Tyr Pro Arg Glu Ala Lys Val Gln Trp Lys Val Asp Asn Ala Leu
        275                 280                 285

Gln Ser Gly Asn Ser Gln Glu Ser Val Thr Glu Gln Asp Ser Lys Asp
290                 295                 300

Ser Thr Tyr Ser Leu Ser Ser Thr Leu Thr Leu Ser Lys Ala Asp Tyr
305                 310                 315                 320

Glu Lys His Lys Val Tyr Ala Cys Glu Val Thr His Gln Gly Leu Ser
                325                 330                 335

Ser Pro Val Thr Lys Ser Phe Asn Arg Gly Glu Cys
            340                 345

<210> SEQ ID NO 35
<211> LENGTH: 491
<212> TYPE: PRT
<213> ORGANISM: Artificial Sequence
<220> FEATURE:
<223> OTHER INFORMATION: Synthetic Polypeptide

<400> SEQUENCE: 35

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Pro Asp His Ile Phe
130                 135                 140

Ser Ile His Trp Met Gln Trp Val Arg Gln Ala Pro Gly Gln Gly Leu
145                 150                 155                 160

Glu Trp Met Gly Glu Ile Phe Pro Gly Ser Gly Thr Thr Asp Tyr Asn
                165                 170                 175

Glu Lys Phe Lys Gly Lys Val Thr Ile Thr Val Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ser Gly Ala Phe Asp Tyr Trp Gly Gln Gly Thr Thr
    210                 215                 220

Val Thr Val Ser Ser Gly Gly Cys Gly Gly Gly Glu Val Ala Ala Cys
225                 230                 235                 240

Glu Lys Glu Val Ala Ala Leu Glu Lys Glu Val Ala Ala Leu Glu Lys
                245                 250                 255

Glu Val Ala Ala Leu Glu Lys Gly Ser Lys Tyr Gly Pro Pro Cys Pro
            260                 265                 270

Pro Cys Pro Ala Pro Glu Phe Leu Gly Gly Pro Ser Val Phe Leu Phe
        275                 280                 285

Pro Pro Lys Pro Lys Asp Thr Leu Tyr Ile Thr Arg Glu Pro Glu Val
290                 295                 300

Thr Cys Val Val Val Asp Val Ser Gln Glu Asp Pro Glu Val Gln Phe
305                 310                 315                 320

Asn Trp Tyr Val Asp Gly Val Glu Val His Asn Ala Lys Thr Lys Pro
                325                 330                 335

Arg Glu Glu Gln Phe Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Gly Leu Pro Ser Ser Ile Glu Lys Thr Ile Ser Lys Ala
    370                 375                 380

Lys Gly Gln Pro Arg Glu Pro Gln Val Tyr Thr Leu Pro Pro Ser Gln
385                 390                 395                 400
```

```
Glu Glu Met Thr Lys Asn Gln Val Ser Leu Thr Cys Leu Val Lys Gly
            405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
            435                 440                 445

Phe Phe Leu Tyr Ser Arg Leu Thr Val Asp Lys Ser Arg Trp Gln Glu
450                 455                 460

Gly Asn Val Phe Ser Cys Ser Val Met His Glu Ala Leu His Asn His
465                 470                 475                 480

Tyr Thr Gln Lys Ser Leu Ser Leu Ser Leu Gly
            485                 490

<210> SEQ ID NO 36
<211> LENGTH: 269
<212> TYPE: PRT
<213> ORGANISM: Artificial Sequence
<220> FEATURE:
<223> OTHER INFORMATION: Synthetic Polypeptide

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Arg
            20                  25                  30

Leu Asn Trp Tyr Gln Gln Lys Pro Gly Lys Ala Pro Lys Arg Leu Ile
        35                  40                  45

Tyr Ala Thr Ser Ser Leu Asp Ser Gly Val Pro Ser Arg Phe Ser Gly
    50                  55                  60

Ser Arg Ser Gly Thr Glu Phe Thr Leu Thr Ile Ser Ser Leu Gln Pro
65                  70                  75                  80

Glu Asp Phe Val Thr Tyr Tyr Cys Leu Gln Tyr Ala Ser Ser Pro Phe
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
    130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
    210                 215                 220

Trp Gly Gln Gly Thr Leu Val Thr Val Ser Ser Gly Gly Cys Gly Gly
225                 230                 235                 240

Gly Lys Val Ala Ala Cys Lys Glu Lys Val Ala Ala Leu Lys Glu Lys
                245                 250                 255

Val Ala Ala Leu Lys Glu Lys Val Ala Ala Leu Lys Glu
            260                 265
```

<210> SEQ ID NO 37
<211> LENGTH: 572
<212> TYPE: PRT
<213> ORGANISM: Artificial Sequence
<220> FEATURE:
<223> OTHER INFORMATION: Synthetic Polypeptide

<400> SEQUENCE: 37

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Ser Phe
    130                 135                 140

Ser Thr Phe Phe Ile His Trp Val Arg Gln Arg Pro Gly Gln Gly Leu
145                 150                 155                 160

Glu Trp Ile Gly Arg Ile Asp Pro Asn Ser Gly Ala Thr Lys Tyr Asn
                165                 170                 175

Glu Lys Phe Glu Ser Lys Val Thr Leu Thr Arg Asp Thr Ser Ile Ser
            180                 185                 190

Thr Ala Tyr Met Glu Leu Ser Arg Leu Arg Ser Asp Asp Thr Ala Val
        195                 200                 205

Tyr Tyr Cys Ala Arg Gly Glu Asp Leu Leu Ile Arg Thr Asp Ala Leu
    210                 215                 220

Asp Tyr Trp Gly Gln Gly Thr Ser Val Thr Val Ser Ser Leu Gly Gly
225                 230                 235                 240

Gly Ser Gly Ala Ser Thr Lys Gly Pro Ser Val Phe Pro Leu Ala Pro
                245                 250                 255

Ser Ser Lys Ser Thr Ser Gly Gly Thr Ala Ala Leu Gly Cys Leu Val
            260                 265                 270

Lys Asp Tyr Phe Pro Glu Pro Val Thr Val Ser Trp Asn Ser Gly Ala
        275                 280                 285

Leu Thr Ser Gly Val His Thr Phe Pro Ala Val Leu Gln Ser Ser Gly
    290                 295                 300

Leu Tyr Ser Leu Ser Ser Val Val Thr Val Pro Ser Ser Ser Leu Gly
305                 310                 315                 320

Thr Gln Thr Tyr Ile Cys Asn Val Asn His Lys Pro Ser Asn Thr Lys
                325                 330                 335

Val Asp Lys Arg Val Glu Pro Lys Ser Cys Asp Lys Thr His Thr Cys
            340                 345                 350

Pro Pro Cys Pro Ala Pro Glu Ala Ala Gly Gly Pro Ser Val Phe Leu
        355                 360                 365
```

```
Phe Pro Pro Lys Pro Lys Asp Thr Leu Tyr Ile Thr Arg Glu Pro Glu
    370             375                 380

Val Thr Cys Val Val Val Asp Val Ser His Glu Asp Pro Glu Val Lys
385                 390                 395                 400

Phe Asn Trp Tyr Val Asp Gly Val Glu Val His Asn Ala Lys Thr Lys
                405                 410                 415

Pro Arg Glu Glu Gln Tyr Asn Ser Thr Tyr Arg Val Val Ser Val Leu
            420                 425                 430

Thr Val Leu His Gln Asp Trp Leu Asn Gly Lys Glu Tyr Lys Cys Lys
            435                 440                 445

Val Ser Asn Lys Ala Leu Pro Ala Pro Ile Glu Lys Thr Ile Ser Lys
450                 455                 460

Ala Lys Gly Gln Pro Arg Glu Pro Gln Val Tyr Thr Leu Pro Pro Ser
465                 470                 475                 480

Arg Glu Glu Met Thr Lys Asn Gln Val Ser Leu Thr Cys Leu Val Lys
                485                 490                 495

Gly Phe Tyr Pro Ser Asp Ile Ala Val Glu Trp Glu Ser Asn Gly Gln
                500                 505                 510

Pro Glu Asn Asn Tyr Lys Thr Thr Pro Pro Val Leu Asp Ser Asp Gly
            515                 520                 525

Ser Phe Phe Leu Tyr Ser Lys Leu Thr Val Asp Lys Ser Arg Trp Gln
530                 535                 540

Gln Gly Asn Val Phe Ser Cys Ser Val Met His Glu Ala Leu His Asn
545                 550                 555                 560

His Tyr Thr Gln Lys Ser Leu Ser Leu Ser Pro Gly
                565                 570

<210> SEQ ID NO 38
<211> LENGTH: 348
<212> TYPE: PRT
<213> ORGANISM: Artificial Sequence
<220> FEATURE:
<223> OTHER INFORMATION: Synthetic Polypeptide

<400> SEQUENCE: 38

Asp Ile Gln Met Thr Gln Ser Pro Ser Ser Leu Ser Ala Ser Val Gly
1               5                   10                  15

Asp Arg Val Ser Ile Thr Cys Lys Ala Ser Gln Asn Ala Gly Ile Asp
            20                  25                  30

Val Ala Trp Phe Gln Gln Lys Pro Gly Lys Ala Pro Lys Leu Leu Ile
            35                  40                  45

Tyr Ser Lys Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Tyr Cys Leu Gln Tyr Arg Ser Tyr Pro Arg
                85                  90                  95

Thr Phe Gly Gly Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
            115                 120                 125

Pro Gly Ser Ser Val Lys Val Ser Cys Lys Ala Ser Gly Tyr Thr Phe
    130                 135                 140

Thr Asp Gln Thr Ile His Trp Met Arg Gln Ala Pro Gly Gln Gly Leu
145                 150                 155                 160
```

Glu Trp Ile Gly Tyr Ile Tyr Pro Arg Asp Ser Pro Lys Tyr Asn
            165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
            195                 200                 205

Tyr Tyr Cys Ala Ile Pro Asp Arg Ser Gly Tyr Ala Trp Phe Ile Tyr
210                 215                 220

Trp Gly Gln Gly Thr Leu Val Thr Val Ser Ser Leu Gly Gly Gly Ser
225                 230                 235                 240

Gly Arg Thr Val Ala Ala Pro Ser Val Phe Ile Phe Pro Pro Ser Asp
            245                 250                 255

Glu Gln Leu Lys Ser Gly Thr Ala Ser Val Val Cys Leu Leu Asn Asn
            260                 265                 270

Phe Tyr Pro Arg Glu Ala Lys Val Gln Trp Lys Val Asp Asn Ala Leu
            275                 280                 285

Gln Ser Gly Asn Ser Gln Glu Ser Val Thr Glu Gln Asp Ser Lys Asp
290                 295                 300

Ser Thr Tyr Ser Leu Ser Ser Thr Leu Thr Leu Ser Lys Ala Asp Tyr
305                 310                 315                 320

Glu Lys His Lys Val Tyr Ala Cys Glu Val Thr His Gln Gly Leu Ser
            325                 330                 335

Ser Pro Val Thr Lys Ser Phe Asn Arg Gly Glu Cys
            340                 345

<210> SEQ ID NO 39
<211> LENGTH: 503
<212> TYPE: PRT
<213> ORGANISM: Artificial Sequence
<220> FEATURE:
<223> OTHER INFORMATION: Synthetic Polypeptide

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
            35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Ser Phe
            130                 135                 140

Ser Thr Phe Phe Ile His Trp Val Arg Gln Arg Pro Gly Gln Gly Leu
145                 150                 155                 160

Glu Trp Ile Gly Arg Ile Asp Pro Asn Ser Gly Ala Thr Lys Tyr Asn
                165                 170                 175

```
Glu Lys Phe Glu Ser Lys Val Thr Leu Thr Arg Asp Thr Ser Ile Ser
                180                 185                 190

Thr Ala Tyr Met Glu Leu Ser Arg Leu Arg Ser Asp Thr Ala Val
            195                 200                 205

Tyr Tyr Cys Ala Arg Gly Glu Asp Leu Leu Ile Arg Thr Asp Ala Leu
        210                 215                 220

Asp Tyr Trp Gly Gln Gly Thr Ser Val Thr Val Ser Ser Gly Gly Cys
225                 230                 235                 240

Gly Gly Gly Glu Val Ala Ala Cys Glu Lys Glu Val Ala Ala Leu Glu
                245                 250                 255

Lys Glu Val Ala Ala Leu Glu Lys Glu Val Ala Ala Leu Glu Lys Leu
                260                 265                 270

Glu Pro Lys Ser Ser Asp Lys Thr His Thr Cys Pro Pro Cys Pro Ala
            275                 280                 285

Pro Glu Ala Ala Gly Gly Pro Ser Val Phe Leu Phe Pro Pro Lys Pro
        290                 295                 300

Lys Asp Thr Leu Tyr Ile Thr Arg Glu Pro Glu Val Thr Cys Val Val
305                 310                 315                 320

Val Asp Val Ser His Glu Asp Pro Glu Val Lys Phe Asn Trp Tyr Val
                325                 330                 335

Asp Gly Val Glu Val His Asn Ala Lys Thr Lys Pro Arg Glu Glu Gln
                340                 345                 350

Tyr Asn Ser Thr Tyr Arg Val Val Ser Val Leu Thr Val Leu His Gln
            355                 360                 365

Asp Trp Leu Asn Gly Lys Glu Tyr Lys Cys Lys Val Ser Asn Lys Ala
370                 375                 380

Leu Pro Ala Pro Ile Glu Lys Thr Ile Ser Lys Ala Lys Gly Gln Pro
385                 390                 395                 400

Arg Glu Pro Gln Val Tyr Thr Leu Pro Pro Ser Arg Glu Glu Met Thr
                405                 410                 415

Lys Asn Gln Val Ser Leu Thr Cys Leu Val Lys Gly Phe Tyr Pro Ser
            420                 425                 430

Asp Ile Ala Val Glu Trp Glu Ser Asn Gly Gln Pro Glu Asn Asn Tyr
        435                 440                 445

Lys Thr Thr Pro Pro Val Leu Asp Ser Asp Gly Ser Phe Phe Leu Tyr
450                 455                 460

Ser Lys Leu Thr Val Asp Lys Ser Arg Trp Gln Gln Gly Asn Val Phe
465                 470                 475                 480

Ser Cys Ser Val Met His Glu Ala Leu His Asn His Tyr Thr Gln Lys
                485                 490                 495

Ser Leu Ser Leu Ser Pro Gly
            500

<210> SEQ ID NO 40
<211> LENGTH: 269
<212> TYPE: PRT
<213> ORGANISM: Artificial Sequence
<220> FEATURE:
<223> OTHER INFORMATION: Synthetic Polypeptide

<400> SEQUENCE: 40

Asp Ile Gln Met Thr Gln Ser Pro Ser Leu Ser Ala Ser Val Gly
1               5                   10                  15

Asp Arg Val Ser Ile Thr Cys Lys Ala Ser Gln Asn Ala Gly Ile Asp
                20                  25                  30
```

Val Ala Trp Phe Gln Gln Lys Pro Gly Lys Ala Pro Lys Leu Leu Ile
            35                  40                  45

Tyr Ser Lys Ser Asn Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Asp Tyr Tyr Cys Leu Gln Tyr Arg Ser Tyr Pro Arg
                85                  90                  95

Thr Phe Gly Gly Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
210                 215                 220

Trp Gly Gln Gly Thr Leu Val Thr Val Ser Ser Gly Cys Gly Gly Gly
225                 230                 235                 240

Gly Lys Val Ala Ala Cys Lys Glu Lys Val Ala Ala Leu Lys Glu Lys
                245                 250                 255

Val Ala Ala Leu Lys Glu Lys Val Ala Ala Leu Lys Glu
            260                 265

<210> SEQ ID NO 41
<211> LENGTH: 569
<212> TYPE: PRT
<213> ORGANISM: Artificial Sequence
<220> FEATURE:
<223> OTHER INFORMATION: Synthetic Polypeptide

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
            35                  40                  45

Tyr Trp Ala Ser Thr Arg His Thr Gly Val Pro Ser Arg Phe Ser Gly
        50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

```
Pro Gly Ala Ser Val Lys Val Ser Cys Lys Ala Ser Gly Tyr Ser Phe
    130                 135                 140
Ser Thr Phe Phe Ile His Trp Val Arg Gln Arg Pro Gly Gln Gly Leu
145                 150                 155                 160
Glu Trp Ile Gly Arg Ile Asp Pro Asn Ser Gly Ala Thr Lys Tyr Asn
                165                 170                 175
Glu Lys Phe Glu Ser Lys Val Thr Leu Thr Arg Asp Thr Ser Ile Ser
            180                 185                 190
Thr Ala Tyr Met Glu Leu Ser Arg Leu Arg Ser Asp Asp Thr Ala Val
        195                 200                 205
Tyr Tyr Cys Ala Arg Gly Glu Asp Leu Leu Ile Arg Thr Asp Ala Leu
    210                 215                 220
Asp Tyr Trp Gly Gln Gly Thr Ser Val Thr Val Ser Ser Leu Gly Gly
225                 230                 235                 240
Gly Ser Gly Ala Ser Thr Lys Gly Pro Ser Val Phe Pro Leu Ala Pro
                245                 250                 255
Cys Ser Arg Ser Thr Ser Glu Ser Thr Ala Ala Leu Gly Cys Leu Val
            260                 265                 270
Lys Asp Tyr Phe Pro Glu Pro Val Thr Val Ser Trp Asn Ser Gly Ala
        275                 280                 285
Leu Thr Ser Gly Val His Thr Phe Pro Ala Val Leu Gln Ser Ser Gly
    290                 295                 300
Leu Tyr Ser Leu Ser Ser Val Val Thr Val Pro Ser Ser Ser Leu Gly
305                 310                 315                 320
Thr Lys Thr Tyr Thr Cys Asn Val Asp His Lys Pro Ser Asn Thr Lys
                325                 330                 335
Val Asp Lys Arg Val Glu Ser Lys Tyr Gly Pro Pro Cys Pro Pro Cys
            340                 345                 350
Pro Ala Pro Glu Phe Leu Gly Gly Pro Ser Val Phe Leu Phe Pro Pro
        355                 360                 365
Lys Pro Lys Asp Thr Leu Tyr Ile Thr Arg Glu Pro Glu Val Thr Cys
    370                 375                 380
Val Val Val Asp Val Ser Gln Glu Asp Pro Glu Val Gln Phe Asn Trp
385                 390                 395                 400
Tyr Val Asp Gly Val Glu Val His Asn Ala Lys Thr Lys Pro Arg Glu
                405                 410                 415
Glu Gln Phe Asn Ser Thr Tyr Arg Val Val Ser Val Leu Thr Val Leu
            420                 425                 430
His Gln Asp Trp Leu Asn Gly Lys Glu Tyr Lys Cys Lys Val Ser Asn
        435                 440                 445
Lys Gly Leu Pro Ser Ser Ile Glu Lys Thr Ile Ser Lys Ala Lys Gly
    450                 455                 460
Gln Pro Arg Glu Pro Gln Val Tyr Thr Leu Pro Pro Ser Gln Glu Glu
465                 470                 475                 480
Met Thr Lys Asn Gln Val Ser Leu Thr Cys Leu Val Lys Gly Phe Tyr
                485                 490                 495
Pro Ser Asp Ile Ala Val Glu Trp Glu Ser Asn Gly Gln Pro Glu Asn
            500                 505                 510
Asn Tyr Lys Thr Thr Pro Pro Val Leu Asp Ser Asp Gly Ser Phe Phe
        515                 520                 525
Leu Tyr Ser Arg Leu Thr Val Asp Lys Ser Arg Trp Gln Glu Gly Asn
    530                 535                 540
```

Val Phe Ser Cys Ser Val Met His Glu Ala Leu His Asn His Tyr Thr
545                 550                 555                 560

Gln Lys Ser Leu Ser Leu Ser Leu Gly
                565

<210> SEQ ID NO 42
<211> LENGTH: 348
<212> TYPE: PRT
<213> ORGANISM: Artificial Sequence
<220> FEATURE:
<223> OTHER INFORMATION: Synthetic Polypeptide

<400> SEQUENCE: 42

Asp Ile Gln Met Thr Gln Ser Pro Ser Ser Leu Ser Ala Ser Val Gly
1               5                   10                  15

Asp Arg Val Ser Ile Thr Cys Lys Ala Ser Gln Asn Ala Gly Ile Asp
            20                  25                  30

Val Ala Trp Phe Gln Gln Lys Pro Gly Lys Ala Pro Lys Leu Leu Ile
        35                  40                  45

Tyr Ser Lys Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Tyr Cys Leu Gln Tyr Arg Ser Tyr Pro Arg
                85                  90                  95

Thr Phe Gly Gly Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
    210                 215                 220

Trp Gly Gln Gly Thr Leu Val Thr Val Ser Ser Leu Gly Gly Gly Ser
225                 230                 235                 240

Gly Arg Thr Val Ala Ala Pro Ser Val Phe Ile Phe Pro Pro Ser Asp
                245                 250                 255

Glu Gln Leu Lys Ser Gly Thr Ala Ser Val Val Cys Leu Leu Asn Asn
            260                 265                 270

Phe Tyr Pro Arg Glu Ala Lys Val Gln Trp Lys Val Asp Asn Ala Leu
        275                 280                 285

Gln Ser Gly Asn Ser Gln Glu Ser Val Thr Glu Gln Asp Ser Lys Asp
    290                 295                 300

Ser Thr Tyr Ser Leu Ser Ser Thr Leu Thr Leu Ser Lys Ala Asp Tyr
305                 310                 315                 320

Glu Lys His Lys Val Tyr Ala Cys Glu Val Thr His Gln Gly Leu Ser
                325                 330                 335

```
Ser Pro Val Thr Lys Ser Phe Asn Arg Gly Glu Cys
            340                 345
```

<210> SEQ ID NO 43
<211> LENGTH: 499
<212> TYPE: PRT
<213> ORGANISM: Artificial Sequence
<220> FEATURE:
<223> OTHER INFORMATION: Synthetic Polypeptide

<400> SEQUENCE: 43

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Ser Phe
130                 135                 140

Ser Thr Phe Phe Ile His Trp Val Arg Gln Arg Pro Gly Gln Gly Leu
145                 150                 155                 160

Glu Trp Ile Gly Arg Ile Asp Pro Asn Ser Gly Ala Thr Lys Tyr Asn
                165                 170                 175

Glu Lys Phe Glu Ser Lys Val Thr Leu Thr Arg Asp Thr Ser Ile Ser
            180                 185                 190

Thr Ala Tyr Met Glu Leu Ser Arg Leu Arg Ser Asp Asp Thr Ala Val
        195                 200                 205

Tyr Tyr Cys Ala Arg Gly Glu Asp Leu Leu Ile Arg Thr Asp Ala Leu
210                 215                 220

Asp Tyr Trp Gly Gln Gly Thr Ser Val Thr Val Ser Ser Gly Gly Cys
225                 230                 235                 240

Gly Gly Gly Glu Val Ala Ala Cys Glu Lys Glu Val Ala Ala Leu Glu
                245                 250                 255

Lys Glu Val Ala Ala Leu Glu Lys Glu Val Ala Ala Leu Glu Lys Glu
            260                 265                 270

Ser Lys Tyr Gly Pro Pro Cys Pro Pro Cys Pro Ala Pro Glu Phe Leu
        275                 280                 285

Gly Gly Pro Ser Val Phe Leu Phe Pro Pro Lys Pro Lys Asp Thr Leu
290                 295                 300

Tyr Ile Thr Arg Glu Pro Glu Val Thr Cys Val Val Val Asp Val Ser
305                 310                 315                 320

Gln Glu Asp Pro Glu Val Gln Phe Asn Trp Tyr Val Asp Gly Val Glu
                325                 330                 335

Val His Asn Ala Lys Thr Lys Pro Arg Glu Glu Gln Phe Asn Ser Thr
            340                 345                 350
```

```
Tyr Arg Val Val Ser Val Leu Thr Val Leu His Gln Asp Trp Leu Asn
            355                 360                 365

Gly Lys Glu Tyr Lys Cys Lys Val Ser Asn Lys Gly Leu Pro Ser Ser
        370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Gln Glu Glu Met Thr Lys Asn Gln Val
                405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
        435                 440                 445

Pro Val Leu Asp Ser Asp Gly Ser Phe Phe Leu Tyr Ser Arg Leu Thr
    450                 455                 460

Val Asp Lys Ser Arg Trp Gln Glu Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Leu Gly

<210> SEQ ID NO 44
<211> LENGTH: 269
<212> TYPE: PRT
<213> ORGANISM: Artificial Sequence
<220> FEATURE:
<223> OTHER INFORMATION: Synthetic Polypeptide

<400> SEQUENCE: 44

Asp Ile Gln Met Thr Gln Ser Pro Ser Ser Leu Ser Ala Ser Val Gly
1               5                   10                  15

Asp Arg Val Ser Ile Thr Cys Lys Ala Ser Gln Asn Ala Gly Ile Asp
            20                  25                  30

Val Ala Trp Phe Gln Gln Lys Pro Gly Lys Ala Pro Lys Leu Leu Ile
        35                  40                  45

Tyr Ser Lys Ser Asn Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Asp Tyr Tyr Cys Leu Gln Tyr Arg Ser Tyr Pro Arg
                85                  90                  95

Thr Phe Gly Gly Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
    130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
```

Trp Gly Gln Gly Thr Leu Val Thr Val Ser Ser Gly Cys Gly Gly
225                 230                 235                 240

Gly Lys Val Ala Ala Cys Lys Glu Lys Val Ala Ala Leu Lys Glu Lys
                245                 250                 255

Val Ala Ala Leu Lys Glu Lys Val Ala Ala Leu Lys Glu
                260                 265

<210> SEQ ID NO 45
<211> LENGTH: 572
<212> TYPE: PRT
<213> ORGANISM: Artificial Sequence
<220> FEATURE:
<223> OTHER INFORMATION: Synthetic Polypeptide

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
                20                  25                  30

Val Ala Trp Tyr Gln Gln Lys Pro Gly Lys Val Pro Lys Leu Leu Ile
            35                  40                  45

Tyr Trp Ala Ser Thr Arg His Thr Gly Val Pro Ser Arg Phe Ser Gly
50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Ser Phe
    130                 135                 140

Ser Thr Phe Phe Ile His Trp Val Arg Gln Ala Pro Gly Gln Gly Leu
145                 150                 155                 160

Glu Trp Ile Gly Arg Ile Asp Pro Asn Ser Gly Ala Thr Lys Tyr Asn
                165                 170                 175

Glu Lys Phe Glu Ser Arg Val Thr Met Thr Arg Asp Thr Ser Ile Ser
            180                 185                 190

Thr Ala Tyr Met Glu Leu Ser Arg Leu Arg Ser Asp Asp Thr Ala Val
        195                 200                 205

Tyr Tyr Cys Ala Arg Gly Glu Asp Leu Leu Ile Arg Thr Asp Ala Leu
    210                 215                 220

Asp Tyr Trp Gly Gln Gly Thr Ser Val Thr Val Ser Ser Leu Gly Gly
225                 230                 235                 240

Gly Ser Gly Ala Ser Thr Lys Gly Pro Ser Val Phe Pro Leu Ala Pro
                245                 250                 255

Ser Ser Lys Ser Thr Ser Gly Gly Thr Ala Ala Leu Gly Cys Leu Val
            260                 265                 270

Lys Asp Tyr Phe Pro Glu Pro Val Thr Val Ser Trp Asn Ser Gly Ala
        275                 280                 285

Leu Thr Ser Gly Val His Thr Phe Pro Ala Val Leu Gln Ser Ser Gly
    290                 295                 300

Leu Tyr Ser Leu Ser Ser Val Val Thr Val Pro Ser Ser Ser Leu Gly

```
              305                 310                 315                 320
Thr Gln Thr Tyr Ile Cys Asn Val Asn His Lys Pro Ser Asn Thr Lys
                325                 330                 335

Val Asp Lys Arg Val Glu Pro Lys Ser Cys Asp Lys Thr His Thr Cys
                340                 345                 350

Pro Pro Cys Pro Ala Pro Glu Ala Gly Gly Pro Ser Val Phe Leu
                355                 360                 365

Phe Pro Pro Lys Pro Lys Asp Thr Leu Tyr Ile Thr Arg Glu Pro Glu
    370                 375                 380

Val Thr Cys Val Val Val Asp Val Ser His Glu Asp Pro Glu Val Lys
385                 390                 395                 400

Phe Asn Trp Tyr Val Asp Gly Val Glu Val His Asn Ala Lys Thr Lys
                405                 410                 415

Pro Arg Glu Glu Gln Tyr Asn Ser Thr Tyr Arg Val Val Ser Val Leu
                420                 425                 430

Thr Val Leu His Gln Asp Trp Leu Asn Gly Lys Glu Tyr Lys Cys Lys
                435                 440                 445

Val Ser Asn Lys Ala Leu Pro Ala Pro Ile Glu Lys Thr Ile Ser Lys
450                 455                 460

Ala Lys Gly Gln Pro Arg Glu Pro Gln Val Tyr Thr Leu Pro Pro Ser
465                 470                 475                 480

Arg Glu Glu Met Thr Lys Asn Gln Val Ser Leu Thr Cys Leu Val Lys
                485                 490                 495

Gly Phe Tyr Pro Ser Asp Ile Ala Val Glu Trp Glu Ser Asn Gly Gln
                500                 505                 510

Pro Glu Asn Asn Tyr Lys Thr Thr Pro Pro Val Leu Asp Ser Asp Gly
                515                 520                 525

Ser Phe Phe Leu Tyr Ser Lys Leu Thr Val Asp Lys Ser Arg Trp Gln
                530                 535                 540

Gln Gly Asn Val Phe Ser Cys Ser Val Met His Glu Ala Leu His Asn
545                 550                 555                 560

His Tyr Thr Gln Lys Ser Leu Ser Leu Ser Pro Gly
                565                 570

<210> SEQ ID NO 46
<211> LENGTH: 348
<212> TYPE: PRT
<213> ORGANISM: Artificial Sequence
<220> FEATURE:
<223> OTHER INFORMATION: Synthetic Polypeptide

<400> SEQUENCE: 46

Asp Ile Gln Met Thr Gln Ser Pro Ser Ser Leu Ser Ala Ser Val Gly
1               5                   10                  15

Asp Arg Val Ser Ile Thr Cys Lys Ala Ser Gln Asn Ala Gly Ile Asp
                20                  25                  30

Val Ala Trp Phe Gln Gln Lys Pro Gly Lys Ala Pro Lys Leu Leu Ile
            35                  40                  45

Tyr Ser Lys Ser Asn Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Arg Ser Tyr Pro Arg
                85                  90                  95

Thr Phe Gly Gln Gly Thr Lys Leu Glu Ile Lys Gly Gly Gly Ser Gly
```

```
            100                 105                 110
Gly Gly Gly Gln Val Gln Leu Val Gln Ser Gly Ala Glu Val Lys Lys
            115                 120                 125

Pro Gly Ser Ser Val Lys Val Ser Cys Lys Ala Ser Gly Tyr Thr Phe
        130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
    210                 215                 220

Trp Gly Gln Gly Thr Leu Val Thr Val Ser Ser Leu Gly Gly Gly Ser
225                 230                 235                 240

Gly Arg Thr Val Ala Ala Pro Ser Val Phe Ile Phe Pro Pro Ser Asp
                245                 250                 255

Glu Gln Leu Lys Ser Gly Thr Ala Ser Val Val Cys Leu Leu Asn Asn
            260                 265                 270

Phe Tyr Pro Arg Glu Ala Lys Val Gln Trp Lys Val Asp Asn Ala Leu
        275                 280                 285

Gln Ser Gly Asn Ser Gln Glu Ser Val Thr Glu Gln Asp Ser Lys Asp
    290                 295                 300

Ser Thr Tyr Ser Leu Ser Ser Thr Leu Thr Leu Ser Lys Ala Asp Tyr
305                 310                 315                 320

Glu Lys His Lys Val Tyr Ala Cys Glu Val Thr His Gln Gly Leu Ser
                325                 330                 335

Ser Pro Val Thr Lys Ser Phe Asn Arg Gly Glu Cys
            340                 345

<210> SEQ ID NO 47
<211> LENGTH: 503
<212> TYPE: PRT
<213> ORGANISM: Artificial Sequence
<220> FEATURE:
<223> OTHER INFORMATION: Synthetic Polypeptide

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
```

```
            115                 120                 125
Pro Gly Ala Ser Val Lys Val Ser Cys Lys Ala Ser Gly Tyr Ser Phe
            130                 135                 140
Ser Thr Phe Phe Ile His Trp Val Arg Gln Ala Pro Gly Gln Gly Leu
145                 150                 155                 160
Glu Trp Ile Gly Arg Ile Asp Pro Asn Ser Gly Ala Thr Lys Tyr Asn
                165                 170                 175
Glu Lys Phe Glu Ser Arg Val Thr Met Thr Arg Asp Thr Ser Ile Ser
            180                 185                 190
Thr Ala Tyr Met Glu Leu Ser Arg Leu Arg Ser Asp Thr Ala Val
            195                 200                 205
Tyr Tyr Cys Ala Arg Gly Glu Asp Leu Leu Ile Arg Thr Asp Ala Leu
            210                 215                 220
Asp Tyr Trp Gly Gln Gly Thr Ser Val Thr Val Ser Ser Gly Gly Cys
225                 230                 235                 240
Gly Gly Gly Glu Val Ala Ala Cys Glu Lys Glu Val Ala Ala Leu Glu
                245                 250                 255
Lys Glu Val Ala Ala Leu Glu Lys Glu Val Ala Ala Leu Glu Lys Leu
            260                 265                 270
Glu Pro Lys Ser Ser Asp Lys Thr His Thr Cys Pro Pro Cys Pro Ala
            275                 280                 285
Pro Glu Ala Ala Gly Gly Pro Ser Val Phe Leu Phe Pro Pro Lys Pro
            290                 295                 300
Lys Asp Thr Leu Tyr Ile Thr Arg Glu Pro Glu Val Thr Cys Val Val
305                 310                 315                 320
Val Asp Val Ser His Glu Asp Pro Glu Val Lys Phe Asn Trp Tyr Val
                325                 330                 335
Asp Gly Val Glu Val His Asn Ala Lys Thr Lys Pro Arg Glu Glu Gln
            340                 345                 350
Tyr Asn Ser Thr Tyr Arg Val Val Ser Val Leu Thr Val Leu His Gln
            355                 360                 365
Asp Trp Leu Asn Gly Lys Glu Tyr Lys Cys Lys Val Ser Asn Lys Ala
            370                 375                 380
Leu Pro Ala Pro Ile Glu Lys Thr Ile Ser Lys Ala Lys Gly Gln Pro
385                 390                 395                 400
Arg Glu Pro Gln Val Tyr Thr Leu Pro Pro Ser Arg Glu Glu Met Thr
                405                 410                 415
Lys Asn Gln Val Ser Leu Thr Cys Leu Val Lys Gly Phe Tyr Pro Ser
            420                 425                 430
Asp Ile Ala Val Glu Trp Glu Ser Asn Gly Gln Pro Glu Asn Asn Tyr
            435                 440                 445
Lys Thr Thr Pro Pro Val Leu Asp Ser Asp Gly Ser Phe Phe Leu Tyr
            450                 455                 460
Ser Lys Leu Thr Val Asp Lys Ser Arg Trp Gln Gln Gly Asn Val Phe
465                 470                 475                 480
Ser Cys Ser Val Met His Glu Ala Leu His Asn His Tyr Thr Gln Lys
                485                 490                 495
Ser Leu Ser Leu Ser Pro Gly
            500

<210> SEQ ID NO 48
<211> LENGTH: 269
<212> TYPE: PRT
<213> ORGANISM: Artificial Sequence
```

<220> FEATURE:
<223> OTHER INFORMATION: Synthetic Polypeptide

<400> SEQUENCE: 48

```
Asp Ile Gln Met Thr Gln Ser Pro Ser Ser Leu Ser Ala Ser Val Gly
1               5                   10                  15

Asp Arg Val Ser Ile Thr Cys Lys Ala Ser Gln Asn Ala Gly Ile Asp
            20                  25                  30

Val Ala Trp Phe Gln Gln Lys Pro Gly Lys Ala Pro Lys Leu Leu Ile
        35                  40                  45

Tyr Ser Lys Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Arg Ser Tyr Pro Arg
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
    210                 215                 220

Trp Gly Gln Gly Thr Leu Val Thr Val Ser Ser Gly Gly Cys Gly Gly
225                 230                 235                 240

Gly Lys Val Ala Ala Cys Lys Glu Lys Val Ala Ala Leu Lys Glu Lys
                245                 250                 255

Val Ala Ala Leu Lys Glu Lys Val Ala Ala Leu Lys Glu
            260                 265
```

<210> SEQ ID NO 49
<211> LENGTH: 569
<212> TYPE: PRT
<213> ORGANISM: Artificial Sequence
<220> FEATURE:
<223> OTHER INFORMATION: Synthetic Polypeptide

<400> SEQUENCE: 49

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
```

```
                65                  70                  75                  80
Glu Asp Val Ala Asp Tyr Phe Cys His Gln Tyr Ser Ser Tyr Pro Phe
                    85                  90                  95

Thr Phe Gly Ser Gly Thr Lys Leu Glu Ile Lys Gly Gly Ser Gly
            100                 105                 110

Gly Gly Gly Gln Val Gln Leu Val Gln Ser Gly Ala Glu Val Lys Lys
            115                 120                 125

Pro Gly Ala Ser Val Lys Val Ser Cys Lys Ala Ser Gly Tyr Ser Phe
            130                 135                 140

Ser Thr Phe Phe Ile His Trp Val Arg Gln Ala Pro Gly Gln Gly Leu
145                 150                 155                 160

Glu Trp Ile Gly Arg Ile Asp Pro Asn Ser Gly Ala Thr Lys Tyr Asn
                165                 170                 175

Glu Lys Phe Glu Ser Arg Val Thr Met Thr Arg Asp Thr Ser Ile Ser
            180                 185                 190

Thr Ala Tyr Met Glu Leu Ser Arg Leu Arg Ser Asp Asp Thr Ala Val
                195                 200                 205

Tyr Tyr Cys Ala Arg Gly Glu Asp Leu Leu Ile Arg Thr Asp Ala Leu
            210                 215                 220

Asp Tyr Trp Gly Gln Gly Thr Ser Val Thr Val Ser Ser Leu Gly Gly
225                 230                 235                 240

Gly Ser Gly Ala Ser Thr Lys Gly Pro Ser Val Phe Pro Leu Ala Pro
                245                 250                 255

Cys Ser Arg Ser Thr Ser Glu Ser Thr Ala Ala Leu Gly Cys Leu Val
            260                 265                 270

Lys Asp Tyr Phe Pro Glu Pro Val Thr Val Ser Trp Asn Ser Gly Ala
            275                 280                 285

Leu Thr Ser Gly Val His Thr Phe Pro Ala Val Leu Gln Ser Ser Gly
            290                 295                 300

Leu Tyr Ser Leu Ser Ser Val Val Thr Val Pro Ser Ser Ser Leu Gly
305                 310                 315                 320

Thr Lys Thr Tyr Thr Cys Asn Val Asp His Lys Pro Ser Asn Thr Lys
                325                 330                 335

Val Asp Lys Arg Val Glu Ser Lys Tyr Gly Pro Pro Cys Pro Pro Cys
            340                 345                 350

Pro Ala Pro Glu Phe Leu Gly Gly Pro Ser Val Phe Leu Phe Pro Pro
            355                 360                 365

Lys Pro Lys Asp Thr Leu Tyr Ile Thr Arg Glu Pro Glu Val Thr Cys
            370                 375                 380

Val Val Val Asp Val Ser Gln Glu Asp Pro Glu Val Gln Phe Asn Trp
385                 390                 395                 400

Tyr Val Asp Gly Val Glu Val His Asn Ala Lys Thr Lys Pro Arg Glu
                405                 410                 415

Glu Gln Phe Asn Ser Thr Tyr Arg Val Val Ser Val Leu Thr Val Leu
            420                 425                 430

His Gln Asp Trp Leu Asn Gly Lys Glu Tyr Lys Cys Lys Val Ser Asn
            435                 440                 445

Lys Gly Leu Pro Ser Ser Ile Glu Lys Thr Ile Ser Lys Ala Lys Gly
            450                 455                 460

Gln Pro Arg Glu Pro Gln Val Tyr Thr Leu Pro Pro Ser Gln Glu Glu
465                 470                 475                 480

Met Thr Lys Asn Gln Val Ser Leu Thr Cys Leu Val Lys Gly Phe Tyr
                485                 490                 495
```

```
Pro Ser Asp Ile Ala Val Glu Trp Glu Ser Asn Gly Gln Pro Glu Asn
                500                 505                 510

Asn Tyr Lys Thr Thr Pro Pro Val Leu Asp Ser Asp Gly Ser Phe Phe
            515                 520                 525

Leu Tyr Ser Arg Leu Thr Val Asp Lys Ser Arg Trp Gln Gln Gly Asn
530                 535                 540

Val Phe Ser Cys Ser Val Met His Glu Ala Leu His Asn His Tyr Thr
545                 550                 555                 560

Gln Lys Ser Leu Ser Leu Ser Leu Gly
                565

<210> SEQ ID NO 50
<211> LENGTH: 348
<212> TYPE: PRT
<213> ORGANISM: Artificial Sequence
<220> FEATURE:
<223> OTHER INFORMATION: Synthetic Polypeptide

<400> SEQUENCE: 50

Asp Ile Gln Met Thr Gln Ser Pro Ser Ser Leu Ser Ala Ser Val Gly
1               5                   10                  15

Asp Arg Val Ser Ile Thr Cys Lys Ala Ser Gln Asn Ala Gly Ile Asp
            20                  25                  30

Val Ala Trp Phe Gln Gln Lys Pro Gly Lys Ala Pro Lys Leu Leu Ile
        35                  40                  45

Tyr Ser Lys Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Arg Ser Tyr Pro Arg
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
    130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
    210                 215                 220

Trp Gly Gln Gly Thr Leu Val Thr Val Ser Ser Leu Gly Gly Gly Ser
225                 230                 235                 240

Gly Arg Thr Val Ala Ala Pro Ser Val Phe Ile Phe Pro Pro Ser Asp
                245                 250                 255

Glu Gln Leu Lys Ser Gly Thr Ala Ser Val Val Cys Leu Leu Asn Asn
            260                 265                 270

Phe Tyr Pro Arg Glu Ala Lys Val Gln Trp Lys Val Asp Asn Ala Leu
        275                 280                 285
```

```
Gln Ser Gly Asn Ser Gln Glu Ser Val Thr Glu Gln Asp Ser Lys Asp
        290                 295                 300

Ser Thr Tyr Ser Leu Ser Ser Thr Leu Thr Leu Ser Lys Ala Asp Tyr
305                 310                 315                 320

Glu Lys His Lys Val Tyr Ala Cys Glu Val Thr His Gln Gly Leu Ser
                325                 330                 335

Ser Pro Val Thr Lys Ser Phe Asn Arg Gly Glu Cys
            340                 345

<210> SEQ ID NO 51
<211> LENGTH: 499
<212> TYPE: PRT
<213> ORGANISM: Artificial Sequence
<220> FEATURE:
<223> OTHER INFORMATION: Synthetic Polypeptide

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Ser Phe
    130                 135                 140

Ser Thr Phe Phe Ile His Trp Val Arg Gln Ala Pro Gly Gln Gly Leu
145                 150                 155                 160

Glu Trp Ile Gly Arg Ile Asp Pro Asn Ser Gly Ala Thr Lys Tyr Asn
                165                 170                 175

Glu Lys Phe Glu Ser Arg Val Thr Met Thr Arg Asp Thr Ser Ile Ser
            180                 185                 190

Thr Ala Tyr Met Glu Leu Ser Arg Leu Arg Ser Asp Asp Thr Ala Val
        195                 200                 205

Tyr Tyr Cys Ala Arg Gly Glu Asp Leu Leu Ile Arg Thr Asp Ala Leu
    210                 215                 220

Asp Tyr Trp Gly Gln Gly Thr Ser Val Thr Val Ser Ser Gly Gly Cys
225                 230                 235                 240

Gly Gly Gly Glu Val Ala Ala Cys Glu Lys Glu Val Ala Ala Leu Glu
                245                 250                 255

Lys Glu Val Ala Ala Leu Glu Lys Glu Val Ala Ala Leu Glu Lys Glu
            260                 265                 270

Ser Lys Tyr Gly Pro Pro Cys Pro Pro Cys Pro Ala Pro Glu Phe Leu
        275                 280                 285

Gly Gly Pro Ser Val Phe Leu Phe Pro Pro Lys Pro Lys Asp Thr Leu
    290                 295                 300
```

-continued

```
Tyr Ile Thr Arg Glu Pro Glu Val Thr Cys Val Val Asp Val Ser
305                 310                 315                 320

Gln Glu Asp Pro Glu Val Gln Phe Asn Trp Tyr Val Asp Gly Val Glu
                325                 330                 335

Val His Asn Ala Lys Thr Lys Pro Arg Glu Glu Gln Phe Asn Ser Thr
            340                 345                 350

Tyr Arg Val Val Ser Val Leu Thr Val Leu His Gln Asp Trp Leu Asn
        355                 360                 365

Gly Lys Glu Tyr Lys Cys Lys Val Ser Asn Lys Gly Leu Pro Ser Ser
    370                 375                 380

Ile Glu Lys Thr Ile Ser Lys Ala Lys Gly Gln Pro Arg Glu Pro Gln
385                 390                 395                 400

Val Tyr Thr Leu Pro Pro Ser Gln Glu Glu Met Thr Lys Asn Gln Val
                405                 410                 415

Ser Leu Thr Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
        435                 440                 445

Pro Val Leu Asp Ser Asp Gly Ser Phe Phe Leu Tyr Ser Arg Leu Thr
    450                 455                 460

Val Asp Lys Ser Arg Trp Gln Glu Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Leu Gly

<210> SEQ ID NO 52
<211> LENGTH: 269
<212> TYPE: PRT
<213> ORGANISM: Artificial Sequence
<220> FEATURE:
<223> OTHER INFORMATION: Synthetic Polypeptide

<400> SEQUENCE: 52

Asp Ile Gln Met Thr Gln Ser Pro Ser Ser Leu Ser Ala Ser Val Gly
1               5                   10                  15

Asp Arg Val Ser Ile Thr Cys Lys Ala Ser Gln Asn Ala Gly Ile Asp
            20                  25                  30

Val Ala Trp Phe Gln Gln Lys Pro Gly Lys Ala Pro Lys Leu Leu Ile
        35                  40                  45

Tyr Ser Lys Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Arg Ser Tyr Pro Arg
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
    130                 135                 140

Thr Asp Gln Thr Ile His Trp Met Arg Gln Ala Pro Gly Gln Gly Leu
145                 150                 155                 160
```

```
Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
    210                 215                 220

Trp Gly Gln Gly Thr Leu Val Thr Val Ser Ser Gly Cys Gly Gly
225                 230                 235                 240

Gly Lys Val Ala Ala Cys Lys Glu Lys Val Ala Ala Leu Lys Glu Lys
                245                 250                 255

Val Ala Ala Leu Lys Glu Lys Val Ala Ala Leu Lys Glu
                260                 265

<210> SEQ ID NO 53
<211> LENGTH: 570
<212> TYPE: PRT
<213> ORGANISM: Artificial Sequence
<220> FEATURE:
<223> OTHER INFORMATION: Synthetic Polypeptide

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Arg
            20                  25                  30

Leu Ser Trp Leu Gln Gln Glu Pro Gly Lys Ala Pro Lys Arg Leu Ile
        35                  40                  45

Tyr Ala Thr Ser Ser Leu Asp Ser Gly Val Pro Ser Arg Phe Ser Gly
    50                  55                  60

Ser Arg Ser Gly Thr Glu Phe Thr Leu Thr Ile Ser Ser Leu Gln Pro
65                  70                  75                  80

Glu Asp Phe Val Thr Tyr Tyr Cys Leu Gln Tyr Ala Ser Ser Pro Phe
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
    130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
    210                 215                 220

Trp Gly Gln Gly Thr Leu Val Thr Val Ser Ser Leu Gly Gly Gly Ser
225                 230                 235                 240

Gly Ala Ser Thr Lys Gly Pro Ser Val Phe Pro Leu Ala Pro Ser Ser
                245                 250                 255
```

Lys Ser Thr Ser Gly Gly Thr Ala Ala Leu Gly Cys Leu Val Lys Asp
            260                 265                 270

Tyr Phe Pro Glu Pro Val Thr Val Ser Trp Asn Ser Gly Ala Leu Thr
            275                 280                 285

Ser Gly Val His Thr Phe Pro Ala Val Leu Gln Ser Ser Gly Leu Tyr
            290                 295                 300

Ser Leu Ser Ser Val Val Thr Val Pro Ser Ser Ser Leu Gly Thr Gln
305                 310                 315                 320

Thr Tyr Ile Cys Asn Val Asn His Lys Pro Ser Asn Thr Lys Val Asp
            325                 330                 335

Lys Arg Val Glu Pro Lys Ser Cys Asp Lys Thr His Thr Cys Pro Pro
            340                 345                 350

Cys Pro Ala Pro Glu Ala Ala Gly Gly Pro Ser Val Phe Leu Phe Pro
            355                 360                 365

Pro Lys Pro Lys Asp Thr Leu Tyr Ile Thr Arg Glu Pro Glu Val Thr
            370                 375                 380

Cys Val Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
            405                 410                 415

Glu Glu Gln Tyr Asn Ser Thr Tyr Arg Val Val Ser Val Leu Thr Val
            420                 425                 430

Leu His Gln Asp Trp Leu Asn Gly Lys Glu Tyr Lys Cys Lys Val Ser
            435                 440                 445

Asn Lys Ala Leu Pro Ala Pro Ile Glu Lys Thr Ile Ser Lys Ala Lys
            450                 455                 460

Gly Gln Pro Arg Glu Pro Gln Val Tyr Thr Leu Pro Pro Ser Arg Glu
465                 470                 475                 480

Glu Met Thr Lys Asn Gln Val Ser Leu Thr Cys Leu Val Lys Gly Phe
            485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
            515                 520                 525

Phe Leu Tyr Ser Lys Leu Thr Val Asp Lys Ser Arg Trp Gln Gln Gly
            530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly
            565                 570

<210> SEQ ID NO 54
<211> LENGTH: 342
<212> TYPE: PRT
<213> ORGANISM: Artificial Sequence
<220> FEATURE:
<223> OTHER INFORMATION: Synthetic Polypeptide

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
            35                  40                  45

Tyr Trp Ala Ser Thr Arg His Thr Gly Val Pro Ser Arg Phe Ser Gly
            50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
            115                 120                 125

Pro Gly Ser Ser Val Lys Val Ser Cys Lys Ala Pro Asp His Ile Phe
130                 135                 140

Ser Ile His Trp Met Gln Trp Val Arg Gln Ala Pro Gly Gln Gly Leu
145                 150                 155                 160

Glu Trp Met Gly Glu Ile Phe Pro Gly Ser Gly Thr Thr Asp Tyr Asn
                165                 170                 175

Glu Lys Phe Lys Gly Lys Val Thr Ile Thr Val Asp Lys Ser Thr Ser
            180                 185                 190

Thr Ala Tyr Met Glu Leu Ser Ser Leu Arg Ser Glu Asp Thr Ala Val
            195                 200                 205

Tyr Tyr Cys Ala Ser Gly Ala Phe Asp Tyr Trp Gly Gln Gly Thr Thr
210                 215                 220

Val Thr Val Ser Ser Leu Gly Gly Gly Ser Gly Arg Thr Val Ala Ala
225                 230                 235                 240

Pro Ser Val Phe Ile Phe Pro Pro Ser Asp Glu Gln Leu Lys Ser Gly
                245                 250                 255

Thr Ala Ser Val Val Cys Leu Leu Asn Asn Phe Tyr Pro Arg Glu Ala
            260                 265                 270

Lys Val Gln Trp Lys Val Asp Asn Ala Leu Gln Ser Gly Asn Ser Gln
            275                 280                 285

Glu Ser Val Thr Glu Gln Asp Ser Lys Asp Ser Thr Tyr Ser Leu Ser
290                 295                 300

Ser Thr Leu Thr Leu Ser Lys Ala Asp Tyr Glu Lys His Lys Val Tyr
305                 310                 315                 320

Ala Cys Glu Val Thr His Gln Gly Leu Ser Ser Pro Val Thr Lys Ser
                325                 330                 335

Phe Asn Arg Gly Glu Cys
            340

<210> SEQ ID NO 55
<211> LENGTH: 567
<212> TYPE: PRT
<213> ORGANISM: Artificial Sequence
<220> FEATURE:
<223> OTHER INFORMATION: Synthetic Polypeptide

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Arg
            20                  25                  30

Leu Ser Trp Leu Gln Gln Glu Pro Gly Lys Ala Pro Lys Arg Leu Ile
        35                  40                  45

Tyr Ala Thr Ser Ser Leu Asp Ser Gly Val Pro Ser Arg Phe Ser Gly
    50                  55                  60

```
Ser Arg Ser Gly Thr Glu Phe Thr Leu Thr Ile Ser Ser Leu Gln Pro
 65                  70                  75                  80

Glu Asp Phe Val Thr Tyr Tyr Cys Leu Gln Tyr Ala Ser Ser Pro Phe
                 85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
    130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
    210                 215                 220

Trp Gly Gln Gly Thr Leu Val Thr Val Ser Ser Leu Gly Gly Gly Ser
225                 230                 235                 240

Gly Ala Ser Thr Lys Gly Pro Ser Val Phe Pro Leu Ala Pro Cys Ser
                245                 250                 255

Arg Ser Thr Ser Glu Ser Thr Ala Ala Leu Gly Cys Leu Val Lys Asp
            260                 265                 270

Tyr Phe Pro Glu Pro Val Thr Val Ser Trp Asn Ser Gly Ala Leu Thr
        275                 280                 285

Ser Gly Val His Thr Phe Pro Ala Val Leu Gln Ser Ser Gly Leu Tyr
    290                 295                 300

Ser Leu Ser Ser Val Val Thr Val Pro Ser Ser Ser Leu Gly Thr Lys
305                 310                 315                 320

Thr Tyr Thr Cys Asn Val Asp His Lys Pro Ser Asn Thr Lys Val Asp
                325                 330                 335

Lys Arg Val Glu Ser Lys Tyr Gly Pro Pro Cys Pro Pro Cys Pro Ala
            340                 345                 350

Pro Glu Phe Leu Gly Gly Pro Ser Val Phe Leu Phe Pro Pro Lys Pro
        355                 360                 365

Lys Asp Thr Leu Tyr Ile Thr Arg Glu Pro Glu Val Thr Cys Val Val
    370                 375                 380

Val Asp Val Ser Gln Glu Asp Pro Glu Val Gln Phe Asn Trp Tyr Val
385                 390                 395                 400

Asp Gly Val Glu Val His Asn Ala Lys Thr Lys Pro Arg Glu Glu Gln
                405                 410                 415

Phe Asn Ser Thr Tyr Arg Val Val Ser Val Leu Thr Val Leu His Gln
            420                 425                 430

Asp Trp Leu Asn Gly Lys Glu Tyr Lys Cys Lys Val Ser Asn Lys Gly
        435                 440                 445

Leu Pro Ser Ser Ile Glu Lys Thr Ile Ser Lys Ala Lys Gly Gln Pro
    450                 455                 460

Arg Glu Pro Gln Val Tyr Thr Leu Pro Pro Ser Gln Glu Glu Met Thr
465                 470                 475                 480

Lys Asn Gln Val Ser Leu Thr Cys Leu Val Lys Gly Phe Tyr Pro Ser
```

```
                    485                 490                 495
Asp Ile Ala Val Glu Trp Glu Ser Asn Gly Gln Pro Glu Asn Asn Tyr
                500                 505                 510

Lys Thr Thr Pro Pro Val Leu Asp Ser Asp Gly Ser Phe Phe Leu Tyr
                515                 520                 525

Ser Arg Leu Thr Val Asp Lys Ser Arg Trp Gln Glu Gly Asn Val Phe
            530                 535                 540

Ser Cys Ser Val Met His Glu Ala Leu His Asn His Tyr Thr Gln Lys
545                 550                 555                 560

Ser Leu Ser Leu Ser Leu Gly
                565

<210> SEQ ID NO 56
<211> LENGTH: 342
<212> TYPE: PRT
<213> ORGANISM: Artificial Sequence
<220> FEATURE:
<223> OTHER INFORMATION: Synthetic Polypeptide

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Pro Asp His Ile Phe
    130                 135                 140

Ser Ile His Trp Met Gln Trp Val Arg Gln Ala Pro Gly Gln Gly Leu
145                 150                 155                 160

Glu Trp Met Gly Glu Ile Phe Pro Gly Ser Gly Thr Thr Asp Tyr Asn
                165                 170                 175

Glu Lys Phe Lys Gly Lys Val Thr Ile Thr Val Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ser Gly Ala Phe Asp Tyr Trp Gly Gln Gly Thr Thr
    210                 215                 220

Val Thr Val Ser Ser Leu Gly Gly Gly Ser Gly Arg Thr Val Ala Ala
225                 230                 235                 240

Pro Ser Val Phe Ile Phe Pro Pro Ser Asp Glu Gln Leu Lys Ser Gly
                245                 250                 255

Thr Ala Ser Val Val Cys Leu Leu Asn Asn Phe Tyr Pro Arg Glu Ala
            260                 265                 270

Lys Val Gln Trp Lys Val Asp Asn Ala Leu Gln Ser Gly Asn Ser Gln
```

```
              275                 280                 285
Glu Ser Val Thr Glu Gln Asp Ser Lys Asp Ser Thr Tyr Ser Leu Ser
        290                 295                 300

Ser Thr Leu Thr Leu Ser Lys Ala Asp Tyr Glu Lys His Lys Val Tyr
305                 310                 315                 320

Ala Cys Glu Val Thr His Gln Gly Leu Ser Ser Pro Val Thr Lys Ser
                325                 330                 335

Phe Asn Arg Gly Glu Cys
            340

<210> SEQ ID NO 57
<211> LENGTH: 570
<212> TYPE: PRT
<213> ORGANISM: Artificial Sequence
<220> FEATURE:
<223> OTHER INFORMATION: Synthetic Polypeptide

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Arg
            20                  25                  30

Leu Asn Trp Tyr Gln Gln Lys Pro Gly Lys Ala Pro Lys Arg Leu Ile
        35                  40                  45

Tyr Ala Thr Ser Ser Leu Asp Ser Gly Val Pro Ser Arg Phe Ser Gly
50                  55                  60

Ser Arg Ser Gly Thr Glu Phe Thr Leu Thr Ile Ser Ser Leu Gln Pro
65                  70                  75                  80

Glu Asp Phe Val Thr Tyr Tyr Cys Leu Gln Tyr Ala Ser Ser Pro Phe
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
210                 215                 220

Trp Gly Gln Gly Thr Leu Val Thr Val Ser Ser Leu Gly Gly Gly Ser
225                 230                 235                 240

Gly Ala Ser Thr Lys Gly Pro Ser Val Phe Pro Leu Ala Pro Ser Ser
            245                 250                 255

Lys Ser Thr Ser Gly Gly Thr Ala Ala Leu Gly Cys Leu Val Lys Asp
        260                 265                 270

Tyr Phe Pro Glu Pro Val Thr Val Ser Trp Asn Ser Gly Ala Leu Thr
275                 280                 285

Ser Gly Val His Thr Phe Pro Ala Val Leu Gln Ser Ser Gly Leu Tyr
```

```
            290                 295                 300
Ser Leu Ser Ser Val Val Thr Val Pro Ser Ser Leu Gly Thr Gln
305                 310                 315                 320

Thr Tyr Ile Cys Asn Val Asn His Lys Pro Ser Asn Thr Lys Val Asp
                325                 330                 335

Lys Arg Val Glu Pro Lys Ser Cys Asp Lys Thr His Thr Cys Pro Pro
                340                 345                 350

Cys Pro Ala Pro Glu Ala Ala Gly Gly Pro Ser Val Phe Leu Phe Pro
                355                 360                 365

Pro Lys Pro Lys Asp Thr Leu Tyr Ile Thr Arg Glu Pro Glu Val Thr
        370                 375                 380

Cys Val Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
                405                 410                 415

Glu Glu Gln Tyr Asn Ser Thr Tyr Arg Val Val Ser Val Leu Thr Val
                420                 425                 430

Leu His Gln Asp Trp Leu Asn Gly Lys Glu Tyr Lys Cys Lys Val Ser
        435                 440                 445

Asn Lys Ala Leu Pro Ala Pro Ile Glu Lys Thr Ile Ser Lys Ala Lys
        450                 455                 460

Gly Gln Pro Arg Glu Pro Gln Val Tyr Thr Leu Pro Pro Ser Arg Glu
465                 470                 475                 480

Glu Met Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
                500                 505                 510

Asn Asn Tyr Lys Thr Thr Pro Pro Val Leu Asp Ser Asp Gly Ser Phe
                515                 520                 525

Phe Leu Tyr Ser Lys Leu Thr Val Asp Lys Ser Arg Trp Gln Gln Gly
        530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly
                565                 570
```

<210> SEQ ID NO 58
<211> LENGTH: 342
<212> TYPE: PRT
<213> ORGANISM: Artificial Sequence
<220> FEATURE:
<223> OTHER INFORMATION: Synthetic Polypeptide

<400> SEQUENCE: 58

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
                20                  25                  30

Val Ala Trp Tyr Gln Gln Lys Pro Gly Lys Val Pro Lys Leu Leu Ile
            35                  40                  45

Tyr Trp Ala Ser Thr Arg His Thr Gly Val Pro Ser Arg Phe Ser Gly
        50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
```

```
                     85                  90                  95

Thr Phe Gly Ser Gly Thr Lys Leu Glu Ile Lys Gly Gly Ser Gly
                100                 105                 110

Gly Gly Gly Gln Val Gln Leu Val Gln Ser Gly Ala Glu Val Lys Lys
            115                 120                 125

Pro Gly Ser Ser Val Lys Val Ser Cys Lys Ala Pro Asp His Ile Phe
        130                 135                 140

Ser Ile His Trp Met Gln Trp Val Arg Gln Ala Pro Gly Gln Gly Leu
145                 150                 155                 160

Glu Trp Met Gly Glu Ile Phe Pro Ser Gly Thr Thr Asp Tyr Asn
                165                 170                 175

Glu Lys Phe Lys Gly Lys Val Thr Ile Thr Val Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ser Gly Ala Phe Asp Tyr Trp Gly Gln Gly Thr Thr
    210                 215                 220

Val Thr Val Ser Ser Leu Gly Gly Ser Gly Arg Thr Val Ala Ala
225                 230                 235                 240

Pro Ser Val Phe Ile Phe Pro Pro Ser Asp Glu Gln Leu Lys Ser Gly
                245                 250                 255

Thr Ala Ser Val Val Cys Leu Leu Asn Asn Phe Tyr Pro Arg Glu Ala
            260                 265                 270

Lys Val Gln Trp Lys Val Asp Asn Ala Leu Gln Ser Gly Asn Ser Gln
        275                 280                 285

Glu Ser Val Thr Glu Gln Asp Ser Lys Asp Ser Thr Tyr Ser Leu Ser
    290                 295                 300

Ser Thr Leu Thr Leu Ser Lys Ala Asp Tyr Glu Lys His Lys Val Tyr
305                 310                 315                 320

Ala Cys Glu Val Thr His Gln Gly Leu Ser Ser Pro Val Thr Lys Ser
                325                 330                 335

Phe Asn Arg Gly Glu Cys
            340

<210> SEQ ID NO 59
<211> LENGTH: 567
<212> TYPE: PRT
<213> ORGANISM: Artificial Sequence
<220> FEATURE:
<223> OTHER INFORMATION: Synthetic Polypeptide

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Arg
            20                  25                  30

Leu Asn Trp Tyr Gln Gln Lys Pro Gly Lys Ala Pro Lys Arg Leu Ile
        35                  40                  45

Tyr Ala Thr Ser Ser Leu Asp Ser Gly Val Pro Ser Arg Phe Ser Gly
    50                  55                  60

Ser Arg Ser Gly Thr Glu Phe Thr Leu Thr Ile Ser Ser Leu Gln Pro
65                  70                  75                  80

Glu Asp Phe Val Thr Tyr Tyr Cys Leu Gln Tyr Ala Ser Ser Pro Phe
                85                  90                  95

Thr Phe Gly Gln Gly Thr Lys Leu Glu Ile Lys Gly Gly Gly Ser Gly
```

```
                100               105                 110
Gly Gly Gly Gln Val Gln Leu Val Gln Ser Gly Ala Glu Val Lys Lys
            115                 120                 125
Pro Gly Ser Ser Val Lys Val Ser Cys Lys Ala Ser Gly Tyr Thr Phe
        130                 135                 140
Thr Asp Gln Thr Ile His Trp Met Arg Gln Ala Pro Gly Gln Gly Leu
145                 150                 155                 160
Glu Trp Ile Gly Tyr Ile Tyr Pro Arg Asp Asp Ser Pro Lys Tyr Asn
                165                 170                 175
Glu Asn Phe Lys Gly Lys Val Thr Ile Thr Ala Asp Lys Ser Thr Ser
            180                 185                 190
Thr Ala Tyr Met Glu Leu Ser Ser Leu Arg Ser Glu Asp Thr Ala Val
        195                 200                 205
Tyr Tyr Cys Ala Ile Pro Asp Arg Ser Gly Tyr Ala Trp Phe Ile Tyr
    210                 215                 220
Trp Gly Gln Gly Thr Leu Val Thr Val Ser Ser Leu Gly Gly Gly Ser
225                 230                 235                 240
Gly Ala Ser Thr Lys Gly Pro Ser Val Phe Pro Leu Ala Pro Cys Ser
                245                 250                 255
Arg Ser Thr Ser Glu Ser Thr Ala Ala Leu Gly Cys Leu Val Lys Asp
            260                 265                 270
Tyr Phe Pro Glu Pro Val Thr Val Ser Trp Asn Ser Gly Ala Leu Thr
        275                 280                 285
Ser Gly Val His Thr Phe Pro Ala Val Leu Gln Ser Ser Gly Leu Tyr
    290                 295                 300
Ser Leu Ser Ser Val Val Thr Val Pro Ser Ser Ser Leu Gly Thr Lys
305                 310                 315                 320
Thr Tyr Thr Cys Asn Val Asp His Lys Pro Ser Asn Thr Lys Val Asp
                325                 330                 335
Lys Arg Val Glu Ser Lys Tyr Gly Pro Pro Cys Pro Pro Cys Pro Ala
            340                 345                 350
Pro Glu Phe Leu Gly Gly Pro Ser Val Phe Leu Phe Pro Pro Lys Pro
        355                 360                 365
Lys Asp Thr Leu Tyr Ile Thr Arg Glu Pro Glu Val Thr Cys Val Val
    370                 375                 380
Val Asp Val Ser Gln Glu Asp Pro Glu Val Gln Phe Asn Trp Tyr Val
385                 390                 395                 400
Asp Gly Val Glu Val His Asn Ala Lys Thr Lys Pro Arg Glu Glu Gln
                405                 410                 415
Phe Asn Ser Thr Tyr Arg Val Val Ser Val Leu Thr Val Leu His Gln
            420                 425                 430
Asp Trp Leu Asn Gly Lys Glu Tyr Lys Cys Lys Val Ser Asn Lys Gly
        435                 440                 445
Leu Pro Ser Ser Ile Glu Lys Thr Ile Ser Lys Ala Lys Gly Gln Pro
    450                 455                 460
Arg Glu Pro Gln Val Tyr Thr Leu Pro Pro Ser Gln Glu Glu Met Thr
465                 470                 475                 480
Lys Asn Gln Val Ser Leu Thr Cys Leu Val Lys Gly Phe Tyr Pro Ser
                485                 490                 495
Asp Ile Ala Val Glu Trp Glu Ser Asn Gly Gln Pro Glu Asn Asn Tyr
            500                 505                 510
Lys Thr Thr Pro Pro Val Leu Asp Ser Asp Gly Ser Phe Phe Leu Tyr
        515                 520                 525
```

```
Ser Arg Leu Thr Val Asp Lys Ser Arg Trp Gln Glu Gly Asn Val Phe
            530                 535                 540

Ser Cys Ser Val Met His Glu Ala Leu His Asn His Tyr Thr Gln Lys
545                 550                 555                 560

Ser Leu Ser Leu Ser Leu Gly
                565
```

<210> SEQ ID NO 60
<211> LENGTH: 342
<212> TYPE: PRT
<213> ORGANISM: Artificial Sequence
<220> FEATURE:
<223> OTHER INFORMATION: Synthetic Polypeptide

<400> SEQUENCE: 60

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Pro Asp His Ile Phe
    130                 135                 140

Ser Ile His Trp Met Gln Trp Val Arg Gln Ala Pro Gly Gln Gly Leu
145                 150                 155                 160

Glu Trp Met Gly Glu Ile Phe Pro Gly Ser Gly Thr Thr Asp Tyr Asn
                165                 170                 175

Glu Lys Phe Lys Gly Lys Val Thr Ile Thr Val Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ser Gly Ala Phe Asp Tyr Trp Gly Gln Gly Thr Thr
    210                 215                 220

Val Thr Val Ser Ser Leu Gly Gly Gly Ser Gly Arg Thr Val Ala Ala
225                 230                 235                 240

Pro Ser Val Phe Ile Phe Pro Pro Ser Asp Glu Gln Leu Lys Ser Gly
                245                 250                 255

Thr Ala Ser Val Val Cys Leu Leu Asn Asn Phe Tyr Pro Arg Glu Ala
            260                 265                 270

Lys Val Gln Trp Lys Val Asp Asn Ala Leu Gln Ser Gly Asn Ser Gln
        275                 280                 285

Glu Ser Val Thr Glu Gln Asp Ser Lys Asp Ser Thr Tyr Ser Leu Ser
    290                 295                 300

Ser Thr Leu Thr Leu Ser Lys Ala Asp Tyr Glu Lys His Lys Val Tyr
305                 310                 315                 320
```

```
Ala Cys Glu Val Thr His Gln Gly Leu Ser Ser Pro Val Thr Lys Ser
                325                 330                 335

Phe Asn Arg Gly Glu Cys
            340

<210> SEQ ID NO 61
<211> LENGTH: 570
<212> TYPE: PRT
<213> ORGANISM: Artificial Sequence
<220> FEATURE:
<223> OTHER INFORMATION: Synthetic Polypeptide

<400> SEQUENCE: 61

Asp Ile Gln Met Thr Gln Ser Pro Ser Ser Leu Ser Ala Ser Val Gly
1               5                   10                  15

Asp Arg Val Ser Ile Thr Cys Lys Ala Ser Gln Asn Ala Gly Ile Asp
            20                  25                  30

Val Ala Trp Phe Gln Gln Lys Pro Gly Lys Ala Pro Lys Leu Leu Ile
        35                  40                  45

Tyr Ser Lys Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Tyr Cys Leu Gln Tyr Arg Ser Tyr Pro Arg
                85                  90                  95

Thr Phe Gly Gly Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
    130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
    210                 215                 220

Trp Gly Gln Gly Thr Leu Val Thr Val Ser Ser Leu Gly Gly Gly Ser
225                 230                 235                 240

Gly Ala Ser Thr Lys Gly Pro Ser Val Phe Pro Leu Ala Pro Ser Ser
                245                 250                 255

Lys Ser Thr Ser Gly Gly Thr Ala Ala Leu Gly Cys Leu Val Lys Asp
            260                 265                 270

Tyr Phe Pro Glu Pro Val Thr Val Ser Trp Asn Ser Gly Ala Leu Thr
        275                 280                 285

Ser Gly Val His Thr Phe Pro Ala Val Leu Gln Ser Ser Gly Leu Tyr
    290                 295                 300

Ser Leu Ser Ser Val Val Thr Val Pro Ser Ser Ser Leu Gly Thr Gln
305                 310                 315                 320

Thr Tyr Ile Cys Asn Val Asn His Lys Pro Ser Asn Thr Lys Val Asp
                325                 330                 335
```

-continued

Lys Arg Val Glu Pro Lys Ser Cys Asp Lys Thr His Thr Cys Pro Pro
            340                 345                 350

Cys Pro Ala Pro Glu Ala Ala Gly Gly Pro Ser Val Phe Leu Phe Pro
            355                 360                 365

Pro Lys Pro Lys Asp Thr Leu Tyr Ile Thr Arg Glu Pro Glu Val Thr
            370                 375                 380

Cys Val Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
            405                 410                 415

Glu Glu Gln Tyr Asn Ser Thr Tyr Arg Val Val Ser Val Leu Thr Val
            420                 425                 430

Leu His Gln Asp Trp Leu Asn Gly Lys Glu Tyr Lys Cys Lys Val Ser
            435                 440                 445

Asn Lys Ala Leu Pro Ala Pro Ile Glu Lys Thr Ile Ser Lys Ala Lys
            450                 455                 460

Gly Gln Pro Arg Glu Pro Gln Val Tyr Thr Leu Pro Pro Ser Arg Glu
465                 470                 475                 480

Glu Met Thr Lys Asn Gln Val Ser Leu Thr Cys Leu Val Lys Gly Phe
            485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
            515                 520                 525

Phe Leu Tyr Ser Lys Leu Thr Val Asp Lys Ser Arg Trp Gln Gln Gly
            530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly
                565                 570

<210> SEQ ID NO 62
<211> LENGTH: 350
<212> TYPE: PRT
<213> ORGANISM: Artificial Sequence
<220> FEATURE:
<223> OTHER INFORMATION: Synthetic Polypeptide

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
            35                  40                  45

Tyr Trp Ala Ser Thr Arg His Thr Gly Val Pro Ser Arg Phe Ser Gly
            50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
            85                  90                  95

Thr Phe Gly Ser Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
            115                 120                 125

Pro Gly Ala Ser Val Lys Val Ser Cys Lys Ala Ser Gly Tyr Ser Phe
            130                 135                 140

Ser Thr Phe Phe Ile His Trp Val Arg Gln Arg Pro Gly Gln Gly Leu
145                 150                 155                 160

Glu Trp Ile Gly Arg Ile Asp Pro Asn Ser Gly Ala Thr Lys Tyr Asn
                165                 170                 175

Glu Lys Phe Glu Ser Lys Val Thr Leu Thr Arg Asp Thr Ser Ile Ser
            180                 185                 190

Thr Ala Tyr Met Glu Leu Ser Arg Leu Arg Ser Asp Asp Thr Ala Val
        195                 200                 205

Tyr Tyr Cys Ala Arg Gly Glu Asp Leu Leu Ile Arg Thr Asp Ala Leu
210                 215                 220

Asp Tyr Trp Gly Gln Gly Thr Ser Val Thr Val Ser Ser Leu Gly Gly
225                 230                 235                 240

Gly Ser Gly Arg Thr Val Ala Ala Pro Ser Val Phe Ile Phe Pro Pro
                245                 250                 255

Ser Asp Glu Gln Leu Lys Ser Gly Thr Ala Ser Val Val Cys Leu Leu
            260                 265                 270

Asn Asn Phe Tyr Pro Arg Glu Ala Lys Val Gln Trp Lys Val Asp Asn
        275                 280                 285

Ala Leu Gln Ser Gly Asn Ser Gln Glu Ser Val Thr Glu Gln Asp Ser
290                 295                 300

Lys Asp Ser Thr Tyr Ser Leu Ser Ser Thr Leu Thr Leu Ser Lys Ala
305                 310                 315                 320

Asp Tyr Glu Lys His Lys Val Tyr Ala Cys Glu Val Thr His Gln Gly
                325                 330                 335

Leu Ser Ser Pro Val Thr Lys Ser Phe Asn Arg Gly Glu Cys
            340                 345                 350

<210> SEQ ID NO 63
<211> LENGTH: 567
<212> TYPE: PRT
<213> ORGANISM: Artificial Sequence
<220> FEATURE:
<223> OTHER INFORMATION: Synthetic Polypeptide

<400> SEQUENCE: 63

Asp Ile Gln Met Thr Gln Ser Pro Ser Ser Leu Ser Ala Ser Val Gly
1               5                   10                  15

Asp Arg Val Ser Ile Thr Cys Lys Ala Ser Gln Asn Ala Gly Ile Asp
            20                  25                  30

Val Ala Trp Phe Gln Gln Lys Pro Gly Lys Ala Pro Lys Leu Leu Ile
        35                  40                  45

Tyr Ser Lys Ser Asn Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Asp Tyr Tyr Cys Leu Gln Tyr Arg Ser Tyr Pro Arg
                85                  90                  95

Thr Phe Gly Gly Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
130                 135                 140

```
Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
    210                 215                 220

Trp Gly Gln Gly Thr Leu Val Thr Val Ser Ser Leu Gly Gly Gly Ser
225                 230                 235                 240

Gly Ala Ser Thr Lys Gly Pro Ser Val Phe Pro Leu Ala Pro Cys Ser
                245                 250                 255

Arg Ser Thr Ser Glu Ser Thr Ala Ala Leu Gly Cys Leu Val Lys Asp
            260                 265                 270

Tyr Phe Pro Glu Pro Val Thr Val Ser Trp Asn Ser Gly Ala Leu Thr
        275                 280                 285

Ser Gly Val His Thr Phe Pro Ala Val Leu Gln Ser Ser Gly Leu Tyr
    290                 295                 300

Ser Leu Ser Ser Val Val Thr Val Pro Ser Ser Ser Leu Gly Thr Lys
305                 310                 315                 320

Thr Tyr Thr Cys Asn Val Asp His Lys Pro Ser Asn Thr Lys Val Asp
                325                 330                 335

Lys Arg Val Glu Ser Lys Tyr Gly Pro Pro Cys Pro Pro Cys Pro Ala
            340                 345                 350

Pro Glu Phe Leu Gly Gly Pro Ser Val Phe Leu Phe Pro Pro Lys Pro
        355                 360                 365

Lys Asp Thr Leu Tyr Ile Thr Arg Glu Pro Glu Val Thr Cys Val Val
    370                 375                 380

Val Asp Val Ser Gln Glu Asp Pro Glu Val Gln Phe Asn Trp Tyr Val
385                 390                 395                 400

Asp Gly Val Glu Val His Asn Ala Lys Thr Lys Pro Arg Glu Glu Gln
                405                 410                 415

Phe Asn Ser Thr Tyr Arg Val Val Ser Val Leu Thr Val Leu His Gln
            420                 425                 430

Asp Trp Leu Asn Gly Lys Glu Tyr Lys Cys Lys Val Ser Asn Lys Gly
        435                 440                 445

Leu Pro Ser Ser Ile Glu Lys Thr Ile Ser Lys Ala Lys Gly Gln Pro
    450                 455                 460

Arg Glu Pro Gln Val Tyr Thr Leu Pro Pro Ser Gln Glu Glu Met Thr
465                 470                 475                 480

Lys Asn Gln Val Ser Leu Thr Cys Leu Val Lys Gly Phe Tyr Pro Ser
                485                 490                 495

Asp Ile Ala Val Glu Trp Glu Ser Asn Gly Gln Pro Glu Asn Asn Tyr
            500                 505                 510

Lys Thr Thr Pro Pro Val Leu Asp Ser Asp Gly Ser Phe Phe Leu Tyr
        515                 520                 525

Ser Arg Leu Thr Val Asp Lys Ser Arg Trp Gln Glu Gly Asn Val Phe
    530                 535                 540

Ser Cys Ser Val Met His Glu Ala Leu His Asn His Tyr Thr Gln Lys
545                 550                 555                 560
```

Ser Leu Ser Leu Ser Leu Gly
            565

<210> SEQ ID NO 64
<211> LENGTH: 350
<212> TYPE: PRT
<213> ORGANISM: Artificial Sequence
<220> FEATURE:
<223> OTHER INFORMATION: Synthetic Polypeptide

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Ser Phe
    130                 135                 140

Ser Thr Phe Phe Ile His Trp Val Arg Gln Arg Pro Gly Gln Gly Leu
145                 150                 155                 160

Glu Trp Ile Gly Arg Ile Asp Pro Asn Ser Gly Ala Thr Lys Tyr Asn
                165                 170                 175

Glu Lys Phe Glu Ser Lys Val Thr Leu Thr Arg Asp Thr Ser Ile Ser
            180                 185                 190

Thr Ala Tyr Met Glu Leu Ser Arg Leu Arg Ser Asp Asp Thr Ala Val
        195                 200                 205

Tyr Tyr Cys Ala Arg Gly Glu Asp Leu Leu Ile Arg Thr Asp Ala Leu
    210                 215                 220

Asp Tyr Trp Gly Gln Gly Thr Ser Val Thr Val Ser Ser Leu Gly Gly
225                 230                 235                 240

Gly Ser Gly Arg Thr Val Ala Ala Pro Ser Val Phe Ile Phe Pro Pro
                245                 250                 255

Ser Asp Glu Gln Leu Lys Ser Gly Thr Ala Ser Val Val Cys Leu Leu
            260                 265                 270

Asn Asn Phe Tyr Pro Arg Glu Ala Lys Val Gln Trp Lys Val Asp Asn
        275                 280                 285

Ala Leu Gln Ser Gly Asn Ser Gln Glu Ser Val Thr Glu Gln Asp Ser
    290                 295                 300

Lys Asp Ser Thr Tyr Ser Leu Ser Ser Thr Leu Thr Leu Ser Lys Ala
305                 310                 315                 320

Asp Tyr Glu Lys His Lys Val Tyr Ala Cys Glu Val Thr His Gln Gly
                325                 330                 335

Leu Ser Ser Pro Val Thr Lys Ser Phe Asn Arg Gly Glu Cys
            340                 345                 350

<210> SEQ ID NO 65
<211> LENGTH: 570
<212> TYPE: PRT
<213> ORGANISM: Artificial Sequence
<220> FEATURE:
<223> OTHER INFORMATION: Synthetic Polypeptide

<400> SEQUENCE: 65

```
Asp Ile Gln Met Thr Gln Ser Pro Ser Ser Leu Ser Ala Ser Val Gly
1               5                   10                  15

Asp Arg Val Ser Ile Thr Cys Lys Ala Ser Gln Asn Ala Gly Ile Asp
            20                  25                  30

Val Ala Trp Phe Gln Gln Lys Pro Gly Lys Ala Pro Lys Leu Leu Ile
        35                  40                  45

Tyr Ser Lys Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Arg Ser Tyr Pro Arg
                85                  90                  95

Thr Phe Gly Gln Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
    130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
                165                 170                 175

Glu Asn Phe Lys Gly Lys Val Thr Ile Thr Ala Asp Lys Ser Thr Ser
            180                 185                 190

Thr Ala Tyr Met Glu Leu Ser Ser Leu Arg Ser Glu Asp Thr Ala Val
        195                 200                 205

Tyr Tyr Cys Ala Ile Pro Asp Arg Ser Gly Tyr Ala Trp Phe Ile Tyr
    210                 215                 220

Trp Gly Gln Gly Thr Leu Val Thr Val Ser Ser Leu Gly Gly Gly Ser
225                 230                 235                 240

Gly Ala Ser Thr Lys Gly Pro Ser Val Phe Pro Leu Ala Pro Ser Ser
                245                 250                 255

Lys Ser Thr Ser Gly Gly Thr Ala Ala Leu Gly Cys Leu Val Lys Asp
            260                 265                 270

Tyr Phe Pro Glu Pro Val Thr Val Ser Trp Asn Ser Gly Ala Leu Thr
        275                 280                 285

Ser Gly Val His Thr Phe Pro Ala Val Leu Gln Ser Ser Gly Leu Tyr
    290                 295                 300

Ser Leu Ser Ser Val Val Thr Val Pro Ser Ser Ser Leu Gly Thr Gln
305                 310                 315                 320

Thr Tyr Ile Cys Asn Val Asn His Lys Pro Ser Asn Thr Lys Val Asp
                325                 330                 335

Lys Arg Val Glu Pro Lys Ser Cys Asp Lys Thr His Thr Cys Pro Pro
            340                 345                 350

Cys Pro Ala Pro Glu Ala Ala Gly Gly Pro Ser Val Phe Leu Phe Pro
        355                 360                 365
```

```
Pro Lys Pro Lys Asp Thr Leu Tyr Ile Thr Arg Glu Pro Glu Val Thr
        370                 375                 380

Cys Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
                405                 410                 415

Glu Glu Gln Tyr Asn Ser Thr Tyr Arg Val Val Ser Val Leu Thr Val
                420                 425                 430

Leu His Gln Asp Trp Leu Asn Gly Lys Glu Tyr Lys Cys Lys Val Ser
                435                 440                 445

Asn Lys Ala Leu Pro Ala Pro Ile Glu Lys Thr Ile Ser Lys Ala Lys
450                 455                 460

Gly Gln Pro Arg Glu Pro Gln Val Tyr Thr Leu Pro Pro Ser Arg Glu
465                 470                 475                 480

Glu Met Thr Lys Asn Gln Val Ser Leu Thr Cys Leu Val Lys Gly Phe
                485                 490                 495

Tyr Pro Ser Asp Ile Ala Val Glu Trp Glu Ser Asn Gly Gln Pro Glu
                500                 505                 510

Asn Asn Tyr Lys Thr Thr Pro Pro Val Leu Asp Ser Asp Gly Ser Phe
                515                 520                 525

Phe Leu Tyr Ser Lys Leu Thr Val Asp Lys Ser Arg Trp Gln Gln Gly
530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly
                565                 570

<210> SEQ ID NO 66
<211> LENGTH: 350
<212> TYPE: PRT
<213> ORGANISM: Artificial Sequence
<220> FEATURE:
<223> OTHER INFORMATION: Synthetic Polypeptide

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
                20                  25                  30

Val Ala Trp Tyr Gln Gln Lys Pro Gly Lys Val Pro Lys Leu Leu Ile
                35                  40                  45

Tyr Trp Ala Ser Thr Arg His Thr Gly Val Pro Ser Arg Phe Ser Gly
50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
                100                 105                 110

Gly Gly Gly Gln Val Gln Leu Val Gln Ser Gly Ala Glu Val Lys Lys
                115                 120                 125

Pro Gly Ala Ser Val Lys Val Ser Cys Lys Ala Ser Gly Tyr Ser Phe
                130                 135                 140

Ser Thr Phe Phe Ile His Trp Val Arg Gln Ala Pro Gly Gln Gly Leu
145                 150                 155                 160
```

Glu Trp Ile Gly Arg Ile Asp Pro Asn Ser Gly Ala Thr Lys Tyr Asn
            165                 170                 175

Glu Lys Phe Glu Ser Arg Val Thr Met Thr Arg Asp Thr Ser Ile Ser
            180                 185                 190

Thr Ala Tyr Met Glu Leu Ser Arg Leu Arg Ser Asp Asp Thr Ala Val
            195                 200                 205

Tyr Tyr Cys Ala Arg Gly Glu Asp Leu Leu Ile Arg Thr Asp Ala Leu
210                 215                 220

Asp Tyr Trp Gly Gln Gly Thr Ser Val Thr Val Ser Ser Leu Gly Gly
225                 230                 235                 240

Gly Ser Gly Arg Thr Val Ala Ala Pro Ser Val Phe Ile Phe Pro Pro
            245                 250                 255

Ser Asp Glu Gln Leu Lys Ser Gly Thr Ala Ser Val Val Cys Leu Leu
            260                 265                 270

Asn Asn Phe Tyr Pro Arg Glu Ala Lys Val Gln Trp Lys Val Asp Asn
            275                 280                 285

Ala Leu Gln Ser Gly Asn Ser Gln Glu Ser Val Thr Glu Gln Asp Ser
            290                 295                 300

Lys Asp Ser Thr Tyr Ser Leu Ser Ser Thr Leu Thr Leu Ser Lys Ala
305                 310                 315                 320

Asp Tyr Glu Lys His Lys Val Tyr Ala Cys Glu Val Thr His Gln Gly
            325                 330                 335

Leu Ser Ser Pro Val Thr Lys Ser Phe Asn Arg Gly Glu Cys
            340                 345                 350

<210> SEQ ID NO 67
<211> LENGTH: 567
<212> TYPE: PRT
<213> ORGANISM: Artificial Sequence
<220> FEATURE:
<223> OTHER INFORMATION: Synthetic Polypeptide

<400> SEQUENCE: 67

Asp Ile Gln Met Thr Gln Ser Pro Ser Ser Leu Ser Ala Ser Val Gly
1               5                   10                  15

Asp Arg Val Ser Ile Thr Cys Lys Ala Ser Gln Asn Ala Gly Ile Asp
            20                  25                  30

Val Ala Trp Phe Gln Gln Lys Pro Gly Lys Ala Pro Lys Leu Leu Ile
        35                  40                  45

Tyr Ser Lys Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Arg Ser Tyr Pro Arg
                85                  90                  95

Thr Phe Gly Gln Gly Thr Lys Leu Glu Ile Lys Gly Gly Ser Gly Gly
            100                 105                 110

Gly Gly Gly Gln Val Gln Leu Val Gln Ser Gly Ala Glu Val Lys Lys
        115                 120                 125

Pro Gly Ser Ser Val Lys Val Ser Cys Lys Ala Ser Gly Tyr Thr Phe
130                 135                 140

Thr Asp Gln Thr Ile His Trp Met Arg Gln Ala Pro Gly Gln Gly Leu
145                 150                 155                 160

Glu Trp Ile Gly Tyr Ile Tyr Pro Arg Asp Asp Ser Pro Lys Tyr Asn
            165                 170                 175

-continued

Glu Asn Phe Lys Gly Lys Val Thr Ile Thr Ala Asp Lys Ser Thr Ser
                180                 185                 190

Thr Ala Tyr Met Glu Leu Ser Ser Leu Arg Ser Glu Asp Thr Ala Val
            195                 200                 205

Tyr Tyr Cys Ala Ile Pro Asp Arg Ser Gly Tyr Ala Trp Phe Ile Tyr
        210                 215                 220

Trp Gly Gln Gly Thr Leu Val Thr Val Ser Ser Leu Gly Gly Gly Ser
225                 230                 235                 240

Gly Ala Ser Thr Lys Gly Pro Ser Val Phe Pro Leu Ala Pro Cys Ser
                245                 250                 255

Arg Ser Thr Ser Glu Ser Thr Ala Ala Leu Gly Cys Leu Val Lys Asp
            260                 265                 270

Tyr Phe Pro Glu Pro Val Thr Val Ser Trp Asn Ser Gly Ala Leu Thr
        275                 280                 285

Ser Gly Val His Thr Phe Pro Ala Val Leu Gln Ser Ser Gly Leu Tyr
    290                 295                 300

Ser Leu Ser Ser Val Val Thr Val Pro Ser Ser Ser Leu Gly Thr Lys
305                 310                 315                 320

Thr Tyr Thr Cys Asn Val Asp His Lys Pro Ser Asn Thr Lys Val Asp
                325                 330                 335

Lys Arg Val Glu Ser Lys Tyr Gly Pro Pro Cys Pro Pro Cys Pro Ala
            340                 345                 350

Pro Glu Phe Leu Gly Gly Pro Ser Val Phe Leu Phe Pro Pro Lys Pro
        355                 360                 365

Lys Asp Thr Leu Tyr Ile Thr Arg Glu Pro Glu Val Thr Cys Val Val
370                 375                 380

Val Asp Val Ser Gln Glu Asp Pro Glu Val Gln Phe Asn Trp Tyr Val
385                 390                 395                 400

Asp Gly Val Glu Val His Asn Ala Lys Thr Lys Pro Arg Glu Glu Gln
                405                 410                 415

Phe Asn Ser Thr Tyr Arg Val Val Ser Val Leu Thr Val Leu His Gln
            420                 425                 430

Asp Trp Leu Asn Gly Lys Glu Tyr Lys Cys Lys Val Ser Asn Lys Gly
        435                 440                 445

Leu Pro Ser Ser Ile Glu Lys Thr Ile Ser Lys Ala Lys Gly Gln Pro
450                 455                 460

Arg Glu Pro Gln Val Tyr Thr Leu Pro Pro Ser Gln Glu Glu Met Thr
465                 470                 475                 480

Lys Asn Gln Val Ser Leu Thr Cys Leu Val Lys Gly Phe Tyr Pro Ser
                485                 490                 495

Asp Ile Ala Val Glu Trp Glu Ser Asn Gly Gln Pro Glu Asn Asn Tyr
            500                 505                 510

Lys Thr Thr Pro Pro Val Leu Asp Ser Asp Gly Ser Phe Phe Leu Tyr
        515                 520                 525

Ser Arg Leu Thr Val Asp Lys Ser Arg Trp Gln Glu Gly Asn Val Phe
530                 535                 540

Ser Cys Ser Val Met His Glu Ala Leu His Asn His Tyr Thr Gln Lys
545                 550                 555                 560

Ser Leu Ser Leu Ser Leu Gly
                565

<210> SEQ ID NO 68
<211> LENGTH: 350
<212> TYPE: PRT

<213> ORGANISM: Artificial Sequence
<220> FEATURE:
<223> OTHER INFORMATION: Synthetic Polypeptide

<400> SEQUENCE: 68

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Gly Gly Gly Ser Gly
            100                 105                 110

Gly Gly Gly Gln Val Gln Leu Val Gln Ser Gly Ala Glu Val Lys Lys
        115                 120                 125

Pro Gly Ala Ser Val Lys Val Ser Cys Lys Ala Ser Gly Tyr Ser Phe
130                 135                 140

Ser Thr Phe Phe Ile His Trp Val Arg Gln Ala Pro Gly Gln Gly Leu
145                 150                 155                 160

Glu Trp Ile Gly Arg Ile Asp Pro Asn Ser Gly Ala Thr Lys Tyr Asn
                165                 170                 175

Glu Lys Phe Glu Ser Arg Val Thr Met Thr Arg Asp Thr Ser Ile Ser
            180                 185                 190

Thr Ala Tyr Met Glu Leu Ser Arg Leu Arg Ser Asp Asp Thr Ala Val
        195                 200                 205

Tyr Tyr Cys Ala Arg Gly Glu Asp Leu Leu Ile Arg Thr Asp Ala Leu
    210                 215                 220

Asp Tyr Trp Gly Gln Gly Thr Ser Val Thr Val Ser Ser Leu Gly Gly
225                 230                 235                 240

Gly Ser Gly Arg Thr Val Ala Ala Pro Ser Val Phe Ile Phe Pro Pro
                245                 250                 255

Ser Asp Glu Gln Leu Lys Ser Gly Thr Ala Ser Val Val Cys Leu Leu
            260                 265                 270

Asn Asn Phe Tyr Pro Arg Glu Ala Lys Val Gln Trp Lys Val Asp Asn
        275                 280                 285

Ala Leu Gln Ser Gly Asn Ser Gln Glu Ser Val Thr Glu Gln Asp Ser
    290                 295                 300

Lys Asp Ser Thr Tyr Ser Leu Ser Ser Thr Leu Thr Leu Ser Lys Ala
305                 310                 315                 320

Asp Tyr Glu Lys His Lys Val Tyr Ala Cys Glu Val Thr His Gln Gly
                325                 330                 335

Leu Ser Ser Pro Val Thr Lys Ser Phe Asn Arg Gly Glu Cys
            340                 345                 350
```

<210> SEQ ID NO 69
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 69

Gly Gly Gly Ser Gly Gly Gly Gly
1               5

<210> SEQ ID NO 70
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 70

Leu Gly Gly Gly Ser Gly
1               5

<210> SEQ ID NO 71
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 71

Phe Asn Arg Gly Glu Cys
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 72

Val Glu Pro Lys Ser Cys
1               5

<210> SEQ ID NO 73
<211> LENGTH: 326
<212> TYPE: PRT
<213> ORGANISM: Artificial Sequence
<220> FEATURE:
<223> OTHER INFORMATION: Synthetic Polypeptide

<400> SEQUENCE: 73

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 74
<211> LENGTH: 326
<212> TYPE: PRT
<213> ORGANISM: Artificial Sequence
<220> FEATURE:
<223> OTHER INFORMATION: Synthetic Polypeptide

<400> SEQUENCE: 74

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Tyr Ile Thr Arg Glu Pro Glu Val Thr Cys Val Val Val
    130                 135                 140

Asp Val Ser Gln Glu Asp Pro Glu Val Gln Phe Asn Trp Tyr Val Asp
145                 150                 155                 160

```
Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Gln Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 75
<211> LENGTH: 329
<212> TYPE: PRT
<213> ORGANISM: Artificial Sequence
<220> FEATURE:
<223> OTHER INFORMATION: Synthetic Polypeptide

<400> SEQUENCE: 75

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

-continued

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 76
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 76

Glu Pro Lys Ser Cys Asp Lys Thr His Thr Cys Pro Pro Cys Pro
1               5                   10                  15

<210> SEQ ID NO 77
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 77

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 78
<211> LENGTH: 330
<212> TYPE: PRT
<213> ORGANISM: Artificial Sequence
<220> FEATURE:
<223> OTHER INFORMATION: Synthetic Polypeptide

<400> SEQUENCE: 78

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Tyr Ile Thr Arg Glu Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 79
<211> LENGTH: 329
<212> TYPE: PRT
<213> ORGANISM: Artificial Sequence
<220> FEATURE:
<223> OTHER INFORMATION: Synthetic Polypeptide

<400> SEQUENCE: 79

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr

```
            20                  25                  30
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 80
<211> LENGTH: 285
<212> TYPE: PRT
<213> ORGANISM: Homo sapiens

<400> SEQUENCE: 80

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60
```

```
Ser Phe Tyr Gln Val Ala Ala Leu Gln Gly Asp Leu Ala Ser Leu Arg
 65                  70                  75                  80

Ala Glu Leu Gln Gly His His Ala Glu Lys Leu Pro Ala Gly Ala Gly
                 85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
    130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
    210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys Leu Leu
        275                 280                 285

<210> SEQ ID NO 81
<211> LENGTH: 189
<212> TYPE: PRT
<213> ORGANISM: Homo sapiens

<400> SEQUENCE: 81

Met Leu Gly Ser Arg Ala Val Met Leu Leu Leu Leu Leu Pro Trp Thr
1               5                   10                  15

Ala Gln Gly Arg Ala Val Pro Gly Gly Ser Ser Pro Ala Trp Thr Gln
            20                  25                  30

Cys Gln Gln Leu Ser Gln Lys Leu Cys Thr Leu Ala Trp Ser Ala His
        35                  40                  45

Pro Leu Val Gly His Met Asp Leu Arg Glu Glu Gly Asp Glu Glu Thr
    50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
        115                 120                 125

Leu Gly Leu Ser Gln Leu Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160
```

Leu Arg Phe Lys Ile Leu Arg Ser Leu Gln Ala Phe Ala Val Ala
                165                 170                 175

Ala Arg Val Phe Ala His Gly Ala Ala Thr Leu Ser Pro
            180                 185

<210> SEQ ID NO 82
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 82

Gly Gly Cys Gly Gly Gly Glu Val Ala Ala Cys Glu Lys Glu Val Ala
1               5                   10                  15

Ala Leu Glu Lys Glu Val Ala Ala Leu Glu Lys Glu Val Ala Ala Leu
            20                  25                  30

Glu Lys

<210> SEQ ID NO 83
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 83

Gly Gly Cys Gly Gly Gly Lys Val Ala Ala Cys Lys Glu Lys Val Ala
1               5                   10                  15

Ala Leu Lys Glu Lys Val Ala Ala Leu Lys Glu Lys Val Ala Ala Leu
            20                  25                  30

Lys Glu

<210> SEQ ID NO 84
<211> LENGTH: 114
<212> TYPE: PRT
<213> ORGANISM: Artificial Sequence
<220> FEATURE:
<223> OTHER INFORMATION: Synthetic Polypeptide

<400> SEQUENCE: 84

Gln Val Gln Leu Val Gln Ser Gly Ala Glu Val Lys Lys Pro Gly Ser
1               5                   10                  15

Ser Val Lys Val Ser Cys Lys Ala Pro Asp His Ile Phe Ser Ile His
            20                  25                  30

Trp Met Gln Trp Val Arg Gln Ala Pro Gly Gln Gly Leu Glu Trp Met
        35                  40                  45

Gly Glu Ile Phe Pro Gly Ser Gly Thr Thr Asp Tyr Asn Glu Lys Phe
    50                  55                  60

Lys Gly Lys Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Ala Phe Asp Tyr Trp Gly Gln Gly Thr Thr Val Thr Val
            100                 105                 110

Ser Ser

<210> SEQ ID NO 85
<211> LENGTH: 107

<212> TYPE: PRT
<213> ORGANISM: Artificial Sequence
<220> FEATURE:
<223> OTHER INFORMATION: Synthetic Polypeptide

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Arg
            20                  25                  30

Leu Ser Trp Leu Gln Gln Glu Pro Gly Lys Ala Pro Lys Arg Leu Ile
        35                  40                  45

Tyr Ala Thr Ser Ser Leu Asp Ser Gly Val Pro Ser Arg Phe Ser Gly
    50                  55                  60

Ser Arg Ser Gly Thr Glu Phe Thr Leu Thr Ile Ser Ser Leu Gln Pro
65                  70                  75                  80

Glu Asp Phe Val Thr Tyr Tyr Cys Leu Gln Tyr Ala Ser Ser Pro Phe
                85                  90                  95

Thr Phe Gly Gln Gly Thr Lys Leu Glu Ile Lys
            100                 105

<210> SEQ ID NO 86
<211> LENGTH: 114
<212> TYPE: PRT
<213> ORGANISM: Artificial Sequence
<220> FEATURE:
<223> OTHER INFORMATION: Synthetic Polypeptide

<400> SEQUENCE: 86

Gln Val Gln Leu Val Gln Ser Gly Ala Glu Val Lys Lys Pro Gly Ser
1               5                   10                  15

Ser Val Lys Val Ser Cys Lys Ala Pro Asp His Ile Phe Ser Ile His
            20                  25                  30

Trp Met Gln Trp Val Arg Gln Ala Pro Gly Gln Gly Leu Glu Trp Met
        35                  40                  45

Gly Glu Ile Phe Pro Gly Ser Gly Thr Thr Asp Tyr Asn Glu Lys Phe
    50                  55                  60

Lys Gly Lys Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Ala Phe Asp Tyr Trp Gly Gln Gly Thr Thr Val Thr Val
            100                 105                 110

Ser Ser

<210> SEQ ID NO 87
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 87

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Gly Asn Arg
            20                  25                  30

Leu Asn Trp Tyr Gln Gln Lys Pro Gly Lys Ala Pro Lys Arg Leu Ile
        35                  40                  45

```
Tyr Ala Thr Ser Ser Leu Asp Ser Gly Val Pro Ser Arg Phe Ser Gly
            50                  55                  60

Ser Arg Ser Gly Thr Glu Phe Thr Leu Thr Ile Ser Ser Leu Gln Pro
65                  70                  75                  80

Glu Asp Phe Val Thr Tyr Tyr Cys Leu Gln Tyr Ala Ser Ser Pro Phe
                85                  90                  95

Thr Phe Gly Gln Gly Thr Lys Leu Glu Ile Lys
            100                 105
```

<210> SEQ ID NO 88
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 88

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Thr Phe
            20                  25                  30

Phe Ile His Trp Val Arg Gln Arg Pro Gly Gln Gly Leu Glu Trp Ile
        35                  40                  45

Gly Arg Ile Asp Pro Asn Ser Gly Ala Thr Lys Tyr Asn Glu Lys Phe
    50                  55                  60

Glu Ser Lys Val Thr Leu Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Gly Glu Asp Leu Leu Ile Arg Thr Asp Ala Leu Asp Tyr Trp
            100                 105                 110

Gly Gln Gly Thr Ser Val Thr Val Ser Ser
        115                 120
```

<210> SEQ ID NO 89
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 89

```
Asp Ile Gln Met Thr Gln Ser Pro Ser Ser Leu Ser Ala Ser Val Gly
1               5                   10                  15

Asp Arg Val Ser Ile Thr Cys Lys Ala Ser Gln Asn Ala Gly Ile Asp
            20                  25                  30

Val Ala Trp Phe Gln Gln Lys Pro Gly Lys Ala Pro Lys Leu Leu Ile
        35                  40                  45

Tyr Ser Lys Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Tyr Cys Leu Gln Tyr Arg Ser Tyr Pro Arg
                85                  90                  95

Thr Phe Gly Gly Gly Thr Lys Leu Glu Ile Lys
            100                 105
```

```
<210> SEQ ID NO 90
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Thr Phe
            20                  25                  30

Phe Ile His Trp Val Arg Gln Ala Pro Gly Gln Gly Leu Glu Trp Ile
        35                  40                  45

Gly Arg Ile Asp Pro Asn Ser Gly Ala Thr Lys Tyr Asn Glu Lys Phe
    50                  55                  60

Glu Ser Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Glu Asp Leu Leu Ile Arg Thr Asp Ala Leu Asp Tyr Trp
            100                 105                 110

Gly Gln Gly Thr Ser Val Thr Val Ser Ser
        115                 120

<210> SEQ ID NO 91
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 91

Asp Ile Gln Met Thr Gln Ser Pro Ser Ser Leu Ser Ala Ser Val Gly
1               5                   10                  15

Asp Arg Val Ser Ile Thr Cys Lys Ala Ser Gln Asn Ala Gly Ile Asp
            20                  25                  30

Val Ala Trp Phe Gln Gln Lys Pro Gly Lys Ala Pro Lys Leu Leu Ile
        35                  40                  45

Tyr Ser Lys Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Arg Ser Tyr Pro Arg
                85                  90                  95

Thr Phe Gly Gln Gly Thr Lys Leu Glu Ile Lys
            100                 105

<210> SEQ ID NO 92
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 92

Gly Gly Thr Phe Asn Asn Asn Ala Ile Asn
1               5                   10

<210> SEQ ID NO 93
```

```
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 93

Gly Ile Ile Pro Met Phe Gly Thr Ala Lys Tyr Ser Gln Asn Phe Gln
1               5                   10                  15
Gly

<210> SEQ ID NO 94
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 94

Ser Arg Asp Leu Leu Leu Phe Pro His His Ala Leu Ser Pro
1               5                   10

<210> SEQ ID NO 95
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 95

Gln Gly Asp Ser Leu Arg Ser Tyr Tyr Ala Ser
1               5                   10

<210> SEQ ID NO 96
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 96

Gly Lys Asn Asn Arg Pro Ser
1               5

<210> SEQ ID NO 97
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 97

Ser Ser Arg Asp Ser Ser Gly Asn His Trp Val
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 98

Gly Tyr Thr Phe Thr Asp Gln Thr Ile His
1               5                   10
```

<210> SEQ ID NO 99
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 99

Tyr Ile Tyr Pro Arg Asp Asp Ser Pro Lys Tyr Asn Glu Asn Phe Lys
1               5                   10                  15

Gly

<210> SEQ ID NO 100
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 100

Pro Asp Arg Ser Gly Tyr Ala Trp Phe Ile Tyr
1               5                   10

<210> SEQ ID NO 101
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 101

Lys Ala Ser Arg Asp Val Ala Ile Ala Val Ala
1               5                   10

<210> SEQ ID NO 102
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 102

Trp Ala Ser Thr Arg His Thr
1               5

<210> SEQ ID NO 103
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 103

His Gln Tyr Ser Ser Tyr Pro Phe Thr
1               5

<210> SEQ ID NO 104
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 104

Asp His Ile Phe Ser Ile His Trp Met Gln
1               5                   10

```
<210> SEQ ID NO 105
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 105

Glu Ile Phe Pro Gly Ser Gly Thr Thr Asp Tyr Asn Glu Lys Phe Lys
1               5                   10                  15

Gly

<210> SEQ ID NO 106
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 106

Gly Ala Phe Asp Tyr
1               5

<210> SEQ ID NO 107
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 107

Arg Ala Ser Gln Asp Ile Gly Asn Arg Leu Ser
1               5                   10

<210> SEQ ID NO 108
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 108

Ala Thr Ser Ser Leu Asp Ser
1               5

<210> SEQ ID NO 109
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 109

Leu Gln Tyr Ala Ser Ser Pro Phe Thr
1               5

<210> SEQ ID NO 110
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 110

Asp His Ile Phe Ser Ile His Trp Met Gln
1               5                   10
```

<210> SEQ ID NO 111
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 111

Glu Ile Phe Pro Gly Ser Gly Thr Thr Asp Tyr Asn Glu Lys Phe Lys
1               5                   10                  15

Gly

<210> SEQ ID NO 112
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 112

Gly Ala Phe Asp Tyr
1               5

<210> SEQ ID NO 113
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 113

Arg Ala Ser Gln Asp Ile Gly Asn Arg Leu Asn
1               5                   10

<210> SEQ ID NO 114
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 114

Ala Thr Ser Ser Leu Asp Ser
1               5

<210> SEQ ID NO 115
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 115

Gly Tyr Ser Phe Ser Thr Phe Phe Ile His
1               5                   10

<210> SEQ ID NO 116
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 116

Arg Ile Asp Pro Asn Ser Gly Ala Thr Lys Tyr Asn Glu Lys Phe Glu

Ser

<210> SEQ ID NO 117
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 117

Gly Glu Asp Leu Leu Ile Arg Thr Asp Ala Leu Asp Tyr
1               5                   10

<210> SEQ ID NO 118
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 118

Lys Ala Ser Gln Asn Ala Gly Ile Asp Val Ala
1               5                   10

<210> SEQ ID NO 119
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 119

Ser Lys Ser Asn Arg Tyr Thr
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 120

Leu Gln Tyr Arg Ser Tyr Pro Arg Thr
1               5

<210> SEQ ID NO 121
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 121

Gly Tyr Ser Phe Ser Thr Phe Phe Ile His
1               5                   10

<210> SEQ ID NO 122
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 122

```
Gly Arg Ile Asp Pro Asn Ser Gly Ala Thr Lys Tyr Asn Glu Lys Phe
1               5                   10                  15

Glu Ser
```

<210> SEQ ID NO 123
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 123

```
Gly Glu Asp Leu Leu Ile Arg Thr Asp Ala Leu Asp Tyr
1               5                   10
```

<210> SEQ ID NO 124
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 124

```
Lys Ala Ser Gln Asn Ala Gly Ile Asp Val Ala
1               5                   10
```

<210> SEQ ID NO 125
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 125

```
Ser Lys Ser Asn Arg Tyr Thr
1               5
```

<210> SEQ ID NO 126
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 126

```
Leu Gln Tyr Arg Ser Tyr Pro Arg Thr
1               5
```

<210> SEQ ID NO 127
<211> LENGTH: 228
<212> TYPE: PRT
<213> ORGANISM: Artificial Sequence
<220> FEATURE:
<223> OTHER INFORMATION: Synthetic Polypeptide

<400> SEQUENCE: 127

```
Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Tyr Ile Thr Arg Glu Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60
```

```
Glu Val His Asn Ala Lys Thr Lys Pro Arg Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225

<210> SEQ ID NO 128
<211> LENGTH: 329
<212> TYPE: PRT
<213> ORGANISM: Artificial Sequence
<220> FEATURE:
<223> OTHER INFORMATION: Synthetic Polypeptide

<400> SEQUENCE: 128

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Tyr Ile Thr Arg Glu Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 129
<211> LENGTH: 232
<212> TYPE: PRT
<213> ORGANISM: Artificial Sequence
<220> FEATURE:
<223> OTHER INFORMATION: Synthetic Polypeptide

<400> SEQUENCE: 129

Leu Glu Pro Lys Ser Ser Asp Lys Thr His Thr Cys Pro Pro Cys Pro
1               5                   10                  15

Ala Pro Glu Ala Ala Gly Gly Pro Ser Val Phe Leu Phe Pro Pro Lys
                20                  25                  30

Pro Lys Asp Thr Leu Tyr Ile Thr Arg Glu Pro Glu Val Thr Cys Val
                35                  40                  45

Val Val Asp Val Ser His Glu Asp Pro Glu Val Lys Phe Asn Trp Tyr
        50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
                100                 105                 110

Ala Leu Pro Ala Pro Ile Glu Lys Thr Ile Ser Lys Ala Lys Gly Gln
            115                 120                 125

Pro Arg Glu Pro Gln Val Tyr Thr Leu Pro Pro Ser Arg Glu Glu Met
        130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
                180                 185                 190

Tyr Ser Lys Leu Thr Val Asp Lys Ser Arg Trp Gln Gln Gly Asn Val
            195                 200                 205

Phe Ser Cys Ser Val Met His Glu Ala Leu His Asn His Tyr Thr Gln
        210                 215                 220

```
Lys Ser Leu Ser Leu Ser Pro Gly
225                 230
```

```
<210> SEQ ID NO 130
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 130

Leu Glu Pro Lys Ser Ser Asp Lys Thr His Thr Cys Pro Pro Cys Pro
1               5                   10                  15
```

```
<210> SEQ ID NO 131
<211> LENGTH: 290
<212> TYPE: PRT
<213> ORGANISM: Artificial Sequence
<220> FEATURE:
<223> OTHER INFORMATION: Synthetic Polypeptide

<400> SEQUENCE: 131

Gly Cys Lys Trp Asp Leu Leu Ile Lys Gln Trp Val Cys Asp Pro Leu
1               5                   10                  15

Gly Ser Gly Ser Ala Thr Gly Gly Ser Gly Ser Thr Ala Ser Ser Gly
                20                  25                  30

Ser Gly Ser Ala Thr His Met Leu Pro Gly Cys Lys Trp Asp Leu Leu
            35                  40                  45

Ile Lys Gln Trp Val Cys Asp Pro Leu Gly Gly Gly Gly Val Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
        115                 120                 125

Asn Ala Lys Thr Lys Pro Arg Glu Glu Gln Tyr Asn Ser Thr Tyr Arg
    130                 135                 140

Val Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
            180                 185                 190

Thr Leu Pro Pro Ser Arg Asp Glu Leu Thr Lys Asn Gln Val Ser Leu
        195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
            260                 265                 270

Glu Ala Leu His Asn His Tyr Thr Gln Lys Ser Leu Ser Leu Ser Pro
        275                 280                 285
```

Gly Lys
    290

<210> SEQ ID NO 132
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 132

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Tyr Tyr Asp Ile Leu Thr Gly Tyr Tyr Tyr Phe Asp Tyr
            100                 105                 110

Trp Gly Gln Gly Thr Leu Val Thr Val Ser Ser
        115                 120

<210> SEQ ID NO 133
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 133

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Ser Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys
            100                 105

<210> SEQ ID NO 134
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 134

```
Glu Ser Lys Tyr Gly Pro Pro Cys Pro Pro Cys Pro
1               5                   10

<210> SEQ ID NO 135
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 135

Gly Gly Cys Gly Gly Gly
1               5

<210> SEQ ID NO 136
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 136

Leu Gly Gly Cys Gly Gly Gly Ser
1               5
```